United States Patent
Mahr et al.

(10) Patent No.: US 12,168,043 B2
(45) Date of Patent: *Dec. 17, 2024

(54) PEPTIDES AND COMBINATION OF PEPTIDES FOR USE IN IMMUNOTHERAPY AGAINST VARIOUS CANCERS

(71) Applicant: Immatics Biotechnologies GmbH, Tuebingen (DE)

(72) Inventors: Andrea Mahr, Tuebingen (DE); Toni Weinschenk, Tuebingen (DE); Colette Song, Tuebingen (DE); Oliver Schoor, Tuebingen (DE); Jens Fritsche, Tuebingen (DE); Harpreet Singh, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 301 days.

This patent is subject to a terminal disclaimer.

(21) Appl. No.: 17/727,244

(22) Filed: Apr. 22, 2022

(65) Prior Publication Data

US 2022/0249635 A1 Aug. 11, 2022

Related U.S. Application Data

(63) Continuation of application No. 17/327,458, filed on May 21, 2021, now abandoned, which is a (Continued)

(30) Foreign Application Priority Data

Dec. 11, 2015 (GB) .................................... 1521894

(51) Int. Cl.
| | | |
|---|---|---|
| *A61K 38/00* | (2006.01) | |
| *A61K 39/00* | (2006.01) | |
| *C07K 7/06* | (2006.01) | |
| *C07K 7/08* | (2006.01) | |
| *C07K 14/47* | (2006.01) | |
| *C07K 14/705* | (2006.01) | |
| *C07K 14/71* | (2006.01) | |

(Continued)

(52) U.S. Cl.
CPC ............ *A61K 39/0011* (2013.01); *C07K 7/06* (2013.01); *C07K 7/08* (2013.01); *C07K 14/47* (2013.01); *C07K 14/4748* (2013.01); *C07K 14/705* (2013.01); *C07K 14/7051* (2013.01); *C07K 14/71* (2013.01); *C07K 14/721* (2013.01); *C07K 14/8135* (2013.01); *C07K 16/18* (2013.01); *C07K 16/28* (2013.01); *C07K 16/2863* (2013.01); *C07K 16/2869* (2013.01); *C07K 16/30* (2013.01); *C07K 16/38* (2013.01); *C07K 16/40* (2013.01); *C12N 5/0636* (2013.01); *C12N 5/0638* (2013.01); *C12N 9/0091* (2013.01); *C12N 9/1264* (2013.01); *C12N 15/115* (2013.01); *C12Q 1/6886* (2013.01); *C12Y 116/01* (2013.01); *C12Y 207/07031* (2013.01); *G01N 33/57484* (2013.01); *G16B 25/00* (2019.02); *G16B 25/10* (2019.02); *A61K 35/17* (2013.01); *A61K 38/00* (2013.01); *A61K 2039/5158* (2013.01); *A61K 2039/572* (2013.01); *C07K 2317/34* (2013.01); *C07K 2317/76* (2013.01); *C07K 2319/40* (2013.01); *C12N 2310/16* (2013.01); *C12N 2502/11* (2013.01); *C12Q 2600/156* (2013.01); *G01N 2333/47* (2013.01)

(58) Field of Classification Search
CPC ....... A61K 39/0011; C07K 7/06; C07K 14/47; C07K 14/4748; C07K 16/30
See application file for complete search history.

(56) References Cited

U.S. PATENT DOCUMENTS

| | | |
|---|---|---|
| 7,060,275 B2 | 6/2006 | Mueller et al. |
| 7,205,121 B2 | 4/2007 | Palka-Hamblin et al. |

(Continued)

FOREIGN PATENT DOCUMENTS

| | | |
|---|---|---|
| CN | 1621414 A | 9/2011 |
| EP | 1118860 A1 | 7/2001 |

(Continued)

OTHER PUBLICATIONS

Accardi, Luisa, et al. "In vivo antitumor effect of an intracellular single-chain antibody fragment against the E7 oncoprotein of human papillomavirus 16" International Journal of Cancer, vol. 134, No. 11, pp. 2742-2747, Jun. 2014.

Albrecht, Jana, et al. "IL-21-treated naive CD45RA+ CD8+ T cells represent a reliable source for producing leukemia-reactive cytotoxic T lymphocytes with high proliferative potential and early differentiation phenotype" Cancer Immunol. Immunotherapy, vol. 60, No. 2, pp. 235-248, Feb. 2011.

Ampie, Leonel, et al. "Immunotherapeutic advancements for glioblastoma" Frontiers in Oncology, vol. 5, Article 12, Jan. 2015.

(Continued)

*Primary Examiner* — Sheela J. Huff
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 34 Drawing Sheets
Specification includes a Sequence Listing.

Related U.S. Application Data continuation of application No. 16/705,042, filed on Dec. 5, 2019, now Pat. No. 11,433,124, which is a continuation of application No. 16/408,653, filed on May 10, 2019, now Pat. No. 10,525,116, which is a continuation of application No. 16/116,323, filed on Aug. 29, 2018, now Pat. No. 10,342,859, which is a continuation of application No. 15/374,882, filed on Dec. 9, 2016, now Pat. No. 10,179,165.

(60) Provisional application No. 62/266,233, filed on Dec. 11, 2015.

(51) Int. Cl.

| | | |
|---|---|---|
| C07K 14/72 | (2006.01) | |
| C07K 14/725 | (2006.01) | |
| C07K 14/81 | (2006.01) | |
| C07K 16/18 | (2006.01) | |
| C07K 16/28 | (2006.01) | |
| C07K 16/30 | (2006.01) | |
| C07K 16/38 | (2006.01) | |
| C07K 16/40 | (2006.01) | |
| C12N 5/0783 | (2010.01) | |
| C12N 9/02 | (2006.01) | |
| C12N 9/12 | (2006.01) | |
| C12N 15/115 | (2010.01) | |
| C12Q 1/6886 | (2018.01) | |
| G01N 33/574 | (2006.01) | |
| G16B 25/00 | (2019.01) | |
| G16B 25/10 | (2019.01) | |
| A61K 35/17 | (2015.01) | |

(56) References Cited

U.S. PATENT DOCUMENTS

| | | |
|---|---|---|
| 7,268,222 B1 | 9/2007 | Harras et al. |
| 7,358,231 B1 | 4/2008 | McCaffey et al. |
| 7,368,531 B2 * | 5/2008 | Rosen .................... G01N 33/68 435/7.1 |
| 7,399,469 B2 | 7/2008 | Zhang et al. |
| 7,608,413 B1 | 10/2009 | Joseloff et al. |
| 7,745,391 B2 | 6/2010 | Mintz et al. |
| 7,820,786 B2 | 10/2010 | Thomson et al. |
| 7,842,467 B1 | 11/2010 | Heidbrink et al. |
| 7,892,770 B2 | 2/2011 | Cao et al. |
| 7,919,467 B2 | 4/2011 | Ramakrishna et al. |
| 7,932,031 B2 | 4/2011 | Lee et al. |
| 7,951,546 B2 | 5/2011 | Frantz et al. |
| 7,960,134 B1 | 6/2011 | Ashwell et al. |
| 7,960,158 B1 | 6/2011 | Ashwell et al. |
| 7,964,365 B2 | 6/2011 | Bottaro et al. |
| 7,968,681 B2 | 6/2011 | Stemmer et al. |
| 7,998,689 B2 | 8/2011 | Joseloff et al. |
| 8,168,602 B2 | 5/2012 | DePinho et al. |
| 8,304,199 B2 | 11/2012 | Bottaro et al. |
| 8,309,315 B2 | 11/2012 | Cao et al. |
| 8,455,623 B2 | 6/2013 | Horst et al. |
| 8,586,006 B2 | 11/2013 | Hood et al. |
| 8,617,831 B2 | 12/2013 | Bottaro et al. |
| 8,647,629 B2 | 2/2014 | Rammensee et al. |
| 9,498,512 B2 | 11/2016 | Rammensee et al. |
| 9,943,579 B2 | 4/2018 | Weinschenk et al. |
| 10,058,598 B2 | 8/2018 | Mahr et al. |
| 10,071,148 B2 | 9/2018 | Weinschenk et al. |
| 10,098,938 B2 | 10/2018 | Mahr et al. |
| 10,179,165 B2 | 1/2019 | Mahr et al. |
| 10,314,896 B2 | 6/2019 | Mahr et al. |
| 10,434,136 B2 | 10/2019 | Rammensee et al. |
| 10,450,356 B2 | 10/2019 | Kessler et al. |
| 10,590,194 B2 | 3/2020 | Wagner et al. |
| 10,723,796 B2 | 7/2020 | Wagner et al. |
| 10,988,754 B2 | 4/2021 | Fotin-Mleczek et al. |
| 11,111,294 B2 | 9/2021 | Wagner et al. |
| 11,224,644 B2 * | 1/2022 | Mahr .................... G16B 25/00 |
| 2005/0239700 A1 | 10/2005 | Kloetzer et al. |
| 2007/0065447 A1 | 3/2007 | Tryggvason et al. |
| 2007/0065888 A1 | 3/2007 | Ring et al. |
| 2008/0025981 A1 | 1/2008 | Young et al. |
| 2008/0063654 A1 | 3/2008 | McNeel et al. |
| 2009/0274714 A1 | 11/2009 | Singh et al. |
| 2009/0275633 A1 | 11/2009 | Esteller |
| 2011/0142842 A1 | 6/2011 | Olweus et al. |
| 2012/0070450 A1 | 3/2012 | Ishikawa et al. |
| 2014/0086943 A1 | 3/2014 | Weinschenk et al. |
| 2014/0234351 A1 | 8/2014 | Bender et al. |
| 2015/0104473 A1 | 4/2015 | Ossendorp et al. |
| 2015/0125477 A1 | 5/2015 | Kuttruff-Coqui et al. |
| 2016/0168200 A1 | 6/2016 | Weinschenk et al. |
| 2017/0202937 A1 | 7/2017 | Weinschenk et al. |
| 2017/0319675 A1 | 11/2017 | Weinschenk et al. |
| 2020/0078439 A1 | 3/2020 | Rammensee et al. |

FOREIGN PATENT DOCUMENTS

| | | | |
|---|---|---|---|
| EP | 1760089 A1 | 3/2007 | |
| EP | 1760088 B1 | 3/2008 | |
| WO | 0190197 A1 | 11/2001 | |
| WO | 2007028574 A2 | 3/2007 | |
| WO | 20070150077 A2 | 12/2007 | |
| WO | 2008118017 A2 | 10/2008 | |
| WO | 2009036246 A2 | 3/2009 | |
| WO | 20090036246 A2 | 3/2009 | |
| WO | 20090059804 A2 | 5/2009 | |
| WO | WO-2009138236 A1 * | 11/2009 | ............ A61K 38/10 |
| WO | 20120178087 A1 | 12/2012 | |
| WO | 2013177533 A2 | 11/2013 | |
| WO | 2015018805 A1 | 2/2015 | |
| WO | 20150018805 A1 | 2/2015 | |
| WO | 2015188839 A2 | 12/2015 | |
| WO | 2017089768 A1 | 6/2017 | |
| WO | 2017096304 A1 | 6/2017 | |
| WO | 2019075385 A1 | 4/2019 | |

OTHER PUBLICATIONS

Arceci, Robert J. "The potential for antitumor vaccination in acute myelogenous leukemia" Journal of Molecular Medicine, vol. 76, pp. 80-93, 1998.

Avigan, David, et al. "Fusion Cell Vaccination of Patients with Metastatic Breast and Renal Cancer Induces Immunological and Clinical Responses" Clinical Cancer Research, vol. 10, pp. 4699-4708, Jul. 15, 2004.

Beatty, Gregory L., et al. "IFN-g-Dependent Inhibition of Tumor Angiogenesis by Tumor-Infiltrating CD41 T Cells Requires Tumor Responsiveness to IFN-y1" Journal of Immunology, vol. 166, No. 4, pp. 2276-2282, Feb. 15, 2001.

Bodey, Bela, et al. "Failure of Cancer Vaccines: The Significant Limitations of the Approach to Immunotherapy" Anticancer Research, vol. 20, No. 4, pp. 2665-2676, Jul.-Aug. 2000.

Braumueller, Heidi, et al. "T-helper-1-cell cytokines drive cancer into senescence" Nature, vol. 494, pp. 361-365, Feb. 2013.

Bray, Freddie, et al. "Global estimates of cancer prevalence for 27 sites in the adult population in 2008" International Journal of Cancer, vol. 132, pp. 1133-1145, 2013.

Brossart, Peter and Bevan, Michael J. "Presentation of Exogenous Protein Antigens on Major Histocompatability Complex Class I Molecules by Dendritic Cells: Pathway of Presentation and Regulation by Cytokines" Blood, vol. 90, No. 4, pp. 1594-1599, Aug. 15, 1997.

Bujas, T., et al. "MAGE-A3/4 and NY-ESO-1 antigens expression in metastatic esophageal squamous cell carcinoma" European Journal Histochem. vol. 55, No. 1, Mar. 2011.

Butterfield, Lisa H., et al., "A Phase I/II Trial Testing Immunization of Hepatocellular Carcinoma Patients with Dendritic Cells Pulsed with Four α-Fetoprotein Peptides", Clinical Cancer Research, vol. 12, No. 9, pp. 2817-2825, May 2006.

(56) References Cited

OTHER PUBLICATIONS

Butterfield, Lisa H., et al., "Determinant Spreading Associated with Clinical Response in Dendritic Cell-based Immunotherapy for Malignant Melanoma", Clinical Cancer Research, vol. 9, pp. 998-1008, Mar. 2003.

Carballido, Estrella, et al. "Immunomodulatory Drugs and Active Immunotherapy for Chronic Lymphocytic eukemia" Cancer Control, vol. 19, Issue 1, pp. 4-76, Jan. 2012.

Chang, A. et al. "Clinical observations on adoptive immunotherapy with vaccine-primed T-lymphocytes secondarily sensitized to tumor in vitro" Cancer Research, vol. 53, No. 5, pp. 1043-1050, Mar. 1993.

Chang, Yong S., et al., "Sorafenib (BAY 43-9006) inhibits tumor growth and vascularization and induces tumor apoptosis and hypoxia in RCC xenograft models", Cancer Chemother. Pharmacol. Vol. 59, No. 5, pp. 561-574, Apr. 2007.

Chapiro, Julius, et al., "Combination of intra-arterial therapies and sorafenib: Is there a clinical benefit?" Radiol. Med. vol. 119, pp. 476-482, Jul. 2014.

Chen, Liya, et al. "Critical role of endoplasmic reticulum aminopeptidase 1 in determining the length and sequence of peptides bound and presented by HLA-B27" Arthritis Rheumatol., vol. 66, No. 2, pp. 284-294, Feb. 2014.

Chen, Ting, et al. "Identification of trypsin-inhibitory site and structure determination of human SPINK2 serine proteinase inhibitor" Proteins, vol. 77, No. 1, pp. 209-219, Oct. 2009.

Coosemans, An, et al. "Wilms' Tumor Gene 1 (WT1)-loaded dendritic cell immunotherapy in patients with uterine tumors: a phase I/II clinical trial" Anticancer Research, vol. 33, No. 12, pp. 5495-5500, Dec. 2013.

Counter, C.M., "Telomerase activity in normal leukocytes and in hematologic malignancies" Blood, vol. 85, No. 9, pp. 2315-2320, May 1995.

Cunha, Fernanda, et al. "Intracellular Peptides as Natural Regulators of Cell Signaling" Journal of Biological Chemistry, vol. 283, No. 36, pp. 24448-59, Sep. 2008.

Dengjel, Jorn, et al. "Unexpected Abundance of HLA Class II Presented Peptides in Primary Renal Cell Carcinomas" Clinical Cancer Research, vol. 12, No. 14, Jul. 15, 2006.

Di Renzo, M.F., et al. "Expression of the Met/HGF receptor in normal and neoplastic human tissues" Oncogenetics, vol. 6, No. 11, pp. 1997-2003, Nov. 1991.

Di Schiavi, et al. "UMODL1/Olfactorin is an extracellular membrane-bound molecule with a restricted spatial expression in olfactory and vomeronasal neurons" European Journal of Neuroscience, vol. 21, No. 12, pp. 3291-3300, Jun. 2005.

Distler, Eva, et al. "Patient-individualized CD8+ cytolytic T-cell therapy effectively combats minimal residual leukemia in immunodeficient mice" International Journal of Cancer, vol. 138, No. 5, Mar. 2016.

Drexler, H. G., et al. "Terminal deoxynucleotidyl transferase (TdT) expression in acute myeloid leukemia" Leukemia, vol. 7, No. 8, pp. 1142-1150, Aug. 1993.

Economopoulou, Panagiota, et al. "The emerging role of immunotherapy in head and neck squamous cell carcinoma (HNSCC): anti-tumor immunity and clinical applications" Annals of Translational Medicine, vol. 4, No. 9, Article 173, May 2016.

Emens, Leisha A. "Breast cancer immunobiology driving immunotherapy: vaccines and immune checkpoint blockade" Expert Review Anticancer Therapy, vol. 12, No. 12, pp. 1597-1611, Dec. 2012.

Estey, Elihu H. "Acute myeloid leukemia: 2014 update on risk-stratification and management" American Journal of Hematology, vol. 89, No. 11, pp. 1063-1081, Nov. 2014.

Farahat, N., et al. "Differential TdT expression in acute leukemia by flow cytometry: a quantitative study" Leukemia., vol. 9, No. 4, pp. 583-587, Apr. 1995.

Ferlay, J., et al. "Cancer incidence and mortality patterns in Europe: Estimates for 40 countries in 2012" European Journal of Cancer, vol. 49, pp. 1374-1403, Apr. 2013.

Fuge, Oliver, et al. "Immunotherapy for bladder cancer" Research and Reports in Urology, vol. 7, pp. 65-79, May 2015.

Gandhi, Ankit V., et al. "Differential expression of cytochrome P450 omega-hydroxylase isoforms and their association with clinicopathological features in pancreatic ductal adenocarcinoma" Annals Surgical Oncology, vol. 20, Suppl. 3, Dec. 2013.

Giannopolous, K., et al. "Peptide vaccination elicits leukemia-associated antigen-specific cytotoxic CD8+ T-cell responses in patients with chronic lymphocytic leukemia" Leukemia, vol. 24, No. 4, pp. 798-805, Apr. 2010.

Giannopoulos, K., et al. "Expression of RHAMM/CD168 and other tumor-associated antigens in patients with B-cell chronic lymphocytic leukemia" International Journal of Oncology, vol. 29, No. 1, pp. 95-103, Jul. 2006.

Gnjatic, Sacha, et al. "Survey of naturally occurring CD4+ T cell responses against NY-ESO-1 in cancer patients: Correlation with antibody responses" PNAS, vol. 100, No. 15, pp. 8862-8867. Jul. 22, 2003.

Goede, Valentin, et al. "Obinutuzumab plus chlorambucil in patients with CLL and coexisting conditions" New England Journal of Medicine, vol. 370, No. 12, pp. 1101-1110, Mar. 2014.

Granziero, L., et al. "Survivin is expressed on CD40 stimulation and interfaces proliferation and apoptosis in B-cell chronic lymphocytic leukemia" Blood, vol. 97, No. 9, pp. 27777-83, May 2001.

Grivas, Petros D., et al. "The biological complexity of urothelial carcinoma: Insights into carcinogenesis, targets and biomarkers of response to therapeutic approaches" Semin Cancer Biol. vol. 35, pp. 125-132, Dec. 2015.

Gunawardana, Chaminda, et al. "South Asian chronic lymphocytic leukemia patients have more rapid disease progression in comparison to White patients." British journal of haematology 142, No. 4 (2008): 606-609.

Gura, Trisha. "Systems for Identifying New Drugs are Often Faulty" Science, vol. 278, No. 5340, pp. 1041-1042, Nov. 1997.

Hallek, M., et al. "Immunochemotherapy with fludarabine (F), cyclophosphamide (C), and rituximab (R) (FCR) versus fludarabine and cyclophosphamide (FC) improves response rates and progression-free survival (PFS) of previously untreated patients (pts) with advanced chronic lymphocytic leukemia (CLL)" Blood (ASH Annual Meeting Abstracts), vol. 112, p. 325, 2008 (Abtsract Only).

Harig, S., et al. "Induction of cytotoxic T-cell responses against immunoglobulin V region-derived peptides modified at human leukocyte antigen-A2 binding residues" Blood, vol. 98, No. 10, pp. 29999-3005, Nov. 2001.

Hilpert, Kai, et al. "Peptide arrays on cellulose support: SPOT sunthesis, a time and cost efficient method for synthesis of large Nos. of peptides in a parallel and addressable fashion" Nat. Protoc. vol. 2, No. 6, pp. 1333-1349, May 2007.

Holtl, Lorenz, et al. "Immunotherapy of Metastatic Renal Cell Carcinoma with Tumor Lysate-pulsed Autologous Dendritic Cells1" Clinical Cancer Research, vol. 8, pp. 3369-3376, Nov. 2002.

Horig, Heidi, et al. "Phase I clinical trial of a recombinant canarypoxvirus (ALVAC) vaccine expressing human carcinoembryonic antigen and the B7.1 co-stimulatory molecule" Cancer Immunology, Immunotherapy, vol. 49, No. 9, pp. 504-514, Nov. 2000.

Hung, Chien-Fu, et al. "Antigen-specific immunotherapy of cervical and ovarian cancer" Immunological Review, vol. 222, pp. 43-69, Apr. 2008.

Hus, Iwona, et al. "Immunotherapy with irradiated autologous leukemic cells in patients with B-CLL in early stages" Oncology Rep. vol. 20, No. 2, pp. 443-451, Aug. 2008.

Hwang. Melissa L., et al. "Cognate memory CD4+ T cells generated with dendritic cell priming influence the expansion, trafficking, and differentiation of secondary CD8+ T cells and enhance tumor control" Journal of Immunology, vol. 179, No. 9, pp. 5829-5838, Nov. 2007.

Inoue, H., et al. "Human esophageal carcinomas frequently express the tumor-rejection antigens of MAGE genes" International Journal of Cancer, vol. 63, No. 4, pp. 523-526, Nov. 1995.

Janakiram, Naveena B., et al. "Adoptive Transfer of Regulatory T Cells Promotes Intestinal Tumorigenesis and is Associated With Decreased NK Cells and IL-22 Binding Protein" Molecular Carcinogenesis, vol. 54, No. 10, pp. 986-998, Oct. 2015.

(56) References Cited

OTHER PUBLICATIONS

Jarmalavicius, Saulius et al., "High Immunogenicity of the Human Leukocyte Antigen Peptidomes of Melanoma Tumor Cells", The Journal of Biological Chemistry, Sep. 28, 2012, pP. 33401-33411, vol. 287, No. 40.

Jones, Robert T., et al. "Pharmacogenomics: Biomarker-Directed Therapy for Bladder Cancer" Urol. Clim North America, vol. 43, No. 1, pp. 77-86, Feb. 2016.

Juncher, Henning, et al. "The Solubility of Oral Preparations of Penicilin V" Antibiotic Med. Clin. Ther. Vol. 4, No. 9, pp. 497-507, Sep. 1957.

Kalos, Michael, et al. "T cells with chimeric antigen receptors have potent antitumor effects and can establish memory in patients with advanced leukemia" Science Translational Medicine, vol. 3, No. 95, Aug. 2011.

Kaufman, Howard L., et al. "Combination Chemotherapy and ALVAC-CEA/B7.1Vaccine in Patients with Metastatic Colorectal Cancer" Clinical Cancer Research, vol. 14, No. 15, pp. 4843-4849, Aug. 1, 2008.

Khong, Hung T., et al. "Natural selection of tumor variants in the generation of "tumor escape" phenotypes" Natural Immunology, vol. 3, No. 11, pp. 999-1005, Nov. 2002.

Kimura, Hitoshi, et al. "Prognostic significance of EpCAM expression in human esophageal cancer" International Journal of Oncology, vol. 30, No. 1, pp. 171-179, Jan. 2007.

Knollman, Hayley, et al. "Muscle-invasive urothelial bladder cancer: an update on systemic therapy" Ther Adv Urol. vol. 7, No. 6, pp. 312-330, Dec. 2015.

Koido, Shigeo, et al. "Immunotherapy for colorectal cancer" World of Gastroenterology, vol. 19, No. 46, pp. 8531-8542, Dec. 2013.

Kono, Koji, et al. "Vaccination with multiple peptides derived from novel cancer-testis antigens can induce specific T-cell responses and clinical responses in advanced esophageal cancer" Cancer Science, vol. 100, No. 8, pp. 1502-1509, Aug. 2009.

Krackhardt, Angela M., et al. "Identification of tumor-associated antigens in chronic lymphocytic leukemia by SEREX" Blood, vol. 100, No. 6, pp. 2123-2131, Sep. 2002.

Kronenberger, Konrad, et al. "A Polyvalent Cellular Vaccine Induces T-cell Responses Against Specific Self-antigens Overexpressed in Chronic Lymphocytic B-cell Leukemia" Journal of Immunotherapy, vol. 31, Issue 8, pp. 723-730, Oct. 2008.

Lee, Wei-Chen, et al., "Vaccination of Advanced Hepatocellular Carcinoma Patients with Tumor Lysate-Pulsed Dendritic Cells: A Clinical Trial" Journal of Immunotherapy, vol. 28, No. 5, pp. 496-504, Sep./Oct. 2005.

Liang, Zhen, et al. "[The expression of 11 cancer/testis (CT) antigen genes in esophageal carcinoma]" Chinese Journal of Oncology, vol. 27, No. 9, pp. 534-537, Sep. 2005 (translation of abstract only).

Liu, Zuqiang, et al. "Potent Tumor-Specific Protection Ignited by Adoptively Transferred CD4+ T Cells" Journal of Immunology, vol. 181, No. 6, pp. 4363-4370, Sep. 2008.

Llovet, Josep M., et al., "Sorafenib in Advanced Hepatocellular Carcinoma" New England Journal of Medicine, vol. 359, pp. 378-390, Dec. 4, 2008.

Lollini, Pier-Luigi, et al. "Cancer immunoprevention: tracking down persistent tumor antigens" Trends in Immunology, vol. 24, No. 2, pp. 62-66, Feb. 2003.

Lollini, P-L., et al. "New target antigens for cancer immunoprevention" Current Cancer Drug targets, vol. 5, No. 3, pp. 221-228, May 2005.

Maerten, Angela, et al. "Therapeutic vaccination against metastatic renal cell carcinoma by autologous dendritic cells: preclinical results and outcome of a first clinical phase I/II trial" Cancer Immunology, Immunotherapy, vol. 51, pp. 637-644, Oct. 2002.

Mantia-Smaldone, Gina M., et al. "Immunotherapy in ovarian cancer" Human Vaccin Innumotherapy, vol. 8, No. 9, pp. 1179-1191, Sep. 2012.

Massari, F., et al. "PD-1 blockade therapy in renal cell carcinoma: Current studies and future promises" Cancer Treatment Reviews, vol. 41, No. 2, pp. 114-121, Feb. 2015.

Matsueda, Satoko, et al. "Immunotherapy in gastric cancer" World Journal of Gastroenterology, vol. 20, Issue 7, pp. 1657-1666, Feb. 21, 2014.

Maus, Marcela V., et al. "Antibody-modified T cells: CARs take the front seat for hematologic malignancies" Blood, vol. 123, No. 17, pp. 2625-2635, Apr. 2014.

Mayr, Christine, et al. "Fibromodulin as a novel tumor-associated antigen (TAA) in chronic lymphocytic leukemia (CLL), which allows expansion of specific CD8+ autologous T lymphocytes" Blood, vol. 105, No. 4, pp. 1566-1573, Feb. 2005.

Mayr, Christine, et al. "MDM2 is recognized as a tumor-associated antigen in chronic lymphocytic leukemia by CD8+ autologous T lymphocytes" Experimental Hematology, vol. 31, No. 1, pp. 44-53, Jan. 2006.

Menoret, Antoine, et al. "Association of Peptides with Heat Shock Protein gp96 Occurs in Vivo and Not after Cell Lysis" Biochemical and Biophysical Research Communications, vol. 262, No. 3, pp. 813-818, Sep. 1999.

Miyagi, Yoshiaki, et al. "Induction of Cellular Immune Responses to Tumor Cells and Peptides in Colorectal Cancer Patients by Vaccination with SART3 Peptides1" Clinical Cancer Research, vol. 7, pp. 3950-3962, Dec. 2001.

Molina, Julian R., et al. "Non-Small Cell Lung Cancer: Epidemiology, Risk Factors, Treatment, and Survivorship" Mayo Clinic Proceedings, vol. 83, No. 5m pp. 584-594, May 2008.

Morozowich, W., et al. "Relationship between In Vitro Dissolution Rates, Solubilities, and LT50s in Mice of Some Salts of Benzphetamine and Etryptamine" Journal of Pharmaceutical Science, vol. 51, No. 10, pp. 993-995, 1962.

Mortara, Lorenzo, et al. "CIITA-Induced MHC Class II Expression in Mammary Adenocarcinoma Leads to a Th1Polarization of the Tumor Microenvironment, Tumor Rejection, and Specific Antitumor Memory" Clinical Cancer Research, vol. 12, No. 11, pp. 3435-3443, Jun. 1, 2006.

Moulton, Hong M., et al. "Active Specific Immunotherapy with a -Human Chorionic Gonadotropin Peptide Vaccine in Patients with Metastatic Colorectal Cancer: Antibody Response Is Associated with Improved Survival1" Clinical Cancer Research, vol. 8, pp. 2044-2051, Jul. 2002.

Mueller, Martin R., et al. "Induction of chronic lymphocytic leukemia (CLL)-specific CD4- and CD8-mediated T-cell responses using RNA-transfected dendritic cells" Blood, vol. 103, No. 5, pp. 1763-1769, Mar. 2004.

Mumberg, Dominik, et al. "CD41 T cells eliminate MHC class II-negative cancer cells in vivo by indirect effects of IFN-γ" Immunology, vol. 96, pp. 8633-8638, Jul. 1999.

Neeley, Yilin C., et al. "Partially Circumventing Peripheral Tolerance for Oncogene-Specific Prostate Cancer Immunotherapy" The Prostate, vol. 68, No. 7, pp. 715-727, May 2008.

O'Connor, Colleen M., et al. "Adoptive T-cell therapy improves treatment of canine non-Hodgkin lymphoma post chemotherapy" Scientific Reports, vol. 2, No. 249, pp. 1-12, 2012.

Ohigashi, Yuichiro, et al. "Clinical significance of programmed death-1 ligand-1 and programmed death-1 ligand-2 expression in human esophageal cancer" Clinical Cancer Research, vol. 11, No. 8, pp. 2947-2953, Apr. 2005.

Okuno, Kiyotaka, et al. "Phase I clinical trial of a novel peptide vaccine in combination with UFT/LV for metastatic colorectal cancer" Experimental and Therapeutic Medicine, vol. 2, pp. 73-79, Jan. 2011.

Palma, M., et al. "Development of a dendritic cell-based vaccine for chronic lymphocytic leukemia" Cancer Immunol. Immunother. vol. 57, No. 11, pp. 1705-1710, Nov. 2008.

Palmer, Daniel H., et al., "A phase II study of adoptive immunotherapy using dendritic cells pulsed with tumor lysate In patients with hepatocellular carcinoma", Hepatology, vol. 49, pp. 124-132, Jan. 2009.

Palomba, M. Lia. "Active immunotherapy: current state of the art in vaccine approaches for NHL" Current Oncology Reports, vol. 14, No. 5, pp. 433-440, Oct. 2012.

(56) References Cited

OTHER PUBLICATIONS

Parikh, Sameer A., et al. "Frontline chemoimmunotherapy with fludarabine, cyclophosphamide, alemtuzumab, and rituximab for high-risk chronic lymphocytic leukemia" Blood, vol. 118, No. 8, pp. 2062, 2068, Aug. 2011.
Phan, Giao Q., et al. "Adoptive cell transfer for patients with metastatic melanoma: the potential and promise of cancer immunotherapy" Cancer Control, vol. 20, No. 4, pp. 289-297, Oct. 2013.
Porter, David L., et al. "Chimeric antigen receptor-modified T cells in chronic lymphoid leukemia" New England Journal of Medicine, vol. 365, No. 8, pp. 725-733, Aug. 2011.
Prato, Sandro, et al. "Rapid Deletion and Inactivation of CTLs upon Recognition of a Number of Target Cells over a Critical Threshold" Journal of Immunology, vol. 191, No. 7, pp. 3534-3544, Oct. 2013.
Pritchard, Antonia L. et al., "Exploration of Peptides Bound to MHC Class I Molecules in Melanoma", Pigment Cell Melanoma Research, vol. 28, No. 3, May 2015 (Abstract Only).
Quillen, V., et al. "Expression of MAGE genes in esophageal squamous-cell carcinoma" Anticancer Research, vol. 17, No. 1A, pp. 387-391, Jan. 1997 (abstract Only).
Quinn, David I., et al. "Immunotherapy for castration-resistant prostate cancer: Progress and new paradigms" Urologic Oncology, vol. 33, No. 5, pp. 245-260, May 2015.
Ramanathan, Sheela, et al "Antigen-nonspecific activation of CD8+ T lymphocytes by cytokines: relevance to Immunity, autoimmunity, and cancer" Arch. Immunol. Ther. Exp. (Warsz), vol. 56, No. 5, pp. 311-323, Sep. 2008.
Search Report from GB Application No. 1521894.4 received Sep. 22, 2016.
GENE (epub Sep. 2015); vol. 575, pp. 438-451, "Analysis of the Fam181 gene family . . . " Marks et al.
International Search Report for PCT/EP2016/079737, mailed May 3, 2017.
Walter et al., "Multipeptide immune response to cancer vaccine IMA901 after single-dose cyclophosphamide associates with longer patient survival", Nature Medicine., vol. 18, No. 8, Aug. 2012 (Aug. 2012), pp. 1254-1265, XP055175088, Nature Publishing Group, New York, NY. ISSN: 1078-8956.
Weinschenk, et al., "Integrated functional genomics approach for the design of patient-individual antitumor vaccines." Cancer Research, American Association for Cancer Research, US. vol. 62, No. 20, Oct. 15, 2002 (Oct. 15, 2002), pp. 5818-5827. XP002266492, 21-29. ISSN: 0008-5472.
Hinrichs et al., Nature Biotechnology vol. 31 p. 999 (2013).
Baruch et al. (Cancer vol. 123 p. 2154 (2017)).
Li et al., "Identification of a new HLA-A*0201-restricted CD8+ T cell epitope from hepatocellular carcinoma-associated antigen HCA587," Clinical and Experimental Immunology, (2005), vol. 140: 310-319.
Reinisch et al., "Prospective Pilot Study of Recombinant Granulocyte-Macrophage Colony-Stimulating Factor and Interferon-y in Patients With Inoperable Hepatocellular Carcinoma" Journal of Immunotherapy, vol. 25, No. 6, pp. 489-499, Nov./Dec. 2002.
Reinmuth, Niels, et al. "[Non-small cell lung cancer: news from immunotherapy]" Dtsch Med Wochenschr, vol. 140, No. 5, pp. 329-333, Mar. 2015.
Restifo, Nicholas P., et al. "Loss of Functional Beta2-Microglobulin in Metastatic Melanomas From Five Patients Receiving Immunotherapy" Journal National Cancer Institute, vol. 88, No. 2, pp. 100-108, Jan. 1996.
Richards, S., et al. "Chemotherapeutic Options in Chronic Lymphocytic Leukemia: a Meta-analysis of the Randomized Trials" J Natl. Cancer Inst vol. 91, pp. 861-868, May 1999.
Robak, Tadeusz, et al. "Anti-CD37 antibodies for chronic lymphocytic leukemia" Expert Opinion on Biological Therapy, vol. 14, No. 5, pp. 651-661, Feb. 2014.
Rock, K.L., et al. "Presentation of exogenous antigen with class I major histocompatibility complex molecules" Science, vol. 249, No. 4971, pp. 918-921, Aug. 1990.

Rosenberg, S.A., "Gene transfer into humans—immunotherapy of patients with advanced melanoma, using tumor- Infiltrating lymphocytes modified by retroviral gene transduction" New England Journal of Medicine, vol. 323, No. 9, pp. 570-578, Aug. 1990.
Rosenberg, Steven A., et al. "Adoptive cell transfer: a clinical path to effective cancer immunotherapy" Nat. Rev. Cancer, vol. 8, No. 4, pp. 299-308, Apr. 2008.
Rouanne, Mathieu, et al. "Novel therapeutic targets in advanced urothelial carcinoma" Critical Review Oncol Hematology, vol. 98, pp. 106-115, Feb. 2016.
Rudolph, Despina, et al. "Potent costimulation of human CD8 T cells by anti-4-1BB and anti-CD28 on synthetic artificial antigen presenting cells" Cancer Immunol. Immunotherapy, vol. 57, No. 2, pp. 175-183, Feb. 2008.
Saesmaa, Tarja, et al. "Dissolution studies on ampicillin embonate and amoxycillin embonate" Journal of Pharmaceutical & Biomedical Analysis, vol. 8, No. 1, pp. 61-65, 1990.
Salman, Bulent, et al. "Vaccine therapy for pancreatic cancer" Oncoimmunology, vol. 2, No. 12, article e26662, Dec. 2013.
Sangro, Bruno, et al., "Phase I Trial of Intratumoral Injection of an Adenovirus Encoding Interleukin-12 for Advanced Digestive Tumors", Journal of Clinical Oncology, vol. 22, No. 8, pp. 1389-1397, Apr. 15, 2004.
Schmidt, Susanne M., et al. "Induction of adipophilin-specific cytotoxic T lymphocytes using a novel HLA-A2-binding peptide that mediates tumor cell lysis" Cancer Research, vol. 64, No. 3, pp. 1164-1170, Feb. 2004.
Schultze, J. L., et al. "A pilot study of combined immunotherapy with autologous adoptive tumour-specific T-cell transfer, vaccination with CD40-activated malignant B cells and interleukin 2" British Journal of Haematology, vol. 113, No. 2, pp. 455-460, May 2001.
Shi, M., "Autologous cytokine-induced killer cell therapy in clinical trial phase I is safe in patients with primary hepatocellular carcinoma", World Journal of Gastroenterology, vol. 10, No. 8, pp. 1146-1151, Apr. 15, 2004.
Siegel, Sandra, et al. "Induction of cytotoxic T-cell responses against the oncofetal antigen-immature laminin receptor for the treatment of hematologic malignancies" Blood, vol. 102, No. 13, pp. 4416-4423, Dec. 2003.
Singh-Jasuja, Harpreet et al. "!The Tuebingen approach: identification, selection, and validation of tumor-associated HLA peptides for cancer therapy" Cancer Immunology, Immunotherapy, vol. 53, pp. 187-185, Jan. 2004.
Slingluff, Craig L., Jr., et al. Melanomas with concordant loss of multiple melanocyctic differentiation proteins: Immune escape that may be overcome by targeting unique or undefined antigens Cancer Immunology Immunotherapy, vol. 48, pp. 661-672, Mar. 2000.
Spaner, David E., et al. "A phase I/II trial of oxidized autologous tumor vaccines during the "watch and wait" phase of chronic lymphocytic leukemia" Cancer Immunol. Immunother. vol. 54, No. 7, pp. 635-646, Jul. 2005.
Srivastava, Neeharika, et al. "Update on benefit of immunotherapy and targeted therapy in melanoma: the changing landscape" Cancer Manag Res. vol. 6, pp. 279-289, Jun. 2014.
Stevanovic, Sanja, et al. "Complete regression of metastatic cervical cancer after treatment with human papillomavirus-targeted tumor-infiltrating T cells" Journal of Clinical Oncology, vol. 33, No. 14, pp. 1543-1550, May 2015.
Stevens, James, et al. "Peptide length preferences for rat and mouse MHC class I molecules using random peptide libraries" European Journal of immunology, vol. 28, No. 4, pp. 1272-1279, Mar. 2013.
Stintzing, Sebastian. "Management of colorectal cancer" F1000Prime Reports, vol. 6, No. 108, Nov. 2014 (12 pages).
Su, Zhen, et al. "Immunological and clinical responses in metastatic renal cancer patients vaccinated with tumor RNA-transfected dendritic cells" Cancer Research, vol. 63, No. 9, pp. 2127-2133, May 2003.
Takayama, "Distribution and therapeutic effect of intraarterially transferred tumor—infiltrating lymphocytes in hepatic malignancies", A Preliminary Report, Cancer, vol. 68 (11), Mar. 19, 1991, pp. 2391-2396.

(56) References Cited

OTHER PUBLICATIONS

Takayama, Tadatoshi, et al., "Adoptive immunotherapy to lower postsurgical recurrence rates of hepatocellular carcinoma: a randomised trial", The Lancet, vol. 356, pp. 802-807, Sep. 2, 2000.

Tanaka, F., et al. "High frequency of the expression of the MAGE gene family in human esophageal carcinoma" International Journal of Oncology, vol. 10, No. 6, pp. 1113-1117, Jun. 1997.

Thakkar, Jigisha P., et al. "Epidemiologic and Molecular Prognostic Review of Glioblastoma" Cancer Epidemiol. Biomarkers Prev. vol. 23, No. 10, pp. 1985-1996, Oct. 2014.

Toh, Uhi, et al. "Locoregional adoptive immunotherapy resulted in regression in distant metastases of a recurrent esophageal cancer" International Journal of Clinical Oncology, vol. 7, No. 6, pp. 372-375, Dec. 2002.

Toh, Uhi, et al. "Locoregional cellular immunotherapy for patients with advanced esophageal cancer" Clinical Cancer Research, vol. 6, No. 12, pp. 4663-4673, Dec. 2000.

Toomey, Paul G., et al. "Immunotherapy for gastrointestinal malignancies" Cancer Control. vol. 20, No. 1, pp. 32-42, Jan. 2013.

Tran, Eric, et al. "Cancer Immunotherapy Based on Mutation-Specific CD4+ T Cells in a Patient with Epithelial Cancer" Science, vol. 344, No. 6184, pp. 641-645, May 2014.

Vici, Patrizia, et al. "Immunologic treatments for precancerous lesions and uterine cervical cancer" Journal Experimental Clinical Cancer Research, vol. 33, No. 1, Mar. 2014.

Von Rundstedt, Friedrich-Carl, et al. "Bacille-Calmette-Guerin non-responders: how to manage" Transl. Androl. Urol. vol. 4, No. 3, pp. 244-253, Jun. 2015.

Vonderheide, Robert H., et al. "Agonistic CD40 antibodies and cancer therapy" Clinical Cancer Research, vol. 19, No. 5, pp. 1035-1043, Mar. 2013.

Wierda, William G., et al. "Ofatumumab is active in patients with fludarabine-refractory CLL irrespective of prior rituximab: results from the phase 2 international study" Blood, vol. 118, No. 19, pp. 5126-5129, Nov. 2011.

Wilhelm et at, "BAY 43-9006 exhibits broad spectrum oral antitumor activity and targets the RAF/MEK/ERK pathway and receptor tyrosine kinases involved in tumor progression and angiogenesis". Cancer Res. Vol. 64, Oct. 1, 2004, pp. 7099-7109.

Wilson, Peter M., et al. "Standing the test of time: targeting thymidylate biosynthesis in cancer therapy" Nature, vol. 11, pp. 282-298, May 2014.

Wittig, B., et al. "Therapeutic vaccination against metastatic carcinoma by expression-modulated and Immunomodified autologous tumor cells: a first clinical phase I/II trial" Human Gene Therapy, vol. 12, No. 3, pp. 267-278, Feb. 2001.

York, Ian A., et al. "The Cytosolic Endopeptidase, Thimet Oligopeptide, Destroys Antigenic Peptides and Limits the Extent of MHC Class I Antigen Presentation" Immunity, vol. 18, No. 3, pp. 429-440, Mar. 2003.

Kessler et al. "Efficient Identification of Novel HLA-A 0201-presented Cytotoxic T Lymphocyte Epitopes in the Widely Expressed Tumor Antigen PRAME by Proteasome-mediated Digestion Analysis," The Journal of Experimental Medicine, Rockefeller University Press, US; 193(1): 73-88 (Jan. 1, 2001).

Xing et al, "Identification of new cytotoxic T-lymphocyte epitopes from cancer testis antigen HCA587," Biochemical and Biophysical Research Communications, vol. 372, No. 2, pp. 331 to 335. Jul. 25, 2008—abstract provided.

Kiessling, A., "Identification of an HLA-A* 0201-restricted T-cell epitope derived from the prostate cancer-associated protein prostein." British journal of cancer vol. 90, No. 5 pp. 1034-1040. (2004).

Pritchard, A.'"Exploration of peptides bound to MHC class I molecules in melanoma." Pigment cell & melanoma research, vol. 28, No. 3, pp. 281-294. (2015).

* cited by examiner

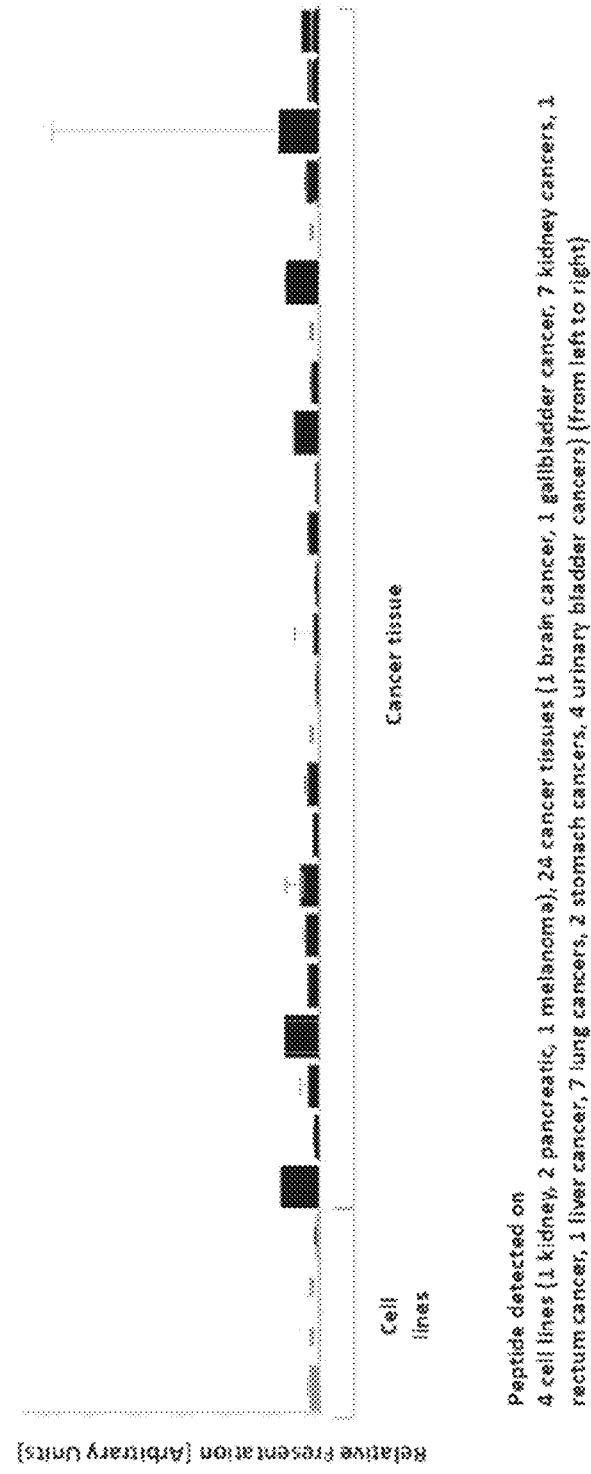

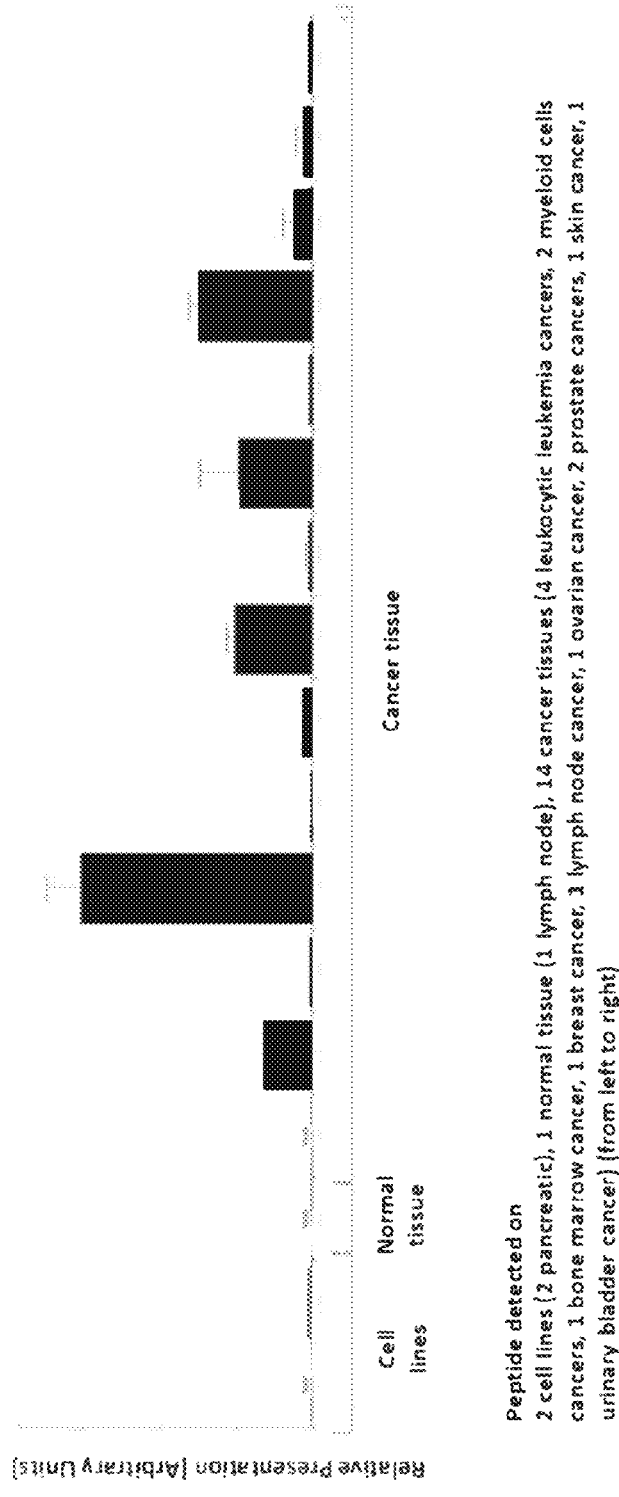

Peptide: HYSQELSLLYL (A*24)
SEQ ID NO: 158

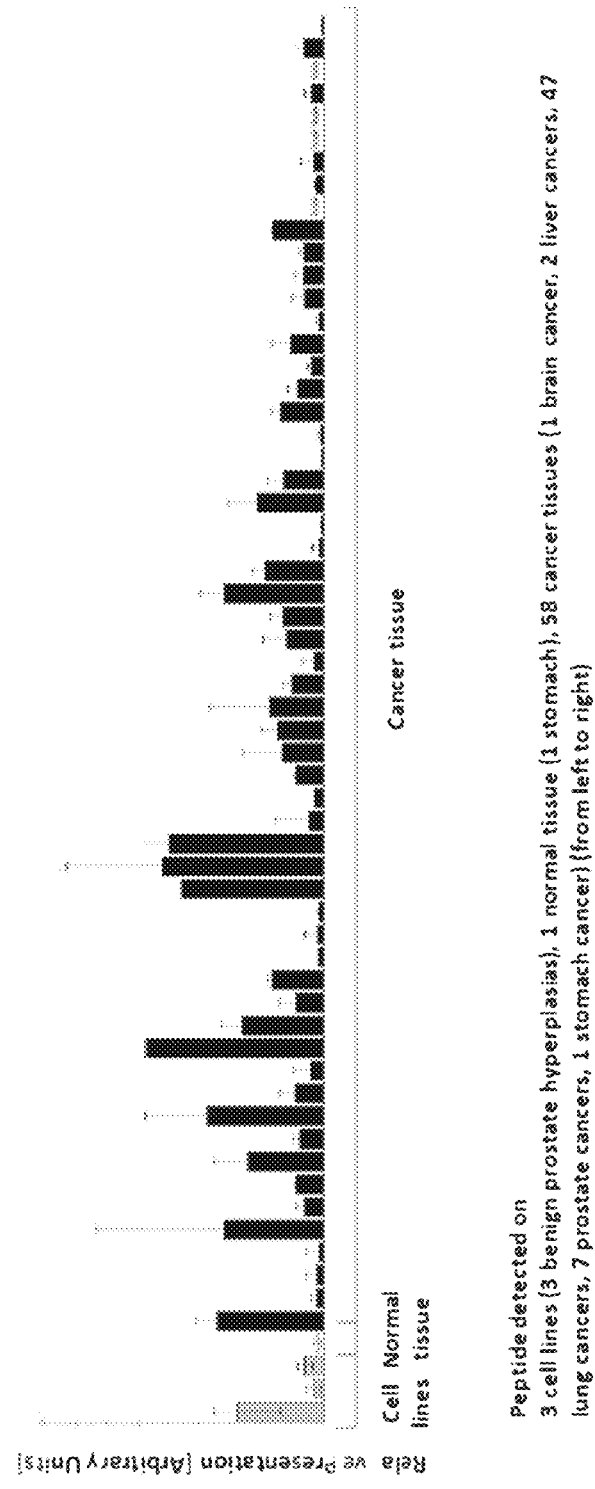

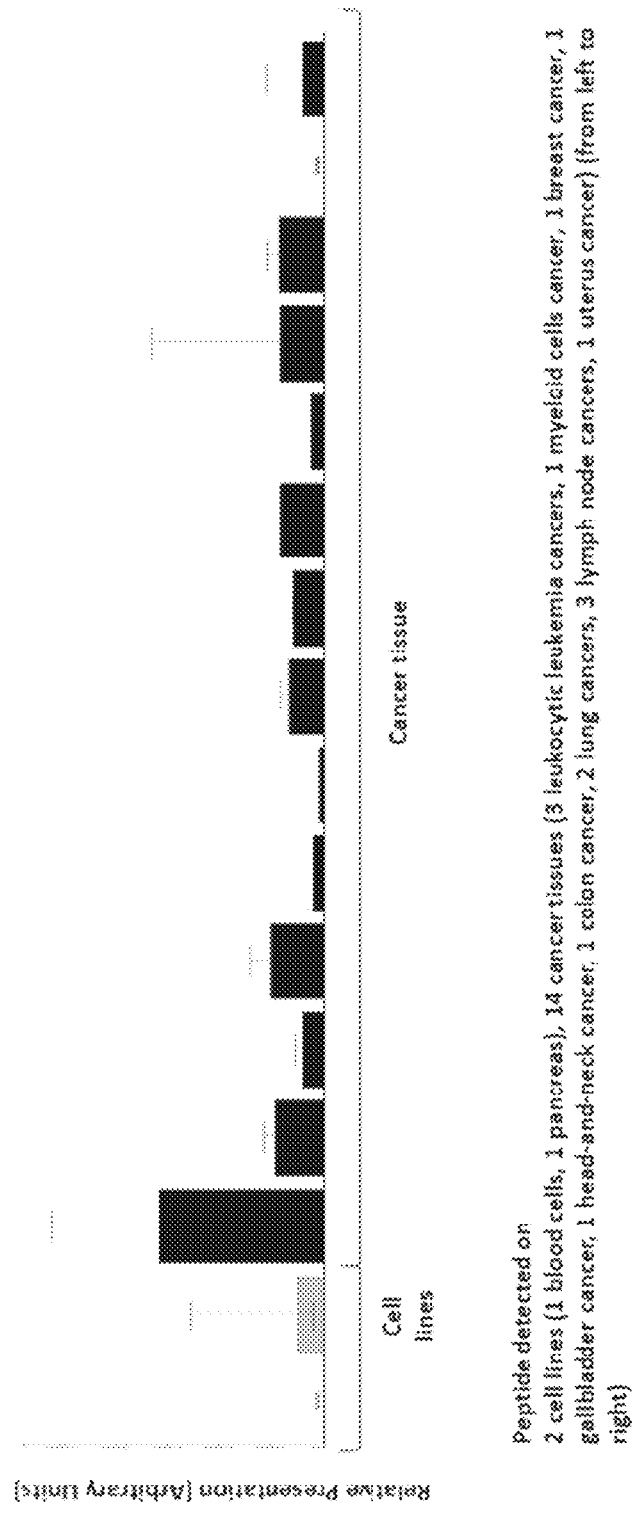

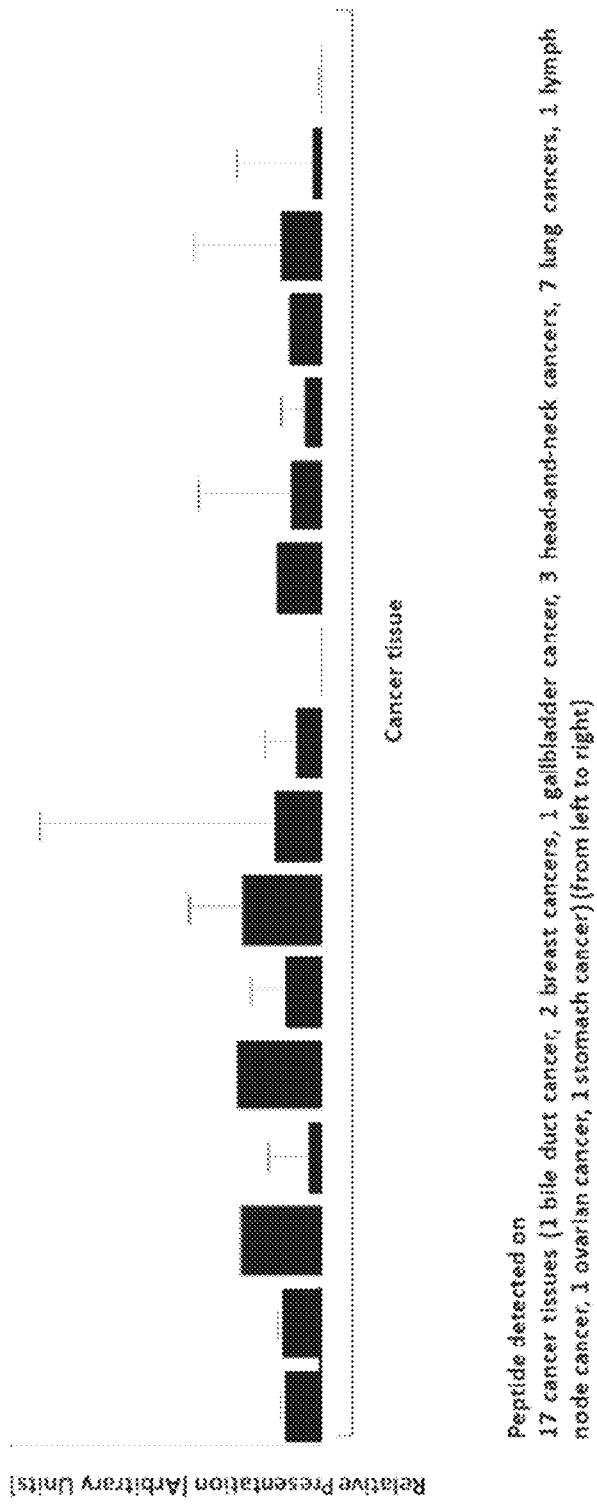

Peptide: ALAPHLDDA (A*02)
SEQ ID NO: 237

Peptide detected on:
1 cell lines (blood cells), 10 cancer tissues (1 myeloid cells cancer, 2 brain cancers, 1 breast cancer, 1 lung cancer, 1 ovarian cancer, 1 skin cancer, 1 urinary bladder cancer, 2 uterus cancers) (from left to right)

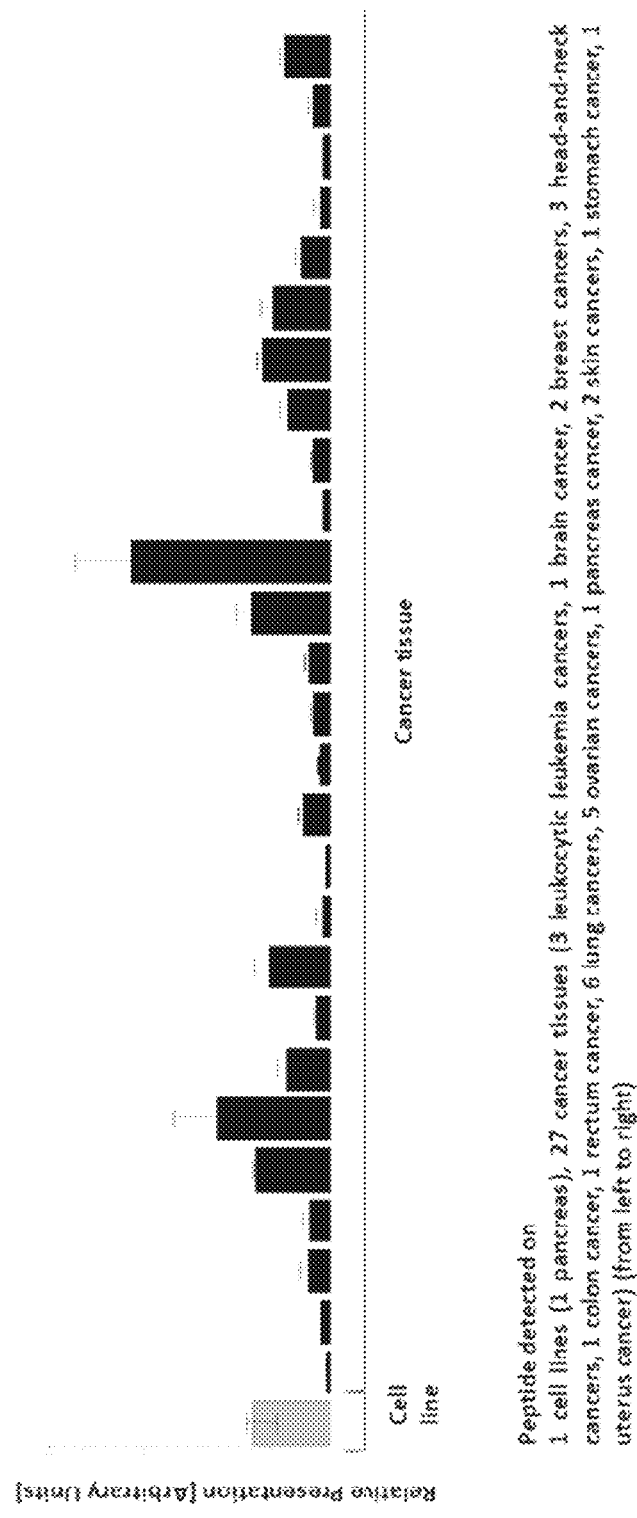

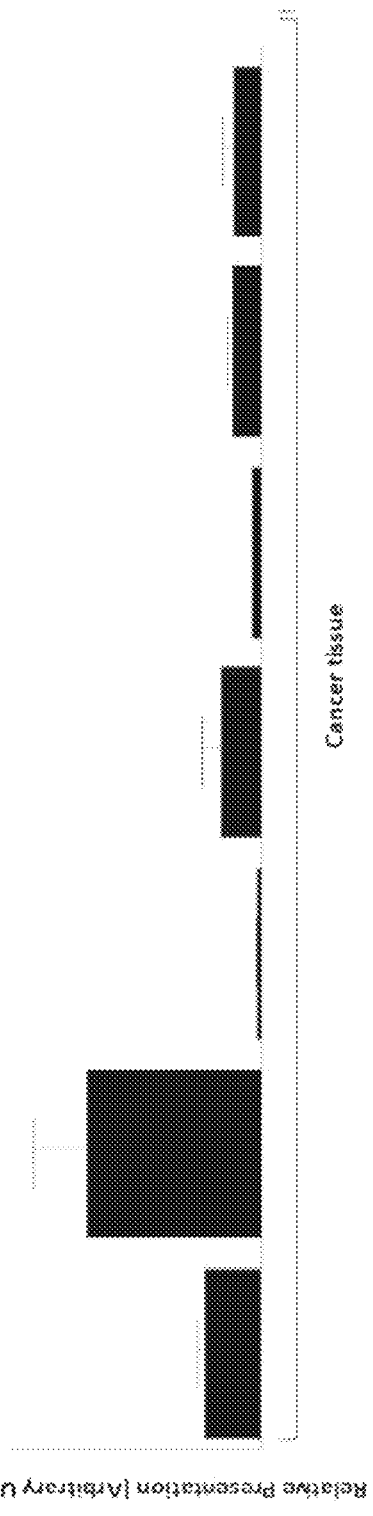

Peptide: VQLDSIEDLEV (A*02)
SEQ ID NO: 32

Peptide: FYSRLLQKF (A*24)
SEQ ID NO: 203

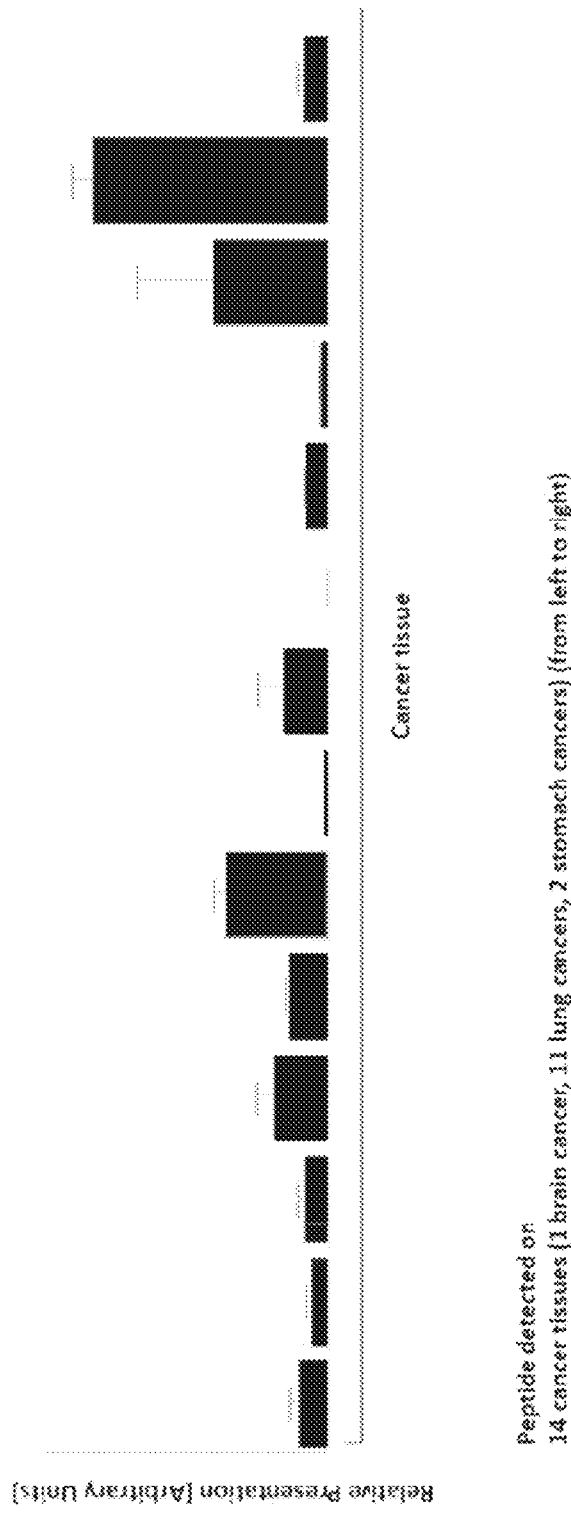

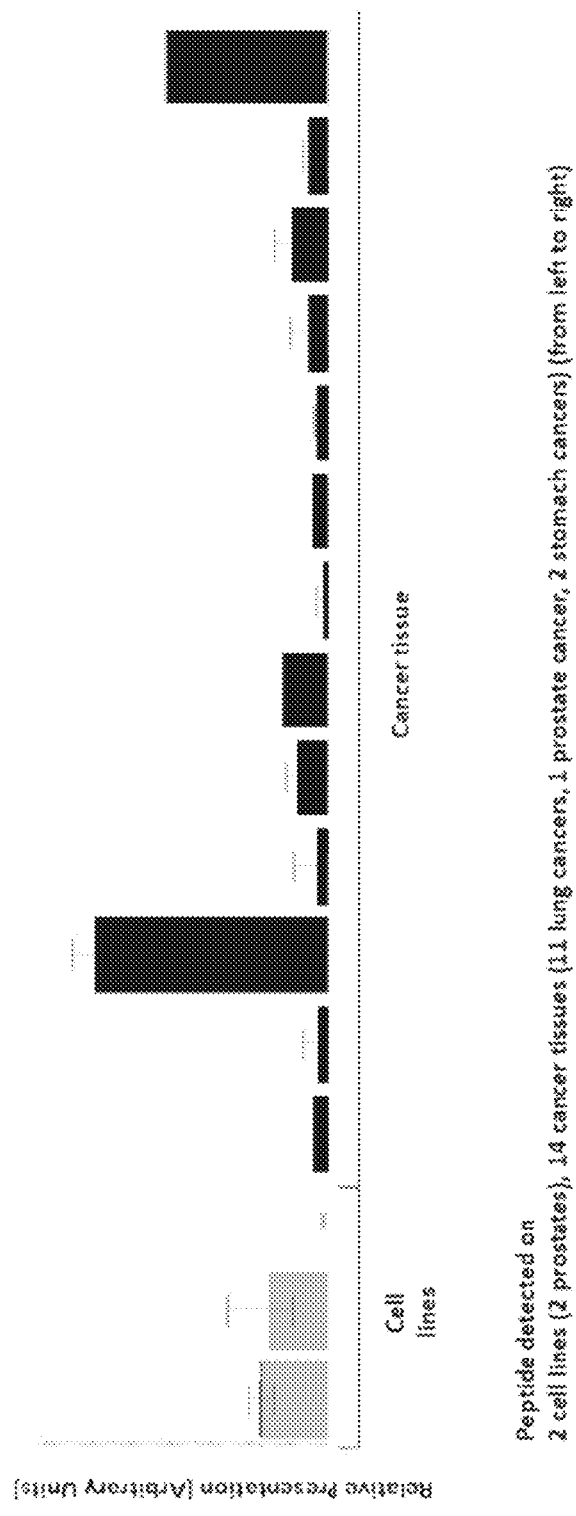

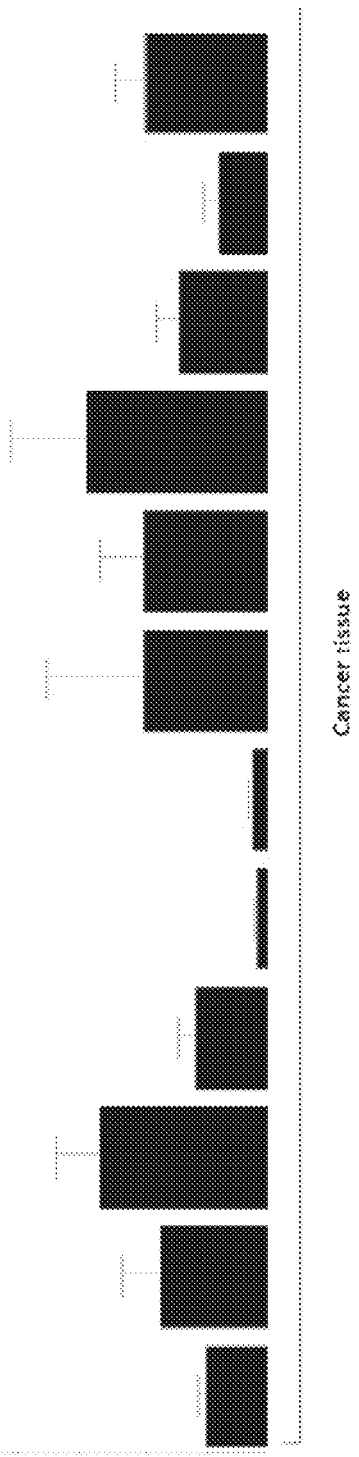

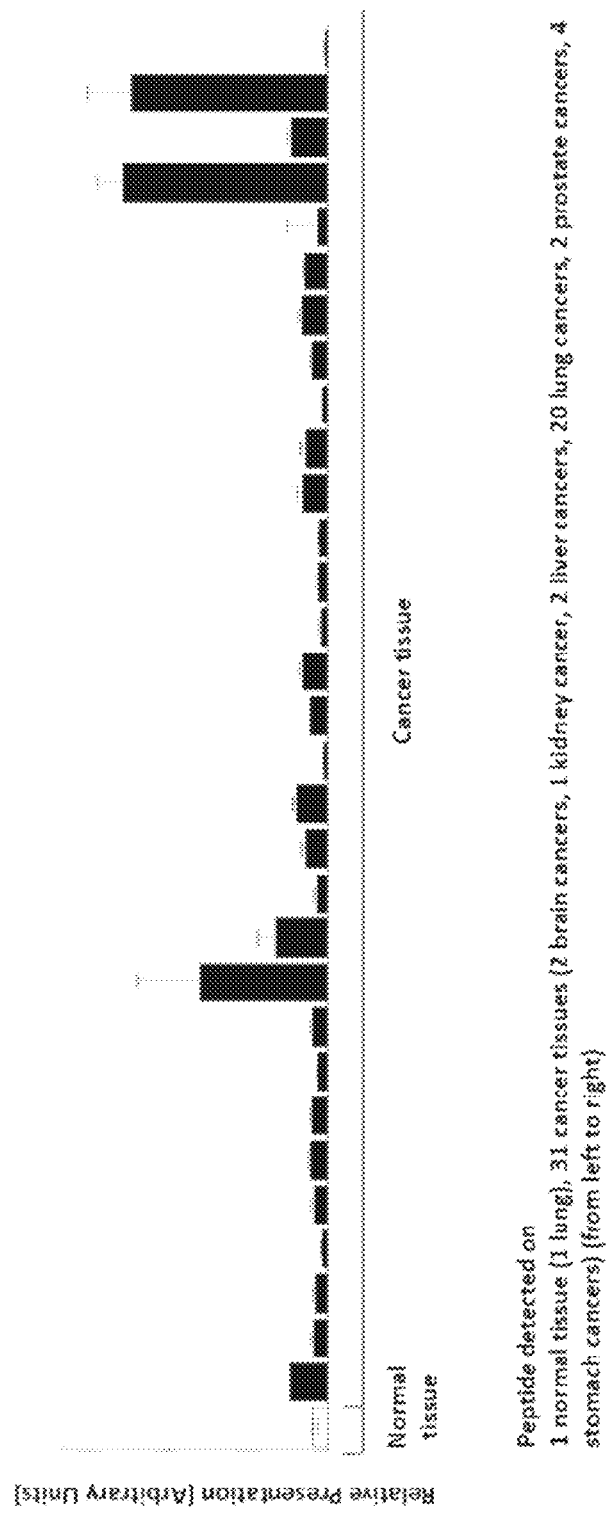

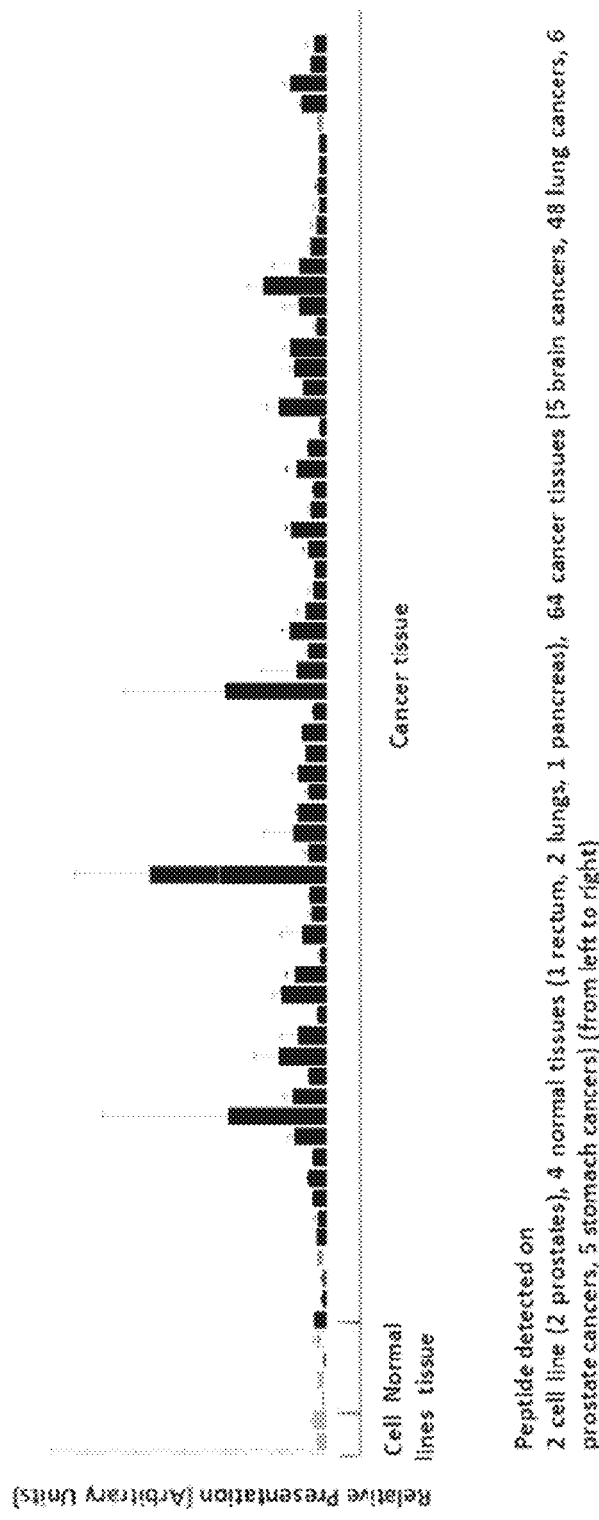

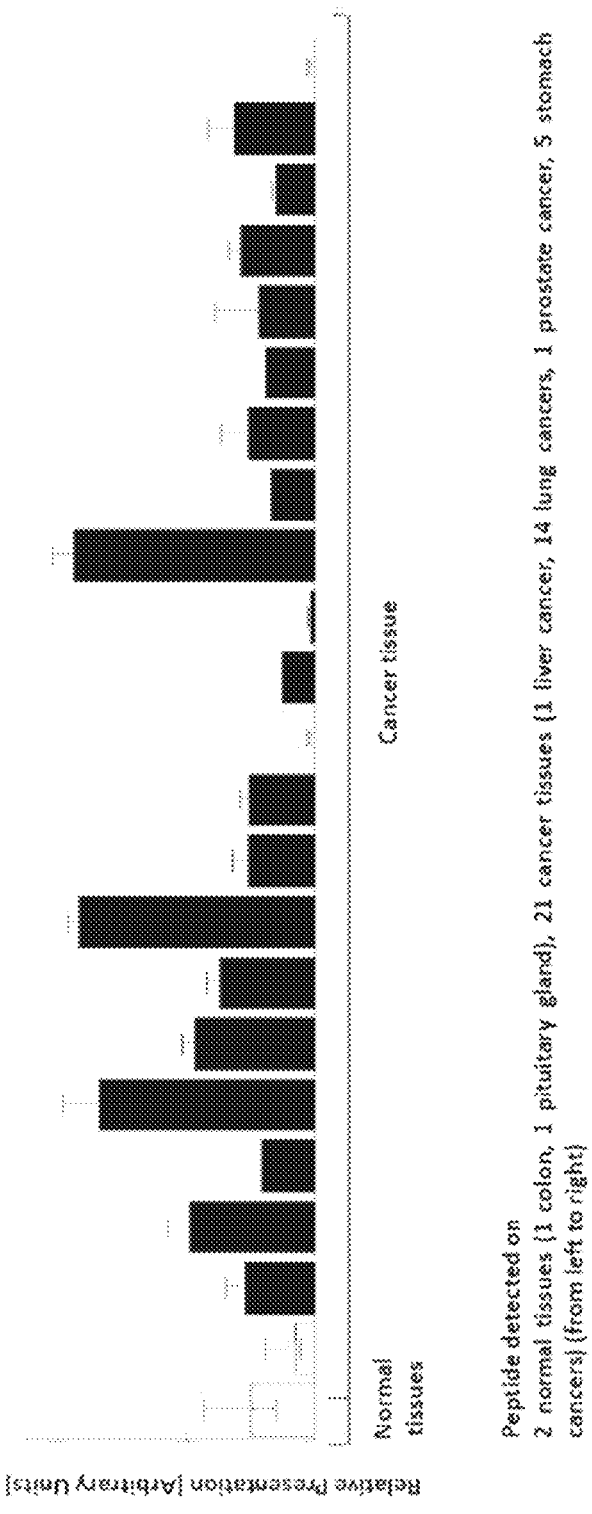

Peptide: VYTLDIPVL (A*24)
SEQ ID NO: 160

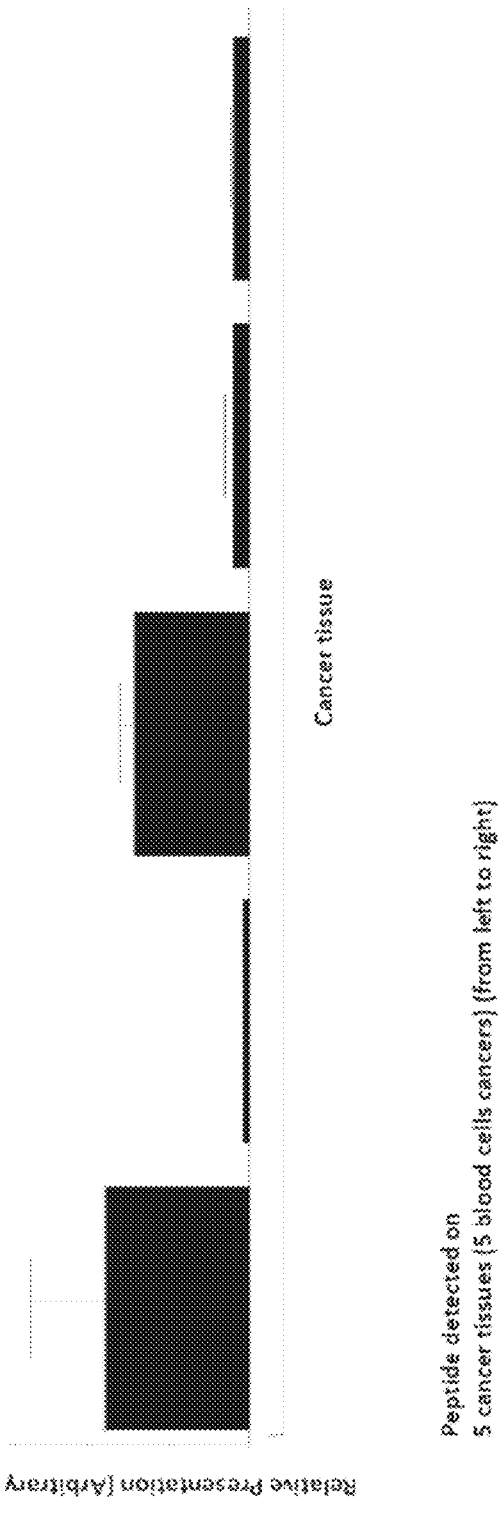

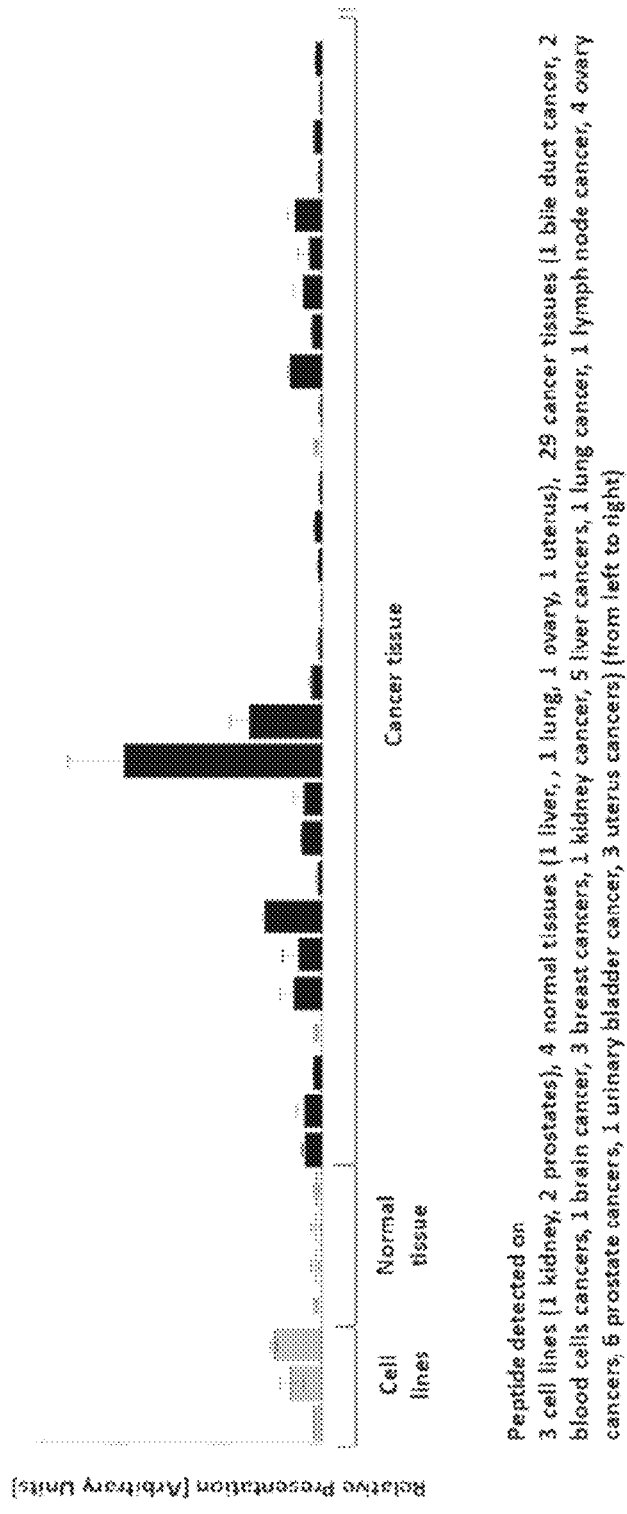

Gene: TNC
Peptide: KLLDPQEFTL
SEQ ID: 59

Gene: LRRC15
Peptide: ILNTHITEL
SEQ ID NO: 149

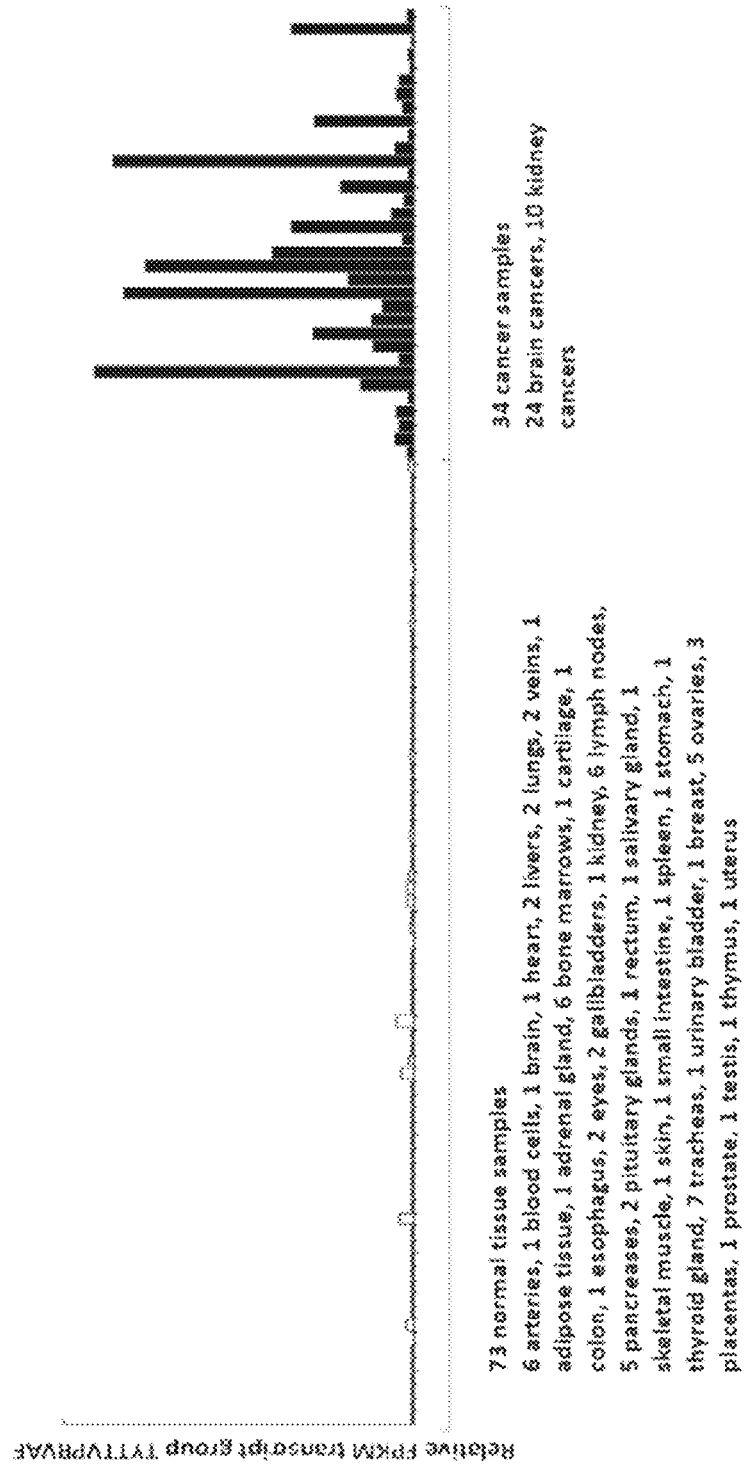

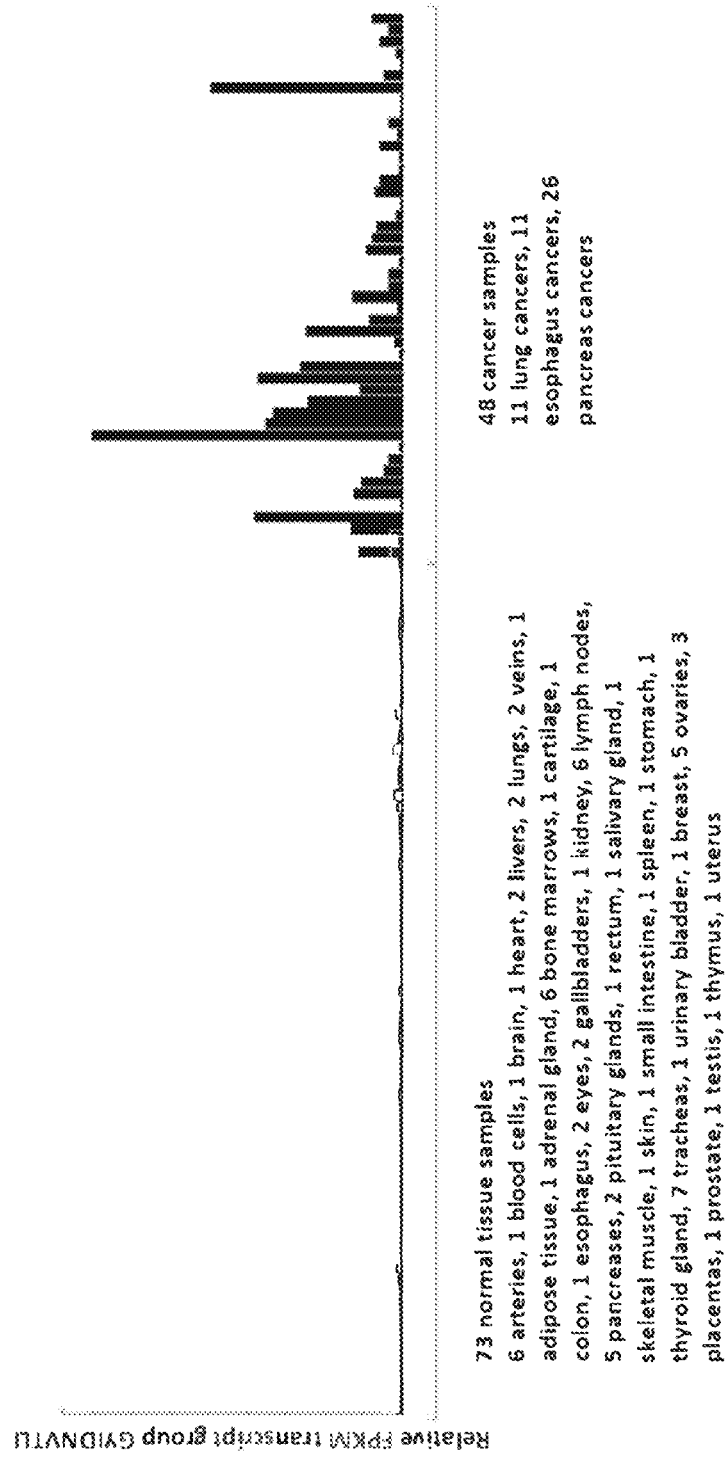

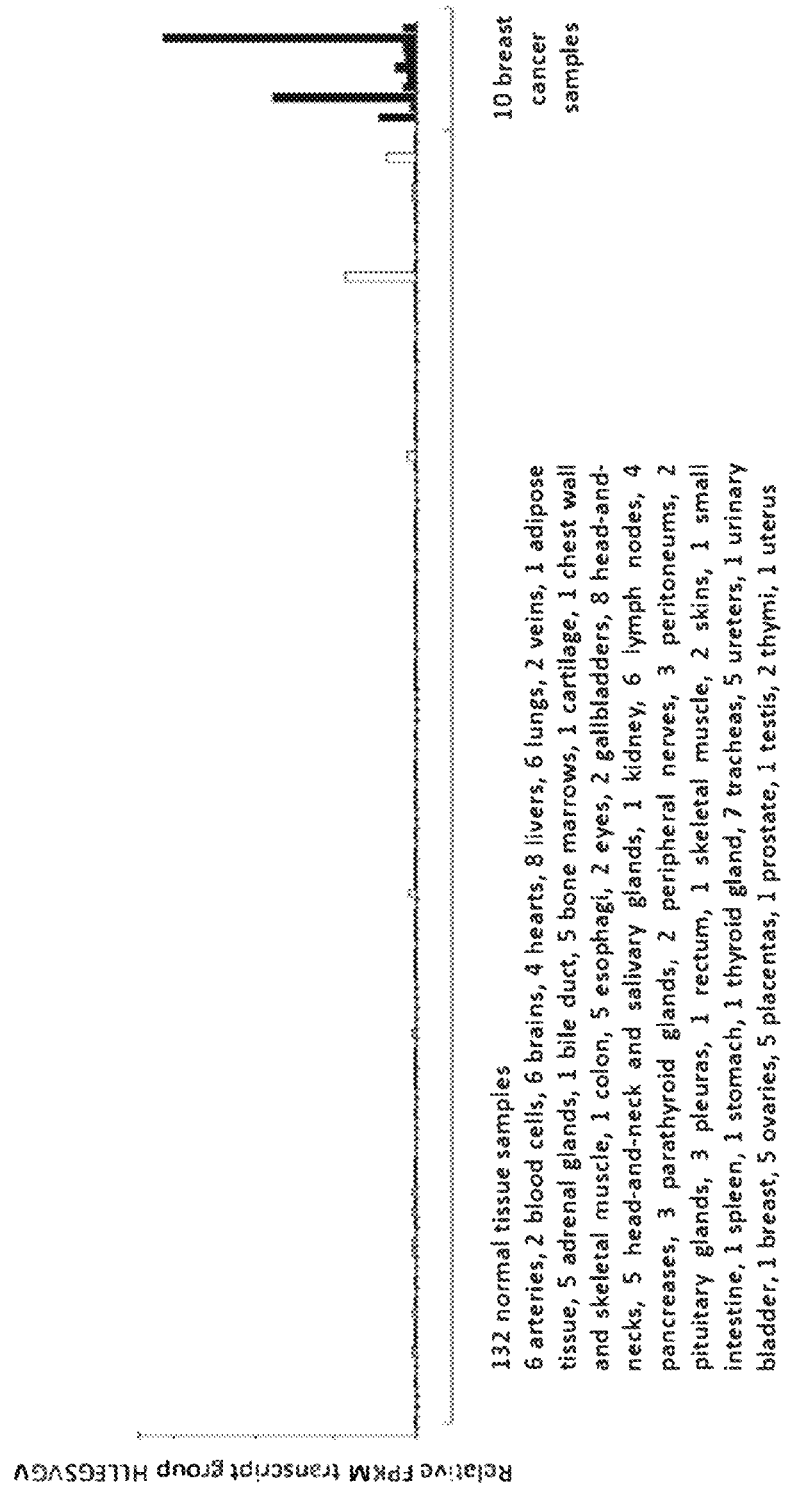

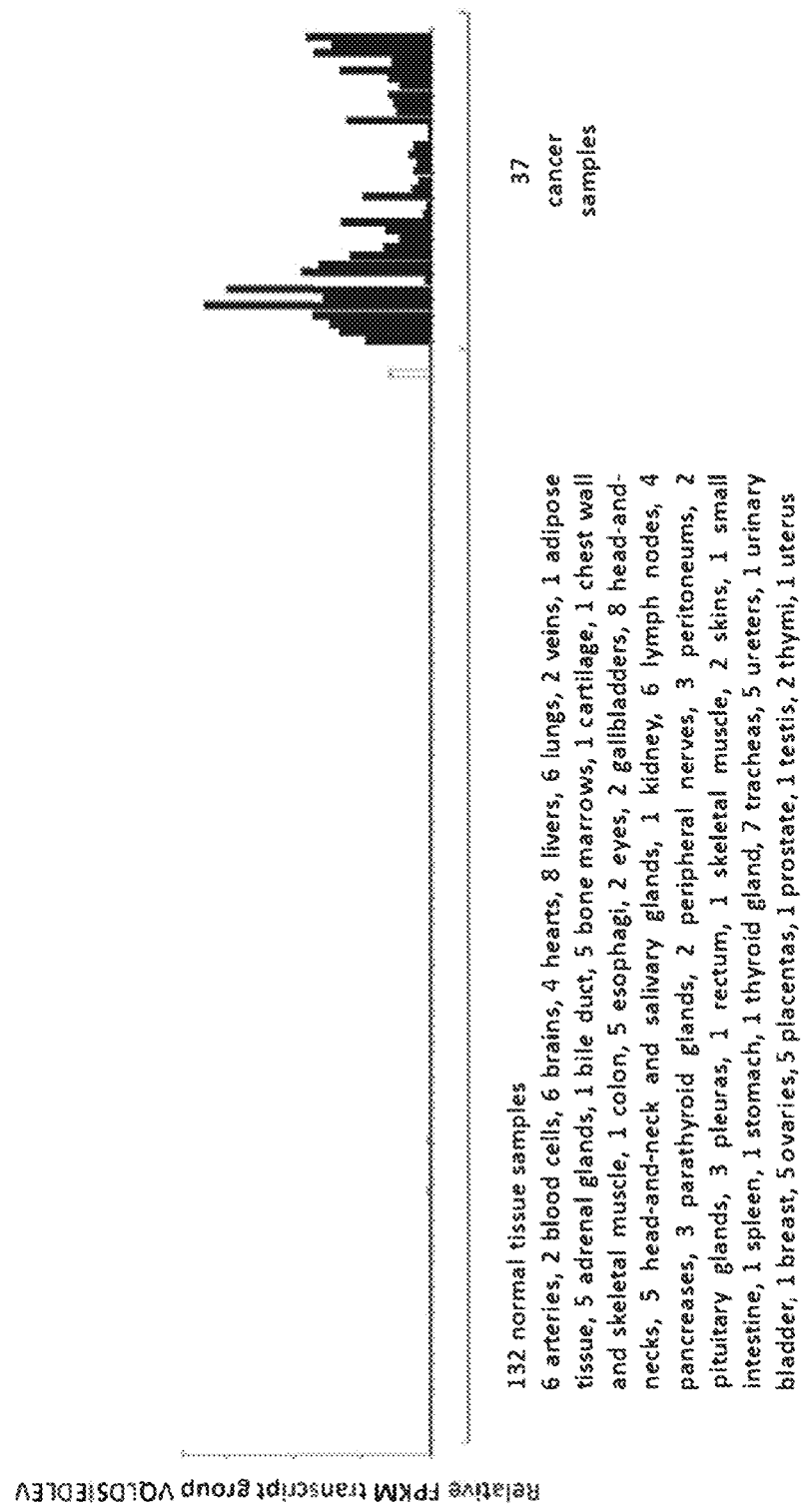

Gene: SPINK2
Peptide: ALSVLRLAL
SEQ ID: 251

Gene: MAGEC2
Peptide: TLDEKVAEL
SEQ ID: 24

Gene: C1orf186
Peptide: FLTAINYLL
SEQ ID NO: 72

SEQUENCE LISTING

<160> NUMBER OF SEQ ID NOS: 306

<210> SEQ ID NO 1
<211> LENGTH: 9
<212> TYPE: PRT
<213> ORGANISM: Homo sapiens

<400> SEQUENCE: 1

Leu Leu Tyr Pro Glu Pro Trp Ser Val
1               5

<210> SEQ ID NO 2
<211> LENGTH: 9
<212> TYPE: PRT
<213> ORGANISM: Homo sapiens

<400> SEQUENCE: 2

Gly Leu Ile Ala Gly Val Val Ser Ile
1               5

<210> SEQ ID NO 3
<211> LENGTH: 10
<212> TYPE: PRT
<213> ORGANISM: Homo sapiens

<400> SEQUENCE: 3

Lys Leu Glu Glu Asn Gly Asp Leu Tyr Leu
1               5                   10

<210> SEQ ID NO 4
<211> LENGTH: 9
<212> TYPE: PRT
<213> ORGANISM: Homo sapiens

<400> SEQUENCE: 4

Lys Leu Met Pro Gly Thr Tyr Thr Leu
1               5

<210> SEQ ID NO 5
<211> LENGTH: 9
<212> TYPE: PRT
<213> ORGANISM: Homo sapiens

<400> SEQUENCE: 5

Gly Ile Val Ala His Ile Gln Glu Val
1               5

<210> SEQ ID NO 6
<211> LENGTH: 9
<212> TYPE: PRT
<213> ORGANISM: Homo sapiens

<400> SEQUENCE: 6

Ala Leu Phe Asp Ser Leu Arg His Val
1               5

<210> SEQ ID NO 7
<211> LENGTH: 9
<212> TYPE: PRT
<213> ORGANISM: Homo sapiens

<400> SEQUENCE: 7

Ile Leu Asp His Glu Val Pro Ser Leu
1               5

```
<210> SEQ ID NO 8
<211> LENGTH: 9
<212> TYPE: PRT
<213> ORGANISM: Homo sapiens

<400> SEQUENCE: 8

Ser Ile Tyr Gln Phe Leu Ile Ala Val
1               5

<210> SEQ ID NO 9
<211> LENGTH: 9
<212> TYPE: PRT
<213> ORGANISM: Homo sapiens

<400> SEQUENCE: 9

Phe Leu Val Asp Gly Ser Tyr Ser Ile
1               5

<210> SEQ ID NO 10
<211> LENGTH: 9
<212> TYPE: PRT
<213> ORGANISM: Homo sapiens

<400> SEQUENCE: 10

Gly Ile Ala Gly Ser Leu Lys Thr Val
1               5

<210> SEQ ID NO 11
<211> LENGTH: 9
<212> TYPE: PRT
<213> ORGANISM: Homo sapiens

<400> SEQUENCE: 11

Ala Leu Ser Pro Ser Tyr Leu Thr Val
1               5

<210> SEQ ID NO 12
<211> LENGTH: 9
<212> TYPE: PRT
<213> ORGANISM: Homo sapiens

<400> SEQUENCE: 12

Gly Leu Leu Pro Leu Leu His Arg Ala
1               5

<210> SEQ ID NO 13
<211> LENGTH: 9
<212> TYPE: PRT
<213> ORGANISM: Homo sapiens

<400> SEQUENCE: 13

Ala Leu Met Ala Met Leu Val Tyr Val
1               5

<210> SEQ ID NO 14
<211> LENGTH: 9
<212> TYPE: PRT
<213> ORGANISM: Homo sapiens

<400> SEQUENCE: 14

Ile Leu Ala Lys Asp Leu Phe Glu Ile
1               5

<210> SEQ ID NO 15
```

```
<211> LENGTH: 9
<212> TYPE: PRT
<213> ORGANISM: Homo sapiens

<400> SEQUENCE: 15

Tyr Leu Asp Leu Ser His Asn Gln Leu
1               5

<210> SEQ ID NO 16
<211> LENGTH: 11
<212> TYPE: PRT
<213> ORGANISM: Homo sapiens

<400> SEQUENCE: 16

Tyr Thr Leu Asp Ile Pro Val Leu Phe Gly Val
1               5                   10

<210> SEQ ID NO 17
<211> LENGTH: 10
<212> TYPE: PRT
<213> ORGANISM: Homo sapiens

<400> SEQUENCE: 17

Ala Val Phe Pro Asp Asp Met Pro Thr Leu
1               5                   10

<210> SEQ ID NO 18
<211> LENGTH: 10
<212> TYPE: PRT
<213> ORGANISM: Homo sapiens

<400> SEQUENCE: 18

Ile Leu Leu Asp Leu Thr Asp Asn Arg Leu
1               5                   10

<210> SEQ ID NO 19
<211> LENGTH: 9
<212> TYPE: PRT
<213> ORGANISM: Homo sapiens

<400> SEQUENCE: 19

Ser Ile Ser Asp Asn Val Trp Glu Val
1               5

<210> SEQ ID NO 20
<211> LENGTH: 9
<212> TYPE: PRT
<213> ORGANISM: Homo sapiens

<400> SEQUENCE: 20

Gly Leu Ser Gln Ile Thr Asn Gln Leu
1               5

<210> SEQ ID NO 21
<211> LENGTH: 9
<212> TYPE: PRT
<213> ORGANISM: Homo sapiens

<400> SEQUENCE: 21

Ala Ile Gln Asp Glu Ile Arg Ser Val
1               5

<210> SEQ ID NO 22
<211> LENGTH: 10
<212> TYPE: PRT
```

<213> ORGANISM: Homo sapiens

<400> SEQUENCE: 22

Phe Val Asp Pro Asn Thr Gln Glu Lys Val
1               5                   10

<210> SEQ ID NO 23
<211> LENGTH: 9
<212> TYPE: PRT
<213> ORGANISM: Homo sapiens

<400> SEQUENCE: 23

Ser Leu Phe Ser Asp Glu Phe Lys Val
1               5

<210> SEQ ID NO 24
<211> LENGTH: 9
<212> TYPE: PRT
<213> ORGANISM: Homo sapiens

<400> SEQUENCE: 24

Thr Leu Asp Glu Lys Val Ala Glu Leu
1               5

<210> SEQ ID NO 25
<211> LENGTH: 9
<212> TYPE: PRT
<213> ORGANISM: Homo sapiens

<400> SEQUENCE: 25

Thr Met Asp Ser Val Leu Val Thr Val
1               5

<210> SEQ ID NO 26
<211> LENGTH: 9
<212> TYPE: PRT
<213> ORGANISM: Homo sapiens

<400> SEQUENCE: 26

Ala Leu Gln Glu Glu Leu Thr Glu Leu
1               5

<210> SEQ ID NO 27
<211> LENGTH: 9
<212> TYPE: PRT
<213> ORGANISM: Homo sapiens

<400> SEQUENCE: 27

Arg Leu Met Glu Glu Asn Trp Asn Ala
1               5

<210> SEQ ID NO 28
<211> LENGTH: 10
<212> TYPE: PRT
<213> ORGANISM: Homo sapiens

<400> SEQUENCE: 28

Ser Leu Pro Asn Gly Lys Pro Val Ser Val
1               5                   10

<210> SEQ ID NO 29
<211> LENGTH: 9
<212> TYPE: PRT
<213> ORGANISM: Homo sapiens

```
<400> SEQUENCE: 29

Tyr Leu Leu Asp Pro Ser Ile Thr Leu
1               5

<210> SEQ ID NO 30
<211> LENGTH: 9
<212> TYPE: PRT
<213> ORGANISM: Homo sapiens

<400> SEQUENCE: 30

Ala Met Ile Glu Glu Val Phe Glu Ala
1               5

<210> SEQ ID NO 31
<211> LENGTH: 9
<212> TYPE: PRT
<213> ORGANISM: Homo sapiens

<400> SEQUENCE: 31

Thr Ile Thr Glu Thr Thr Val Glu Val
1               5

<210> SEQ ID NO 32
<211> LENGTH: 11
<212> TYPE: PRT
<213> ORGANISM: Homo sapiens

<400> SEQUENCE: 32

Val Gln Leu Asp Ser Ile Glu Asp Leu Glu Val
1               5                   10

<210> SEQ ID NO 33
<211> LENGTH: 9
<212> TYPE: PRT
<213> ORGANISM: Homo sapiens

<400> SEQUENCE: 33

Tyr Ile Lys Thr Glu Leu Ile Ser Val
1               5

<210> SEQ ID NO 34
<211> LENGTH: 10
<212> TYPE: PRT
<213> ORGANISM: Homo sapiens

<400> SEQUENCE: 34

Phe Leu Leu Ala Thr Glu Val Val Thr Val
1               5                   10

<210> SEQ ID NO 35
<211> LENGTH: 10
<212> TYPE: PRT
<213> ORGANISM: Homo sapiens

<400> SEQUENCE: 35

Phe Leu Leu Pro Phe Ser Thr Val Tyr Leu
1               5                   10

<210> SEQ ID NO 36
<211> LENGTH: 11
<212> TYPE: PRT
<213> ORGANISM: Homo sapiens

<400> SEQUENCE: 36
```

```
Ser Leu Ala Asp Thr Asn Ser Leu Ala Val Val
1               5                   10
```

<210> SEQ ID NO 37
<211> LENGTH: 9
<212> TYPE: PRT
<213> ORGANISM: Homo sapiens

<400> SEQUENCE: 37

```
Ile Leu Ala Pro Phe Ser Val Asp Leu
1               5
```

<210> SEQ ID NO 38
<211> LENGTH: 9
<212> TYPE: PRT
<213> ORGANISM: Homo sapiens

<400> SEQUENCE: 38

```
Phe Leu Gly Pro Arg Ile Ile Gly Leu
1               5
```

<210> SEQ ID NO 39
<211> LENGTH: 9
<212> TYPE: PRT
<213> ORGANISM: Homo sapiens

<400> SEQUENCE: 39

```
His Leu Leu Glu Gly Ser Val Gly Val
1               5
```

<210> SEQ ID NO 40
<211> LENGTH: 11
<212> TYPE: PRT
<213> ORGANISM: Homo sapiens

<400> SEQUENCE: 40

```
Val Leu Ile Asp Pro Gln Trp Val Leu Thr Ala
1               5                   10
```

<210> SEQ ID NO 41
<211> LENGTH: 9
<212> TYPE: PRT
<213> ORGANISM: Homo sapiens

<400> SEQUENCE: 41

```
Ala Leu Phe Glu Asn Thr Pro Lys Ala
1               5
```

<210> SEQ ID NO 42
<211> LENGTH: 8
<212> TYPE: PRT
<213> ORGANISM: Homo sapiens

<400> SEQUENCE: 42

```
Leu Leu Asp Ser Val Ser Arg Leu
1               5
```

<210> SEQ ID NO 43
<211> LENGTH: 9
<212> TYPE: PRT
<213> ORGANISM: Homo sapiens

<400> SEQUENCE: 43

```
Lys Ala Ile Glu Val Leu Leu Thr Leu
1               5
```

```
<210> SEQ ID NO 44
<211> LENGTH: 9
<212> TYPE: PRT
<213> ORGANISM: Homo sapiens

<400> SEQUENCE: 44

Ser Leu Phe Glu Thr Ala Trp Glu Ala
1               5

<210> SEQ ID NO 45
<211> LENGTH: 9
<212> TYPE: PRT
<213> ORGANISM: Homo sapiens

<400> SEQUENCE: 45

Ser Leu Thr Glu Val Ser Leu Pro Leu
1               5

<210> SEQ ID NO 46
<211> LENGTH: 9
<212> TYPE: PRT
<213> ORGANISM: Homo sapiens

<400> SEQUENCE: 46

Ser Gln Phe Pro Leu Pro Leu Ala Val
1               5

<210> SEQ ID NO 47
<211> LENGTH: 10
<212> TYPE: PRT
<213> ORGANISM: Homo sapiens

<400> SEQUENCE: 47

Ala Leu Leu Glu Arg Gly Glu Leu Phe Val
1               5                   10

<210> SEQ ID NO 48
<211> LENGTH: 9
<212> TYPE: PRT
<213> ORGANISM: Homo sapiens

<400> SEQUENCE: 48

Gln Val Ile Glu Asp Ser Thr Gly Val
1               5

<210> SEQ ID NO 49
<211> LENGTH: 9
<212> TYPE: PRT
<213> ORGANISM: Homo sapiens

<400> SEQUENCE: 49

Ala Leu Asn Ile Ala Thr His Val Leu
1               5

<210> SEQ ID NO 50
<211> LENGTH: 9
<212> TYPE: PRT
<213> ORGANISM: Homo sapiens

<400> SEQUENCE: 50

Ile Leu Phe His Gly Val Phe Tyr Ala
1               5
```

```
<210> SEQ ID NO 51
<211> LENGTH: 9
<212> TYPE: PRT
<213> ORGANISM: Homo sapiens

<400> SEQUENCE: 51

Leu Leu Phe Ser Arg Leu Cys Gly Ala
1               5

<210> SEQ ID NO 52
<211> LENGTH: 9
<212> TYPE: PRT
<213> ORGANISM: Homo sapiens

<400> SEQUENCE: 52

Arg Leu Ala Val Leu Phe Ser Gly Ala
1               5

<210> SEQ ID NO 53
<211> LENGTH: 9
<212> TYPE: PRT
<213> ORGANISM: Homo sapiens

<400> SEQUENCE: 53

Lys Met Val Gly Leu Val Val Ala Ile
1               5

<210> SEQ ID NO 54
<211> LENGTH: 9
<212> TYPE: PRT
<213> ORGANISM: Homo sapiens

<400> SEQUENCE: 54

Val Leu Asn Pro Leu Ile Thr Ala Val
1               5

<210> SEQ ID NO 55
<211> LENGTH: 9
<212> TYPE: PRT
<213> ORGANISM: Homo sapiens

<400> SEQUENCE: 55

Ser Leu Ala Thr Lys Ile Val Glu Ala
1               5

<210> SEQ ID NO 56
<211> LENGTH: 11
<212> TYPE: PRT
<213> ORGANISM: Homo sapiens

<400> SEQUENCE: 56

Phe Leu His Asp Glu Lys Glu Gly Ile Tyr Ile
1               5                   10

<210> SEQ ID NO 57
<211> LENGTH: 10
<212> TYPE: PRT
<213> ORGANISM: Homo sapiens

<400> SEQUENCE: 57

Thr Val Phe Thr Asp His Met Leu Thr Val
1               5                   10

<210> SEQ ID NO 58
<211> LENGTH: 9
```

```
<212> TYPE: PRT
<213> ORGANISM: Homo sapiens

<400> SEQUENCE: 58

Tyr Leu Leu Pro Leu Leu Pro Ala Leu
1               5

<210> SEQ ID NO 59
<211> LENGTH: 10
<212> TYPE: PRT
<213> ORGANISM: Homo sapiens

<400> SEQUENCE: 59

Lys Leu Leu Asp Pro Gln Glu Phe Thr Leu
1               5                   10

<210> SEQ ID NO 60
<211> LENGTH: 9
<212> TYPE: PRT
<213> ORGANISM: Homo sapiens

<400> SEQUENCE: 60

Ala Leu Phe Ala Pro Leu Val His Leu
1               5

<210> SEQ ID NO 61
<211> LENGTH: 9
<212> TYPE: PRT
<213> ORGANISM: Homo sapiens

<400> SEQUENCE: 61

Ala Ile Val Lys Glu Ile Val Asn Ile
1               5

<210> SEQ ID NO 62
<211> LENGTH: 9
<212> TYPE: PRT
<213> ORGANISM: Homo sapiens

<400> SEQUENCE: 62

Ala Leu Asn Pro Glu Leu Val Gln Ala
1               5

<210> SEQ ID NO 63
<211> LENGTH: 9
<212> TYPE: PRT
<213> ORGANISM: Homo sapiens

<400> SEQUENCE: 63

Ser Gln Ile Pro Ala Gln Pro Ser Val
1               5

<210> SEQ ID NO 64
<211> LENGTH: 9
<212> TYPE: PRT
<213> ORGANISM: Homo sapiens

<400> SEQUENCE: 64

Ser Leu Phe Pro Asp Ser Leu Ile Val
1               5

<210> SEQ ID NO 65
<211> LENGTH: 9
<212> TYPE: PRT
<213> ORGANISM: Homo sapiens
```

```
<400> SEQUENCE: 65

Ser Val Val Pro Asp Val Arg Ser Val
1               5

<210> SEQ ID NO 66
<211> LENGTH: 9
<212> TYPE: PRT
<213> ORGANISM: Homo sapiens

<400> SEQUENCE: 66

Lys Leu Ile Phe Ser Val Glu Ala Val
1               5

<210> SEQ ID NO 67
<211> LENGTH: 9
<212> TYPE: PRT
<213> ORGANISM: Homo sapiens

<400> SEQUENCE: 67

Thr Leu Leu Gln Arg Leu Thr Glu Val
1               5

<210> SEQ ID NO 68
<211> LENGTH: 9
<212> TYPE: PRT
<213> ORGANISM: Homo sapiens

<400> SEQUENCE: 68

Ser Leu Ser Asn Arg Leu Tyr Tyr Leu
1               5

<210> SEQ ID NO 69
<211> LENGTH: 9
<212> TYPE: PRT
<213> ORGANISM: Homo sapiens

<400> SEQUENCE: 69

Phe Leu Ala Val Gly Leu Val Asp Val
1               5

<210> SEQ ID NO 70
<211> LENGTH: 10
<212> TYPE: PRT
<213> ORGANISM: Homo sapiens

<400> SEQUENCE: 70

Leu Leu Leu Gly Asp Ser Ala Leu Tyr Leu
1               5                   10

<210> SEQ ID NO 71
<211> LENGTH: 9
<212> TYPE: PRT
<213> ORGANISM: Homo sapiens

<400> SEQUENCE: 71

Val Leu His Ser Lys Phe Trp Val Val
1               5

<210> SEQ ID NO 72
<211> LENGTH: 9
<212> TYPE: PRT
<213> ORGANISM: Homo sapiens

<400> SEQUENCE: 72
```

```
Phe Leu Thr Ala Ile Asn Tyr Leu Leu
1               5

<210> SEQ ID NO 73
<211> LENGTH: 9
<212> TYPE: PRT
<213> ORGANISM: Homo sapiens

<400> SEQUENCE: 73

Tyr Thr Leu Arg Glu Val Asp Thr Val
1               5

<210> SEQ ID NO 74
<211> LENGTH: 9
<212> TYPE: PRT
<213> ORGANISM: Homo sapiens

<400> SEQUENCE: 74

Thr Leu Phe Gly Tyr Ser Val Val Leu
1               5

<210> SEQ ID NO 75
<211> LENGTH: 9
<212> TYPE: PRT
<213> ORGANISM: Homo sapiens

<400> SEQUENCE: 75

Ala Val Ile Lys Phe Leu Glu Leu Leu
1               5

<210> SEQ ID NO 76
<211> LENGTH: 9
<212> TYPE: PRT
<213> ORGANISM: Homo sapiens

<400> SEQUENCE: 76

Ala Val Gly Pro Val His Asn Ser Val
1               5

<210> SEQ ID NO 77
<211> LENGTH: 11
<212> TYPE: PRT
<213> ORGANISM: Homo sapiens

<400> SEQUENCE: 77

Thr Leu Ile Asp Glu Gln Asp Ile Pro Leu Val
1               5                   10

<210> SEQ ID NO 78
<211> LENGTH: 9
<212> TYPE: PRT
<213> ORGANISM: Homo sapiens

<400> SEQUENCE: 78

Thr Val Val Thr Arg Leu Asp Glu Ile
1               5

<210> SEQ ID NO 79
<211> LENGTH: 9
<212> TYPE: PRT
<213> ORGANISM: Homo sapiens

<400> SEQUENCE: 79

Val Thr Phe Lys Glu Tyr Val Thr Val
```

```
<210> SEQ ID NO 80
<211> LENGTH: 9
<212> TYPE: PRT
<213> ORGANISM: Homo sapiens

<400> SEQUENCE: 80

Lys Leu Tyr Glu Ala Asp Phe Val Leu
1               5

<210> SEQ ID NO 81
<211> LENGTH: 9
<212> TYPE: PRT
<213> ORGANISM: Homo sapiens

<400> SEQUENCE: 81

Asn Ala Leu Asp Lys Val Leu Ser Val
1               5

<210> SEQ ID NO 82
<211> LENGTH: 9
<212> TYPE: PRT
<213> ORGANISM: Homo sapiens

<400> SEQUENCE: 82

Phe Ile Phe Asp Glu Ala Glu Lys Leu
1               5

<210> SEQ ID NO 83
<211> LENGTH: 9
<212> TYPE: PRT
<213> ORGANISM: Homo sapiens

<400> SEQUENCE: 83

Gly Gln Ala Ser Tyr Phe Tyr Val Ala
1               5

<210> SEQ ID NO 84
<211> LENGTH: 9
<212> TYPE: PRT
<213> ORGANISM: Homo sapiens

<400> SEQUENCE: 84

Ala Leu Cys Pro Arg Ile His Glu Val
1               5

<210> SEQ ID NO 85
<211> LENGTH: 9
<212> TYPE: PRT
<213> ORGANISM: Homo sapiens

<400> SEQUENCE: 85

Val Leu Asn Asp Ile Leu Val Arg Ala
1               5

<210> SEQ ID NO 86
<211> LENGTH: 9
<212> TYPE: PRT
<213> ORGANISM: Homo sapiens

<400> SEQUENCE: 86

Ser Val Asp Ser His Phe Gln Glu Val
1               5
```

```
<210> SEQ ID NO 87
<211> LENGTH: 9
<212> TYPE: PRT
<213> ORGANISM: Homo sapiens

<400> SEQUENCE: 87

Thr Ile Tyr Lys Asp Phe Val Tyr Ile
1               5

<210> SEQ ID NO 88
<211> LENGTH: 9
<212> TYPE: PRT
<213> ORGANISM: Homo sapiens

<400> SEQUENCE: 88

Ala Gln Ala Asp His Leu Pro Gln Leu
1               5

<210> SEQ ID NO 89
<211> LENGTH: 9
<212> TYPE: PRT
<213> ORGANISM: Homo sapiens

<400> SEQUENCE: 89

Gln Leu Ala Pro Val Phe Gln Arg Val
1               5

<210> SEQ ID NO 90
<211> LENGTH: 9
<212> TYPE: PRT
<213> ORGANISM: Homo sapiens

<400> SEQUENCE: 90

Phe Leu Gln Asp Leu Glu Gln Arg Leu
1               5

<210> SEQ ID NO 91
<211> LENGTH: 9
<212> TYPE: PRT
<213> ORGANISM: Homo sapiens

<400> SEQUENCE: 91

Lys Leu Phe Asp Glu Ser Ile Leu Ile
1               5

<210> SEQ ID NO 92
<211> LENGTH: 9
<212> TYPE: PRT
<213> ORGANISM: Homo sapiens

<400> SEQUENCE: 92

Gly Leu Leu Phe Ser Leu Arg Ser Val
1               5

<210> SEQ ID NO 93
<211> LENGTH: 10
<212> TYPE: PRT
<213> ORGANISM: Homo sapiens

<400> SEQUENCE: 93

Gln Val Leu Glu Leu Asp Val Ala Asp Ile
1               5                   10

<210> SEQ ID NO 94
```

```
<211> LENGTH: 10
<212> TYPE: PRT
<213> ORGANISM: Homo sapiens

<400> SEQUENCE: 94

Leu Leu Leu Pro Ala Val Pro Val Gly Ala
1               5                   10

<210> SEQ ID NO 95
<211> LENGTH: 9
<212> TYPE: PRT
<213> ORGANISM: Homo sapiens

<400> SEQUENCE: 95

Gly Leu Leu Gly Ser Leu Phe Phe Leu
1               5

<210> SEQ ID NO 96
<211> LENGTH: 9
<212> TYPE: PRT
<213> ORGANISM: Homo sapiens

<400> SEQUENCE: 96

Leu Leu Val Ser His Leu Tyr Leu Val
1               5

<210> SEQ ID NO 97
<211> LENGTH: 9
<212> TYPE: PRT
<213> ORGANISM: Homo sapiens

<400> SEQUENCE: 97

Ser Thr Leu Pro Lys Ser Leu Ser Leu
1               5

<210> SEQ ID NO 98
<211> LENGTH: 12
<212> TYPE: PRT
<213> ORGANISM: Homo sapiens

<400> SEQUENCE: 98

Arg Leu Phe Pro Asp Phe Phe Thr Arg Val Ala Leu
1               5                   10

<210> SEQ ID NO 99
<211> LENGTH: 11
<212> TYPE: PRT
<213> ORGANISM: Homo sapiens

<400> SEQUENCE: 99

Tyr Leu Leu Gln Ser Val Asn Gln Leu Leu Leu
1               5                   10

<210> SEQ ID NO 100
<211> LENGTH: 10
<212> TYPE: PRT
<213> ORGANISM: Homo sapiens

<400> SEQUENCE: 100

Ala Leu Leu Gly Met Ile Ile Val Gly Val
1               5                   10

<210> SEQ ID NO 101
<211> LENGTH: 9
<212> TYPE: PRT
```

```
<213> ORGANISM: Homo sapiens

<400> SEQUENCE: 101

Ala Leu Ala Asp Phe Met Leu Ser Leu
1               5

<210> SEQ ID NO 102
<211> LENGTH: 11
<212> TYPE: PRT
<213> ORGANISM: Homo sapiens

<400> SEQUENCE: 102

Val Leu Leu Asp Ile Gln Glu Val Phe Gln Ile
1               5                   10

<210> SEQ ID NO 103
<211> LENGTH: 9
<212> TYPE: PRT
<213> ORGANISM: Homo sapiens

<400> SEQUENCE: 103

Tyr Leu Val Ser Glu Ile Phe Lys Ala
1               5

<210> SEQ ID NO 104
<211> LENGTH: 10
<212> TYPE: PRT
<213> ORGANISM: Homo sapiens

<400> SEQUENCE: 104

Ala Leu Ile Ser Trp Gln Pro Pro Arg Ala
1               5                   10

<210> SEQ ID NO 105
<211> LENGTH: 9
<212> TYPE: PRT
<213> ORGANISM: Homo sapiens

<400> SEQUENCE: 105

Ala Leu Leu Gly Thr Lys Ile Leu Leu
1               5

<210> SEQ ID NO 106
<211> LENGTH: 9
<212> TYPE: PRT
<213> ORGANISM: Homo sapiens

<400> SEQUENCE: 106

Phe Ile Asn Asp Ser Ile Val Tyr Leu
1               5

<210> SEQ ID NO 107
<211> LENGTH: 11
<212> TYPE: PRT
<213> ORGANISM: Homo sapiens

<400> SEQUENCE: 107

Leu Leu Val Pro Thr Ser Gly Ile Tyr Phe Val
1               5                   10

<210> SEQ ID NO 108
<211> LENGTH: 9
<212> TYPE: PRT
<213> ORGANISM: Homo sapiens
```

<400> SEQUENCE: 108

Ile Leu Leu Lys Asn Leu Val Thr Ile
1               5

<210> SEQ ID NO 109
<211> LENGTH: 9
<212> TYPE: PRT
<213> ORGANISM: Homo sapiens

<400> SEQUENCE: 109

Ser Leu Asp Pro Ser Val Thr His Leu
1               5

<210> SEQ ID NO 110
<211> LENGTH: 9
<212> TYPE: PRT
<213> ORGANISM: Homo sapiens

<400> SEQUENCE: 110

Phe Leu Leu Gly Val Ser Lys Glu Val
1               5

<210> SEQ ID NO 111
<211> LENGTH: 9
<212> TYPE: PRT
<213> ORGANISM: Homo sapiens

<400> SEQUENCE: 111

Ala Ile Val Asp Leu Ile His Asp Ile
1               5

<210> SEQ ID NO 112
<211> LENGTH: 9
<212> TYPE: PRT
<213> ORGANISM: Homo sapiens

<400> SEQUENCE: 112

Ser Leu Gly Lys Phe Thr Phe Asp Val
1               5

<210> SEQ ID NO 113
<211> LENGTH: 9
<212> TYPE: PRT
<213> ORGANISM: Homo sapiens

<400> SEQUENCE: 113

Phe Leu Glu Arg Gly Leu Glu Ser Ala
1               5

<210> SEQ ID NO 114
<211> LENGTH: 9
<212> TYPE: PRT
<213> ORGANISM: Homo sapiens

<400> SEQUENCE: 114

Gln Leu Ile Gln Thr Leu His Ala Val
1               5

<210> SEQ ID NO 115
<211> LENGTH: 10
<212> TYPE: PRT
<213> ORGANISM: Homo sapiens

<400> SEQUENCE: 115

```
Ser Leu Asp Pro Asp Thr Leu Pro Ala Val
1               5                   10
```

<210> SEQ ID NO 116
<211> LENGTH: 9
<212> TYPE: PRT
<213> ORGANISM: Homo sapiens

<400> SEQUENCE: 116

```
Thr Ile Asp Glu Ser Gly Ser Ile Leu
1               5
```

<210> SEQ ID NO 117
<211> LENGTH: 9
<212> TYPE: PRT
<213> ORGANISM: Homo sapiens

<400> SEQUENCE: 117

```
Lys Met Pro Asp Val Glu Leu Phe Val
1               5
```

<210> SEQ ID NO 118
<211> LENGTH: 9
<212> TYPE: PRT
<213> ORGANISM: Homo sapiens

<400> SEQUENCE: 118

```
Gln Leu Trp Gln Phe Leu Val Thr Leu
1               5
```

<210> SEQ ID NO 119
<211> LENGTH: 11
<212> TYPE: PRT
<213> ORGANISM: Homo sapiens

<400> SEQUENCE: 119

```
Phe Ile Ile Gln Gly Leu Arg Ser Val Gly Ala
1               5                   10
```

<210> SEQ ID NO 120
<211> LENGTH: 9
<212> TYPE: PRT
<213> ORGANISM: Homo sapiens

<400> SEQUENCE: 120

```
Val Thr Pro Val Thr Val Ser Ala Val
1               5
```

<210> SEQ ID NO 121
<211> LENGTH: 9
<212> TYPE: PRT
<213> ORGANISM: Homo sapiens

<400> SEQUENCE: 121

```
Phe Thr Ile Phe Arg Thr Ile Ser Val
1               5
```

<210> SEQ ID NO 122
<211> LENGTH: 9
<212> TYPE: PRT
<213> ORGANISM: Homo sapiens

<400> SEQUENCE: 122

```
Gly Val Val Asp Pro Val His Gly Val
1               5
```

```
<210> SEQ ID NO 123
<211> LENGTH: 10
<212> TYPE: PRT
<213> ORGANISM: Homo sapiens

<400> SEQUENCE: 123

Val Leu Asp Pro Ala Leu Pro Ala Leu Val
1               5                   10

<210> SEQ ID NO 124
<211> LENGTH: 9
<212> TYPE: PRT
<213> ORGANISM: Homo sapiens

<400> SEQUENCE: 124

Lys Val Met Ala Thr Ile Glu Lys Val
1               5

<210> SEQ ID NO 125
<211> LENGTH: 9
<212> TYPE: PRT
<213> ORGANISM: Homo sapiens

<400> SEQUENCE: 125

Ser Leu Ala Asp Tyr Glu His Phe Val
1               5

<210> SEQ ID NO 126
<211> LENGTH: 9
<212> TYPE: PRT
<213> ORGANISM: Homo sapiens

<400> SEQUENCE: 126

Gln Met Phe Gln Tyr Phe Ile Thr Val
1               5

<210> SEQ ID NO 127
<211> LENGTH: 9
<212> TYPE: PRT
<213> ORGANISM: Homo sapiens

<400> SEQUENCE: 127

Lys Leu Asp Gly Asn Glu Leu Asp Leu
1               5

<210> SEQ ID NO 128
<211> LENGTH: 9
<212> TYPE: PRT
<213> ORGANISM: Homo sapiens

<400> SEQUENCE: 128

Thr Gln Ser Pro Ala Thr Leu Ser Val
1               5

<210> SEQ ID NO 129
<211> LENGTH: 9
<212> TYPE: PRT
<213> ORGANISM: Homo sapiens

<400> SEQUENCE: 129

Arg Leu Gln Asp Ile Leu Trp Phe Leu
1               5
```

```
<210> SEQ ID NO 130
<211> LENGTH: 10
<212> TYPE: PRT
<213> ORGANISM: Homo sapiens

<400> SEQUENCE: 130

Ser Leu Leu Gly Gly Thr Phe Val Gly Ile
1               5                   10

<210> SEQ ID NO 131
<211> LENGTH: 10
<212> TYPE: PRT
<213> ORGANISM: Homo sapiens

<400> SEQUENCE: 131

Val Thr Ser Asn Ser Gly Ile Leu Gly Val
1               5                   10

<210> SEQ ID NO 132
<211> LENGTH: 9
<212> TYPE: PRT
<213> ORGANISM: Homo sapiens

<400> SEQUENCE: 132

Ile Leu Gly Glu Val Leu Ala Gln Leu
1               5

<210> SEQ ID NO 133
<211> LENGTH: 9
<212> TYPE: PRT
<213> ORGANISM: Homo sapiens

<400> SEQUENCE: 133

Ala Leu Leu Pro Arg Leu His Gln Leu
1               5

<210> SEQ ID NO 134
<211> LENGTH: 9
<212> TYPE: PRT
<213> ORGANISM: Homo sapiens

<400> SEQUENCE: 134

Gly Leu Ala Val Pro Thr Pro Ser Val
1               5

<210> SEQ ID NO 135
<211> LENGTH: 9
<212> TYPE: PRT
<213> ORGANISM: Homo sapiens

<400> SEQUENCE: 135

His Leu Ser Thr Ile Ile His Glu Ala
1               5

<210> SEQ ID NO 136
<211> LENGTH: 10
<212> TYPE: PRT
<213> ORGANISM: Homo sapiens

<400> SEQUENCE: 136

Phe Leu Phe Gly Gly Val Leu Met Thr Leu
1               5                   10

<210> SEQ ID NO 137
<211> LENGTH: 9
```

```
<212> TYPE: PRT
<213> ORGANISM: Homo sapiens

<400> SEQUENCE: 137

Glu Ile Ala Ser Ile Thr Glu Gln Leu
1               5

<210> SEQ ID NO 138
<211> LENGTH: 9
<212> TYPE: PRT
<213> ORGANISM: Homo sapiens

<400> SEQUENCE: 138

Ala Leu Leu Ala Lys Ile Leu Gln Ile
1               5

<210> SEQ ID NO 139
<211> LENGTH: 9
<212> TYPE: PRT
<213> ORGANISM: Homo sapiens

<400> SEQUENCE: 139

Phe Leu Leu Pro Thr Gly Ala Glu Ala
1               5

<210> SEQ ID NO 140
<211> LENGTH: 9
<212> TYPE: PRT
<213> ORGANISM: Homo sapiens

<400> SEQUENCE: 140

Val Leu Leu Glu Glu Leu Glu Ala Leu
1               5

<210> SEQ ID NO 141
<211> LENGTH: 9
<212> TYPE: PRT
<213> ORGANISM: Homo sapiens

<400> SEQUENCE: 141

Phe Leu Asp Lys Val Leu Val Ala Ala
1               5

<210> SEQ ID NO 142
<211> LENGTH: 9
<212> TYPE: PRT
<213> ORGANISM: Homo sapiens

<400> SEQUENCE: 142

Ile Leu Val Glu Gly Ile Ser Thr Val
1               5

<210> SEQ ID NO 143
<211> LENGTH: 9
<212> TYPE: PRT
<213> ORGANISM: Homo sapiens

<400> SEQUENCE: 143

Ala Leu Leu Pro Glu Leu Arg Glu Val
1               5

<210> SEQ ID NO 144
<211> LENGTH: 9
<212> TYPE: PRT
<213> ORGANISM: Homo sapiens
```

<400> SEQUENCE: 144

Ala Leu Leu Ala Phe Phe Pro Gly Leu
1               5

<210> SEQ ID NO 145
<211> LENGTH: 9
<212> TYPE: PRT
<213> ORGANISM: Homo sapiens

<400> SEQUENCE: 145

Tyr Leu Trp Ala Thr Ile Gln Arg Ile
1               5

<210> SEQ ID NO 146
<211> LENGTH: 9
<212> TYPE: PRT
<213> ORGANISM: Homo sapiens

<400> SEQUENCE: 146

Ala Leu His Phe Ser Glu Asp Glu Ile
1               5

<210> SEQ ID NO 147
<211> LENGTH: 9
<212> TYPE: PRT
<213> ORGANISM: Homo sapiens

<400> SEQUENCE: 147

Tyr Leu Met Asp Asp Thr Val Glu Ile
1               5

<210> SEQ ID NO 148
<211> LENGTH: 9
<212> TYPE: PRT
<213> ORGANISM: Homo sapiens

<400> SEQUENCE: 148

Met Leu Ala Gly Ile Ala Ile Thr Val
1               5

<210> SEQ ID NO 149
<211> LENGTH: 9
<212> TYPE: PRT
<213> ORGANISM: Homo sapiens

<400> SEQUENCE: 149

Ile Leu Asn Thr His Ile Thr Glu Leu
1               5

<210> SEQ ID NO 150
<211> LENGTH: 9
<212> TYPE: PRT
<213> ORGANISM: Homo sapiens

<400> SEQUENCE: 150

Val Leu Tyr Asp Arg Pro Leu Lys Ile
1               5

<210> SEQ ID NO 151
<211> LENGTH: 9
<212> TYPE: PRT
<213> ORGANISM: Homo sapiens

<400> SEQUENCE: 151

Ser Val Leu Asp Ser Thr Ala Lys Val
1               5

<210> SEQ ID NO 152
<211> LENGTH: 9
<212> TYPE: PRT
<213> ORGANISM: Homo sapiens

<400> SEQUENCE: 152

Met Met Val Gly Asp Leu Leu Glu Val
1               5

<210> SEQ ID NO 153
<211> LENGTH: 9
<212> TYPE: PRT
<213> ORGANISM: Homo sapiens

<400> SEQUENCE: 153

Phe Ile Ser Glu Arg Val Glu Val Val
1               5

<210> SEQ ID NO 154
<211> LENGTH: 9
<212> TYPE: PRT
<213> ORGANISM: Homo sapiens

<400> SEQUENCE: 154

Arg Leu Leu Gly Thr Glu Phe Gln Val
1               5

<210> SEQ ID NO 155
<211> LENGTH: 9
<212> TYPE: PRT
<213> ORGANISM: Homo sapiens

<400> SEQUENCE: 155

Leu Leu Asn Pro Val Val Glu Phe Val
1               5

<210> SEQ ID NO 156
<211> LENGTH: 9
<212> TYPE: PRT
<213> ORGANISM: Homo sapiens

<400> SEQUENCE: 156

Ile Leu Gly Asp Leu Ser His Leu Leu
1               5

<210> SEQ ID NO 157
<211> LENGTH: 9
<212> TYPE: PRT
<213> ORGANISM: Homo sapiens

<400> SEQUENCE: 157

Thr Leu Thr Ser Leu Leu Ala Gln Ala
1               5

<210> SEQ ID NO 158
<211> LENGTH: 11
<212> TYPE: PRT
<213> ORGANISM: Homo sapiens

<400> SEQUENCE: 158

His Tyr Ser Gln Glu Leu Ser Leu Leu Tyr Leu

```
                 1               5                    10
```

<210> SEQ ID NO 159
<211> LENGTH: 9
<212> TYPE: PRT
<213> ORGANISM: Homo sapiens

<400> SEQUENCE: 159

Leu Tyr Asn Lys Gly Phe Ile Tyr Leu
1               5

<210> SEQ ID NO 160
<211> LENGTH: 9
<212> TYPE: PRT
<213> ORGANISM: Homo sapiens

<400> SEQUENCE: 160

Val Tyr Thr Leu Asp Ile Pro Val Leu
1               5

<210> SEQ ID NO 161
<211> LENGTH: 9
<212> TYPE: PRT
<213> ORGANISM: Homo sapiens

<400> SEQUENCE: 161

Ile Tyr Leu Val Ser Ile Pro Glu Leu
1               5

<210> SEQ ID NO 162
<211> LENGTH: 9
<212> TYPE: PRT
<213> ORGANISM: Homo sapiens

<400> SEQUENCE: 162

Val Phe Thr Arg Val Ser Ser Phe Leu
1               5

<210> SEQ ID NO 163
<211> LENGTH: 9
<212> TYPE: PRT
<213> ORGANISM: Homo sapiens

<400> SEQUENCE: 163

Asp Tyr Leu Lys Gly Leu Ala Ser Phe
1               5

<210> SEQ ID NO 164
<211> LENGTH: 9
<212> TYPE: PRT
<213> ORGANISM: Homo sapiens

<400> SEQUENCE: 164

Lys Phe Ser Ser Phe Ser Leu Phe Phe
1               5

<210> SEQ ID NO 165
<211> LENGTH: 9
<212> TYPE: PRT
<213> ORGANISM: Homo sapiens

<400> SEQUENCE: 165

Asp Tyr Thr Thr Trp Thr Ala Leu Leu
1               5

<210> SEQ ID NO 166
<211> LENGTH: 9
<212> TYPE: PRT
<213> ORGANISM: Homo sapiens

<400> SEQUENCE: 166

Tyr Tyr Val Glu Ser Gly Lys Leu Phe
1               5

<210> SEQ ID NO 167
<211> LENGTH: 9
<212> TYPE: PRT
<213> ORGANISM: Homo sapiens

<400> SEQUENCE: 167

Asn Tyr Ile Asn Arg Ile Leu Lys Leu
1               5

<210> SEQ ID NO 168
<211> LENGTH: 9
<212> TYPE: PRT
<213> ORGANISM: Homo sapiens

<400> SEQUENCE: 168

Lys Tyr Gln Asp Ile Leu Glu Thr Ile
1               5

<210> SEQ ID NO 169
<211> LENGTH: 9
<212> TYPE: PRT
<213> ORGANISM: Homo sapiens

<400> SEQUENCE: 169

Ala Tyr Thr Leu Ile Ala Pro Asn Ile
1               5

<210> SEQ ID NO 170
<211> LENGTH: 9
<212> TYPE: PRT
<213> ORGANISM: Homo sapiens

<400> SEQUENCE: 170

Val Tyr Glu Asp Gln Val Gly Lys Phe
1               5

<210> SEQ ID NO 171
<211> LENGTH: 11
<212> TYPE: PRT
<213> ORGANISM: Homo sapiens

<400> SEQUENCE: 171

Leu Phe Ile Pro Ser Ser Lys Leu Leu Phe Leu
1               5                   10

<210> SEQ ID NO 172
<211> LENGTH: 10
<212> TYPE: PRT
<213> ORGANISM: Homo sapiens

<400> SEQUENCE: 172

Thr Tyr Thr Thr Val Pro Arg Val Ala Phe
1               5                   10

<210> SEQ ID NO 173

```
<211> LENGTH: 9
<212> TYPE: PRT
<213> ORGANISM: Homo sapiens

<400> SEQUENCE: 173

Ile Tyr Ser Trp Ile Leu Asp His Phe
1               5

<210> SEQ ID NO 174
<211> LENGTH: 11
<212> TYPE: PRT
<213> ORGANISM: Homo sapiens

<400> SEQUENCE: 174

Val Tyr Val Gly Gly Gly Gln Ile Ile His Leu
1               5                   10

<210> SEQ ID NO 175
<211> LENGTH: 9
<212> TYPE: PRT
<213> ORGANISM: Homo sapiens

<400> SEQUENCE: 175

Tyr Tyr Glu Val His Lys Glu Leu Phe
1               5

<210> SEQ ID NO 176
<211> LENGTH: 9
<212> TYPE: PRT
<213> ORGANISM: Homo sapiens

<400> SEQUENCE: 176

Glu Tyr Asn Gln Trp Phe Thr Lys Leu
1               5

<210> SEQ ID NO 177
<211> LENGTH: 9
<212> TYPE: PRT
<213> ORGANISM: Homo sapiens

<400> SEQUENCE: 177

Val Tyr Pro Trp Leu Gly Ala Leu Leu
1               5

<210> SEQ ID NO 178
<211> LENGTH: 9
<212> TYPE: PRT
<213> ORGANISM: Homo sapiens

<400> SEQUENCE: 178

Ile Phe Ile Glu Val Phe Ser His Phe
1               5

<210> SEQ ID NO 179
<211> LENGTH: 9
<212> TYPE: PRT
<213> ORGANISM: Homo sapiens

<400> SEQUENCE: 179

Met Tyr Asp Ser Tyr Trp Arg Gln Phe
1               5

<210> SEQ ID NO 180
<211> LENGTH: 12
<212> TYPE: PRT
```

```
<213> ORGANISM: Homo sapiens

<400> SEQUENCE: 180

Ile Tyr Asp Asp Ser Phe Ile Arg Pro Val Thr Phe
1               5                   10

<210> SEQ ID NO 181
<211> LENGTH: 9
<212> TYPE: PRT
<213> ORGANISM: Homo sapiens

<400> SEQUENCE: 181

Leu Tyr Leu Asp Ile Ile Asn Leu Phe
1               5

<210> SEQ ID NO 182
<211> LENGTH: 9
<212> TYPE: PRT
<213> ORGANISM: Homo sapiens

<400> SEQUENCE: 182

Ile Tyr Gln Leu Asp Thr Ala Ser Ile
1               5

<210> SEQ ID NO 183
<211> LENGTH: 9
<212> TYPE: PRT
<213> ORGANISM: Homo sapiens

<400> SEQUENCE: 183

Val Phe Thr Ser Thr Ala Arg Ala Phe
1               5

<210> SEQ ID NO 184
<211> LENGTH: 9
<212> TYPE: PRT
<213> ORGANISM: Homo sapiens

<400> SEQUENCE: 184

Val Phe Gln Asn Phe Pro Leu Leu Phe
1               5

<210> SEQ ID NO 185
<211> LENGTH: 9
<212> TYPE: PRT
<213> ORGANISM: Homo sapiens

<400> SEQUENCE: 185

Ile Tyr Lys Val Gly Ala Pro Thr Ile
1               5

<210> SEQ ID NO 186
<211> LENGTH: 9
<212> TYPE: PRT
<213> ORGANISM: Homo sapiens

<400> SEQUENCE: 186

Ile Phe Pro Gln Phe Leu Tyr Gln Phe
1               5

<210> SEQ ID NO 187
<211> LENGTH: 9
<212> TYPE: PRT
<213> ORGANISM: Homo sapiens
```

```
<400> SEQUENCE: 187

Thr Tyr Leu Arg Asp Gln His Phe Leu
1               5

<210> SEQ ID NO 188
<211> LENGTH: 8
<212> TYPE: PRT
<213> ORGANISM: Homo sapiens

<400> SEQUENCE: 188

Arg Tyr Phe Lys Gly Leu Val Phe
1               5

<210> SEQ ID NO 189
<211> LENGTH: 9
<212> TYPE: PRT
<213> ORGANISM: Homo sapiens

<400> SEQUENCE: 189

Trp Tyr Val Asn Gly Val Asn Tyr Phe
1               5

<210> SEQ ID NO 190
<211> LENGTH: 9
<212> TYPE: PRT
<213> ORGANISM: Homo sapiens

<400> SEQUENCE: 190

Gly Phe Phe Ile Phe Asn Glu Arg Phe
1               5

<210> SEQ ID NO 191
<211> LENGTH: 9
<212> TYPE: PRT
<213> ORGANISM: Homo sapiens

<400> SEQUENCE: 191

Val Phe Lys Ala Ser Lys Ile Thr Phe
1               5

<210> SEQ ID NO 192
<211> LENGTH: 9
<212> TYPE: PRT
<213> ORGANISM: Homo sapiens

<400> SEQUENCE: 192

Ser Tyr Ala Leu Leu Thr Tyr Met Ile
1               5

<210> SEQ ID NO 193
<211> LENGTH: 9
<212> TYPE: PRT
<213> ORGANISM: Homo sapiens

<400> SEQUENCE: 193

Arg Phe His Pro Thr Pro Leu Leu Leu
1               5

<210> SEQ ID NO 194
<211> LENGTH: 10
<212> TYPE: PRT
<213> ORGANISM: Homo sapiens

<400> SEQUENCE: 194
```

```
Glu Phe Gly Ser Leu His Leu Glu Phe Leu
1               5                   10

<210> SEQ ID NO 195
<211> LENGTH: 9
<212> TYPE: PRT
<213> ORGANISM: Homo sapiens

<400> SEQUENCE: 195

Thr Tyr Ser Val Ser Phe Pro Met Phe
1               5

<210> SEQ ID NO 196
<211> LENGTH: 10
<212> TYPE: PRT
<213> ORGANISM: Homo sapiens

<400> SEQUENCE: 196

Leu Tyr Ile Asp Arg Pro Leu Pro Tyr Leu
1               5                   10

<210> SEQ ID NO 197
<211> LENGTH: 11
<212> TYPE: PRT
<213> ORGANISM: Homo sapiens

<400> SEQUENCE: 197

Glu Tyr Ser Leu Phe Pro Gly Gln Val Val Ile
1               5                   10

<210> SEQ ID NO 198
<211> LENGTH: 9
<212> TYPE: PRT
<213> ORGANISM: Homo sapiens

<400> SEQUENCE: 198

Leu Tyr Leu Asp Lys Ala Thr Leu Ile
1               5

<210> SEQ ID NO 199
<211> LENGTH: 9
<212> TYPE: PRT
<213> ORGANISM: Homo sapiens

<400> SEQUENCE: 199

Arg Tyr Ala Glu Glu Val Gly Ile Phe
1               5

<210> SEQ ID NO 200
<211> LENGTH: 9
<212> TYPE: PRT
<213> ORGANISM: Homo sapiens

<400> SEQUENCE: 200

Tyr Tyr Gly Pro Ser Leu Phe Leu Leu
1               5

<210> SEQ ID NO 201
<211> LENGTH: 9
<212> TYPE: PRT
<213> ORGANISM: Homo sapiens

<400> SEQUENCE: 201

Ile Tyr Ala Thr Glu Ala His Val Phe
1               5
```

<210> SEQ ID NO 202
<211> LENGTH: 11
<212> TYPE: PRT
<213> ORGANISM: Homo sapiens

<400> SEQUENCE: 202

Val Tyr Trp Asp Ser Ala Gly Ala Ala His Phe
1               5                   10

<210> SEQ ID NO 203
<211> LENGTH: 9
<212> TYPE: PRT
<213> ORGANISM: Homo sapiens

<400> SEQUENCE: 203

Phe Tyr Ser Arg Leu Leu Gln Lys Phe
1               5

<210> SEQ ID NO 204
<211> LENGTH: 9
<212> TYPE: PRT
<213> ORGANISM: Homo sapiens

<400> SEQUENCE: 204

Thr Tyr Glu Leu Arg Tyr Phe Gln Ile
1               5

<210> SEQ ID NO 205
<211> LENGTH: 9
<212> TYPE: PRT
<213> ORGANISM: Homo sapiens

<400> SEQUENCE: 205

Val His Ile Pro Glu Val Tyr Leu Ile
1               5

<210> SEQ ID NO 206
<211> LENGTH: 9
<212> TYPE: PRT
<213> ORGANISM: Homo sapiens

<400> SEQUENCE: 206

Glu Tyr Gln Glu Asn Phe Leu Ser Phe
1               5

<210> SEQ ID NO 207
<211> LENGTH: 9
<212> TYPE: PRT
<213> ORGANISM: Homo sapiens

<400> SEQUENCE: 207

Ala Tyr Val Val Phe Val Ser Thr Leu
1               5

<210> SEQ ID NO 208
<211> LENGTH: 9
<212> TYPE: PRT
<213> ORGANISM: Homo sapiens

<400> SEQUENCE: 208

Thr Tyr Thr Gln Asp Phe Asn Lys Phe
1               5

```
<210> SEQ ID NO 209
<211> LENGTH: 10
<212> TYPE: PRT
<213> ORGANISM: Homo sapiens

<400> SEQUENCE: 209

Thr Tyr Lys Asp Glu Gly Asn Asp Tyr Phe
1               5                   10

<210> SEQ ID NO 210
<211> LENGTH: 9
<212> TYPE: PRT
<213> ORGANISM: Homo sapiens

<400> SEQUENCE: 210

Ile Tyr Thr Met Ile Tyr Arg Asn Leu
1               5

<210> SEQ ID NO 211
<211> LENGTH: 10
<212> TYPE: PRT
<213> ORGANISM: Homo sapiens

<400> SEQUENCE: 211

Tyr Tyr Leu Glu Val Gly Lys Thr Leu Ile
1               5                   10

<210> SEQ ID NO 212
<211> LENGTH: 9
<212> TYPE: PRT
<213> ORGANISM: Homo sapiens

<400> SEQUENCE: 212

Tyr Tyr Thr Phe His Phe Leu Tyr Phe
1               5

<210> SEQ ID NO 213
<211> LENGTH: 8
<212> TYPE: PRT
<213> ORGANISM: Homo sapiens

<400> SEQUENCE: 213

Ile Phe Asp Glu Ala Glu Lys Leu
1               5

<210> SEQ ID NO 214
<211> LENGTH: 9
<212> TYPE: PRT
<213> ORGANISM: Homo sapiens

<400> SEQUENCE: 214

Leu Tyr Leu Lys Leu Trp Asn Leu Ile
1               5

<210> SEQ ID NO 215
<211> LENGTH: 8
<212> TYPE: PRT
<213> ORGANISM: Homo sapiens

<400> SEQUENCE: 215

Tyr Phe Asp Lys Val Val Thr Leu
1               5

<210> SEQ ID NO 216
<211> LENGTH: 9
```

```
<212> TYPE: PRT
<213> ORGANISM: Homo sapiens

<400> SEQUENCE: 216

Gln Tyr Ser Ser Val Phe Lys Ser Leu
1               5

<210> SEQ ID NO 217
<211> LENGTH: 12
<212> TYPE: PRT
<213> ORGANISM: Homo sapiens

<400> SEQUENCE: 217

Phe Phe Pro Pro Thr Arg Gln Met Gly Leu Leu Phe
1               5                   10

<210> SEQ ID NO 218
<211> LENGTH: 9
<212> TYPE: PRT
<213> ORGANISM: Homo sapiens

<400> SEQUENCE: 218

Tyr Tyr Lys Ser Thr Ser Ser Ala Phe
1               5

<210> SEQ ID NO 219
<211> LENGTH: 9
<212> TYPE: PRT
<213> ORGANISM: Homo sapiens

<400> SEQUENCE: 219

Glu Tyr Pro Leu Val Ile Asn Thr Leu
1               5

<210> SEQ ID NO 220
<211> LENGTH: 9
<212> TYPE: PRT
<213> ORGANISM: Homo sapiens

<400> SEQUENCE: 220

Gly Tyr Ile Asp Asn Val Thr Leu Ile
1               5

<210> SEQ ID NO 221
<211> LENGTH: 11
<212> TYPE: PRT
<213> ORGANISM: Homo sapiens

<400> SEQUENCE: 221

Arg Tyr Ser Thr Gly Leu Ala Gly Asn Leu Leu
1               5                   10

<210> SEQ ID NO 222
<211> LENGTH: 9
<212> TYPE: PRT
<213> ORGANISM: Homo sapiens

<400> SEQUENCE: 222

Thr Phe Ser Val Ser Ser His Leu Phe
1               5

<210> SEQ ID NO 223
<211> LENGTH: 9
<212> TYPE: PRT
<213> ORGANISM: Homo sapiens
```

<400> SEQUENCE: 223

Lys Tyr Ile Pro Tyr Lys Tyr Val Ile
1               5

<210> SEQ ID NO 224
<211> LENGTH: 9
<212> TYPE: PRT
<213> ORGANISM: Homo sapiens

<400> SEQUENCE: 224

Gln Tyr Leu Glu Asn Leu Glu Lys Leu
1               5

<210> SEQ ID NO 225
<211> LENGTH: 9
<212> TYPE: PRT
<213> ORGANISM: Homo sapiens

<400> SEQUENCE: 225

Tyr Tyr Val Tyr Ile Met Asn His Leu
1               5

<210> SEQ ID NO 226
<211> LENGTH: 10
<212> TYPE: PRT
<213> ORGANISM: Homo sapiens

<400> SEQUENCE: 226

Val Tyr Arg Asp Glu Thr Gly Glu Leu Phe
1               5                   10

<210> SEQ ID NO 227
<211> LENGTH: 12
<212> TYPE: PRT
<213> ORGANISM: Homo sapiens

<400> SEQUENCE: 227

Ile Phe Leu Asp Tyr Glu Ala Gly Thr Leu Ser Phe
1               5                   10

<210> SEQ ID NO 228
<211> LENGTH: 9
<212> TYPE: PRT
<213> ORGANISM: Homo sapiens

<400> SEQUENCE: 228

Lys Tyr Thr Ser Trp Tyr Val Ala Leu
1               5

<210> SEQ ID NO 229
<211> LENGTH: 9
<212> TYPE: PRT
<213> ORGANISM: Homo sapiens

<400> SEQUENCE: 229

Ala Ile Leu Ala His Leu Asn Thr Val
1               5

<210> SEQ ID NO 230
<211> LENGTH: 9
<212> TYPE: PRT
<213> ORGANISM: Homo sapiens

<400> SEQUENCE: 230

```
Lys Leu Gln Asn Ile Met Met Leu Leu
1               5

<210> SEQ ID NO 231
<211> LENGTH: 9
<212> TYPE: PRT
<213> ORGANISM: Homo sapiens

<400> SEQUENCE: 231

Met Leu Asp Lys Tyr Ser His Tyr Leu
1               5

<210> SEQ ID NO 232
<211> LENGTH: 10
<212> TYPE: PRT
<213> ORGANISM: Homo sapiens

<400> SEQUENCE: 232

Lys Ile Phe Pro Ala Ala Leu Gln Leu Val
1               5                   10

<210> SEQ ID NO 233
<211> LENGTH: 9
<212> TYPE: PRT
<213> ORGANISM: Homo sapiens

<400> SEQUENCE: 233

His Leu Phe Asp Ala Phe Val Ser Val
1               5

<210> SEQ ID NO 234
<211> LENGTH: 9
<212> TYPE: PRT
<213> ORGANISM: Homo sapiens

<400> SEQUENCE: 234

Leu Leu Ser Pro His Asn Pro Ala Leu
1               5

<210> SEQ ID NO 235
<211> LENGTH: 9
<212> TYPE: PRT
<213> ORGANISM: Homo sapiens

<400> SEQUENCE: 235

Lys Ile Ile Asp Phe Leu Ser Ala Leu
1               5

<210> SEQ ID NO 236
<211> LENGTH: 9
<212> TYPE: PRT
<213> ORGANISM: Homo sapiens

<400> SEQUENCE: 236

Ser Thr Ile Ala Ile Leu Asn Ser Val
1               5

<210> SEQ ID NO 237
<211> LENGTH: 9
<212> TYPE: PRT
<213> ORGANISM: Homo sapiens

<400> SEQUENCE: 237

Ala Leu Ala Pro His Leu Asp Asp Ala
```

```
1               5

<210> SEQ ID NO 238
<211> LENGTH: 9
<212> TYPE: PRT
<213> ORGANISM: Homo sapiens

<400> SEQUENCE: 238

Gly Leu Tyr Glu Arg Pro Thr Ala Ala
1               5

<210> SEQ ID NO 239
<211> LENGTH: 9
<212> TYPE: PRT
<213> ORGANISM: Homo sapiens

<400> SEQUENCE: 239

Lys Met Asn Glu Ser Thr Arg Ser Val
1               5

<210> SEQ ID NO 240
<211> LENGTH: 11
<212> TYPE: PRT
<213> ORGANISM: Homo sapiens

<400> SEQUENCE: 240

Tyr Met Gly Glu Glu Lys Leu Ile Ala Ser Val
1               5                   10

<210> SEQ ID NO 241
<211> LENGTH: 9
<212> TYPE: PRT
<213> ORGANISM: Homo sapiens

<400> SEQUENCE: 241

Lys Thr Ile Gln Gln Leu Glu Thr Val
1               5

<210> SEQ ID NO 242
<211> LENGTH: 9
<212> TYPE: PRT
<213> ORGANISM: Homo sapiens

<400> SEQUENCE: 242

Trp Leu Tyr Gly Glu Asp His Gln Ile
1               5

<210> SEQ ID NO 243
<211> LENGTH: 9
<212> TYPE: PRT
<213> ORGANISM: Homo sapiens

<400> SEQUENCE: 243

Phe Met Ala Asp Asp Ile Phe Ser Val
1               5

<210> SEQ ID NO 244
<211> LENGTH: 9
<212> TYPE: PRT
<213> ORGANISM: Homo sapiens

<400> SEQUENCE: 244

Tyr Leu Leu Glu Lys Asn Arg Val Val
1               5
```

```
<210> SEQ ID NO 245
<211> LENGTH: 9
<212> TYPE: PRT
<213> ORGANISM: Homo sapiens

<400> SEQUENCE: 245

Ser Leu Leu Asp Leu Pro Leu Ser Leu
1               5

<210> SEQ ID NO 246
<211> LENGTH: 9
<212> TYPE: PRT
<213> ORGANISM: Homo sapiens

<400> SEQUENCE: 246

Thr Val Ser Asp Val Leu Asn Ser Val
1               5

<210> SEQ ID NO 247
<211> LENGTH: 9
<212> TYPE: PRT
<213> ORGANISM: Homo sapiens

<400> SEQUENCE: 247

Ala Leu Tyr Glu Gly Tyr Ala Thr Val
1               5

<210> SEQ ID NO 248
<211> LENGTH: 9
<212> TYPE: PRT
<213> ORGANISM: Homo sapiens

<400> SEQUENCE: 248

Tyr Leu Asp Arg Phe Leu Ala Gly Val
1               5

<210> SEQ ID NO 249
<211> LENGTH: 9
<212> TYPE: PRT
<213> ORGANISM: Homo sapiens

<400> SEQUENCE: 249

Gly Leu Cys Glu Arg Leu Val Ser Leu
1               5

<210> SEQ ID NO 250
<211> LENGTH: 9
<212> TYPE: PRT
<213> ORGANISM: Homo sapiens

<400> SEQUENCE: 250

Ser Leu Ala Pro Ala Thr Pro Glu Val
1               5

<210> SEQ ID NO 251
<211> LENGTH: 9
<212> TYPE: PRT
<213> ORGANISM: Homo sapiens

<400> SEQUENCE: 251

Ala Leu Ser Val Leu Arg Leu Ala Leu
1               5

<210> SEQ ID NO 252
```

```
<211> LENGTH: 9
<212> TYPE: PRT
<213> ORGANISM: Homo sapiens

<400> SEQUENCE: 252

Arg Leu Met Glu Ile Cys Glu Ser Leu
1               5

<210> SEQ ID NO 253
<211> LENGTH: 10
<212> TYPE: PRT
<213> ORGANISM: Homo sapiens

<400> SEQUENCE: 253

Ala Leu Ala Glu Leu Ile Asp Asn Ser Leu
1               5                   10

<210> SEQ ID NO 254
<211> LENGTH: 9
<212> TYPE: PRT
<213> ORGANISM: Homo sapiens

<400> SEQUENCE: 254

Lys Leu Gln Gly Lys Leu Pro Glu Leu
1               5

<210> SEQ ID NO 255
<211> LENGTH: 9
<212> TYPE: PRT
<213> ORGANISM: Homo sapiens

<400> SEQUENCE: 255

Ser Leu Leu His Phe Thr Glu Asn Leu
1               5

<210> SEQ ID NO 256
<211> LENGTH: 9
<212> TYPE: PRT
<213> ORGANISM: Homo sapiens

<400> SEQUENCE: 256

Ser Leu Gly Glu Glu Gln Phe Ser Val
1               5

<210> SEQ ID NO 257
<211> LENGTH: 9
<212> TYPE: PRT
<213> ORGANISM: Homo sapiens

<400> SEQUENCE: 257

Gly Leu Tyr Thr Asp Pro Cys Gly Val
1               5

<210> SEQ ID NO 258
<211> LENGTH: 9
<212> TYPE: PRT
<213> ORGANISM: Homo sapiens

<400> SEQUENCE: 258

Leu Leu Ser Glu Arg Phe Ile Asn Val
1               5

<210> SEQ ID NO 259
<211> LENGTH: 9
<212> TYPE: PRT
```

<213> ORGANISM: Homo sapiens

<400> SEQUENCE: 259

Ile Leu Leu Pro Arg Ile Ile Glu Ala
1               5

<210> SEQ ID NO 260
<211> LENGTH: 9
<212> TYPE: PRT
<213> ORGANISM: Homo sapiens

<400> SEQUENCE: 260

Ile Leu Leu Glu Lys Ile Leu Ser Leu
1               5

<210> SEQ ID NO 261
<211> LENGTH: 9
<212> TYPE: PRT
<213> ORGANISM: Homo sapiens

<400> SEQUENCE: 261

Gln Leu Gln Asp Arg Val Tyr Ala Leu
1               5

<210> SEQ ID NO 262
<211> LENGTH: 9
<212> TYPE: PRT
<213> ORGANISM: Homo sapiens

<400> SEQUENCE: 262

Phe Met Val Asp Lys Ala Ile Tyr Leu
1               5

<210> SEQ ID NO 263
<211> LENGTH: 11
<212> TYPE: PRT
<213> ORGANISM: Homo sapiens

<400> SEQUENCE: 263

Val Leu Leu Ser Glu Gln Gly Asp Val Lys Leu
1               5                   10

<210> SEQ ID NO 264
<211> LENGTH: 10
<212> TYPE: PRT
<213> ORGANISM: Homo sapiens

<400> SEQUENCE: 264

Lys Leu Phe Pro Gln Glu Thr Leu Phe Leu
1               5                   10

<210> SEQ ID NO 265
<211> LENGTH: 9
<212> TYPE: PRT
<213> ORGANISM: Homo sapiens

<400> SEQUENCE: 265

Asn Thr Cys Pro Tyr Val His Asn Ile
1               5

<210> SEQ ID NO 266
<211> LENGTH: 9
<212> TYPE: PRT
<213> ORGANISM: Homo sapiens

```
<400> SEQUENCE: 266

Tyr Ala Ile Gly Leu Val Met Arg Leu
1               5

<210> SEQ ID NO 267
<211> LENGTH: 9
<212> TYPE: PRT
<213> ORGANISM: Homo sapiens

<400> SEQUENCE: 267

Lys Tyr Met Val Tyr Pro Gln Thr Phe
1               5

<210> SEQ ID NO 268
<211> LENGTH: 9
<212> TYPE: PRT
<213> ORGANISM: Homo sapiens

<400> SEQUENCE: 268

Gln Tyr Leu Gly Gln Ile Gln His Ile
1               5

<210> SEQ ID NO 269
<211> LENGTH: 12
<212> TYPE: PRT
<213> ORGANISM: Homo sapiens

<400> SEQUENCE: 269

Tyr Phe Ile Asp Ser Thr Asn Leu Lys Thr His Phe
1               5                   10

<210> SEQ ID NO 270
<211> LENGTH: 10
<212> TYPE: PRT
<213> ORGANISM: Homo sapiens

<400> SEQUENCE: 270

Asn Tyr Tyr Glu Val His Lys Glu Leu Phe
1               5                   10

<210> SEQ ID NO 271
<211> LENGTH: 9
<212> TYPE: PRT
<213> ORGANISM: Homo sapiens

<400> SEQUENCE: 271

Leu Tyr His Asp Ile Phe Ser Arg Leu
1               5

<210> SEQ ID NO 272
<211> LENGTH: 9
<212> TYPE: PRT
<213> ORGANISM: Homo sapiens

<400> SEQUENCE: 272

Gln Tyr Leu Gln Asp Ala Tyr Ser Phe
1               5

<210> SEQ ID NO 273
<211> LENGTH: 9
<212> TYPE: PRT
<213> ORGANISM: Homo sapiens

<400> SEQUENCE: 273
```

```
Thr Tyr Ile Lys Pro Ile Ser Lys Leu
1               5
```

<210> SEQ ID NO 274
<211> LENGTH: 9
<212> TYPE: PRT
<213> ORGANISM: Homo sapiens

<400> SEQUENCE: 274

```
Ala Tyr Leu His Ser His Ala Leu Ile
1               5
```

<210> SEQ ID NO 275
<211> LENGTH: 11
<212> TYPE: PRT
<213> ORGANISM: Homo sapiens

<400> SEQUENCE: 275

```
Glu Tyr Ile Asn Gln Gly Asp Leu His Glu Phe
1               5                   10
```

<210> SEQ ID NO 276
<211> LENGTH: 9
<212> TYPE: PRT
<213> ORGANISM: Homo sapiens

<400> SEQUENCE: 276

```
Val Tyr Gly Phe Gln Trp Arg His Phe
1               5
```

<210> SEQ ID NO 277
<211> LENGTH: 9
<212> TYPE: PRT
<213> ORGANISM: Homo sapiens

<400> SEQUENCE: 277

```
Val Tyr Gln Gly His Thr Ala Leu Leu
1               5
```

<210> SEQ ID NO 278
<211> LENGTH: 11
<212> TYPE: PRT
<213> ORGANISM: Homo sapiens

<400> SEQUENCE: 278

```
Arg Tyr Ile Ser Asp Gln Leu Phe Thr Asn Phe
1               5                   10
```

<210> SEQ ID NO 279
<211> LENGTH: 9
<212> TYPE: PRT
<213> ORGANISM: Homo sapiens

<400> SEQUENCE: 279

```
Thr Tyr Ile Glu Ser Ala Ser Glu Leu
1               5
```

<210> SEQ ID NO 280
<211> LENGTH: 11
<212> TYPE: PRT
<213> ORGANISM: Homo sapiens

<400> SEQUENCE: 280

```
Arg Tyr Pro Asp Asn Leu Lys His Leu Tyr Leu
1               5                   10
```

<210> SEQ ID NO 281
<211> LENGTH: 9
<212> TYPE: PRT
<213> ORGANISM: Homo sapiens

<400> SEQUENCE: 281

Pro Tyr Arg Leu Ile Phe Glu Lys Phe
1               5

<210> SEQ ID NO 282
<211> LENGTH: 9
<212> TYPE: PRT
<213> ORGANISM: Homo sapiens

<400> SEQUENCE: 282

Lys Phe Val Asp Ser Thr Phe Tyr Leu
1               5

<210> SEQ ID NO 283
<211> LENGTH: 11
<212> TYPE: PRT
<213> ORGANISM: Homo sapiens

<400> SEQUENCE: 283

Thr Tyr Gly Asp Ala Gly Leu Thr Tyr Thr Phe
1               5                   10

<210> SEQ ID NO 284
<211> LENGTH: 9
<212> TYPE: PRT
<213> ORGANISM: Homo sapiens

<400> SEQUENCE: 284

Arg Tyr Leu Asn Lys Ala Phe His Ile
1               5

<210> SEQ ID NO 285
<211> LENGTH: 9
<212> TYPE: PRT
<213> ORGANISM: Homo sapiens

<400> SEQUENCE: 285

His Tyr Pro Pro Val Gln Val Leu Phe
1               5

<210> SEQ ID NO 286
<211> LENGTH: 9
<212> TYPE: PRT
<213> ORGANISM: Homo sapiens

<400> SEQUENCE: 286

Arg Tyr Pro Asp Asn Leu Lys His Leu
1               5

<210> SEQ ID NO 287
<211> LENGTH: 9
<212> TYPE: PRT
<213> ORGANISM: Homo sapiens

<400> SEQUENCE: 287

Leu Tyr Ile Thr Glu Pro Lys Thr Ile
1               5

```
<210> SEQ ID NO 288
<211> LENGTH: 9
<212> TYPE: PRT
<213> ORGANISM: Homo sapiens

<400> SEQUENCE: 288

Val Tyr Val Ser Asp Ile Gln Glu Leu
1               5

<210> SEQ ID NO 289
<211> LENGTH: 9
<212> TYPE: PRT
<213> ORGANISM: Homo sapiens

<400> SEQUENCE: 289

Lys Tyr Pro Val Glu Trp Ala Lys Phe
1               5

<210> SEQ ID NO 290
<211> LENGTH: 9
<212> TYPE: PRT
<213> ORGANISM: Homo sapiens

<400> SEQUENCE: 290

Lys Ile Val Asp Phe Ser Tyr Ser Val
1               5

<210> SEQ ID NO 291
<211> LENGTH: 9
<212> TYPE: PRT
<213> ORGANISM: Homo sapiens

<400> SEQUENCE: 291

Lys Leu Asp Glu Thr Gly Asn Ser Leu
1               5

<210> SEQ ID NO 292
<211> LENGTH: 9
<212> TYPE: PRT
<213> ORGANISM: Homo sapiens

<400> SEQUENCE: 292

Gly Met Met Thr Ala Ile Leu Gly Val
1               5

<210> SEQ ID NO 293
<211> LENGTH: 9
<212> TYPE: PRT
<213> ORGANISM: Homo sapiens

<400> SEQUENCE: 293

Phe Leu Val Asp Gly Ser Trp Ser Ile
1               5

<210> SEQ ID NO 294
<211> LENGTH: 9
<212> TYPE: PRT
<213> ORGANISM: Homo sapiens

<400> SEQUENCE: 294

Gly Leu Met Lys Tyr Ile Gly Glu Val
1               5

<210> SEQ ID NO 295
<211> LENGTH: 9
```

```
<212> TYPE: PRT
<213> ORGANISM: Homo sapiens

<400> SEQUENCE: 295

Tyr Tyr Pro Gly Val Ile Leu Gly Phe
1               5

<210> SEQ ID NO 296
<211> LENGTH: 9
<212> TYPE: PRT
<213> ORGANISM: Homo sapiens

<400> SEQUENCE: 296

Thr Tyr Val Asp Ser Ser His Thr Ile
1               5

<210> SEQ ID NO 297
<211> LENGTH: 9
<212> TYPE: PRT
<213> ORGANISM: Homo sapiens

<400> SEQUENCE: 297

Pro Phe Leu Gln Ala Ser Pro His Phe
1               5

<210> SEQ ID NO 298
<211> LENGTH: 9
<212> TYPE: PRT
<213> ORGANISM: Homo sapiens

<400> SEQUENCE: 298

Arg Tyr Leu Glu Gly Thr Ser Cys Ile
1               5

<210> SEQ ID NO 299
<211> LENGTH: 9
<212> TYPE: PRT
<213> ORGANISM: Homo sapiens

<400> SEQUENCE: 299

Val Tyr Phe Val Ala Pro Ala Lys Phe
1               5

<210> SEQ ID NO 300
<211> LENGTH: 9
<212> TYPE: PRT
<213> ORGANISM: Homo sapiens

<400> SEQUENCE: 300

Ala Tyr Val Leu Arg Leu Glu Thr Leu
1               5

<210> SEQ ID NO 301
<211> LENGTH: 9
<212> TYPE: PRT
<213> ORGANISM: Homo sapiens

<400> SEQUENCE: 301

Ala Tyr Lys Pro Gly Ala Leu Thr Phe
1               5

<210> SEQ ID NO 302
<211> LENGTH: 10
<212> TYPE: PRT
<213> ORGANISM: Homo sapiens
```

```
<400> SEQUENCE: 302

Arg Tyr Met Pro Pro Ala His Arg Asn Phe
1               5                   10

<210> SEQ ID NO 303
<211> LENGTH: 10
<212> TYPE: PRT
<213> ORGANISM: Homo sapiens

<400> SEQUENCE: 303

Glu Leu Ala Gly Ile Gly Ile Leu Thr Val
1               5                   10

<210> SEQ ID NO 304
<211> LENGTH: 9
<212> TYPE: PRT
<213> ORGANISM: Homo sapiens

<400> SEQUENCE: 304

Tyr Leu Leu Pro Ala Ile Val His Ile
1               5

<210> SEQ ID NO 305
<211> LENGTH: 9
<212> TYPE: PRT
<213> ORGANISM: Homo sapiens

<400> SEQUENCE: 305

Lys Leu Phe Thr Ser Val Phe Gly Val
1               5

<210> SEQ ID NO 306
<211> LENGTH: 9
<212> TYPE: PRT
<213> ORGANISM: Homo sapiens

<400> SEQUENCE: 306

Ala Leu Leu Ser Ser Leu Asn Glu Leu
1               5
```

PEPTIDES AND COMBINATION OF PEPTIDES FOR USE IN IMMUNOTHERAPY AGAINST VARIOUS CANCERS

CROSS REFERENCE TO RELATED APPLICATIONS

This application is a continuation of U.S. application Ser. No. 17/327,458, filed on 21 May 2021, which is a continuation of U.S. application Ser. No. 16/705,042, filed on 5 Dec. 2019, which is a continuation of U.S. patent application Ser. No. 16/408,653, filed 10 May 2019, now U.S. Pat. No. 10,525,116, issued on 7 Jan. 2020, which is a continuation of U.S. patent application Ser. No. 16/116,323, filed 29 Aug. 2018, now U.S. Pat. No. 10,342,859, issued 9 Jul. 2019, which is a continuation of U.S. patent application Ser. No. 15/374,882, filed 9 Dec. 2016, now U.S. Pat. No. 10,179,165, issued 15 Jan. 2019, which claims the benefit of U.S. Provisional Application Ser. No. 62/266,233, filed 11 Dec. 2015, and Great Britain Application No. 1521894.4, filed 11 Dec. 2015, the content of each of these applications is herein incorporated by reference in their entirety.

This application is related to PCT/EP2016/079737, filed 5 Dec. 2016, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_listing_2912919-059030_ST25.txt" created on 22 Apr. 2022, and 47,325 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

According to the World Health Organization (WHO), cancer ranged among the four major non-communicable deadly diseases worldwide in 2012. For the same year, colorectal cancer, breast cancer and respiratory tract cancers were listed within the top 10 causes of death in high income countries Epidemiology In 2012, 14.1 million new cancer cases, 32.6 million patients suffering from cancer (within 5 years of diagnosis) and 8.2 million cancer deaths were estimated worldwide (Ferlay et al., 2013; Bray et al., 2013). Table 1 and Table 2 provide an overview of the estimated incidence, 5 year prevalence and mortality in different cancer types relevant for the present intervention, worldwide and in selected regions, respectively.

TABLE 1

Estimated incidence, 5 year prevalence and mortality of different cancer types (adult population, both sexes) worldwide in 2012 (Ferlay et al., 2013; Bray et al., 2013).

| Cancer | Incidence | Prevalence (5 year) | Mortality |
| --- | --- | --- | --- |
| Brain, nervous system | 256213 | 342914 | 189382 |
| Breast | 1671149 | 6232108 | 521907 |
| Colorectum | 1360602 | 3543582 | 693933 |
| Esophagus | 455784 | 464063 | 400169 |
| Kidney | 337860 | 906746 | 143406 |
| Leukemia | 351965 | 500934 | 265471 |
| Liver | 782451 | 633170 | 745533 |
| Lung | 1824701 | 1893078 | 1589925 |
| Melanoma | 232130 | 869754 | 55488 |
| Ovary | 238719 | 586624 | 151917 |
| Pancreas | 337872 | 211544 | 330391 |
| Prostate | 1094916 | 3857500 | 307481 |
| Stomach | 951594 | 1538127 | 723073 |
| Gallbladder | 178101 | 205646 | 142823 |
| Bladder | 429793 | 1319749 | 165084 |
| Corpus uteri | 319605 | 1216504 | 76160 |
| Non-Hodgkin lymphoma | 385741 | 832843 | 199670 |

TABLE 2

Estimated incidence, 5 year prevalence and mortality of different cancer types (adult population, both sexes) in the USA, EU-28, China and Japan in 2012 (Ferlay et al., 2013; Bray et al., 2013).

| Cancer | Incidence | Prevalence (5 year) | Mortality |
| --- | --- | --- | --- |
| Brain, nervous system | 135884 | 172497 | 100865 |
| Breast | 837245 | 3358034 | 197279 |
| Colorectum | 845797 | 2334303 | 396066 |
| Esophagus | 294734 | 323723 | 255752 |
| Kidney | 226733 | 631350 | 83741 |
| Leukemia | 178296 | 309154 | 129500 |
| Liver | 513172 | 441007 | 488485 |
| Lung | 1274568 | 1394735 | 1107546 |
| Melanoma | 163043 | 636364 | 32999 |
| Ovary | 108947 | 270204 | 65130 |
| Pancreas | 220842 | 134864 | 214886 |
| Prostate | 681069 | 2586710 | 136419 |
| Stomach | 615641 | 1076332 | 447735 |
| Gallbladder | 106202 | 118588 | 81391 |
| Bladder | 270335 | 879140 | 91553 |
| Corpus uteri | 199211 | 765101 | 41734 |
| Non-Hodgkin lymphoma | 205955 | 515154 | 90092 |

Within the groups of brain cancer, leukemia and lung cancer the current invention specifically focuses on glioblastoma (GB), chronic lymphocytic leukemia (CLL) and acute myeloid leukemia (AML), non-small cell and small cell lung cancer (NSCLC and SCLC), respectively.

GB is the most common central nervous system malignancy with an age-adjusted incidence rate of 3.19 per 100,000 inhabitants within the United States. GB has a very poor prognosis with a 1-year survival rate of 35% and a 5-year survival rate lower than 5%. Male gender, older age and ethnicity appear to be risk factors for GB (Thakkar et al., 2014).

CLL is the most common leukemia in the Western world where it comprises about one third of all leukemia. Incidence rates are similar in the US and Europe, and estimated new cases are about 16,000 per year. CLL is more common in Caucasians than in Africans, rarer in Hispanics and Native Americans and seldom in Asians. In people of Asian origin, CLL incidence rates are 3 fold lower than in Caucasians (Gunawardana et al., 2008). The five-year overall survival for patients with CLL is about 79%.

AML is the second most common type of leukemia diagnosed in both adults and children. Estimated new cases in the United States are about 21,000 per year. The five-year survival rate of people with AML is approximately 25%.

Lung cancer is the most common type of cancer worldwide and the leading cause of death from cancer in many countries. Lung cancer is subdivided into small cell lung cancer and non-small cell lung cancer. NSCLC includes the histological types adenocarcinoma, squamous cell carcinoma and large cell carcinoma and accounts for 85% of all lung cancers in the United States. The incidence of NSCLC is closely correlated with smoking prevalence, including current and former smokers and the five year survival rate was reported to be 15% (World Cancer Report, 2014; Molina et al., 2008).

Therapy
Breast Cancer

Breast cancer is an immunogenic cancer entity and different types of infiltrating immune cells in primary tumors exhibit distinct prognostic and predictive significance. A large number of early phase immunotherapy trials have been conducted in breast cancer patients. Most of the completed vaccination studies targeted HER2 and carbohydrate antigens like MUC-1 and revealed rather disappointing results. Clinical data on the effects of immune checkpoint modulation with ipilimumab and other T cell-activating antibodies in breast cancer patients are emerging (Emens, 2012).

Chronic Lymphocytic Leukemia

While CLL is not curable at present, many patients show only slow progression of the disease or worsening of symptoms. As patients do not benefit from an early onset of treatment, the initial approach is "watch and wait" (Richards et al., 1999). For patients with symptomatic or rapidly progressing disease, several treatment options are available. These include chemotherapy, targeted therapy, immune-based therapies like monoclonal antibodies, chimeric antigen-receptors (CARs) and active immunotherapy, and stem cell transplants.

Monoclonal antibodies are widely used in hematologic malignancies. This is due to the knowledge of suitable antigens based on the good characterization of immune cell surface molecules and the accessibility of tumor cells in blood or bone marrow. Common monoclonal antibodies used in CLL therapy target either CD20 or CD52. Rituximab, the first monoclonal anti-CD20 antibody originally approved by the FDA for treatment of NHLs, is now widely used in CLL therapy. Combinational treatment with rituximab/fludarabine/cyclophosphamide leads to higher CR rates and improved overall survival (OS) compared to the combination fludarabine/cyclophosphamide and has become the preferred treatment option (Hallek et al., 2008). Ofatumomab targets CD20 and is used for therapy of refractory CLL patients (Wierda et al., 2011). Obinutuzumab is another monoclonal anti-CD20 antibody used in first-line treatment in combination with chlorambucil (Goede et al., 2014).

Alemtuzumab is an anti-CD52 antibody used for treatment of patients with chemotherapy-resistant disease or patients with poor prognostic factors as del 17p or p53 mutations (Parikh et al., 2011). Novel monoclonal antibodies target CD37 (otlertuzumab, BI 836826, IMGN529 and (177)Lu-tetulomab) or CD40 (dacetuzumab and lucatumumab) and are tested in pre-clinical settings (Robak and Robak, 2014).

Several completed and ongoing trials are based on engineered autologous chimeric antigen receptor (CAR)-modified T cells with CD19 specificity (Maus et al., 2014). So far, only the minority of patients showed detectable or persistent CARs. One partial response (PR) and two complete responses (CR) have been detected in the CAR T-cell trials by Porter et al. and Kalos et al. (Kalos et al., 2011; Porter et al., 2011).

Active immunotherapy includes the following strategies: gene therapy, whole modified tumor cell vaccines, DC-based vaccines and tumor associated antigen (TAA)-derived peptide vaccines.

Approaches in gene therapy make use of autologous genetically modified tumor cells. These B-CLL cells are transfected with immuno-(co-)stimulatory genes like IL-2, IL-12, TNF-alpha, GM-CSF, CD80, CD40L, LFA-3 and ICAM-1 to improve antigen presentation and T cell activation (Carballido et al., 2012). While specific T-cell responses and reduction in tumor cells are readily observed, immune responses are only transient.

Several studies have used autologous DCs as antigen presenting cells to elicit anti-tumor responses. DCs have been loaded ex vivo with tumor associated peptides, whole tumor cell lysate and tumor-derived RNA or DNA. Another strategy uses whole tumor cells for fusion with DCs and generation of DC-B-CLL-cell hybrids. Transfected DCs initiated both CD4+ and CD8+ T-cell responses (Muller et al., 2004). Fusion hybrids and DCs loaded with tumor cell lysate or apoptotic bodies increased tumor-specific CD8+ T-cell responses. Patients that showed a clinical response had increased IL-12 serum levels and reduced numbers of Tregs (Palma et al., 2008).

Different approaches use altered tumor cells to initiate or increase CLL-specific immune responses. An example for this strategy is the generation of trioma cells: B-CLL cells are fused to anti-Fc receptor expressing hybridoma cells that have anti-APC specificity. Trioma cells induced CLL-specific T-cell responses in vitro (Kronenberger et al., 2008).

Another strategy makes use of irradiated autologous CLL cells with Bacillus Calmette-Guérin as an adjuvant as a vaccine. Several patients showed a reduction in leukocyte levels or stable disease (Hus et al., 2008).

Besides isolated CLL cells, whole blood from CLL patients has been used as a vaccine after preparation in a blood treatment unit. The vaccine elicited CLL-specific T-cell responses and led to partial clinical responses or stable disease in several patients (Spaner et al., 2005).

Several TAAs are over-expressed in CLL and are suitable for vaccinations. These include fibromodulin (Mayr et al., 2005), RHAMM/CD168 (Giannopoulos et al., 2006), MDM2 (Mayr et al., 2006), hTERT (Counter et al., 1995), the oncofetal antigen-immature laminin receptor protein (OFAiLRP) (Siegel et al., 2003), adipophilin (Schmidt et al., 2004), survivin (Granziero et al., 2001), KW1 to KW14 (Krackhardt et al., 2002) and the tumor-derived IgVHCDR3 region (Harig et al., 2001; Carballido et al., 2012). A phase I clinical trial was conducted using the RHAMM-derived R3 peptide as a vaccine. 5 of 6 patients had detectable R3-specific CD8+ T-cell responses (Giannopoulos et al., 2010).

Colorectal Cancer

Depending on the colorectal cancer (CRC) stage, different standard therapies are available for colon and rectal cancer. Standard procedures include surgery, radiation therapy, chemotherapy and targeted therapy for CRC (Berman et al., 2015a; Berman et al., 2015b).

Removal of the tumor is essential for the treatment of CRC. For chemotherapeutic treatment, the drugs capecitabine or 5-fluorouracil (5-FU) are used. For combinational chemotherapy, a cocktail containing 5-FU, leucovorin and oxaliplatin (FOLFOX) is recommended (Stintzing, 2014; Berman et al., 2015b). In addition to chemotherapeutic drugs, several monoclonal antibodies targeting the epidermal growth factor receptor (EGFR, cetuximab, panitumumab) or the vascular endothelial growth factor-A (VEGF-A, bevacizumab) are administered to patients with high stage disease. For second-line and later treatment the inhibitor for VEGF aflibercept, the tyrosine kinase inhibitor regorafenib and the thymidylate-synthetase inhibitor TAS-102 and the dUTPase inhibitor TAS-114 can be used (Stintzing, 2014; Wilson et al., 2014).

Latest clinical trials analyze active immunotherapy as a treatment option against CRC. Those strategies include the vaccination with peptides from tumor-associated antigens (TAAs), whole tumor cells, dendritic cell (DC) vaccines and viral vectors (Koido et al., 2013).

Peptide vaccines have so far been directed against carcinoembryonic antigen (CEA), mucin 1, EGFR, squamous cell carcinoma antigen recognized by T cells 3 (SART3), beta-human chorionic gonadotropin (beta-hCG), Wilms' Tumor antigen 1 (WT1), Survivin-2B, MAGE3, p53, ring finger protein 43 and translocase of the outer mitochondrial membrane 34 (TOMM34), or mutated KRAS. In several phase I and II clinical trials patients showed antigen-specific CTL responses or antibody production. In contrast to immunological responses, many patients did not benefit from peptide vaccines on the clinical level (Koido et al., 2013; Miyagi et al., 2001; Moulton et al., 2002; Okuno et al., 2011).

Dendritic cell vaccines comprise DCs pulsed with either TAA-derived peptides, tumor cell lysates, apoptotic tumor cells, or tumor RNA or DC-tumor cell fusion products. While many patients in phase I/II trials showed specific immunological responses, only the minority had a clinical benefit (Koido et al., 2013).

Whole tumor cell vaccines consist of autologous tumor cells modified to secrete GM-CSF, modified by irradiation or virus-infected, irradiated cells. Most patients showed no clinical benefit in several phase II/III trials (Koido et al., 2013).

Vaccinia virus or replication-defective avian poxvirus encoding CEA as well as B7.1, ICAM-1 and LFA-3 have been used as vehicles in viral vector vaccines in phase I clinical trials. A different study used non-replicating canary pox virus encoding CEA and B7.1. Besides the induction of CEA-specific T cell responses 40% of patients showed objective clinical responses (Horig et al., 2000; Kaufman et al., 2008).

Esophageal Cancer

Immunotherapy may be a promising novel approach to treat advanced esophageal cancer. Several cancer-associated genes and cancer-testis antigens were shown to be over-expressed in esophageal cancer, including different MAGE genes, NY-ESO-1 and EpCAM (Kimura et al., 2007; Liang et al., 2005; Inoue et al., 1995; Bujas et al., 2011; Tanaka et al., 1997; Quillien et al., 1997). Those genes represent very interesting targets for immunotherapy and most of them are under investigation for the treatment of other malignancies (ClinicalTrials.gov, 2015). Furthermore, up-regulation of PD-L1 and PD-L2 was described in esophageal cancer, which correlated with poorer prognosis. Thus, esophageal cancer patients with PD-L1-positive tumors might benefit from anti-PD-L1 immunotherapy (Ohigashi et al., 2005).

Clinical data on immunotherapeutic approaches in esophageal cancer are still relatively scarce at present, as only a very limited number of early phase clinical trials have been completed. A vaccine consisting of three peptides derived from three different cancer-testis antigens (TTK protein kinase, lymphocyte antigen 6 complex locus K and insulin-like growth factor (IGF)-II mRNA binding protein 3) was administered to patients with advanced esophageal cancer in a phase I trial with moderate results. Intra-tumoral injection of activated T cells after in vitro challenge with autologous malignant cells elicited complete or partial tumor responses in four of eleven patients in a phase I/II study (Toomey et al., 2013). A vaccine consisting of three peptides derived from three different cancer-testis antigens (TTK protein kinase, lymphocyte antigen 6 complex locus K and insulin-like growth factor (IGF)-II mRNA binding protein 3) was administered to patients with advanced esophageal cancer in a phase I trial with moderate results (Kono et al., 2009). Intra-tumoral injection of activated T cells after in vitro challenge with autologous malignant cells and interleukin 2 elicited complete or partial tumor responses in four of eleven patients in a phase I/II study (Toh et al., 2000; Toh et al., 2002). Further clinical trials are currently performed to evaluate the impact of different immunotherapies on esophageal cancer, including adoptive cellular therapy (NCT01691625, NCT01691664, NCT01795976, NCT02096614, NCT02457650) vaccination strategies (NCT01143545, NCT01522820) and anti-PD-L1 therapy (NCT02340975) (ClinicalTrials.gov, 2015).

Gastric Cancer

The efficacy of current therapeutic regimens for advanced GC is poor, resulting in low 5-year survival rates. Immunotherapy might be an alternative approach to ameliorate the survival of GC patients. Adoptive transfer of tumor-associated lymphocytes and cytokine induced killer cells, peptide-based vaccines targeting HER2/neu, MAGE-3 or vascular endothelial growth factor receptor 1 and 2 and dendritic cell-based vaccines targeting HER2/neu showed promising results in clinical GC trials. Immune checkpoint inhibition and engineered T cells might represent additional therapeutic options, which is currently evaluated in pre-clinical and clinical studies (Matsueda and Graham, 2014).

Glioblastoma

The therapeutic options for glioblastoma (WHO grade IV) are very limited. Different immunotherapeutic approaches are investigated for the treatment of GB, including immune-checkpoint inhibition, vaccination and adoptive transfer of engineered T cells.

Antibodies directed against inhibitory T cell receptors or their ligands were shown to efficiently enhance T cell-mediated anti-tumor immune responses in different cancer types, including melanoma and bladder cancer. The effects of T cell activating antibodies like ipilimumab and nivolumab are therefore assessed in clinical GB trials, but preliminary data indicate autoimmune-related adverse events.

Different vaccination strategies for GB patients are currently investigated, including peptide-based vaccines, heat-shock protein vaccines, autologous tumor cell vaccines, dendritic cell-based vaccines and viral protein-based vaccines. In these approaches peptides derived from GB-associated proteins like epidermal growth factor receptor variant III (EGFRvIII) or heat shock proteins or dendritic cells pulsed with autologous tumor cell lysate or cytomegalo virus components are applied to induce an anti-tumor immune response in GB patients. Several of these studies reveal good safety and tolerability profiles as well as promising efficacy data.

Adoptive transfer of genetically modified T cells is an additional immunotherapeutic approach for the treatment of GB. Different clinical trials currently evaluate the safety and efficacy of chimeric antigen receptor bearing T cells directed against HER2, IL-13 receptor alpha 2 and EGFRvIII (Ampie et al., 2015).

Liver Cancer

Therapeutic options in advanced non-resectable HCC are limited to Sorafenib, a multi-tyrosine kinase inhibitor (Chang et al., 2007; Wilhelm et al., 2004). Sorafenib is the only systemic drug confirmed to increase survival by about 3 months and currently represents the only experimental treatment option for such patients (Chapiro et al., 2014; Llovet et al., 2008). Lately, a limited number of immunotherapy trials for HCC have been conducted. Cytokines have been used to activate subsets of immune cells and/or increase the tumor immunogenicity (Reinisch et al., 2002; Sangro et al., 2004). Other trials have focused on the infusion of Tumor-infiltrating lymphocytes or activated peripheral blood lymphocytes (Shi et al., 2004; Takayama et al., 1991; Takayama et al., 2000).

So far, a small number of therapeutic vaccination trials have been executed. Butterfield et al. conducted two trials using peptides derived from alpha-fetoprotein (AFP) as a vaccine or DCs loaded with AFP peptides ex vivo (Butterfield et al., 2003; Butterfield et al., 2006). In two different studies, autologous dendritic cells (DCs) were pulsed ex vivo with autologous tumor lysate (Lee et al., 2005) or lysate of the hepatoblastoma cell line HepG2 (Palmer et al., 2009). So far, vaccination trials have only shown limited improvements in clinical outcomes.

Melanoma

Enhancing the anti-tumor immune responses appears to be a promising strategy for the treatment of advanced melanoma. In the United States the immune checkpoint inhibitor ipilimumab as well as the BRAF kinase inhibitors vemurafenib and dabrafenib and the MEK inhibitor trametinib are already approved for the treatment of advanced melanoma. Both approaches increase the patient's anti-tumor immunity—ipilimumab directly by reducing T cell inhibition and the kinase inhibitors indirectly by enhancing the expression of melanocyte differentiation antigens. Additional checkpoint inhibitors (nivolumab and lambrolizumab) are currently investigated in clinical studies with first encouraging results. Additionaly, different combination therapies targeting the anti-tumor immune response are tested in clinical trials including ipilimumab plus nivolumab, ipilimumab plus a gp100-derived peptide vaccine, ipilimumab plus dacarbazine, ipilimumab plus IL-2 and iplimumab plus GM-CSF (Srivastava and McDermott, 2014).

Several different vaccination approaches have already been evaluated in patients with advanced melanoma. So far, phase III trials revealed rather disappointing results and vaccination strategies clearly need to be improved. Therefore, new clinical trials, like the OncoVEX GM-CSF trial or the DERMA trial, aim at improving clinical efficacy without reducing tolerability.

Adoptive T cell transfer shows great promise for the treatment of advanced stage melanoma. In vitro expanded autologous tumor infiltrating lymphocytes as well as T cells harboring a high affinity T cell receptor for the cancer-testis antigen NY-ESO-1 had significant beneficial and low toxic effects upon transfer into melanoma patients. Unfortunately, T cells with high affinity T cell receptors for the melanocyte specific antigens MART1 and gp100 and the cancer-testis antigen MAGEA3 induced considerable toxic effects in clinical trials. Thus, adoptive T cell transfer has high therapeutic potential, but safety and tolerability of these treatments needs to be further increased (Phan and Rosenberg, 2013; Hinrichs and Restifo, 2013).

Non-Small Cell Lung Cancer

Because the disease has usually spread by the time it is discovered, radiation therapy and chemotherapy are often used, sometimes in combination with surgery (S3-Leitlinie Lungenkarzinom, 2011). To expand the therapeutic options for NSCLC, different immunotherapeutic approaches have been studied or are still under investigation. While vaccination with L-BLP25 or MAGEA3 failed to demonstrate a vaccine-mediated survival advantage in NSCLC patients, an allogeneic cell line-derived vaccine showed promising results in clinical studies. Additionally, further vaccination trials targeting gangliosides, the epidermal growth factor receptor and several other antigens are currently ongoing. An alternative strategy to enhance the patient's anti-tumor T cell response consists of blocking inhibitory T cell receptors or their ligands with specific antibodies. The therapeutic potential of several of these antibodies, including ipilimumab, nivolumab, pembrolizumab, MPDL3280A and MEDI-4736, in NSCLC is currently evaluated in clinical trials (Reinmuth et al., 2015).

Ovarian Cancer

Immunotherapy appears to be a promising strategy to ameliorate the treatment of ovarian cancer patients, as the presence of pro-inflammatory tumor infiltrating lymphocytes, especially CD8-positive T cells, correlates with good prognosis and T cells specific for tumor-associated antigens can be isolated from cancer tissue.

Therefore, a lot of scientific effort is put into the investigation of different immunotherapies in ovarian cancer. A considerable number of pre-clinical and clinical studies have already been performed and further studies are currently ongoing. Clinical data are available for cytokine therapy, vaccination, monoclonal antibody treatment, adoptive cell transfer and immunomodulation.

Cytokine therapy with interleukin-2, interferon-alpha, interferon-gamma or granulocyte-macrophage colony stimulating factor aims at boosting the patient's own anti-tumor immune response and these treatments have already shown promising results in small study cohorts.

Phase I and II vaccination studies, using single or multiple peptides, derived from several tumor-associated proteins (Her2/neu, NY-ESO-1, p53, Wilms tumor-1) or whole tumor antigens, derived from autologous tumor cells revealed good safety and tolerability profiles, but only low to moderate clinical effects.

Monoclonal antibodies that specifically recognize tumor-associated proteins are thought to enhance immune cell-mediated killing of tumor cells. The anti-CA-125 antibodies oregovomab and abagovomab as well as the anti-EpCAM antibody catumaxomab achieved promising results in phase II and III studies. In contrast, the anti-MUC1 antibody HMFG1 failed to clearly enhance survival in a phase III study.

An alternative approach uses monoclonal antibodies to target and block growth factor and survival receptors on tumor cells. While administration of trastuzumab (anti-HER2/neu antibody) and MOv18 and MORAb-003 (anti-folate receptor alpha antibodies) only conferred limited clinical benefit to ovarian cancer patients, addition of bevacizumab (anti-VEGF antibody) to the standard chemotherapy in advanced ovarian cancer appears to be advantageous.

Adoptive transfer of immune cells achieved heterogeneous results in clinical trials. Adoptive transfer of autologous, in vitro expanded tumor infiltrating T cells was shown to be a promising approach in a pilot trial. In contrast, transfer of T cells harboring a chimeric antigen receptor specific for folate receptor alpha did not induce a significant clinical response in a phase I trial. Dendritic cells pulsed with tumor cell lysate or tumor-associated proteins in vitro were shown to enhance the anti-tumor T cell response upon transfer, but the extent of T cell activation did not correlate with clinical effects. Transfer of natural killer cells caused significant toxicities in a phase II study.

Intrinsic anti-tumor immunity as well as immunotherapy are hampered by an immunosuppressive tumor microenvironment. To overcome this obstacle immunomodulatory drugs, like cyclophosphamide, anti-CD25 antibodies and pegylated liposomal doxorubicin are tested in combination with immunotherapy. Most reliable data are currently available for ipilimumab, an anti-CTLA4 antibody, which enhances T cell activity. Ipilimumab was shown to exert significant anti-tumor effects in ovarian cancer patients (Mantia-Smaldone et al., 2012).

Pancreatic Cancer

Therapeutic options for pancreatic cancer patients are very limited. One major problem for effective treatment is the typically advanced tumor stage at diagnosis. Vaccination strategies are investigated as further innovative and promising alternative for the treatment of pancreatic cancer. Peptide-based vaccines targeting KRAS mutations, reactive telomerase, gastrin, survivin, CEA and MUC1 have already been evaluated in clinical trials, partially with promising results. Furthermore, clinical trials for dendritic cell-based vaccines, allogeneic GM-CSF-secreting vaccines and algenpantucel-L in pancreatic cancer patients also revealed beneficial effects of immunotherapy. Additional clinical trials further investigating the efficiency of different vaccination protocols are currently ongoing (Salman et al., 2013).

Prostate Cancer

The dendritic cell-based vaccine sipuleucel-T was the first anti-cancer vaccine to be approved by the FDA. Due to its positive effect on survival in patients with CRPC, much effort is put into the development of further immunotherapies. Regarding vaccination strategies, the peptide vaccine prostate-specific antigen (PSA)-TRICOM, the personalized peptide vaccine PPV, the DNA vaccine pTVG-HP and the whole cell vaccine expressing GM-CSF GVAX showed promising results in different clinical trials. Furthermore, dendritic cell-based vaccines other than sipuleucel-T, namely BPX-101 and DCVAC/Pa were shown to elicited clinical responses in prostate cancer patients. Immune checkpoint inhibitors like ipilimumab and nivolumab are currently evaluated in clinical studies as monotherapy as well as in combination with other treatments, including androgen deprivation therapy, local radiation therapy, PSA-TRICOM and GVAX. The immunomodulatory substance tasquinimod, which significantly slowed progression and increased progression free survival in a phase II trial, is currently further investigated in a phase III trial. Lenalidomide, another immunomodulator, induced promising effects in early phase clinical studies, but failed to improve survival in a phase III trial. Despite these disappointing results further lenalidomide trials are ongoing (Quinn et al., 2015).

Renal Cell Carcinoma

The known immunogenity of RCC has represented the basis supporting the use of immunotherapy and cancer vaccines in advanced RCC. The interesting correlation between lymphocytes PD-1 expression and RCC advanced stage, grade and prognosis, as well as the selective PD-L1 expression by RCC tumor cells and its potential association with worse clinical outcomes, have led to the development of new anti PD-1/PD-L1 agents, alone or in combination with anti-angiogenic drugs or other immunotherapeutic approaches, for the treatment of RCC (Massari et al., 2015). In advanced RCC, a phase III cancer vaccine trial called TRIST study evaluates whether TroVax (a vaccine using a tumor-associated antigen 5T4, with a pox virus vector), added to first-line standard of care therapy, prolongs survival of patients with locally advanced or mRCC. Median survival had not been reached in either group with 399 patients (54%) remaining on study however analysis of the data confirms prior clinical results, demonstrating that TroVax is both immunologically active and that there is a correlation between the strength of the 5T4-specific antibody response and improved survival. Further there are several studies searching for peptide vaccines using epitopes being overexpressed in RCC.

Various approaches of tumor vaccines have been under investigation. Studies using whole-tumor approaches, including tumor cell lysates, fusions of dendritic cells with tumor cells, or whole-tumor RNA were done in RCC patients, and remissions of tumor lesions were reported in some of these trials (Avigan et al., 2004; Holtl et al., 2002; Marten et al., 2002; Su et al., 2003; Wittig et al., 2001).

Small Cell Lung Cancer

Innovations occurred regarding detection, diagnosis and treatment of SCLC. It was shown that the usage of CT scans instead of x-rays for early cancer detection lowered the risk of death from lung cancer. Nowadays, the diagnosis of SCLC can be supported by fluorescence or virtual bronchoscopy; the real-time tumor imagining can be implemented by the radiation treatment. The novel anti-angiogenesis drugs like bevacizumab (Avastin), sunitinib (Sutent) and nintedanib (BIBF 1120) were shown to have therapeutically effects in treatment of SCLC (American Cancer Society, 2015). The immune therapy presents an excessively investigated field of cancer therapy. Various approaches are studded in the treatment of SCLC. One of the approaches targets the blocking of CTLA-4, a natural human immune suppressor. The inhibition of CTLA-4 intends to boost the immune system to combat the cancer. Recently, the development of promising immune check point inhibitors for treatment of SCLC has been started. Another approach is based on anti-cancer vaccines which is currently available for treatment of SCLC in clinical studies (American Cancer Society, 2015; National Cancer Institute (NCI), 2011).

Acute Myeloid Leukemia

One treatment option is targeting CD33 with antibody-drug conjugates (anti-CD33+calechiamicin, SGN-CD33a, anti-CD33+actinium-225), bispecific antibodies (recognition of CD33+CD3 (AMG 330) or CD33+CD16) and chimeric antigen receptors (CARs) (Estey, 2014).

Non-Hodgkin Lymphoma

Treatment of NHL depends on the histologic type and stage (National Cancer Institute, 2015). Spontaneous tumor regression can be observed in lymphoma patients. Therefore, active immunotherapy is a therapy option (Palomba, 2012). An important vaccination option includes Id vaccines. B lymphocytes express surface immunoglobulins with a specific amino acid sequence in the variable regions of their heavy and light chains, unique to each cell clone (=idiotype, Id). The idiotype functions as a tumor associated antigen. Passive immunization includes the injection of recombinant murine anti-Id monoclonal antibodies alone or in combination with IFNalpha, IL2 or chlorambucil.

Active immunization includes the injection of recombinant protein (Id) conjugated to an adjuvant (KLH), given together with GM-CSF as an immune adjuvant. Tumor-specific Id is produced by hybridoma cultures or using recombinant DNA technology (plasmids) by bacterial, insect or mammalian cell culture. Three phase III clinical trials have been conducted (Biovest, Genitope, Favrille). In two trials patients had received rituximab. GM-CSF was administered in all three trials. Biovest used hybridoma-produced protein, Genitope and Favrille used recombinant protein. In all three trials Id was conjugated to KLH. Only Biovest had a significant result.

Vaccines other than Id include the cancer-testis antigens MAGE, NY-ESO1 and PASD-1, the B-cell antigen CD20 or cellular vaccines. The latest mentioned consist of DCs pulsed with apoptotic tumor cells, tumor cell lysate, DC-tumor cell fusion or DCs pulsed with tumor-derived RNA. In situ vaccination involves the vaccination with intratumoral CpG in combination with chemotherapy or irradiated tumor cells grown in the presence of GM-CSF and collection/expansion/re-infusion of T cells. Vaccination with antibodies that alter immunologic checkpoints are comprised of anti-CD40, anti-OX40, anti-41BB, anti-CD27, anti-GITR (agonist antibodies that directly enhance anti-tumor response) or anti-PD1, anti-CTLA-4 (blocking antibodies that inhibit the checkpoint that would hinder the immune response). Examples are ipilimumab (anti-CTLA-4) and CT-011 (anti-PD1) (Palomba, 2012).

Uterine Cancer

There are also some immunotherapeutic approaches that are currently being tested. In a Phase I/II Clinical Trial patients suffering from uterine cancer were vaccinated with autologous dendritic cells (DCs) electroporated with Wilms' tumor gene 1 (WT1) mRNA. Besides one case of local allergic reaction to the adjuvant, no adverse side effects were observed and 3 out of 6 patients showed an immunological response (Coosemans et al., 2013).

As stated above, HPV infections provoke lesions that may ultimately lead to cervical cancer. Therefore, the HPV viral oncoproteins E6 and E7 that are constitutively expressed in high-grade lesions and cancer and are required for the onset and maintenance of the malignant phenotype are considered promising targets for immunotherapeutic approaches (Hung et al., 2008; Vici et al., 2014). One study performed Adoptive T-cell therapy (ACT) in patients with metastatic cervical cancer. Patients receive an infusion with E6 and E7 reactive tumor-infiltrating T cells (TILs) resulting in complete regression in 2 and a partial response in 1 out of 9 patients (Stevanovic et al., 2015). Furthermore, an intracellular antibody targeting E7 was reported to block tumor growth in mice (Accardi et al., 2014). Also peptide, DNA and DC-based vaccines targeting HPV E6 and E7 are in clinical trials (Vici et al., 2014).

Gallbladder Adenocarcinoma and Cholangiocarcinoma

Cholangiocarcinoma (CCC) is mostly identified in advanced stages because it is difficult to diagnose. Gallbladder cancer (GBC) is the most common and aggressive malignancy of the biliary tract worldwide. As for GBC only 10% of tumors are resectable and even with surgery most progress to metastatic disease, prognosis is even worse than for CCC with a 5-year survival of less than 5%. Although most tumors are unresectable there is still no effective adjuvant therapy (Rakic et al., 2014). Some studies showed that combination of chemotherapeutic drugs or combination of targeted therapy (anti-VEGFR/EGFR) with chemotherapy led to an increased overall survival and might be promising treatment options for the future (Kanthan et al., 2015). Due to the rarity of carcinomas of the biliary tract in general there are only a few GBC or CCC specific studies, while most of them include all biliary tract cancers. This is the reason why treatment did not improve during the last decades and R0 resection still is the only curative treatment option.

Urinary Bladder Cancer

The standard treatment for bladder cancer includes surgery, radiation therapy, chemotherapy and immunotherapy.

An effective immunotherapeutic approach is established in the treatment of aggressive non-muscle invasive bladder cancer (NMIBC). Thereby, a weakened form of the bacterium *Mycobacterium bovis* (bacillus Calmette-Guérin=BCG) is applied as an intravesical solution. The major effect of BCG treatment is a significant long-term (up to 10 years) protection from cancer recurrence and reduced progression rate. In principle, the treatment with BCG induces a local inflammatory response which stimulates the cellular immune response. The immune response to BCG is based on the following key steps: infection of urothelial and bladder cancer cells by BCG, followed by increased expression of antigen-presenting molecules, induction of immune response mediated via cytokine release, induction of anti-tumor activity via involvement of various immune cells (thereunder cytotoxic T lymphocytes, neutrophils, natural killer cells, and macrophages) (Fuge et al., 2015; Gandhi et al., 2013).

BCG treatment is in general well tolerated by patients but can be fatal especially by the immunocompromised patients. BCG refractory is observed in about 30-40% of patients (Fuge et al., 2015; Steinberg et al., 2016a). The treatment of patients who failed the BCG therapy is challenging. The patients who failed the BCG treatment are at high risk for developing of muscle-invasive disease. Radical cystectomy is the preferable treatment option for non-responders (Steinberg et al., 2016b; von Rundstedt and Lerner, 2015). The FDA approved second line therapy of BCG-failed NMIBC for patients who desire the bladder preservation is the chemotherapeutic treatment with valrubicin. A number of other second line therapies are available or being currently under investigation as well, thereunder immunotherapeutic approaches like combined BCG-interferon or BCG-check point inhibitor treatments, pre-BCG transdermal vaccination, treatment with *Mycobacterium phlei* cell wall-nucleic acid (MCNA) complex, mono- or combination chemotherapy with various agents like mitomycin C, gemcitabine, docetaxel, nab-paclitaxel, epirubicin, mitomycin/gemcitabine, gemcitabine/docetaxel, and device-assisted chemotherapies like thermochemo-, radiochemo-, electromotive or photodynamic therapies (Fuge et al., 2015; Steinberg et al., 2016b; von Rundstedt and Lerner, 2015). Further evaluation of available therapies in clinical trials is still required.

The alternative treatment options for advanced bladder cancer are being investigated in ongoing clinical trials. The current clinical trials focused on the development of molecularly targeted therapies and immunotherapies. The targeted therapies investigate the effects of cancerogenesis related pathway inhibitors (i.e. mTOR, vascular endothelial, fibroblast, or epidermal growth factor receptors, anti-angiogenesis or cell cycle inhibitors) in the treatment of bladder cancer. The development of molecularly targeted therapies remains challenging due to high degree of genetic diversity of bladder cancer. The main focus of the current immunotherapy is the development of checkpoint blockage agents like anti-PD1 monoclonal antibody and adoptive T-cell transfer (Knollman et al., 2015; Grivas et al., 2015; Jones et al., 2016; Rouanne et al., 2016).

Head and Neck Squamous Cell Carcinoma

Head and neck squamous cell carcinomas (HNSCC) are heterogeneous tumors with differences in epidemiology, etiology and treatment (Economopoulou et al., 2016). Treatment for early HNSCC involves single-modality therapy with either surgery or radiation (World Health Organization, 2014). Advanced cancers are treated by a combination of chemotherapy with surgery and/or radiation therapy.

HNSCC is considered an immunosuppressive disease, characterized by the dysregulation of immunocompetent cells and impaired cytokine secretion (Economopoulou et al., 2016). Immunotherapeutic strategies differ between HPV-negative and HPV-positive tumors.

In HPV-positive tumors, the viral oncoproteins E6 and E7 represent good targets, as they are continuously expressed by tumor cells and are essential to maintain the transformation status of HPV-positive cancer cells. Several vaccination therapies are currently under investigation in HPV-positive HNSCC, including DNA vaccines, peptide vaccines and vaccines involving dendritic cells (DCs). Additionally, an ongoing phase II clinical trial investigates the efficacy of lymphodepletion followed by autologous infusion of TILs in patients with HPV-positive tumors (Economopoulou et al., 2016).

In HPV-negative tumors, several immunotherapeutic strategies are currently used and under investigation. The chimeric IgG1 anti-EGFR monoclonal antibody cetuximab has been approved by the FDA in combination with chemotherapy as standard first line treatment for recurring/metastatic HNSCC. Other anti-EGFR monoclonal antibodies, including panitumumab, nimotuzumab and zalutumumab, are evaluated in HNSCC. Several immune checkpoint inhibitors are investigated in clinical trials for their use in HNSCC. They include the following antibodies: Ipilimumab (anti-CTLA-4), tremelimumab (anti-CTLA-4), pembrolizumab (anti-PD-1), nivolumab (anti-PD-1), durvalumab (anti-PD-1), anti-KIR, urelumab (anti-CD137), and anti-LAG-3.

Two clinical studies with HNSCC patients evaluated the use of DCs loaded with p53 peptides or apoptotic tumor cells. The immunological responses were satisfactory and side effects were acceptable. Several studies have been conducted using adoptive T cell therapy (ACT). T cells were induced against either irradiated autologous tumor cells or EBV. Results in disease control and overall survival were promising (Economopoulou et al., 2016).

Considering the severe side-effects and expense associated with treating cancer, there is a need to identify factors that can be used in the treatment of cancer in general and glioblastoma (GB), breast cancer (BRCA), colorectal cancer (CRC), renal cell carcinoma (RCC), chronic lymphocytic leukemia (CLL), hepatocellular carcinoma (HCC), non-small cell and small cell lung cancer (NSCLC, SCLC), Non-Hodgkin lymphoma (NHL), acute myeloid leukemia (AML), ovarian cancer (OC), pancreatic cancer (PC), prostate cancer (PCA), esophageal cancer including cancer of the gastric-esophageal junction (OSCAR), gallbladder cancer and cholangiocarcinoma (GBC, CCC), melanoma (MEL), gastric cancer (GC), urinary bladder cancer (UBC), head and neck squamous cell carcinoma (HNSCC), and uterine cancer (UEC) in particular. There is also a need to identify factors representing biomarkers for cancer in general and the above-mentioned cancer types in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, and leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 289, SEQ ID NO: 305, and SEQ ID NO: 306 or a variant sequence thereof which is at least 77%, preferably at least 88%, homologous (preferably at least 77% or at least 88% identical) to SEQ ID NO: 1 to SEQ ID NO: 289, SEQ ID NO: 305, and SEQ ID NO: 306, wherein said variant binds to MHC and/or induces T cells cross-reacting with said peptide, or a pharmaceutical acceptable salt thereof, wherein said peptide is not the underlying full-length polypeptide.

While the most important criterion for a peptide to function as cancer therapy target is its over-presentation on primary tumor tissues as compared to normal tissues, also the RNA expression profile of the corresponding gene or exon can help to select appropriate peptides. Particularly, some peptides are hard to detect by mass spectrometry, either due to their chemical properties or to their low copy numbers on cells, and a screening approach focusing on detection of peptide presentation may fail to identify these targets. However, these targets may be detected by an alternative approach starting with analysis of gene and exon expression in tumor tissues and in normal tissues and secondarily assessing peptide presentation in tumors. This approach was realized in this invention using two mRNA databases (TCGA Research Network for tumor samples and GTEX database (Lonsdale, 2013) for normal tissue samples), as well as peptide presentation data. If the mRNA of a gene or exon is over-expressed in tumor tissues compared to normal tissues, it is considered as tumor associated. Such peptides, even if identified on only a small percentage of tumor tissues, represent interesting targets. Routine mass spectrometry analysis is not sensitive enough to assess target coverage on the peptide level. Rather, tumor mRNA expression can be used to assess coverage. For detection of the peptide itself, a targeted mass spectrometry approach with higher sensitivity than in the routine screening may be necessary and may lead to a better estimation of coverage on the level of peptide presentation.

The present invention further relates to a peptide of the present invention comprising a sequence that is selected from the group consisting of SEQ ID NO: 1 to SEQ ID NO: 289, SEQ ID NO: 305, and SEQ ID NO: 306 or a variant thereof, which is at least 77%, preferably at least 88%, homologous (preferably at least 77% or at least 88% identical) to SEQ ID NO: 1 to SEQ ID NO: 289, SEQ ID NO: 305, and SEQ ID NO: 306, wherein said peptide or variant thereof has an overall length of between 8 and 100, preferably between 8 and 30, and most preferred of between 8 and 14 amino acids.

The present invention further relates to a peptide of the present invention consisting of a sequence that is selected from the group consisting of SEQ ID NO: 2, 24, 32, 39, 64, 72, 106, 149, 251, 305, and 306.

The following tables show the peptides according to the present invention, their respective SEQ ID NOs, and the prospective source (underlying) genes for these peptides. All peptides in Table 3, Table 5 and Table 7 (A+B) bind to HLA-A*02. All peptides in Table 4, Table 6 and Table 8 bind to HLA-A*24. The peptides in Table 5 and Table 6 have been disclosed before in large listings as results of high-throughput screenings with high error rates or calculated using algorithms, but have not been associated with cancer at all before. The peptides in Table 7 (A+B) and Table 8 are additional peptides that may be useful in combination with the other peptides of the invention.

TABLE 3

Peptides according to the present invention, HLA-A*02-binding.

| SEQ ID No. | Sequence | GeneID(s) | Official Gene Symbol(s) |
|---|---|---|---|
| 1 | LLYPEPWSV | 220382 | FAM181B |
| 2 | GLIAGVVSI | 4233 | MET |
| 3 | KLEENGDLYL | 55255 | WDR41 |
| 4 | KLMPGTYTL | 2201 | FBN2 |
| 5 | GIVAHIQEV | 440193 | CCDC88C |
| 6 | ALFDSLRHV | 220382 | FAM181B |
| 7 | ILDHEVPSL | 199990 | C1orf86 |
| 8 | SIYQFLIAV | 2237 | FEN1 |
| 9 | FLVDGSYSI | 1303 | COL12A1 |
| 10 | GIAGSLKTV | 3720 | JARID2 |

TABLE 3-continued

Peptides according to the present invention, HLA-A*02-binding.

| SEQ ID No. | Sequence | GeneID(s) | Official Gene Symbol(s) |
|---|---|---|---|
| 11 | ALSPSYLTV | 57674 | RNF213 |
| 12 | GLLPLLHRA | 100529261, 2342, 91612 | CHURC1-FNTB, FNTB, CHURC1 |
| 13 | ALMAMLVYV | 91319 | DERL3 |
| 14 | ILAKDLFEI | 83990 | BRIP1 |
| 15 | YLDLSHNQL | 10333, 79883 | PODNL1, TLR6 |
| 16 | YTLDIPVLFGV | 29028 | ATAD2 |
| 17 | AVFPDDMPTL | 4297 | MLL |
| 18 | ILLDLTDNRL | 135228 | CD109 |
| 19 | SISDNVWEV | 55589 | BMP2K |
| 20 | GLSQITNQL | 9736 | USP34 |
| 21 | AIQDEIRSV | 4085 | MAD2L1 |
| 22 | FVDPNTQEKV | 83481 | EPPK1 |
| 23 | SLFSDEFKV | 102 | ADAM10 |
| 24 | TLDEKVAEL | 51438 | MAGEC2 |
| 25 | TMDSVLVTV | 94025 | MUC16 |
| 26 | ALQEELTEL | 22995 | CEP152 |
| 27 | RLMEENWNA | 7784 | ZP3 |
| 28 | SLPNGKPVSV | 23682 | RAB38 |
| 29 | YLLDPSITL | 10102 | TSFM |
| 30 | AMIEEVFEA | 221443 | OARD1 |
| 31 | TITETTTVEV | 7143 | TNR |
| 32 | VQLDSIEDLEV | 23532 | FRAME |
| 33 | YIKTELISV | 6772 | STAT1 |
| 34 | FLLATEVVTV | 10075 | HUWE1 |
| 35 | FLLPFSTVYL | 9204 | ZMYM6 |
| 36 | SLADTNSLAVV | 6490 | PMEL |
| 37 | ILAPFSVDL | 85413 | SLC22A16 |
| 38 | FLGPRIIGL | 202309 | GAPT |
| 39 | HLLEGSVGV | 85320 | ABCC11 |
| 40 | VLIDPQWVLTA | 3003 | GZMK |
| 41 | ALFENTPKA | 5260 | PHKG1 |
| 42 | LLDSVSRL | 3918 | LAMC2 |
| 43 | KAIEVLLTL | 57650 | KIAA1524 |
| 44 | SLFETAWEA | 9735 | KNTC1 |
| 45 | SLTEVSLPL | 580 | BARD1 |
| 46 | SQFPLPLAV | 80055 | PGAP1 |
| 47 | ALLERGELFV | 79050 | NOC4L |
| 48 | QVIEDSTGV | 64778 | FNDC3B |
| 49 | ALNIATHVL | 24140 | FTSJ1 |
| 50 | ILFHGVFYA | 55744 | COA1 |
| 51 | LLFSRLCGA | 25945 | PVRL3 |
| 52 | RLAVLFSGA | 968 | CD68 |
| 53 | KMVGLVVAI | 80324 | PUS1 |
| 54 | VLNPLITAV | 10827 | FAM114A2 |
| 55 | SLATKIVEA | 152110 | NEK10 |
| 56 | FLHDEKEGIYI | 10225 | CD96 |
| 57 | TVFTDHMLTV | 586 | BCAT1 |
| 58 | YLLPLLPAL | 338645 | LUZP2 |
| 59 | KLLDPQEFTL | 3371 | TNC |
| 60 | ALFAPLVHL | 26251 | KCNG2 |
| 61 | AIVKEIVNI | 4436 | MSH2 |
| 62 | ALNPELVQA | 4233 | MET |
| 63 | SQIPAQPSV | 23215 | PRRC2C |
| 64 | SLFPDSLIV | 261729 | STEAP2 |
| 65 | SVVPDVRSV | 6605 | SMARCE1 |
| 66 | KLIFSVEAV | 65985 | AACS |
| 67 | TLLQRLTEV | 11064 | CNTRL |
| 68 | SLSNRLYYL | 9271 | PIWIL1 |
| 69 | FLAVGLVDV | 28559 | TRBV28 |
| 70 | LLLGDSALYL | 28609, 28610 | TRBV5-6, TRBV5-5 |
| 71 | VLHSKFWVV | 122618 | PLD4 |
| 72 | FLTAINYLL | 440712 | C1orf186 |
| 73 | YTLREVDTV | 4521 | NUDT1 |
| 74 | TLFGYSVVL | 3676 | ITGA4 |
| 75 | AVIKFLELL | 4436 | MSH2 |
| 76 | AVGPVHNSV | 57448 | BIRC6 |
| 77 | TLIDEQDIPLV | 116225 | ZMYND19 |
| 78 | TVVTRLDEI | 9459 | ARHGEF6 |
| 79 | VTFKEYVTV | 8535 | CBX4 |
| 80 | KLYEADFVL | 55501 | CHST12 |
| 81 | NALDKVLSV | 79053 | ALG8 |
| 82 | FIFDEAEKL | 64222 | TOR3A |

TABLE 3-continued

Peptides according to the present invention, HLA-A*02-binding.

| SEQ ID No. | Sequence | GeneID(s) | Official Gene Symbol(s) |
|---|---|---|---|
| 83 | GQASYFYVA | 4486 | MST1R |
| 84 | ALCPRIHEV | 1762 | DMWD |
| 85 | VLNDILVRA | 5016 | OVGP1 |
| 86 | SVDSHFQEV | 4968 | OGG1 |
| 87 | TIYKDFVYI | 79786 | KLHL36 |
| 88 | AQADHLPQL | 64689 | GORASP1 |
| 89 | QLAPVFQRV | 84342 | COG8 |
| 90 | FLQDLEQRL | 128272 | ARHGEF19 |
| 91 | KLFDESILI | 8295 | TRRAP |
| 92 | GLLFSLRSV | 79064 | TMEM223 |
| 93 | QVLELDVADI | 9675 | TTI1 |
| 94 | LLLPAVPVGA | 1953 | MEGF6 |
| 95 | GLLGSLFFL | 91319 | DERL3 |
| 96 | LLVSHLYLV | 84885 | ZDHHC12 |
| 97 | STLPKSLSL | 4605 | MYBL2 |
| 98 | RLFPDFFTRVAL | 5657 | PRTN3 |
| 99 | YLLQSVNQLLL | 23347 | SMCHD1 |
| 100 | ALLGMIIVGV | 6571 | SLC18A2 |
| 101 | ALADFMLSL | 2854 | GPR32 |
| 102 | VLLDIQEVFQI | 201305 | SPNS3 |
| 103 | YLVSEIFKA | 6005 | RHAG |
| 104 | ALISWQPPRA | 7143 | TNR |
| 105 | ALLGTKILL | 147945 | NLRP4 |
| 106 | FINDSIVYL | 89766 | UMODL1 |
| 107 | LLVPTSGIYFV | 4049 | LTA |
| 108 | ILLKNLVTI | 129868, 653192 | TRIM43, TRIM43B |
| 109 | SLDPSVTHL | 250, 251 | ALPPL2, ALPP |
| 110 | FLLGVSKEV | 23251 | KIAA1024 |
| 111 | AIVDLIHDI | 23225 | NUP210 |
| 112 | SLGKFTFDV | 6676 | SPAG4 |
| 113 | FLERGLESA | 10535 | RNASEH2A |
| 114 | QLIQTLHAV | 1004 | CDH6 |
| 115 | SLDPDTLPAV | 352954, 389523, 729438 | GATSL2, GATS, GATSL1 |
| 116 | TIDESGSIL | 29127 | RACGAP1 |
| 117 | KMPDVELFV | 79070 | KDELC1 |
| 118 | QLWQFLVTL | 2119 | ETV5 |
| 119 | FIIQGLRSVGA | 3117, 3118 | HLA-DQA2, HLA-DQA1 |
| 120 | VTPVTVSAV | 3054 | HCFC1 |
| 121 | FTIFRTISV | 83743 | GRWD1 |
| 122 | GVVDPVHGV | 83481 | EPPK1 |
| 123 | VLDPALPALV | 4486 | MST1R |
| 124 | KVMATIEKV | 9274 | BCL7C |
| 125 | SLADYEHFV | 357 | SHROOM2 |
| 126 | QMFQYFITV | 51290 | ERGIC2 |
| 127 | KLDGNELDL | 55379 | LRRC59 |
| 128 | TQSPATLSV | 28299, 28875, 28902, 28913, 3514, 50802 | IGKV1-5, IGKV3-15, IGKV3D-15, IGKC, IGKV1D-13, IGK@ |
| 129 | RLQDILWFL | 150771 | ITPRIPL1 |
| 130 | SLLGGTFVGI | 55266 | TMEM19 |
| 131 | VTSNSGILGV | 22828 | SCAF8 |
| 132 | ILGEVLAQL | 124044 | SPATA2L |
| 133 | ALLPRLHQL | 85414 | SLC45A3 |
| 134 | GLAVPTPSV | 647024 | C6orf132 |
| 135 | HLSTIIHEA | 1147 | CHUK |
| 136 | FLFGGVLMTL | 91319 | DERL3 |
| 137 | EIASITEQL | 55183 | RIF1 |
| 138 | ALLAKILQI | 5591 | PRKDC |
| 139 | FLLPTGAEA | 1511 | CTSG |
| 140 | VLLEELEAL | 10142 | AKAP9 |
| 141 | FLDKVLVAA | 54497 | HEATR5B |
| 142 | ILVEGISTV | 1462 | VCAN |
| 143 | ALLPELREV | 1140 | CHRNB1 |
| 144 | ALLAFFPGL | 80267 | EDEM3 |
| 145 | YLWATIQRI | 2650 | GCNT1 |
| 146 | ALHFSEDEI | 6097 | RORC |
| 147 | YLMDDTVEI | 114327 | EFHC1 |
| 148 | MLAGIAITV | 63826 | SRR |
| 149 | ILNTHITEL | 131578 | LRRC15 |
| 150 | VLYDRPLKI | 64783 | RBM15 |
| 151 | SVLDSTAKV | 54885 | TBC1D8B |

TABLE 3-continued

Peptides according to the present invention, HLA-A*02-binding.

| SEQ ID No. | Sequence | GeneID(s) | Official Gene Symbol(s) |
|---|---|---|---|
| 152 | MMVGDLLEV | 5927 | KDM5A |
| 153 | FISERVEVV | 128869 | PIGU |
| 154 | RLLGTEFQV | 51151 | SLC45A2 |
| 155 | LLNPVVEFV | 5591 | PRKDC |
| 156 | ILGDLSHLL | 11015 | KDELR3 |
| 157 | TLTSLLAQA | 83481 | EPPK1 |

TABLE 4

Peptides according to the present invention, HLA-A*24-binding.

| SEQ ID No. | Sequence | GeneID(s) | Official Gene Symbol(s) |
|---|---|---|---|
| 158 | HYSQELSLLYL | 5591 | PRKDC |
| 159 | LYNKGFIYL | 157769 | FAM91A1 |
| 160 | VYTLDIPVL | 29028 | ATAD2 |
| 161 | IYLVSIPEL | 23545 | ATP6V0A2 |
| 162 | VFTRVSSFL | 1511 | CTSG |
| 163 | DYLKGLASF | 1130 | LYST |
| 164 | KFSSFSLFF | 3003 | GZMK |
| 165 | DYTTWTALL | 10615 | SPAG5 |
| 166 | YYVESGKLF | 23279 | NUP160 |
| 167 | NYINRILKL | 51691 | NAA38 |
| 168 | KYQDILETI | 79730 | NSUN7 |
| 169 | AYTLIAPNI | 94240 | EPSTI1 |
| 170 | VYEDQVGKF | 23065 | EMC1 |
| 171 | LFIPSSKLLFL | 101060416, 101060589, 23049, 440345, 440354, 552900, 641298 | LOC101060416, SMG1, BOLA2, 61E3.4, LOC101060589, SMG1P1, LOC440354 |
| 172 | TYTTVPRVAF | 10882 | C1QL1 |
| 173 | IYSWILDHF | 3344 | FOXN2 |
| 174 | VYVGGGQIIHL | 151354 | FAM84A |
| 175 | YYEVHKELF | 9055 | PRC1 |
| 176 | EYNQWFTKL | 55604 | LRRC16A |
| 177 | VYPWLGALL | 54905 | CYP2W1 |
| 178 | IFIEVFSHF | 284293 | HMSD |
| 179 | MYDSYWRQF | 143686 | SESN3 |
| 180 | IYDDSFIRPVTF | 56886 | UGGT1 |
| 181 | LYLDIINLF | 51643 | TMBIM4 |
| 182 | IYQLDTASI | 55003 | PAK1IP1 |
| 183 | VFTSTARAF | 10225 | CD96 |
| 184 | VFQNFPLLF | 56890 | MDM1 |
| 185 | IYKVGAPTI | 10978 | CLP1 |
| 186 | IFPQFLYQF | 23250 | ATP11A |
| 187 | TYLRDQHFL | 898 | CCNE1 |
| 188 | RYFKGLVF | 166614 | DCLK2 |
| 189 | WYVNGVNYF | 79054 | TRPM8 |
| 190 | GFFIFNERF | 10206 | TRIM13 |
| 191 | VFKASKITF | 5803 | PTPRZ1 |
| 192 | SYALLTYMI | 7298 | TYMS |
| 193 | RFHPTPLLL | 51605 | TRMT6 |
| 194 | EFGSLHLEFL | 57134 | MAN1C1 |
| 195 | TYSVSFPMF | 257202, 2882 | GPX6, GPX7 |
| 196 | LYIDRPLPYL | 253725, 387680, 55747 | FAM21C, FAM21B, FAM21A |
| 197 | EYSLFPGQVVI | 23649 | POLA2 |
| 198 | LYLDKATLI | 55916 | NXT2 |
| 199 | RYAEEVGIF | 54187 | NANS |
| 200 | YYGPSLFLL | 10075 | HUWE1 |
| 201 | IYATEAHVF | 55706 | TMEM48 |
| 202 | VYWDSAGAAHF | 55501 | CHST12 |
| 203 | FYSRLLQKF | 55055 | ZWILCH |
| 204 | TYELRYFQI | 200916 | RPL22L1 |
| 205 | VHIPEVYLI | 57705 | WDFY4 |
| 206 | EYQENFLSF | 441027 | TMEM150C |
| 207 | AYVVFVSTL | 25938 | HEATR5A |
| 208 | TYTQDFNKF | 796 | CALCA |
| 209 | TYKDEGNDYF | 7268 | TTC4 |
| 210 | IYTMIYRNL | 4193 | MDM2 |
| 211 | YYLEVGKTLI | 80267 | EDEM3 |
| 212 | YYTFHFLYF | 26273 | FBXO3 |

TABLE 4-continued

Peptides according to the present invention, HLA-A*24-binding.

| SEQ ID No. | Sequence | GeneID(s) | Official Gene Symbol(s) |
|---|---|---|---|
| 213 | IFDEAEKL | 64222 | TOR3A |
| 214 | LYLKLWNLI | 11274, 373856 | USP18, USP41 |
| 215 | YFDKVVTL | 374654 | KIF7 |
| 216 | QYSSVFKSL | 25938 | HEATR5A |
| 217 | FFPPTRQMGLLF | 85415 | RHPN2 |
| 218 | YYKSTSSAF | 79690 | GAL3ST4 |
| 219 | EYPLVINTL | 100129460, 23333 | DPY19L1P1, DPY19L1 |
| 220 | GYIDNVTLI | 3918 | LAMC2 |
| 221 | RYSTGLAGNLL | 54921 | CHTF8 |
| 222 | TFSVSSHLF | 90874 | ZNF697 |
| 223 | KYIPYKYVI | 57674 | RNF213 |
| 224 | QYLENLEKL | 101060589, 23049, 440345, 641298 | 61E3.4, SMG1P1, SMG1, LOC101060589 |
| 225 | YYVYIMNHL | 10655 | DMRT2 |
| 226 | VYRDETGELF | 84455 | EFCAB7 |
| 227 | IFLDYEAGTLSF | 202658, 56658 | TRIM39, TRIM39-RPP21 |
| 228 | KYTSWYVAL | 2247 | FGF2 |

TABLE 5

Additional peptides according to the present invention with no prior known cancer association, HLA-A*02-binding.

| SEQ ID No. | Sequence | GeneID(s) | Official Gene Symbol(s) |
|---|---|---|---|
| 229 | AILAHLNTV | 8914 | TIMELESS |
| 230 | KLQNIMMLL | 3070 | HELLS |
| 231 | MLDKYSHYL | 139818 | DOCK11 |
| 232 | KIFPAALQLV | 2618 | GART |
| 233 | HLFDAFVSV | 55789 | DEPDC1B |
| 234 | LLSPHNPAL | 10884 | MRPS30 |
| 235 | KIIDFLSAL | 2956 | MSH6 |
| 236 | STIAILNSV | 23310 | NCAPD3 |
| 237 | ALAPHLDDA | 54919 | HEATR2 |
| 238 | GLYERPTAA | 2672 | GFI1 |
| 239 | KMNESTRSV | 4173 | MCM4 |
| 240 | YMGEEKLIASV | 23404 | EXOSC2 |
| 241 | KTIQQLETV | 55127 | HEATR1 |
| 242 | WLYGEDHQI | 586 | BCAT1 |
| 243 | FMADDIFSV | 50615 | IL21R |
| 244 | YLLEKNRVV | 4651 | MYO10 |
| 245 | SLLDLPLSL | 9487 | PIGL |
| 246 | TVSDVLNSV | 22796 | COG2 |
| 247 | ALYEGYATV | 10072, 582 | DPP3, BBS1 |
| 248 | YLDRFLAGV | 894 | CCND2 |
| 249 | GLCERLVSL | 5591 | PRKDC |
| 250 | SLAPATPEV | 9308 | CD83 |
| 251 | ALSVLRLAL | 6691 | SPINK2 |
| 252 | RLMEICESL | 1063 | CENPF |
| 253 | ALAELIDNSL | 23347 | SMCHD1 |
| 254 | KLQGKLPEL | 5198 | PFAS |
| 255 | SLLHFTENL | 157570 | ESCO2 |
| 256 | SLGEEQFSV | 157570 | ESCO2 |
| 257 | GLYTDPCGV | 55007 | FAM118A |
| 258 | LLSERFINV | 56647 | BCCIP |
| 259 | ILLPRIIEA | 83959 | SLC4A11 |
| 260 | ILLEKILSL | 9373 | PLAA |
| 261 | QLQDRVYAL | 55374 | TMCO6 |
| 262 | FMVDKAIYL | 55068 | ENOX1 |
| 263 | VLLSEQGDVKL | 10494, 51765, 6788 | STK25, MST4, STK3 |
| 264 | KLFPQETLFL | 11124 | FAF1 |
| 265 | NTCPYVHNI | 51728 | POLR3K |
| 266 | YAIGLVMRL | 401494 | PTPLAD2 |

TABLE 6

Additional peptides according to the present invention with no prior known cancer association, HLA-A*24-binding.

| SEQ ID No. | Sequence | GeneID(s) | Official Gene Symbol(s) |
|---|---|---|---|
| 267 | KYMVYPQTF | 10884 | MRPS30 |
| 268 | QYLGQIQHI | 7298 | TYMS |
| 269 | YFIDSTNLKTHF | 51042 | ZNF593 |
| 270 | NYYEVHKELF | 9055 | PRC1 |

TABLE 6-continued

Additional peptides according to the present invention with no prior known cancer association, HLA-A*24-binding.

| SEQ ID No. | Sequence | GeneID(s) | Official Gene Symbol(s) |
|---|---|---|---|
| 271 | LYHDIFSRL | 9603 | NFE2L3 |
| 272 | QYLQDAYSF | 9918 | NCAPD2 |
| 273 | TYIKPISKL | 4644 | MY05A |
| 274 | AYLHSHALI | 51347 | TAOK3 |
| 275 | EYINQGDLHEF | 4919 | ROR1 |
| 276 | VYGFQWRHF | 7298 | TYMS |
| 277 | VYQGHTALL | 5754 | PTK7 |
| 278 | RYISDQLFTNF | 23268 | DNMBP |
| 279 | TYIESASEL | 79623 | GALNT14 |
| 280 | RYPDNLKHLYL | 29080 | CCDC59 |
| 281 | PYRLIFEKF | 5591 | PRKDC |
| 282 | KFVDSTFYL | 9688 | NUP93 |
| 283 | TYGDAGLTYTF | 121642 | ALKBH2 |
| 284 | RYLNKAFHI | 23310 | NCAPD3 |
| 285 | HYPPVQVLF | 2956 | MSH6 |
| 286 | RYPDNLKHL | 29080 | CCDC59 |
| 287 | LYITEPKTI | 11219, 55559 | TREX2, HAUS7 |
| 288 | VYVSDIQEL | 23225, 255330 | NUP210P1, NUP210 |
| 289 | KYPVEWAKF | 51101 | ZC2HC1A |

TABLE 7A

Peptides useful for e.g. personalized cancer therapies, HLA-A*02-binding.

| SEQ ID No. | Sequence | GeneID(s) | Official Gene Symbol(s) |
|---|---|---|---|
| 290 | KIVDFSYSV | 701 | BUB1B |
| 291 | KLDETGNSL | 7153 | TOP2A |
| 292 | GMMTAILGV | 79939 | SLC35E1 |
| 293 | FLVDGSWSI | 57642 | COL20A1 |
| 294 | GLMKYIGEV | 79054 | TRPM8 |

TABLE 7B

Peptides useful for e.g. personalized cancer therapies, HLA-A*02-binding.

| SEQ ID No. | Sequence | GeneID(s) | Official Gene Symbol(s) |
|---|---|---|---|
| 305 | KLFTSVFGV | 1791 | DNTT |
| 306 | ALLSSLNEL | 367 | AR |

TABLE 8

Peptides useful for e.g. personalized cancer therapies, HLA-A*24-binding.

| SEQ ID No. | Sequence | GeneID(s) | Official Gene Symbol(s) |
|---|---|---|---|
| 295 | YYPGVILGF | 55026 | TMEM255A |
| 296 | TYVDSSHTI | 1462 | VCAN |
| 297 | PFLQASPHF | 84985 | FAM83A |
| 298 | RYLEGTSCI | 83481 | EPPK1 |
| 299 | VYFVAPAKF | 3918 | LAMC2 |
| 300 | AYVLRLETL | 10687 | PNMA2 |
| 301 | AYKPGALTF | 84883 | A1FM2 |
| 302 | RYMPPAHRNF | 3620 | IDO1 |

BRIEF DESCRIPTION OF THE DRAWINGS

FIGS. 2A-2I describe relative group of various peptides of the present disclosure.

DETAILED DESCRIPTION OF A PREFERRED EMBODIMENT

Figure 1C:
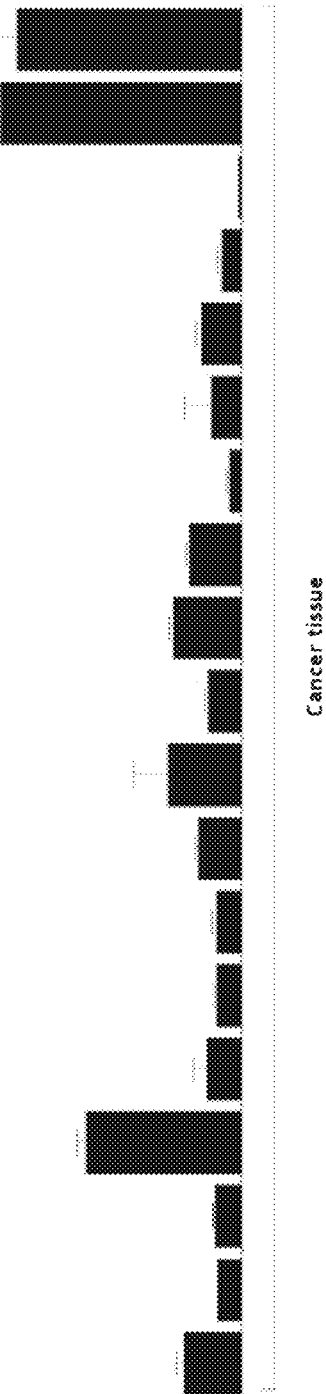
FIGS. 1A-1T describe relative presentation of various peptides of the present disclosure.

The present invention furthermore generally relates to the peptides according to the present invention for use in the treatment of proliferative diseases, such as, for example, glioblastoma (GB), breast cancer (BRCA), colorectal cancer (CRC), renal cell carcinoma (RCC), chronic lymphocytic leukemia (CLL), hepatocellular carcinoma (HCC), non-small cell and small cell lung cancer (NSCLC, SCLC), Non-Hodgkin lymphoma (NHL), acute myeloid leukemia (AML), ovarian cancer (OC), pancreatic cancer (PC), prostate cancer (PCA), esophageal cancer including cancer of the gastric-esophageal junction (OSCAR), gallbladder cancer and cholangiocarcinoma (GBC, CCC), melanoma (MEL), gastric cancer (GC), urinary bladder cancer (UBC), head- and neck squamous cell carcinoma (HNSCC), and uterine cancer (UEC).

Particularly preferred are the peptides—alone or in combination—according to the present invention selected from the group consisting of SEQ ID NO: 1 to SEQ ID NO: 289, SEQ ID NO: 305, and SEQ ID NO: 306. More preferred are the peptides—alone or in combination—selected from the group consisting of SEQ ID NO: 1 to SEQ ID NO: 149 (see Table 3), SEQ ID NO: 158 to SEQ ID NO: 213 (see Table 4), and SEQ ID NO: 305, and SEQ ID NO: 306, in particular consisting of a sequence that is selected from the group consisting of SEQ ID NO: 2, 24, 32, 39, 64, 72, 106, 149, 251, 305, and 306, and their uses in the immunotherapy of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head- and neck squamous cell carcinoma (HNSCC), or uterine cancer.

As shown in Example 1, many of the peptides according to the present invention are found on various tumor types and can, thus, be used in the immunotherapy of other indications. Over-expression of the underlying polypeptides in a variety of cancers, as shown in Example 2, hints towards the usefulness of these peptides in various other oncological indications.

Thus, another aspect of the present invention relates to the use of the peptides according to the present invention for the—preferably combined—treatment of a proliferative disease selected from the group of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head- and neck squamous cell carcinoma, or uterine cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 289, SEQ ID NO: 305, and SEQ ID NO: 306.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 289, preferably containing SEQ ID NO: 1 to SEQ ID NO: 149, SEQ ID NO: 158 to SEQ ID NO: 213, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head- and neck squamous cell carcinoma, or uterine cancer cells.

The present invention further relates to biomarkers based on the peptides according to the present invention, herein called "targets", that can be used in the diagnosis of cancer, preferably glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head- and neck squamous cell carcinoma, or uterine cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these targets in the context of cancer treatment.

A single nucleotide polymorphism of ABCC11 was shown to be associated with a shorter relapse-free survival in patients with non-small cell lung cancer who were treated with S-1 adjuvant chemotherapy (Tsuchiya et al., 2016). ABCC11 was described as a promoter of a multi-drug resistance phenotype in breast cancer. Furthermore, high expression of ABCC11 in breast tumors was shown to be associated with aggressive subtypes and low disease-free survival (Honorat et al., 2013; Yamada et al., 2013). ABCC11 transcript levels in colorectal cancer patients were shown to be significantly lower in non-responders to palliative chemotherapy in comparison with responders which associated with significantly shorter disease-free intervals (Hlavata et al., 2012). ABCC11 was described as a potential biomarker for pemetrexed (MTA) treatment in lung adenocarcinomas (Uemura et al., 2010). ABCC11 up-regulation in acute myeloid leukemia was shown to be associated with a low probability of overall survival assessed over 4 years and may serve as a predictive marker (Guo et al., 2009). ABCC11 was shown to be up-regulated in hepatocellular carcinoma (Borel et al., 2012).

AR encodes for the androgen receptor gene which is more than 90 kb long and codes for a protein that has 3 major functional domains: the N-terminal domain, DNA-binding domain, and androgen-binding domain. The protein functions as a steroid-hormone activated transcription factor. Upon binding the hormone ligand, the receptor dissociates from accessory proteins, translocates into the nucleus, dimerizes, and then stimulates transcription of androgen responsive genes. This gene contains 2 polymorphic trinucleotide repeat segments that encode polyglutamine and polyglycine tracts in the N-terminal transactivation domain of its protein. Expansion of the polyglutamine tract from the normal 9-34 repeats to the pathogenic 38-62 repeats causes spinal bulbar muscular atrophy (Kennedy disease). Mutations in this gene are also associated with complete androgen insensitivity (CAIS). Two alternatively spliced variants encoding distinct isoforms have been described. US20150306197 A1 discloses SQ ID NO. 305 as an AR LBD (ligand-binding domain) peptide epitope that was identified by scanning the protein sequence of the AR LBD for 9-mer or 10-mer peptides that fit the HLA-A2 consensus binding sequence and by their predicted binding affinity to HLA-A2. The peptide is exclusively proposed for a prostate cancer vaccine.

C1orf186 encodes chromosome 1 open reading frame 186 and is located on chromosome 1q32.1 (RefSeq, 2002). Krüppel-like factor 9 inhibits C1orf186 expression in endometrial carcinoma cells (Simmen et al., 2008). C1orf186 is associated with ER-positive breast cancer (Triulzi et al., 2015).

DNTT encodes for DNA nucleotidylexotransferase. In vivo, the encoded protein is expressed in a restricted population of normal and malignant pre-B and pre-T lymphocytes during early differentiation, where it generates antigen receptor diversity by synthesizing non-germ line elements (N-regions) at the junctions of rearranged Ig heavy chain and T cell receptor gene segments. Alternatively spliced transcript variants encoding different isoforms of this gene have been described. US20110142842 A1 predicts the peptide of SEQ ID NO. 305 as binding to HLA-A*0201 as a sequences of hematopoietic cell-specific proteins. The peptide is not tested further, and the publication speculates about the treatment of many different types of cancer including leukemia, lymphomas such as non-Hodgkin lymphoma and multiple myeloma.

LRRC15 encodes leucine rich repeat containing 15 and is located on chromosome 3q29 (RefSeq, 2002). EWSR1-WT1 is an oncogenic transcription factor that was shown to affect the expression of LRRC15 (Cliteur et al., 2012; Reynolds et al., 2003). LRRC15 is a tumor antigen which is over-expressed in a variety of entities (O'Prey et al., 2008). LRRC15 is associated with breast cancer invasion (Schuetz et al., 2006). LRRC15 is associated with aggressive behavior of androgen-independent metastatic prostate tumors (Stanbrough et al., 2006). Autoantibodies against LRRC15 are inversely correlated with breast cancer (Evans et al., 2014).

MAGEC2 encodes MAGE family member C2, a gene clustered on chromosome Xq26-q27 like the other MAGEC genes (RefSeq, 2002). Over-expression of MAGEC2 increases the level of cyclin E and promotes G1-S transition and cell proliferation (Hao et al., 2015). MAGEC2 promotes proliferation and resistance to apoptosis in Multiple Myeloma suggesting that MAGEC2-specific immunotherapies have the potential to eradicate the most malignant cells (Lajmi et al., 2015). MAGEC2, an epithelial-mesenchymal transition inducer, is associated with breast cancer metastasis. Multivariate analyses showed that MAGEC2 expression was an independent risk factor for patient overall survival and metastasis-free survival (Yang et al., 2014).

MET encodes the hepatocyte growth factor receptor and encodes tyrosine-kinase activity (RefSeq, 2002). MET was shown to be up-regulated in dedifferentiated liposarcoma and is associated with melanocytic tumors, hepatocellular carcinoma, non-small cell lung cancer, hereditary papillary kidney cancers and gastric adenocarcinomas (Petrini, 2015; Finocchiaro et al., 2015; Steinway et al., 2015; Bill et al., 2015; Yeh et al., 2015).

PRAME encodes an antigen that is preferentially expressed in human melanomas and acts as a repressor of retinoic acid receptor, likely conferring a growth advantage to cancer cell via this function (RefSeq, 2002). PRAME was shown to be up-regulated in multiple myeloma, clear cell renal cell carcinoma, breast cancer, acute myeloid leukemia, melanoma, chronic myeloid leukemia, head and neck squamous cell carcinoma and osteosarcoma cell lines (Dannenmann et al., 2013; Yao et al., 2014; Zou et al., 2012; Szczepanski and Whiteside, 2013; Zhang et al., 2013; Beard et al., 2013; Abdelmalak et al., 2014; Qin et al., 2014). PRAME is associated with myxoid and round-cell liposarcoma (Hemminger et al., 2014). PRAME is associated with shorter progression-free survival and chemotherapeutic response in diffuse large B-cell lymphoma treated with R-CHOP, markers of poor prognosis in head and neck squamous cell carcinoma, poor response to chemotherapy in urothelial carcinoma and poor prognosis and lung metastasis in osteosarcoma (Tan et al., 2012; Dyrskjot et al., 2012; Szczepanski et al., 2013; Mitsuhashi et al., 2014). PRAME is associated with lower relapse, lower mortality and overall survival in acute lymphoblastic leukemia (Abdelmalak et al., 2014). PRAME may be a prognostic marker for diffuse large B-cell lymphoma treated with R-CHOP therapy (Mitsuhashi et al., 2014).

SPINK2 encodes a member of the family of serine protease inhibitors of the Kazal type which acts as a trypsin and acrosin inhibitor in the genital tract and is localized in the spermatozoa (RefSeq, 2002). SPINK2 was shown to be significantly up-regulated in most leukemia cell lines except B-lymphoblast TK-6 cells, and was suggested to play an important role in tumor progression and response to treatment (Chen et al., 2009).

STEAP2 encodes STEAP2 metalloreductase which encodes a multi-pass membrane protein that localizes to the Golgi complex, the plasma membrane, and the vesicular tubular structures in the cytosol. Increased transcriptional expression of the human gene is associated with prostate cancer progression (RefSeq, 2002). STEAP2 is induced upon TNF-alpha and repressed upon NF-kappaB treatment. Silencing of NF-kappaB leads to an over-expression of the anti-apoptotic protein STEAP2 which subsequently represses p53 (Gonen-Korkmaz et al., 2014). STEAP2 is over-expressed in many cancer entities like prostate, bladder, colon, pancreas, ovary, testis, breast, cervix, and Ewing sarcoma (Wang et al., 2010; Gomes et al., 2012; Grunewald et al., 2012). STEAP2 may drive prostate cancer cell migration and invasion. Over-expression of STEAP2 is associated with locally advanced disease state (Whiteland et al., 2014). STEAP2 has a greater proportion of unspliced RNA in castration-resistant prostate cancer (Sowalsky et al., 2015). STEAP2 can be used as biomarker for prostate cancer (Edwards et al., 2005). STEAP2 is associated with simvastatin and lovastatin resistance (Savas et al., 2011).

UMODL1 encodes uromodulin like 1 and is located on chromosome 21q22.3 (RefSeq, 2002). UMODL1 may drive lung adenocarcinoma metastasis (Tan et al., 2016). A long non-coding RNA chimera, UMODL1-AS1, can be used as prognostic factor for breast cancer recurrence (Liu et al., 2016).

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (elongated variants of the peptides of the invention) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 9

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |

TABLE 9-continued

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02 or A*24. A vaccine may also include pan-binding MHC class II peptides. Therefore, the vaccine of the invention can be used to treat cancer in patients that are A*02 or A*24 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86%.

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
 (i) each base or amino acid in the Reference Sequence that does not have a corresponding aligned base or amino acid in the Compared Sequence and
 (ii) each gap in the Reference Sequence and
 (iii) each aligned base or amino acid in the Reference Sequence that is different from an aligned base or amino acid in the Compared Sequence, constitutes a difference and
 (iiii) the alignment has to start at position 1 of the aligned sequences;
 and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 289 or a variant thereof which is 88% homologous to SEQ ID NO: 1 to SEQ ID NO: 289, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 289. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO: 289, 305, and 306, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 10

Variants and motif of the HLA-A*02-binding peptides according to SEQ ID NO: 1, 2, and 3.

| | Position | | | | | | | | | |
|---|---|---|---|---|---|---|---|---|---|---|
| | 1 | 2 | 3 | 4 | 5 | 6 | 7 | 8 | 9 | 10 |
| SEQ ID NO. 1 Variant | L | L | Y | P | E | P | W | S | V | |
| | | | | | | | | | I | |
| | | | | | | | | | L | |
| | | | | | | | | | A | |
| | | M | | | | | | | | |
| | | M | | | | | | | I | |
| | | M | | | | | | | L | |
| | | M | | | | | | | A | |
| | | A | | | | | | | | |
| | | A | | | | | | | I | |
| | | A | | | | | | | L | |
| | | A | | | | | | | A | |
| | | V | | | | | | | | |
| | | V | | | | | | | I | |
| | | V | | | | | | | L | |
| | | V | | | | | | | A | |
| | | T | | | | | | | | |
| | | T | | | | | | | I | |
| | | T | | | | | | | L | |
| | | T | | | | | | | A | |
| | | Q | | | | | | | | |
| | | a | | | | | | | I | |
| | | a | | | | | | | L | |
| | | Q | | | | | | | A | |
| SEQ ID NO. 2 Variant | G | L | I | A | G | V | V | S | I | |
| | | | | | | | | | V | |
| | | | | | | | | | L | |
| | | | | | | | | | A | |
| | | M | | | | | | | V | |
| | | M | | | | | | | | |
| | | M | | | | | | | L | |
| | | M | | | | | | | A | |
| | | A | | | | | | | V | |
| | | A | | | | | | | | |
| | | A | | | | | | | L | |
| | | A | | | | | | | A | |
| | | V | | | | | | | V | |
| | | V | | | | | | | | |
| | | V | | | | | | | L | |
| | | V | | | | | | | A | |
| | | T | | | | | | | V | |
| | | T | | | | | | | | |
| | | T | | | | | | | L | |
| | | T | | | | | | | A | |
| | | Q | | | | | | | V | |
| | | Q | | | | | | | | |
| | | Q | | | | | | | L | |
| | | Q | | | | | | | A | |
| SEQ ID NO. 3 Variant | K | L | E | E | N | G | D | L | Y | L |
| | | | | | | | | | | V |
| | | | | | | | | | | I |
| | | | | | | | | | | A |
| | | M | | | | | | | | V |
| | | M | | | | | | | | I |
| | | M | | | | | | | | |
| | | M | | | | | | | | A |
| | | A | | | | | | | | V |
| | | A | | | | | | | | I |
| | | A | | | | | | | | |

TABLE 10-continued

Variants and motif of the HLA-A*02-binding peptides according to SEQ ID NO: 1, 2, and 3.

| | Position | | | | | | | | | |
|---|---|---|---|---|---|---|---|---|---|---|
| | 1 | 2 | 3 | 4 | 5 | 6 | 7 | 8 | 9 | 10 |
| | | A | | | | | | | | A |
| | | V | | | | | | | | V |
| | | V | | | | | | | | I |
| | | V | | | | | | | | |
| | | V | | | | | | | | A |
| | | T | | | | | | | | V |
| | | T | | | | | | | | I |
| | | T | | | | | | | | |
| | | T | | | | | | | | A |
| | | Q | | | | | | | | V |
| | | Q | | | | | | | | I |
| | | Q | | | | | | | | |
| | | Q | | | | | | | | A |

TABLE 11

Variants and motif of the HLA-A*24-binding peptides according to SEQ ID NO: 158, 159, and 160.

| | Position | | | | | | | | | | |
|---|---|---|---|---|---|---|---|---|---|---|---|
| | 1 | 2 | 3 | 4 | 5 | 6 | 7 | 8 | 9 | 10 | 11 |
| SEQ ID NO. 158 Variant | H | Y | S | Q | E | L | S | L | L | Y | L |
| | | | | | | | | | | | I |
| | | | | | | | | | | | F |
| | | | | | F | | | | | | I |
| | | | | | F | | | | | | |
| | | | | | F | | | | | | F |
| SEQ ID NO. 159 Variant | L | Y | N | K | G | F | I | Y | L | | |
| | | | | | | | | | I | | |
| | | | | | | | | | F | | |
| | | | | | F | | | | I | | |
| | | | | | F | | | | | | |
| | | | | | F | | | | F | | |
| SEQ ID NO. 160 Variant | V | Y | T | L | D | I | P | V | L | | |
| | | | | | | | | | I | | |
| | | | | | | | | | F | | |
| | | | | | F | | | | I | | |
| | | | | | F | | | | | | |
| | | | | | F | | | | F | | |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 12.

TABLE 12

Combinations of the elongations of peptides of the invention

| C-terminus | N-terminus |
| --- | --- |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
| --- | --- |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 289, 305, and 306.

"Consisting essentially of" shall mean that a peptide according to the present invention, in addition to the sequence according to any of SEQ ID NO: 1 to SEQ ID NO: 289, 305, and 306 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention.

Another embodiment of the present invention relates to a non-naturally occurring peptide wherein said peptide consists or consists essentially of an amino acid sequence according to SEQ ID No: 1 to SEQ ID No: 289, SEQ ID NO: 305, and SEQ ID NO: 306 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)_2Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$), such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

For the identification of peptides of the present invention, two databases of RNA expression data were compared together: RNASeq tumor data generated by the TCGA Research Network and RNASeq data (GTEx) covering around 3000 normal (healthy) tissue samples (Lonsdale, 2013). Genes were screened, with were over-expressed in tumor tissues samples compared with the normal (healthy) tissue samples. Then, cancer-associated peptides derived from the protein products of these genes were identified by mass spectrometry using the XPRESIDENT™ platform as described herein.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1, FIGS. 1A-1T).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from cancer samples (N=450 A*02-positive samples, N=211 A*24-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from A*02 and/or A*24-positive cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from tissue samples were purified and HLA-associated peptides were isolated and analyzed by LC-MS (see examples). All TUMAPs contained in the present application were identified with this approach on primary cancer samples confirming their presentation on primary glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, or uterine cancer.

TUMAPs identified on multiple cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Furthermore, the discovery pipeline XPRESIDENT® v2.1 allows the direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 22)

This combined analysis of RNA expression and mass spectrometry data resulted in the 289 peptides of the present invention.

Besides over-presentation of the peptide, mRNA expression of the underlying gene was tested. mRNA data were obtained via RNASeq analyses of normal tissues and cancer tissues (cf. Example 2, FIGS. 2A-2I). An additional source of normal tissue data was a database of publicly available RNA expression data from around 3000 normal tissue samples (Lonsdale, 2013). Peptides which are derived from proteins whose coding mRNA is highly expressed in cancer tissue, but very low or absent in vital normal tissues, were preferably included in the present invention.

The present invention provides peptides that are useful in treating cancers/tumors, preferably glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, and uterine cancer that over- or exclusively present the peptides of the invention. These peptides were shown by mass spectrometry to be naturally presented by HLA molecules on primary human cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy cells or tissue derived from the same organ as the tumor, or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from cancer, but not on normal tissues (see Example 1).

HLA-bound peptides can be recognized by the immune system, specifically T lymphocytes. T cells can destroy the cells presenting the recognized HLA/peptide complex, e.g. glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, or uterine cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3). Furthermore, the peptides when complexed with the respective MHC can be used for the production of antibodies and/or TCRs, in particular sTCRs, according to the present invention, as well. Respective methods are well known to the person of skill, and can be found in the respective literature as well (see also below). Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient. In this context, particularly preferred are the peptides of the invention selected from the group consisting of SEQ ID NO: 2, 24, 32, 39, 64, 72, 106, 149, 251, 305, and 306.

The present description further relates to T-cell receptors (TCRs) comprising an alpha chain and a beta chain ("alpha/beta TCRs"). Also provided are peptides according to the invention capable of binding to TCRs and antibodies when presented by an MHC molecule. The present description also relates to nucleic acids, vectors and host cells for expressing TCRs and peptides of the present description; and methods of using the same. Again, particularly preferred in this context are the peptides of the invention selected from the group consisting of SEQ ID NO: 2, 24, 32, 39, 64, 72, 106, 149, 251, 305, and 306.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to peptides can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with a peptide, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced (Schmitt et al., 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion) (Schmitt et al., 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 289, 305, and 306, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, CN, USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, NJ, USA. An example of an inducible mammalian expression vector is pMSG, also available from Pharmacia. Useful yeast plasmid vectors are pRS403-406 and pRS413-416 and are generally available from Stratagene Cloning Systems, La Jolla, CA 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, MD, USA, and RR1 available from the American Type Culture Collection (ATCC) of Rockville, MD, USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, CA 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, MD 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 289, 305, and 306, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen (preferably a peptide according to the present invention), the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is thus a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 289, 305, and 306, or a variant thereof which is at least 88% homologous (preferably identical) to SEQ ID NO: 1 to SEQ ID NO: 289, 305, and 306 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 289, 305, and 306 or a variant thereof which is at least 88% homologous (preferably identical) to SEQ ID NO: 1 to SEQ ID NO: 289, 305, and 306, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 289, 305, and 306.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of cancers such as glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 289, 305, and 306 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are cells or other solid or haematological tumor cells such as glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer cells.

The present invention further relates to particular marker proteins and biomarkers based on the peptides according to the present invention, herein called "targets" that can be used in the diagnosis and/or prognosis of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer marker (poly)peptide, delivery of a toxin to a cancer cell expressing a cancer marker gene at an increased level, and/or inhibiting the activity of a cancer marker polypeptide) according to the invention.

Whenever possible, the antibodies of the invention may be purchased from commercial sources. The antibodies of the invention may also be generated using well-known methods. The skilled artisan will understand that either full length glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 289, 305, and 306 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the marker polypeptide for above-mentioned cancers used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (µg/kg to up to 100 mg/kg of body weight or more per day, depending on the factors mentioned above. Following administration of an antibody, preferably for treating glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^3$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than $1 \times 10$ µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Maryland 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 289, 305, and 306, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, and vaccinia-infected target cells.

In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO: 289, 305, and 306.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use.

Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, or uterine cancer, the medicament of the invention is preferably used to treat glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer patients with various HLA-A HLA-B and HLA-C alleles. It may contain MHC class I and MHC class II peptides or elongated MHC class I peptides. In addition to the tumor associated peptides collected from several cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, urinary bladder cancer, head and neck squamous cell carcinoma, or uterine cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

Figure 1G:
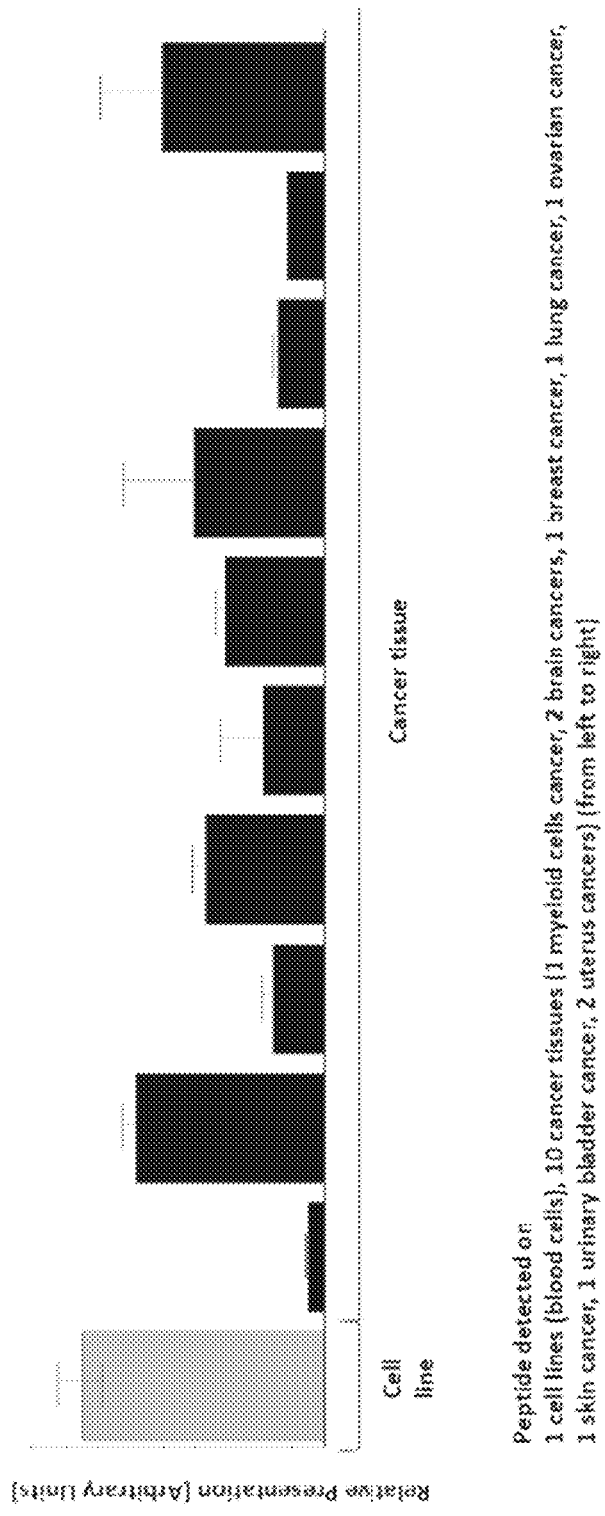
Figure 1J:
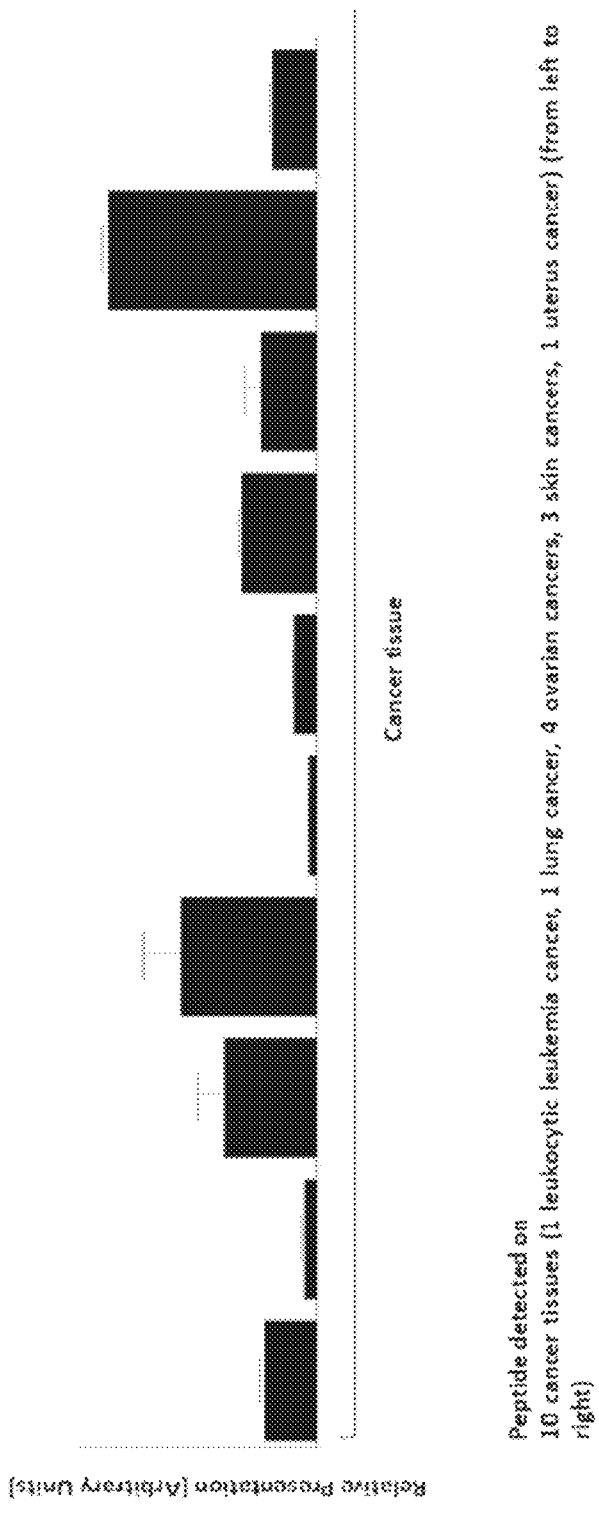
Figure 1K:
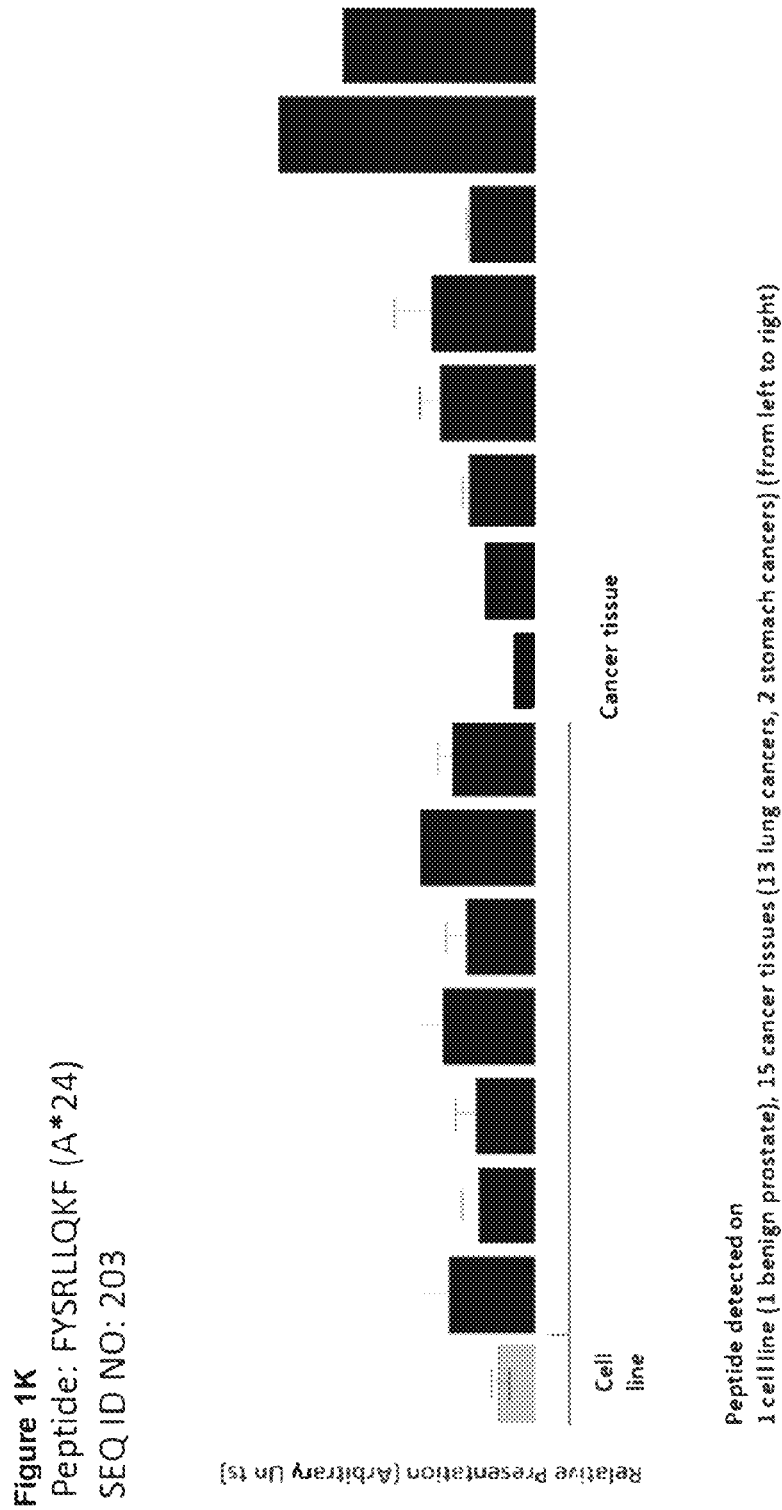
Figure 1R:
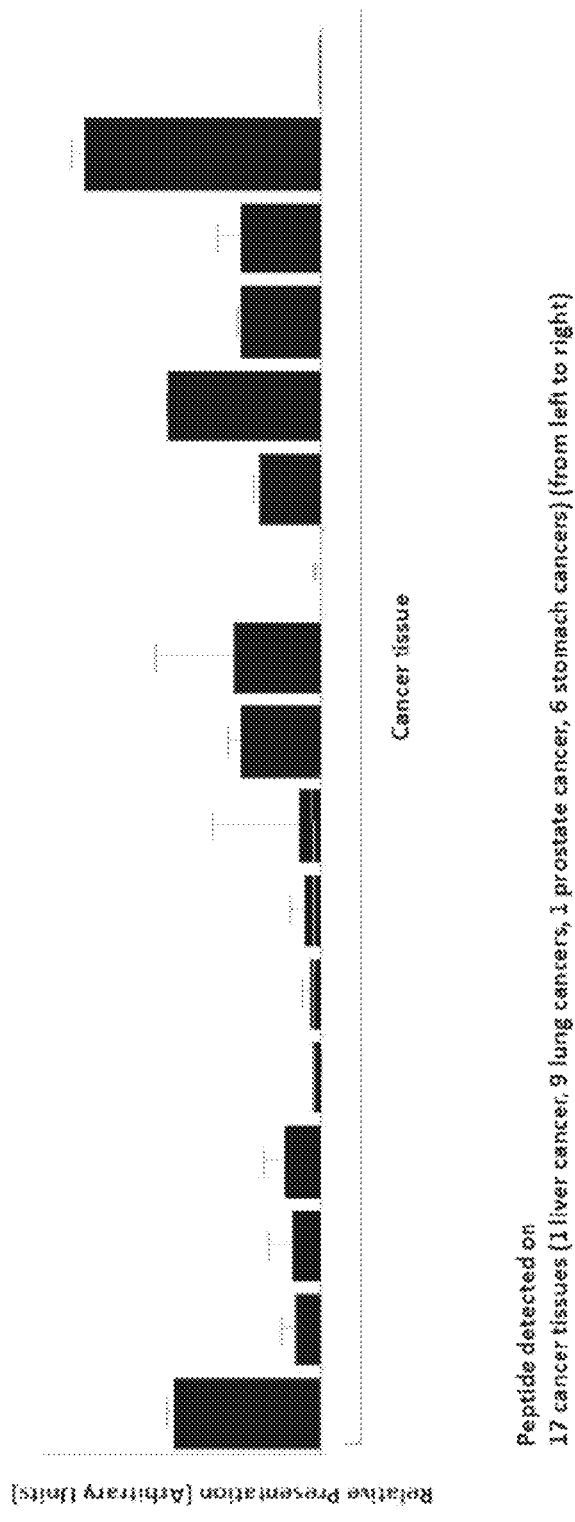

FIGS. 1A to 1T show the over-presentation of various peptides in normal tissues (white bars) and different cancers (black bars). FIG. 1A—MET, Peptide: GLIAGVVSI (SEQ ID NO.: 2)—Tissues from left to right: 4 cell lines (1 kidney, 2 pancreatic, 1 melanoma), 24 cancer tissues (1 brain cancer, 1 gallbladder cancer, 7 kidney cancers, 1 rectum cancer, 1 liver cancer, 7 lung cancers, 2 stomach cancers, 4 urinary bladder cancers); FIG. 1B—TMEM223, Peptide: GLLFSLRSV (SEQ ID NO.: 92)—Tissues from left to right: 2 cell lines (2 pancreatic), 1 normal tissue (1 lymph node), 14 cancer tissues (4 leukocytic leukemia cancers, 2 myeloid cells cancers, 1 bone marrow cancer, 1 breast cancer, 1 lymph node cancer, 1 ovarian cancer, 2 prostate cancers, 1 skin cancer, 1 urinary bladder cancer); FIG. 1C—PRKDC, Peptide: HYSQELSLLYL (SEQ ID NO.: 158)—Tissues from left to right: 19 cancer tissues (1 brain cancer, 1 kidney cancer, 2 liver cancers, 9 lung cancers, 2 prostate cancers, 4 stomach cancers); FIG. 1D—GPX6, GPX7, Peptide: TYSVSFPMF (SEQ ID NO.: 195)—Tissues from left to right: 3 cell lines (3 benign prostate hyperplasias), 1 normal tissue (1 stomach), 58 cancer tissues (1 brain cancer, 2 liver cancers, 47 lung cancers, 7 prostate cancers, 1 stomach cancer). FIGS. 1E to 1R show the over-presentation of various peptides in different cancer tissues compared to normal tissues. The analyses included data from more than 490 A*02 positive normal tissue samples and 70 A*24 positive normal tissue samples, 543 A*02 positive cancer samples and 200 A*24 positive cancer samples. Shown are only samples where the peptide was found to be presented. FIG. 1E) Gene symbol: FEN1, Peptide: SIYQFLIAV (SEQ ID NO: 8)—Tissues from left to right: 2 cell lines (1 blood cells, 1 pancreas), 14 cancer tissues (3 leukocytic leukemia cancers, 1 myeloid cells cancer, 1 breast cancer, 1 gallbladder cancer, 1 head-and-neck cancer, 1 colon cancer, 2 lung cancers, 3 lymph node cancers, 1 uterus cancer); FIG. 1F) Gene symbol: DERL3, Peptide: ALMAMLVYV (SEQ ID NO: 13)—Tissues from left to right: 17 cancer tissues (1 bile duct cancer, 2 breast cancers, 1 gallbladder cancer, 3 head-and-neck cancers, 7 lung cancers, 1 lymph node cancer, 1 ovarian cancer, 1 stomach cancer); FIG. 1G) Gene symbol: HEATR2, Peptide: ALAPHLDDA (SEQ ID NO: 237)—Tissues from left to right: 1 cell lines (blood cells), 10 cancer tissues (1 myeloid cells cancer, 2 brain cancers, 1 breast cancer, 1 lung cancer, 1 ovarian cancer, 1 skin cancer, 1 urinary bladder cancer, 2 uterus cancers); FIG. 1H) Gene symbol: SLC4A11, Peptide: ILLPRIIEA (SEQ ID NO: 259)—Tissues from left to right: 1 cell lines (1 pancreas), 27 cancer tissues (3 leukocytic leukemia cancers, 1 brain cancer, 2 breast cancers, 3 head-and-neck cancers, 1 colon cancer, 1 rectum cancer, 6 lung cancers, 5 ovarian cancers, 1 pancreas cancer, 2 skin cancers, 1 stomach cancer, 1 uterus cancer); FIG. 1I) Gene symbol: ABCC11, Peptide: HLLEGSVGV (SEQ ID NO: 39)—Tissues from left to right: 7 cancer tissues (5 breast cancers, 1 liver cancer, 1 skin cancer); FIG. 1J) Gene symbol: PRAME, Peptide: VQLDSIEDLEV (SEQ ID NO: 32)—Tissues from left to right: 10 cancer tissues (1 leukocytic leukemia cancer, 1 lung cancer, 4 ovarian cancers, 3 skin cancers, 1 uterus cancer); FIG. 1K) Gene symbol: ZWILCH, Peptide: FYSRLLQKF (SEQ ID NO: 203)—Tissues from left to right: 1 cell line (1 benign prostate hyperplasia), 15 cancer tissues (13 lung cancers, 2 stomach cancers); FIG. 1L) Gene symbol: PRC1, Peptide: NYYEVHKELF (SEQ ID NO: 270)—Tissues from left to right: 14 cancer tissues (1 brain cancer, 11 lung cancers, 2 stomach cancers); FIG. 1M) Gene symbol: GZMK, Peptide: KFSSFSLFF (SEQ ID NO: 164)—Tissues from left to right: 2 cell lines (2 benign prostate hyperplasias), 14 cancer tissues (11 lung cancers, 1 prostate cancer, 2 stomach cancers); FIG. 1N) Gene symbols: TREX2, HAUS7, Peptide: LYITEPKTI (SEQ ID NO: 287)—Tissues from left to right: 12 cancer tissues (3 brain cancers, 1 liver cancer, 7 lung cancers, 1 stomach cancer); FIG. 1O) Gene symbol: DNMBP, Peptide: RYISDQLFTNF (SEQ ID NO: 278)—Tissues from left to right: 1 normal tissue (1 lung), 31 cancer tissues (2 brain cancers, 1 kidney cancer, 2 liver cancers, 20 lung cancers, 2 prostate cancers, 4 stomach cancers); FIG. 1P) Gene symbol: PTK7, Peptide: VYQGHTALL (SEQ ID NO: 277)—Tissues from left to right: 2 cell line (2 benign prostate hyperplasias), 4 normal tissues (1 rectum, 2 lungs, 1 pancreas), 64 cancer tissues (5 brain cancers, 48 lung cancers, 6 prostate cancers, 5 stomach cancers); FIG. 1Q) Gene symbols: NUP210P1, NUP210, Peptide: VYVSDIQEL (SEQ ID NO: 288)—Tissues from left to right: 2 normal tissues (1 colon, 1 pituitary gland), 21 cancer tissues (1 liver cancer, 14 lung cancers, 1 prostate cancer, 5 stomach cancers); FIG. 1R) Gene symbol: ATAD2, Peptide: VYTLDIPVL (SEQ ID NO: 160)—Tissues from left to right: 17 cancer tissues (1 liver cancer, 9 lung cancers, 1 prostate cancer, 6 stomach cancers); FIG. 1S) Gene symbol: DNTT, Peptide: KLFTSVFGV (SEQ ID NO: 305)—Tissues from left to right: 5 cancer tissues (5 blood cells cancers); FIG. 1T) Gene symbol: AR, Peptide: ALLSSLNEL (SEQ ID NO: 306)—Tissues from left to right: 3 cell lines (1 kidney, 2 prostates), 4 normal tissues (1 liver, 1 lung, 1 ovary, 1 uterus), 29 cancer tissues (1 bile duct cancer, 2 blood cells cancers, 1 brain cancer, 3 breast cancers, 1 kidney cancer, 5 liver cancers, 1 lung cancer, 1 lymph node cancer, 4 ovary cancers, 6 prostate cancers, 1 urinary bladder cancer, 3 uterus cancers).

Figure 2A:
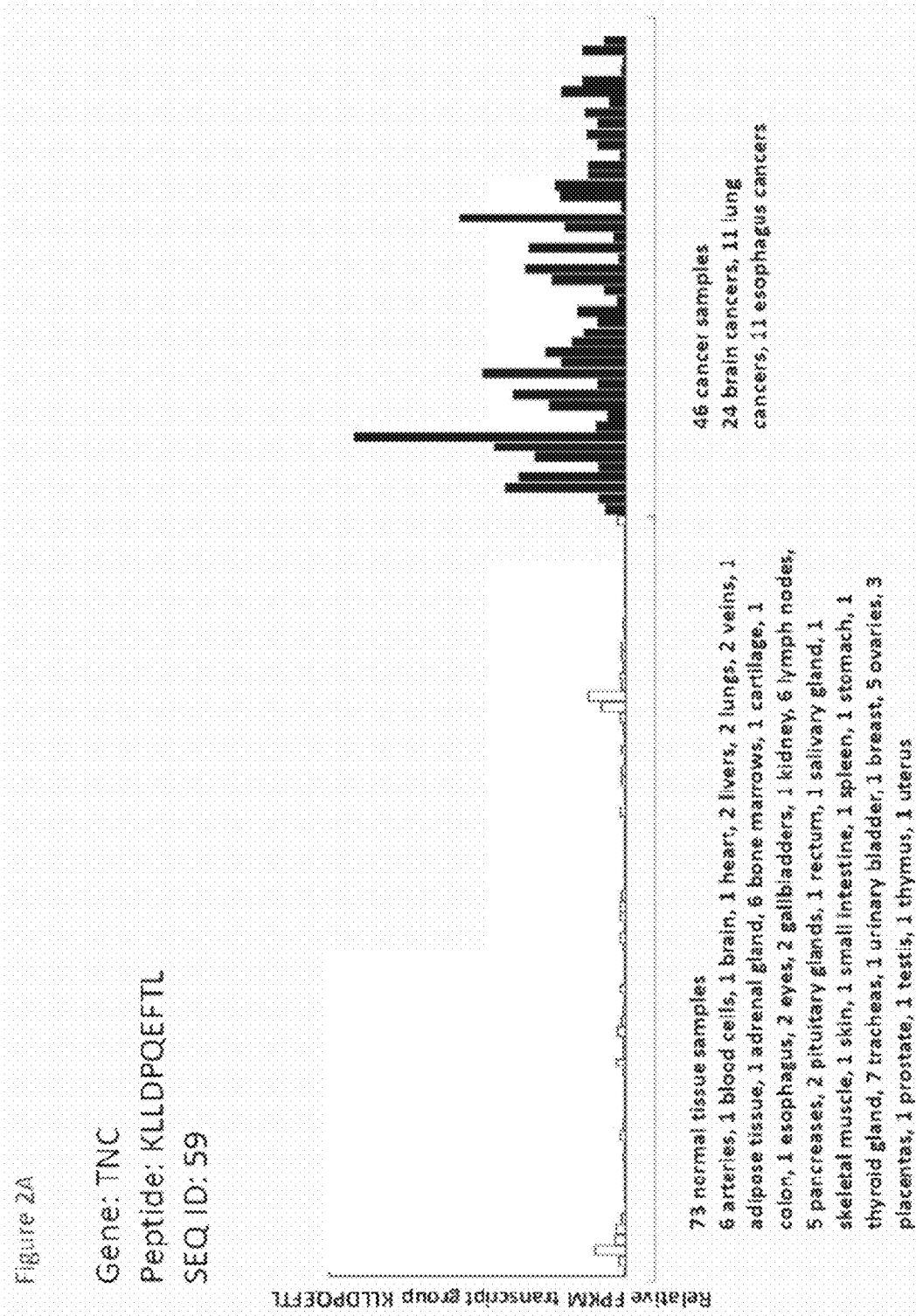
Figure 28:
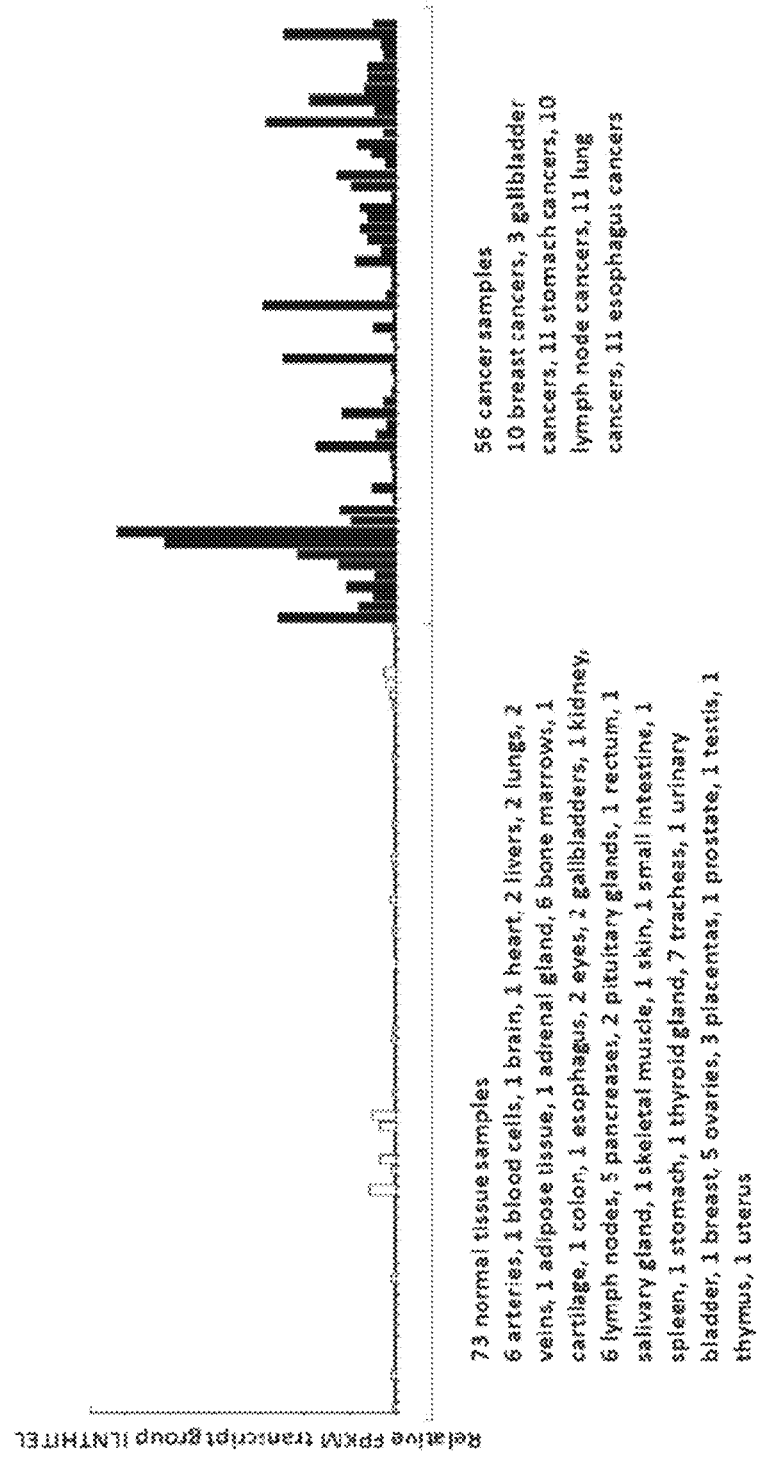
Figure 2G:
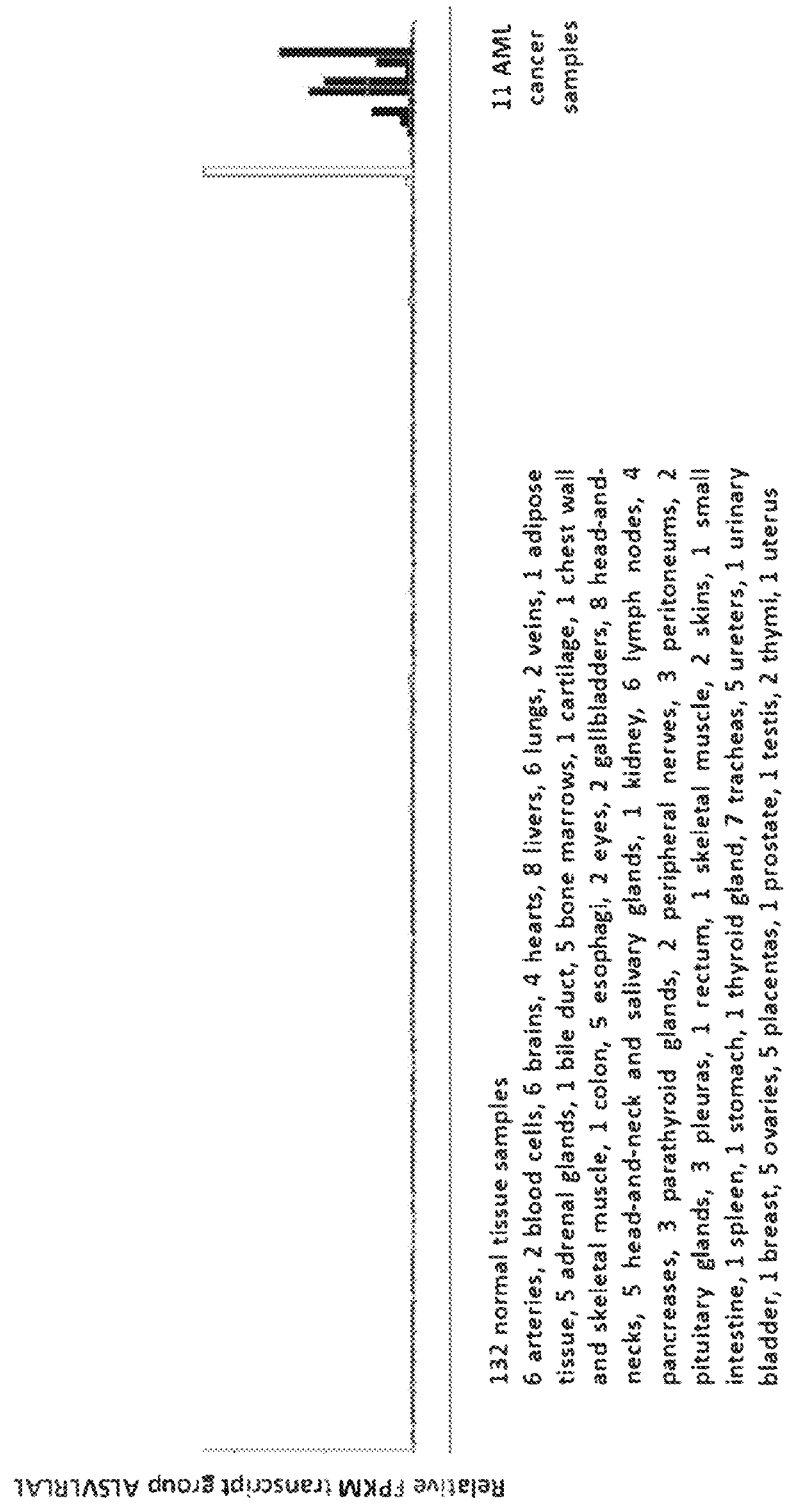
Figure 2H:
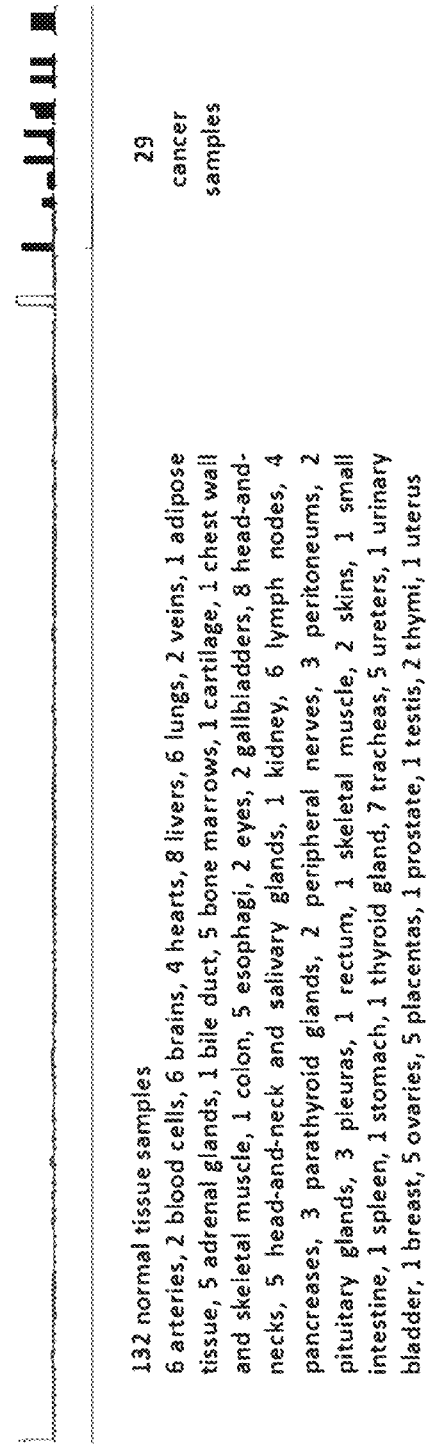
Figure 2I:
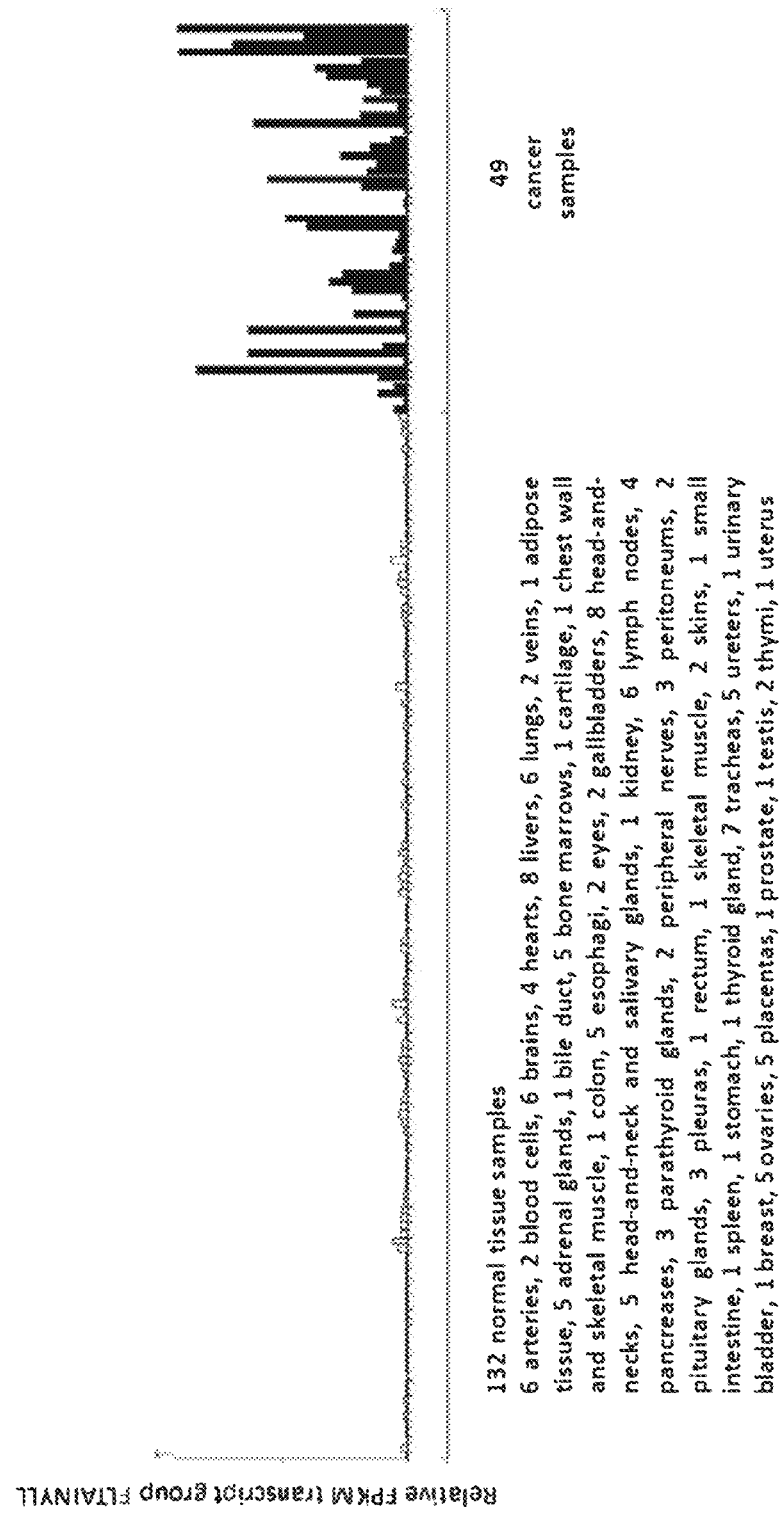

FIGS. 2A to 2I show exemplary expression profiles of source genes of the present invention that are highly over-expressed or exclusively expressed in different cancers in a panel of normal tissues (white bars) and different cancers samples (black bars). FIG. 2A—TNC, Peptide: KLLDPQEFTL, (SEQ ID NO.: 59)—Tissues from left to right: 73 normal tissue samples (6 arteries, 1 blood cells, 1 brain, 1 heart, 2 livers, 2 lungs, 2 veins, 1 adipose tissue, 1 adrenal gland, 6 bone marrows, 1 cartilage, 1 colon, 1 esophagus, 2 eyes, 2 gallbladders, 1 kidney, 6 lymph nodes, 5 pancreases, 2 pituitary glands, 1 rectum, 1 salivary gland, 1 skeletal muscle, 1 skin, 1 small intestine, 1 spleen, 1 stomach, 1 thyroid gland, 7 tracheas, 1 urinary bladder, 1 breast, 5 ovaries, 3 placentas, 1 prostate, 1 testis, 1 thymus, 1 uterus) and 46 cancer samples (24 brain cancers, 11 lung cancers, 11 esophagus cancers); FIG. 2B—LRRC15, Peptide: ILNTHITEL, (SEQ ID NO.: 149)—Tissues from left to right: 73 normal tissue samples (6 arteries, 1 blood cells, 1 brain, 1 heart, 2 livers, 2 lungs, 2 veins, 1 adipose tissue, 1 adrenal gland, 6 bone marrows, 1 cartilage, 1 colon, 1 esophagus, 2 eyes, 2 gallbladders, 1 kidney, 6 lymph nodes, 5 pancreases, 2 pituitary glands, 1 rectum, 1 salivary gland, 1 skeletal muscle, 1 skin, 1 small intestine, 1 spleen, 1 stomach, 1 thyroid gland, 7 tracheas, 1 urinary bladder, 1 breast, 5 ovaries, 3 placentas, 1 prostate, 1 testis, 1 thymus, 1 uterus) and 56 cancer samples (10 breast cancers, 3 gallbladder cancers, 11 stomach cancers, 10 lymph node cancers, 11 lung cancers, 11 esophagus cancers); FIG. 2C—C1QL1, Peptide: TYTTVPRVAF, (SEQ ID NO.: 172)—Tissues from left to right: 73 normal tissue samples (6 arteries, 1 blood cells, 1 brain, 1 heart, 2 livers, 2 lungs, 2 veins, 1 adipose tissue, 1 adrenal gland, 6 bone marrows, 1 cartilage, 1 colon, 1 esophagus, 2 eyes, 2 gallbladders, 1 kidney, 6 lymph nodes, 5 pancreases, 2 pituitary glands, 1 rectum, 1 salivary gland, 1 skeletal muscle, 1 skin, 1 small intestine, 1 spleen, 1 stomach, 1 thyroid gland, 7 tracheas, 1 urinary bladder, 1 breast, 5 ovaries, 3 placentas, 1 prostate, 1 testis, 1 thymus, 1 uterus) and 34 cancer samples (24 brain cancers, 10 kidney cancers); FIG. 2D—AMC2, Peptide: GYIDNVTLI, (SEQ ID NO.: 220)—Tissues from left to right: 73 normal tissue samples (6 arteries, 1 blood cells, 1 brain, 1 heart, 2 livers, 2 lungs, 2 veins, 1 adipose tissue, 1 adrenal gland, 6 bone marrows, 1 cartilage, 1 colon, 1 esophagus, 2 eyes, 2 gallbladders, 1 kidney, 6 lymph nodes, 5 pancreases, 2 pituitary glands, 1 rectum, 1 salivary gland, 1 skeletal muscle, 1 skin, 1 small intestine, 1 spleen, 1 stomach, 1 thyroid gland, 7 tracheas, 1 urinary bladder, 1 breast, 5 ovaries, 3 placentas, 1 prostate, 1 testis, 1 thymus, 1 uterus) and 48 cancer samples (11 lung cancers, 11 esophagus cancers, 26 pancreas cancers). FIG. 2E—ABCC11, Peptide: HLLEGSVGV, (SEQ ID NO.: 39)—Tissues from left to right: 6 arteries, 2 blood cellss, 6 brains, 4 hearts, 8 livers, 6 lungs, 2 veins, 1 adipose tissue, 5 adrenal glands, 1 bile duct, 5 bone marrows, 1 cartilage, 1 chest wall and skeletal muscle, 1 colon, 5 esophagi, 2 eyes, 2 gallbladders, 8 head-and-necks, 5 head-and-neck and salivary glands, 1 kidney, 6 lymph nodes, 4 pancreases, 3 parathyroid glands, 2 peripheral nerves, 3 peritoneums, 2 pituitary glands, 3 pleuras, 1 rectum, 1 skeletal muscle, 2 skins, 1 small intestine, 1 spleen, 1 stomach, 1 thyroid gland, 7 tracheas, 5 ureters, 1 urinary bladder, 1 breast, 5 ovaries, 5 placentas, 1 prostate, 1 testis, 2 thymi, 1 uterus, and 10 breast cancers samples. FIG. 2F—PRAME, Peptide: VQLDSIEDLEV, (SEQ ID NO.: 32)—Tissues from left to right: 6 arteries, 2 blood cellss, 6 brains, 4 hearts, 8 livers, 6 lungs, 2 veins, 1 adipose tissue, 5 adrenal glands, 1 bile duct, 5 bone marrows, 1 cartilage, 1 chest wall and skeletal muscle, 1 colon, 5 esophagi, 2 eyes, 2 gallbladders, 8 head-and-necks, 5 head-and-neck and salivary glands, 1 kidney, 6 lymph nodes, 4 pancreases, 3 parathyroid glands, 2 peripheral nerves, 3 peritoneums, 2 pituitary glands, 3 pleuras, 1 rectum, 1 skeletal muscle, 2 skins, 1 small intestine, 1 spleen, 1 stomach, 1 thyroid gland, 7 tracheas, 5 ureters, 1 urinary bladder, 1 breast, 5 ovaries, 5 placentas, 1 prostate, 1 testis, 2 thymi, 1 uterus, and 37 cancer samples (10 melanoma cancers, 17 ovarian cancers, 10 uterine cancers). FIG. 2G—SPINK2, Peptide: ALSVLRLAL, (SEQ ID NO.: 251)—Tissues from left to right: 6 arteries, 2 blood cellss, 6 brains, 4 hearts, 8 livers, 6 lungs, 2 veins, 1 adipose tissue, 5 adrenal glands, 1 bile duct, 5 bone marrows, 1 cartilage, 1 chest wall and skeletal muscle, 1 colon, 5 esophagi, 2 eyes, 2 gallbladders, 8 head-and-necks, 5 head-and-neck and salivary glands, 1 kidney, 6 lymph nodes, 4 pancreases, 3 parathyroid glands, 2 peripheral nerves, 3 peritoneums, 2 pituitary glands, 3 pleuras, 1 rectum, 1 skeletal muscle, 2 skins, 1 small intestine, 1 spleen, 1 stomach, 1 thyroid gland, 7 tracheas, 5 ureters, 1 urinary bladder, 1 breast, 5 ovaries, 5 placentas, 1 prostate, 1 testis, 2 thymi, 1 uterus, and 11 acute myeloid leukemia samples. FIG. 2H—MAGEC2, Peptide: TLDEKVAEL, (SEQ ID NO.: 24)—Tissues from left to right: 6 arteries, 2 blood cellss, 6 brains, 4 hearts, 8 livers, 6 lungs, 2 veins, 1 adipose tissue, 5 adrenal glands, 1 bile duct, 5 bone marrows, 1 cartilage, 1 chest wall and skeletal muscle, 1 colon, 5 esophagi, 2 eyes, 2 gallbladders, 8 head-and-necks, 5 head-and-neck and salivary glands, 1 kidney, 6 lymph nodes, 4 pancreases, 3 parathyroid glands, 2 peripheral nerves, 3 peritoneums, 2 pituitary glands, 3 pleuras, 1 rectum, 1 skeletal muscle, 2 skins, 1 small intestine, 1 spleen, 1 stomach, 1 thyroid gland, 7 tracheas, 5 ureters, 1 urinary bladder, 1 breast, 5 ovaries, 5 placentas, 1 prostate, 1 testis, 2 thymi, 1 uterus, and 29 cancer samples (19 liver cancers, 10 melanoma cancers). FIG. 2I—C1orf186, Peptide: FLTAINYLL, (SEQ ID NO.: 72)—Tissues from left to right: 6 arteries, 2 blood cellss, 6 brains, 4 hearts, 8 livers, 6 lungs, 2 veins, 1 adipose tissue, 5 adrenal glands, 1 bile duct, 5 bone marrows, 1 cartilage, 1 chest wall and skeletal muscle, 1 colon, 5 esophagi, 2 eyes, 2 gallbladders, 8 head-and-necks, 5 head-and-neck and salivary glands, 1 kidney, 6 lymph nodes, 4 pancreases, 3 parathyroid glands, 2 peripheral nerves, 3 peritoneums, 2 pituitary glands, 3 pleuras, 1 rectum, 1 skeletal muscle, 2 skins, 1 small intestine, 1 spleen, 1 stomach, 1 thyroid gland, 7 tracheas, 5 ureters, 1 urinary bladder, 1 breast, 5 ovaries, 5 placentas, 1 prostate, 1 testis, 2 thymi, 1 uterus, and 49 cancer samples (11 acute myeloid leukemia samples, 17 ovarian cancer samples, 11 renal cell carcinoma samples, 10 uterine cancer samples).

Figure 3A:
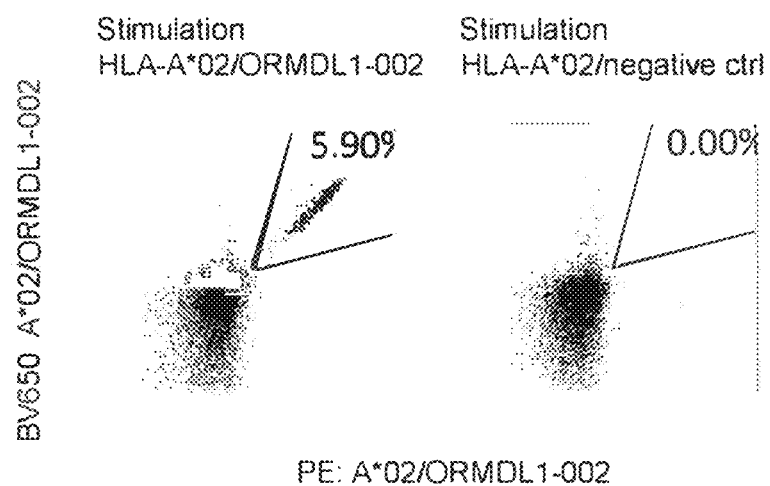
FIGS. 3A and 3B describe simulation graphs of various peptides of the present disclosure.
Figure 3B:
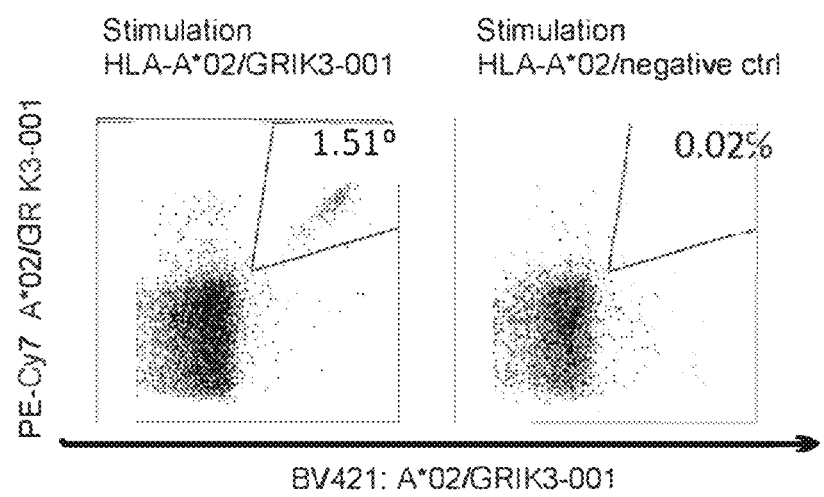

FIGS. 3A and 3B show exemplary immunogenicity data: flow cytometry results after peptide-specific multimer staining.

Figure 4A:
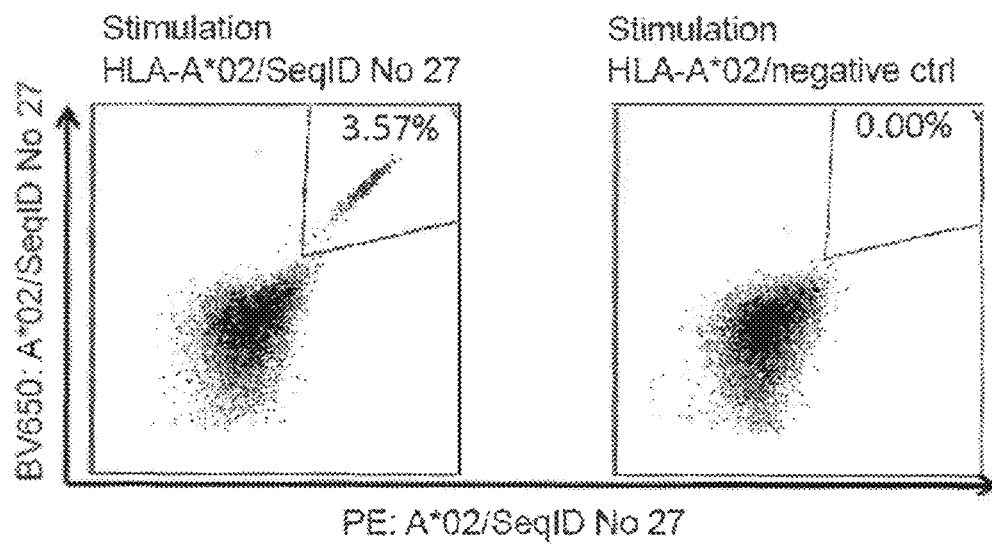
FIGS. 4A-4D describe simulation graphs of various peptides of the present disclosure.
Figure 4B:
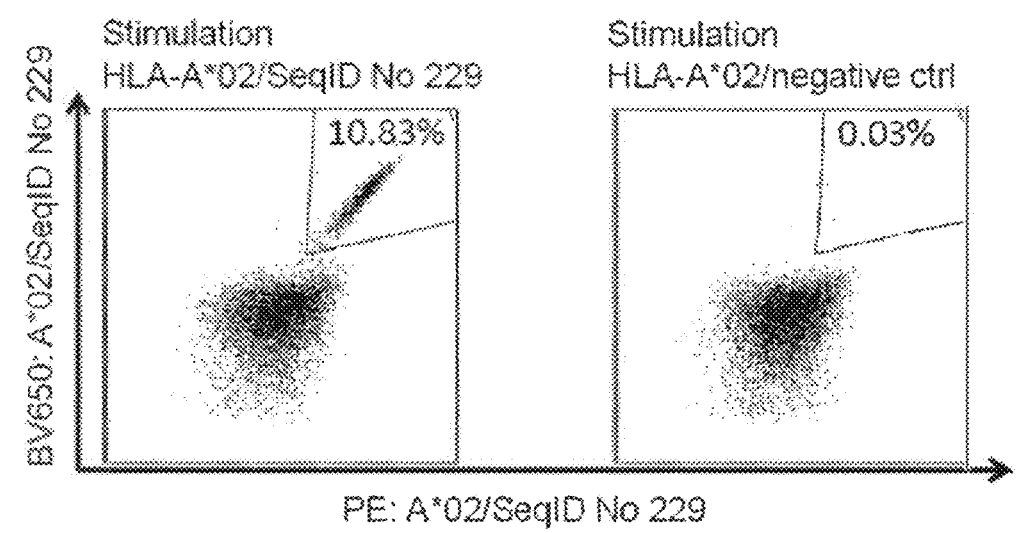
Figure 4C:
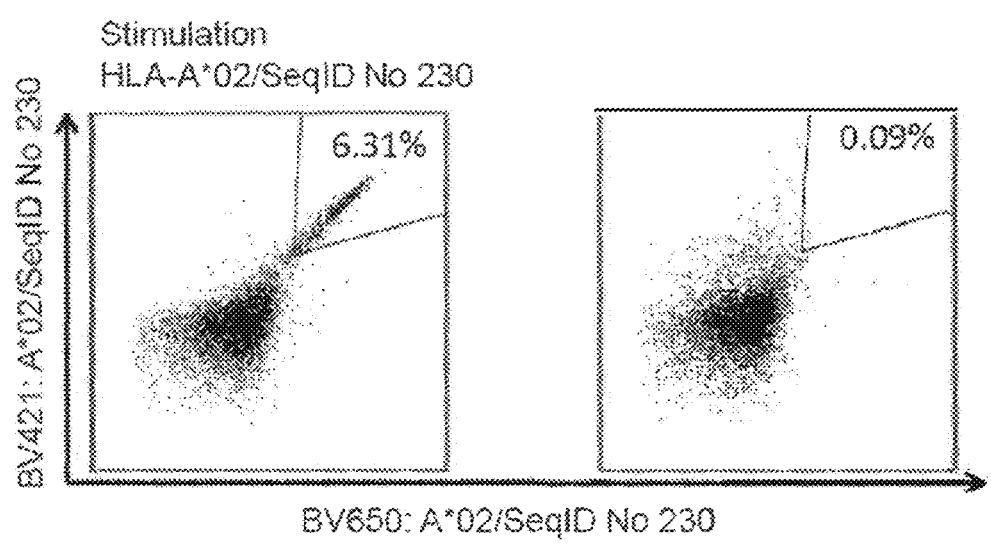
Figure 4D:
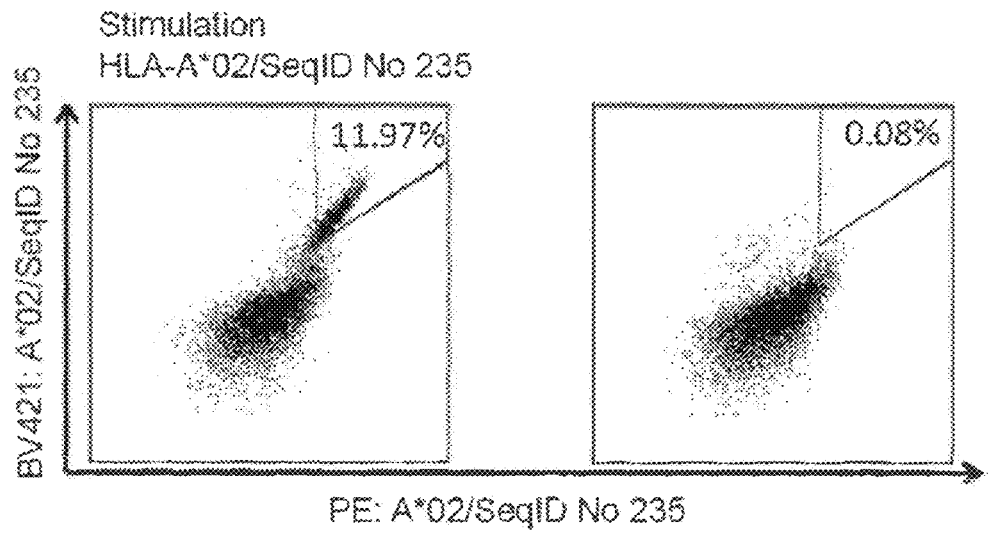

FIGS. 4A to 4D show exemplary results of peptide-specific in vitro CD8+ T cell responses of a healthy HLA-A*02+donor. CD8+ T cells were primed using artificial APCs coated with anti-CD28 mAb and HLA-A*02 in complex with SeqID No 27 peptide (FIG. 4A, left panel), SeqID No 229 peptide (FIG. 4B, left panel), SeqID No 230 peptide (FIG. 4C, left panel) and SeqID No 235 peptide (FIG. 4D, left panel), respectively. After three cycles of stimulation, the detection of peptide-reactive cells was performed by 2D multimer staining with A*02/SeqID No 27 (FIG. 4A), A*02/SeqID No 229 (FIG. 4B), A*02/SeqID No 230 (FIG. 4C) or A*02/SeqID No 235 (FIG. 4D). Right panels (FIGS. 4A, 4B, 4C and 4D) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 5A:
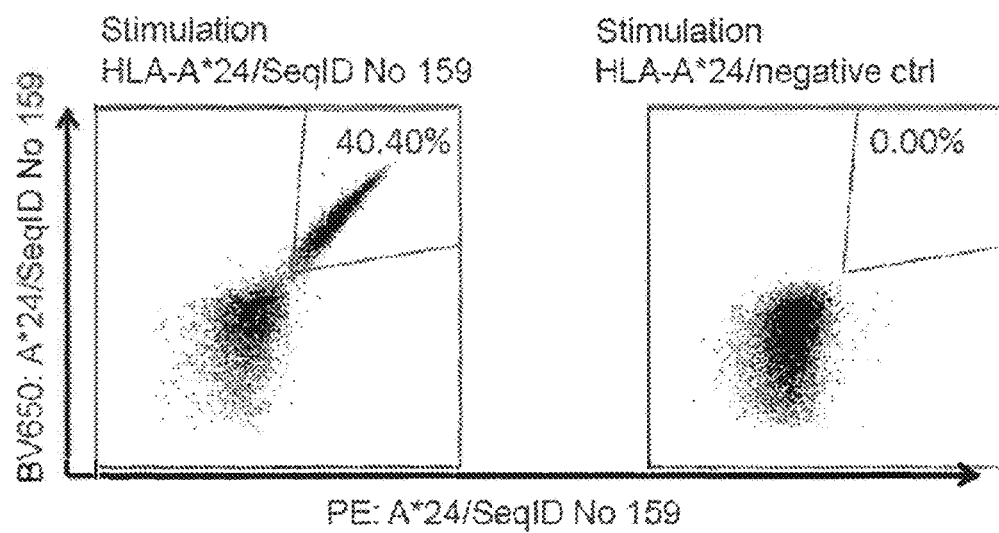
FIGS. 5A-5C describe simulation graphs of various peptides of the present disclosure.
Figure 5B:
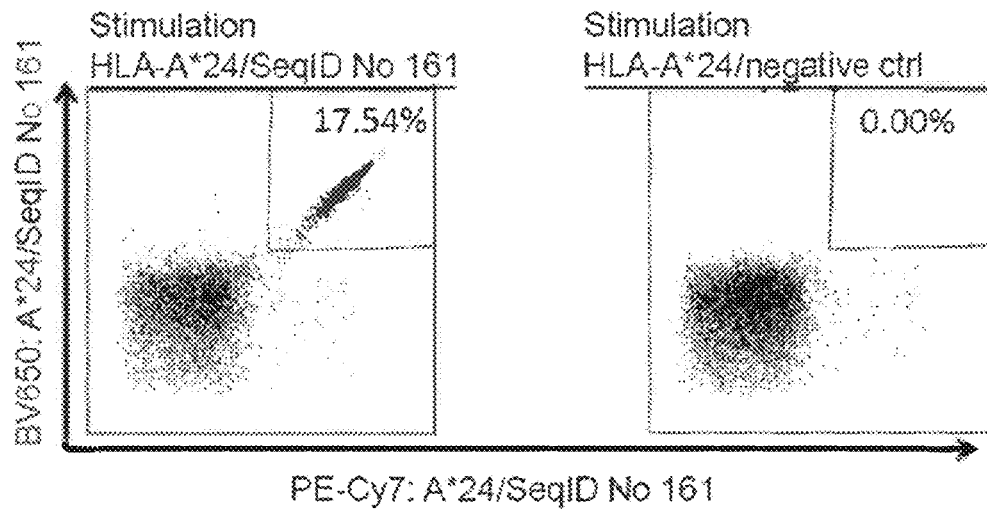
Figure 5C:
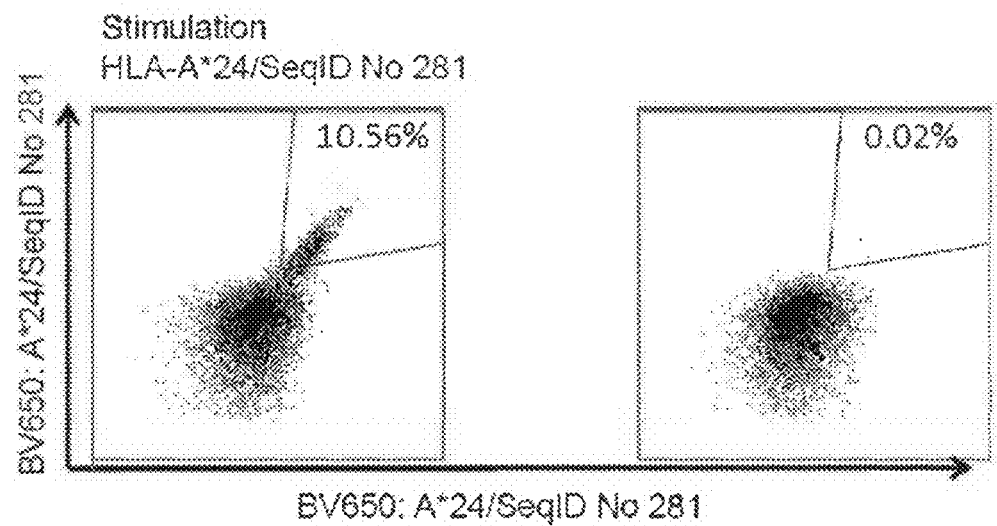

FIGS. 5A to 5C show exemplary results of peptide-specific in vitro CD8+ T cell responses of a healthy HLA-A*24+donor. CD8+ T cells were primed using artificial APCs coated with anti-CD28 mAb and HLA-A*24 in complex with SeqID No 159 peptide (FIG. 5A, left panel), SeqID No 161 peptide (FIG. 5B, left panel) and SeqID No 281 peptide (FIG. 5C, left panel), respectively. After three cycles of stimulation, the detection of peptide-reactive cells was performed by 2D multimer staining with A*24/SeqID No 159 (FIG. 5A), A*24/SeqID No 161 (FIG. 5B) or A*24/SeqID No 281 (FIG. 5C). Right panels (FIGS. 5A, 5B and 5C) show control staining of cells stimulated with irrelevant A*24/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1

Identification and Quantitation of Tumor Associated Peptides Presented on the Cell Surface Tissue Samples Patients' tumor tissues were obtained from:

Asterand (Detroit, MI, USA & Royston, Herts, UK); Bio-Options Inc. (Brea, CA, USA); BioServe (Beltsville, MD, USA); Center for cancer immune therapy (CCIT), Herlev Hospital (Herlev, Denmark); Geneticist Inc. (Glendale, CA, USA); Indivumed GmbH (Hamburg, Germany); Istituto Nazionale Tumori "Pascale" (Naples, Italy); Kyoto Prefectural University of Medicine (KPUM) (Kyoto, Japan); Leiden University Medical Center (LUMC) (Leiden, Netherlands); ProteoGenex Inc. (Culver City, CA, USA); Saint Savas Hospital (Athens, Greece); Stanford Cancer Center (Stanford, CA, USA); Tissue Solutions Ltd (Glasgow, UK); University Hospital Bonn (Bonn, Germany); University Hospital Geneva (Geneva, Switzerland); University Hospital Heidelberg (Heidelberg, Germany); University Hospital Munich (Munich, Germany); Osaka City University (OCU) (Osaka, Japan); University Hospital Tübingen (Tübingen, Germany); Val d'Hebron University Hospital (Barcelona, Spain).

Normal Tissues were Obtained from

Asterand (Detroit, MI, USA & Royston, Herts, UK); BioCat GmbH (Heidelberg, Germany); Bio-Options Inc. (Brea, CA, USA); BioServe (Beltsville, MD, USA); Capital BioScience Inc. (Rockville, MD, USA); Geneticist Inc. (Glendale, CA, USA); Kyoto Prefectural University of Medicine (KPUM) (Kyoto, Japan); ProteoGenex Inc. (Culver City, CA, USA); Tissue Solutions Ltd (Glasgow, UK); University Hospital Geneva (Geneva, Switzerland); University Hospital Heidelberg (Heidelberg, Germany); University Hospital Munich (Munich, Germany); Osaka City University (OCU) (Osaka, Japan); University Hospital Tübingen (Tübingen, Germany).

Written informed consents of all patients had been given before surgery or autopsy. Tissues were shock-frozen immediately after excision and stored until isolation of TUMAPs at −70° C. or below.

Peptides were selected if three conditions were true: (1) Its underlying transcript(s) and/or exon(s) are expressed at low levels, i.e. the median reads per kilobase per million reads (RPKM) was required to be less than 10 for the following organs: brain, blood vessel, heart, liver, lung, blood. In addition, the median RPKM was required to be less than 50 for the following organs: urinary bladder, salivary gland, stomach, adrenal gland, colon, small intestine, spleen, bone marrow, pancreas, muscle, adipose tissue, skin, esophagus, kidney, thyroid gland, pituitary gland, nerve. (2) Its underlying transcript(s) and/or exon(s) are considered over-expressed if the highest 90% percentile of expression level in a tumor sample (based on data generated by the TCGA Research Network) was more than 6-fold above the highest 75% percentile of expression levels determined from normal samples based on a database of RNASeq data covering around 3000 normal tissue samples (Lonsdale, 2013). (3) The peptide was tumor-associated, i.e. found specifically or on tumors or over-expressed compared to a baseline of normal tissues (cf. Example 1).

Sample numbers for HLA-A*02 TUMAP selection were: for pancreatic cancer N=16, for renal cancer N=20, for colorectal cancer N=28, for esophageal carcinoma including cancer of the gastric-esophageal junction N=17, for prostate tumors N=39, for hepatocellular carcinoma N=16, for non-small cell lung cancer N=90, for gastric cancer N=29, for breast cancer N=17, for melanoma N=7, for ovarian cancer N=20, for chronic lymphocytic leukemia N=17, for urinary bladder cancer N=16, for small-cell lung cancer N=19, for gallbladder cancer and cholangiocarcinoma N=6, for acute myeloid leukemia N=18, for glioblastoma N=41, for testis cancer N=1, for Non-Hodgkin lymphoma N=18, for uterine cancer N=15, and for normal tissues N=262.

Sample numbers for HLA-A*24 TUMAP selection were: for gastric cancer N=44, for prostate tumors N=40, for non-small cell lung cancer N=91, for hepatocellular carcinoma N=15, for renal cancer N=2, for colorectal cancer N=1, for glioblastoma N=18 and for normal tissues N=70.

FIGS. 1A-1T also show results for cell lines including kidney cancer cell lines, melanoma cell lines, pancreatic cancer cell lines and benign prostate hyperplasias.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the Orbitrap (R=30 000), which was followed by MS/MS scans also in the Orbitrap (R=7500) on the five most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose different cancer samples to a baseline of normal tissue samples.

Presentation profiles of exemplary over-presented peptides are shown in FIGS. 1A-1T. Presentation scores for exemplary peptides are shown in Table 15 and Table 16.

Table 13 (A and B) and Table 14 (A and B) show the presentation on various cancer entities for selected peptides, and thus the particular relevance of the peptides as mentioned for the diagnosis and/or treatment of the cancers as indicated (e.g. peptide SEQ ID No. 1 for glioblastoma, non-small cell lung cancer, and ovarian cancer, peptide SEQ ID No. 2 for glioblastoma, gastric cancer, non-small cell lung cancer, urinary bladder cancer, gallbladder adenocarcinoma and cholangiocarcinoma, renal cell carcinoma, colorectal cancer and pancreatic cancer).

Overview of presentation of selected HLA-A*02-binding tumor-associated peptides of the present invention across entities.

| SEQ ID No. | Sequence | Peptide Presentation on cancer entities |
|---|---|---|
| 1 | LLYPEPWSV | GB, NSCLC, OC |
| 2 | GLIAGVVSI | GB, GC, NSCLC, UBC, GBC_CCC, RCC, CRC, PC |
| 3 | KLEENGDLYL | NSCLC, OC, SCLC, UBC, BRCA, GBC_CCC, MEL, NHL |
| 4 | KLMPGTYTL | NSCLC, OC, UEC, AML, NHL |
| 5 | GIVAHIQEV | GC, NSCLC, PCA, CLL, OSCAR, OC, CRC, AML, NHL |
| 6 | ALFDSLRHV | GB |
| 7 | ILDHEVPSL | NSCLC, CLL, OSCAR, OC, UBC, MEL, RCC, AML, |

Overview of presentation of selected HLA-A*02-binding tumor-associated peptides of the present invention across entities.

| SEQ ID No. | Sequence | Peptide Presentation on cancer entities |
|---|---|---|
| 8 | SIYQFLIAV | NSCLC, CLL, GBC_CCC, AML, NHL |
| 9 | FLVDGSYSI | NSCLC, OSCAR, GBC_CCC, CRC |
| 10 | GIAGSLKTV | NSCLC, OSCAR, UBC, UEC, CRC, AML |
| 11 | ALSPSYLTV | GC, NSCLC, CLL, BRCA, GBC_CCC, NHL |
| 12 | GLLPLLHRA | GB, NSCLC, UEC, RCC |
| 13 | ALMAMLVYV | GC, NSCLC, OC, SCLC, BRCA, GBC_CCC |
| 14 | ILAKDLFEI | NSCLC, HCC, OSCAR, UBC, AML, NHL |
| 15 | YLDLSHNQL | NSCLC, CLL, BRCA, GBCCCC |
| 16 | YTLDIPVLFGV | NSCLC, HCC, CLL, MEL, NHL |
| 17 | AVFPDDMPTL | GC, NSCLC, OSCAR, OC, NHL |
| 18 | ILLDLTDNRL | NSCLC, OSCAR, UBC, BRCA, MEL, RCC, CRC |
| 19 | SISDNVWEV | GB, OSCAR, OC, UEC, BRCA, MEL, NHL |
| 20 | GLSQITNQL | CLL, UBC, NHL |
| 21 | AIQDEIRSV | GB, NSCLC, OSCAR, OC, BRCA, NHL |
| 22 | FVDPNTQEKV | GC, HCC, OSCAR, OC, UBC, BRCA, |
| 23 | SLFSDEFKV | NSCLC, OSCAR, UBC, RCC, CRC, AML, |
| 24 | TLDEKVAEL | NSCLC, HCC, OSCAR, MEL, |
| 25 | TMDSVLVTV | OC, UEC |
| 26 | ALQEELTEL | BRCA, GBC_CCC, MEL, AML, NHL |
| 27 | RLMEENWNA | NSCLC, OSCAR, OC, UEC, CRC |
| 28 | SLPNGKPVSV | NSCLC, OC, UBC, NHL |
| 29 | YLLDPSITL | NSCLC, CLL, BRCA, GBC_CCC, AML, NHL |
| 30 | AMIEEVFEA | PCA, OC, SCLC, UBC, BRCA, MEL |
| 31 | TITETTVEV | GB |
| 32 | VQLDSIEDLEV | CLL, OC |
| 33 | YIKTELISV | GC, NSCLC, OSCAR, OC, NHL |
| 34 | FLLATEVVTV | OC, SCLC, AML, NHL |
| 35 | FLLPFSTVYL | NSCLC, CLL, OC, AML, NHL |
| 36 | SLADTNSLAVV | SCLC, MEL |
| 37 | ILAPFSVDL | AML |
| 38 | FLGPRIIGL | CLL, AML, NHL |
| 39 | HLLEGSVGV | BRCA |
| 40 | VLIDPQWVLTA | OC, NHL |
| 41 | ALFENTPKA | GB |
| 42 | LLDSVSRL | NSCLC, GBC_CCC, CRC |
| 43 | KAIEVLLTL | GC, OSCAR, AML |
| 44 | SLFETAWEA | NSCLC, MEL, AML, NHL |
| 45 | SLTEVSLPL | OC, GBC_CCC, AML, NHL |
| 46 | SQFPLPLAV | GC, NSCLC, OSCAR, UBC |
| 47 | ALLERGELFV | NSCLC, CLL, OC, NHL |
| 48 | QVIEDSTGV | GC, NSCLC, OSCAR, OC |
| 49 | ALNIATHVL | NSCLC, CLL, UBC, NHL |
| 50 | ILFHGVFYA | NSCLC, OC, UBC, BRCA |
| 51 | LLFSRLCGA | GB, NSCLC |
| 52 | RLAVLFSGA | GC, NSCLC, OSCAR, OC |
| 53 | KMVGLVVAI | CLL, AML, NHL |
| 54 | VLNPLITAV | NSCLC, PCA, AML, NHL |
| 55 | SLATKIVEA | PCA, OC, BRCA, AML |
| 56 | FLHDEKEGIYI | NSCLC, OC, NHL |
| 57 | TVFTDHMLTV | NSCLC, OSCAR, OC, NHL |
| 58 | YLLPLLPAL | GB |
| 59 | KLLDPQEFTL | GB, NSCLC |
| 60 | ALFAPLVHL | AML |
| 61 | AIVKEIVNI | GC, NSCLC, OSCAR |
| 62 | ALNPELVQA | GB, NSCLC, RCC |
| 63 | SQIPAQPSV | GC, NSCLC, OSCAR |
| 64 | SLFPDSLIV | PCA |

Overview of presentation of selected HLA-A*02-binding tumor-associated peptides of the present invention across entities.

| SEQ ID No. | Sequence | Peptide Presentation on cancer entities |
|---|---|---|
| 65 | SVVPDVRSV | GC, NSCLC, OSCAR |
| 66 | KLIFSVEAV | NSCLC, SCLC, UEC, BRCA |
| 67 | TLLQRLTEV | NSCLC, CLL, RCC, AML |
| 68 | SLSNRLYYL | GC, OSCAR, CRC |
| 69 | FLAVGLVDV | AML, NHL |
| 70 | LLLGDSALYL | RCC, NHL |
| 71 | VLHSKFWVV | CLL, NHL |
| 72 | FLTAINYLL | OC, RCC |
| 73 | YTLREVDTV | NSCLC, OSCAR, OC |
| 74 | TLFGYSVVL | AML |
| 75 | AVIKFLELL | GC, NSCLC, OSCAR |
| 76 | AVGPVHNSV | GC, OSCAR |
| 77 | TLIDEQDIPLV | NSCLC, OC, SCLC |
| 78 | TVVTRLDEI | GC, OSCAR, OC |
| 79 | VTFKEYVTV | GC, NSCLC, OSCAR |
| 80 | KLYEADFVL | NSCLC, AML, NHL |
| 81 | NALDKVLSV | GC, NSCLC, OSCAR |
| 82 | FIFDEAEKL | GC, NSCLC, OSCAR |
| 83 | GQASYFYVA | CRC, AML |
| 84 | ALCPRIHEV | GB |
| 85 | VLNDILVRA | OC, UEC |
| 86 | SVDSHFQEV | GC, OSCAR, OC |
| 87 | TIYKDFVYI | GC, NSCLC, OSCAR |
| 88 | AQADHLPQL | GC, NSCLC, OSCAR |
| 89 | QLAPVFQRV | CLL, OC, NHL |
| 90 | FLQDLEQRL | GC, NSCLC, PCA, CLL, OSCAR, OC, SCLC, UBC, UEC, BRCA, GBC_CCC, CRC, NHL |
| 91 | KLFDESILI | GC, NSCLC, PCA, CLL, OSCAR, OC, SCLC, UEC, BRCA, AML, NHL |
| 92 | GLLFSLRSV | NSCLC, HCC, PCA, CLL, OSCAR, OC, UBC, BRCA, MEL, RCC, CRC, AML, NHL |
| 93 | QVLELDVADI | GC, NSCLC, PCA, SCLC, UBC, UEC, BRCA, CRC, AML, NHL |
| 94 | LLLPAVPVGA | GB, NSCLC, OC, UBC, CRC, AML |
| 95 | GLLGSLFFL | NSCLC, OC, SCLC, UEC, BRCA, GBC_CCC, AML, NHL |
| 96 | LLVSHLYLV | NSCLC, CLL, OC, UBC, NHL |
| 97 | STLPKSLSL | GB, GC, NSCLC, HCC, PCA, OSCAR, OC, BRCA, NHL |
| 98 | RLFPDFFTRVAL | NSCLC |
| 99 | YLLQSVNQLLL | NSCLC, CLL, NHL |
| 100 | ALLGMIIVGV | PCA, SCLC, BRCA |
| 101 | ALADFMLSL | AML |
| 102 | VLLDIQEVFQI | AML |
| 103 | YLVSEIFKA | AML |
| 104 | ALISWQPPRA | GB |
| 105 | ALLGTKILL | NHL |
| 106 | FINDSIVYL | AML |
| 107 | LLVPTSGIYFV | NHL |
| 108 | ILLKNLVTI | BRCA |
| 109 | SLDPSVTHL | UEC |
| 110 | FLLGVSKEV | MEL |
| 111 | AIVDLIHDI | GC, NSCLC, OSCAR |
| 112 | SLGKFTFDV | NSCLC, UEC |
| 113 | FLERGLESA | GC, OSCAR, UBC |
| 114 | QLIQTLHAV | OC, RCC |
| 115 | SLDPDTLPAV | NSCLC, OC |
| 116 | TIDESGSIL | UBC, NHL |
| 117 | KMPDVELFV | NSCLC |
| 118 | QLWQFLVTL | OC |
| 119 | FIIQGLRSVGA | NSCLC, OC |
| 120 | VTPVTVSAV | GC, OSCAR |
| 121 | FTIFRTISV | CLL |
| 122 | GVVDPVHGV | GC, NSCLC, OSCAR |
| 123 | VLDPALPALV | OC, UBC |
| 124 | KVMATIEKV | NSCLC, OC |
| 125 | SLADYEHFV | GB, PCA |

Overview of presentation of selected HLA-A*02-binding tumor-associated peptides of the present invention across entities.

| SEQ ID No. | Sequence | Peptide Presentation on cancer entities |
|---|---|---|
| 126 | QMFQYFITV | NSCLC, CLL |
| 127 | KLDGNELDL | NSCLC |
| 128 | TQSPATLSV | GC, OSCAR |
| 129 | RLQDILWFL | NSCLC, AML |
| 130 | SLLGGTFVGI | UBC |
| 131 | VTSNSGILGV | CLL, NHL |
| 132 | ILGEVLAQL | CLL, NHL |
| 133 | ALLPRLHQL | PCA |
| 134 | GLAVPTPSV | NSCLC, OC |
| 135 | HLSTIIHEA | NSCLC, CLL |
| 136 | FLFGGVLMTL | OC, NHL |
| 137 | EIASITEQL | GB, NSCLC |
| 138 | ALLAKILQI | GB, GC, NSCLC, HCC, PCA, CLL, OSCAR, OC, SCLC, UBC, BRCA, GBC_CCC, MEL, RCC, CRC, AML, NHL |
| 139 | FLLPTGAEA | GC, NSCLC, HCC, PCA, CLL, OSCAR, OC, SCLC, UBC, UEC, BRCA, MEL, RCC, CRC, PC, AML, NHL |
| 140 | VLLEELEAL | NSCLC, PCA, CLL, OSCAR, OC, SCLC, UEC, BRCA, GBC_CCC, MEL, AML, NHL |
| 141 | FLDKVLVAA | GC, NSCLC, PCA, CLL, OSCAR, UBC, RCC, AML, NHL |
| 142 | ILVEGISTV | GB, NSCLC, PCA, OC, SCLC, BRCA, GBC_CCC |
| 143 | ALLPELREV | GB, GC, NSCLC, HCC, BRCA, GBC_CCC, RCC, CRC |
| 144 | ALLAFFPGL | GB, GC, NSCLC, OSCAR, OC, UBC, BRCA, MEL, CRC, PC, AML, NHL |
| 145 | YLWATIQRI | NSCLC, OSCAR, OC, AML |
| 146 | ALHFSEDEI | PCA, UEC |
| 147 | YLMDDTVEI | OC, GBC_CCC |
| 148 | MLAGIAITV | GB, GBC_CCC |
| 149 | ILNTHITEL | NHL |
| 150 | VLYDRPLKI | NSCLC, CLL, OSCAR, OC, MEL, RCC, CRC, NHL |
| 151 | SVLDSTAKV | GC, NSCLC, OSCAR, OC, UBC, BRCA, RCC, CRC, NHL |
| 152 | MMVGDLLEV | GB, GC, NSCLC, CLL, MEL, CRC, AML, NHL |
| 153 | FISERVEVV | NSCLC, PCA, CLL, OSCAR, OC, UBC, NHL |
| 154 | RLLGTEFQV | NSCLC, HCC, MEL, |
| 155 | LLNPVVEFV | CLL, OC, GBC_CCC, NHL |
| 156 | ILGDLSHLL | NSCLC, PC |
| 157 | TLTSLLAQA | UBC |
| 229 | AILAHLNTV | GB, NSCLC, HCC, CLL, OSCAR, OC, SCLC, UBC, BRCA, CRC, AML, NHL |
| 230 | KLQNIMMLL | NSCLC, HCC, CLL, UBC, BRCA, GBC_CCC, RCC, CRC, AML, NHL |
| 231 | MLDKYSHYL | NSCLC, CLL, OSCAR, OC, NHL |
| 232 | KIFPAALQLV | NSCLC, HCC, CLL, OC, SCLC, UBC, UEC, GBC_CCC, CRC, NHL |
| 233 | HLFDAFVSV | NSCLC, UBC, BRCA, CRC, AML, NHL |
| 234 | LLSPHNPAL | NSCLC, CLL, OSCAR, OC, UBC, BRCA, NHL |
| 235 | KIIDFLSAL | OC, UEC, AML, NHL |
| 236 | STIAILNSV | GB, GC, NSCLC, PCA, CLL, OSCAR, NHL |
| 237 | ALAPHLDDA | GB, NSCLC, HCC, OC, UBC, UEC, BRCA, MEL |
| 238 | GLYERPTAA | NSCLC, PCA, PC, AML |
| 239 | KMNESTRSV | NSCLC, GBC_CCC, NHL |
| 240 | YMGEEKLIASV | NSCLC, CLL, OC, UBC, MEL, |
| 241 | KTIQQLETV | NSCLC, OC, NHL |
| 242 | WLYGEDHQI | NSCLC, UEC, AML |
| 243 | FMADDIFSV | NHL |
| 244 | YLLEKNRVV | NSCLC, OSCAR, OC |
| 245 | SLLDLPLSL | CLL, NHL |
| 246 | TVSDVLNSV | GB, NSCLC, CLL |

Overview of presentation of selected HLA-A*02-binding tumor-associated peptides of the present invention across entities.

| SEQ ID No. | Sequence | Peptide Presentation on cancer entities |
|---|---|---|
| 247 | ALYEGYATV | NSCLC, HCC, CLL, OSCAR, OC, SCLC, UBC, UEC, BRCA, GBC_CCC, MEL, RCC, CRC, PC, NHL |
| 248 | YLDRFLAGV | GB, NSCLC, PCA, CLL, CRC, AML, NHL |
| 249 | GLCERLVSL | GB, NSCLC, CLL, RCC, CRC |
| 250 | SLAPATPEV | MEL, NHL |
| 251 | ALSVLRLAL | AML |
| 252 | RLMEICESL | AML |
| 253 | ALAELIDNSL | CLL |
| 254 | KLQGKLPEL | NSCLC, NHL |
| 255 | SLLHFTENL | AML, NHL |
| 256 | SLGEEQFSV | MEL, NHL |
| 257 | GLYTDPCGV | NSCLC, NHL |
| 258 | LLSERFINV | HCC, PCA |
| 259 | ILLPRIIEA | NSCLC, OC |
| 260 | ILLEKILSL | NSCLC, CRC |
| 261 | QLQDRVYAL | NSCLC, HCC, CLL, OSCAR, OC, SCLC, UBC, BRCA, RCC, CRC, NHL |
| 262 | FMVDKAIYL | GC, NSCLC, PCA, OSCAR, OC, SCLC, BRCA, GBC_CCC, CRC, PC, NHL |
| 263 | VLLSEQGDVKL | NSCLC, PCA, CLL, OSCAR, OC, MEL, NHL |
| 264 | KLFPQETLFL | NSCLC, CLL, OSCAR, AML, NHL |
| 265 | NTCPYVHNI | GB, CLL |
| 266 | YAIGLVMRL | CLL, BRCA, AML |
| 290 | KIVDFSYSV | GB, GC, NSCLC, HCC, OSCAR, OC, SCLC, UBC, UEC, BRCA, MEL, CRC, AML, NHL |
| 291 | KLDETGNSL | GB, GC, NSCLC, HCC, CLL, OSCAR, OC, SCLC, UBC, UEC, MEL, RCC, CRC, PC, AML, NHL |
| 292 | GMMTAILGV | GB, GC, NSCLC, HCC, PCA, CLL, UEC, GBC_CCC, RCC, CRC, PC, AML, NHL |
| 293 | FLVDGSWSI | GB |
| 294 | GLMKYIGEV | PCA |

GB = glioblastoma,
BRCA = breast cancer,
CRC = colorectal cancer,
RCC = renal cell carcinoma,
CLL = chronic lymphocytic leukemia,
HCC = hepatocellular carcinoma,
NSCLC = non-small cell lung cancer,
SCLC = small cell lung cancer,
NHL = non-Hodgkin lymphoma,
AML = acute myeloid leukemia,
OC = ovarian cancer,
PC = pancreatic cancer,
PCA = prostate cancer and benign prostate hyperplasia,
OSCAR = esophageal cancer, including cancer of the gastric-esophageal junction,
GBC_CCC = gallbladder adenocarcinoma and cholangiocarcinoma,
MEL = melanoma,
GC = gastric cancer,
UBC = urinary bladder cancer,
UEC = uterine cancer.

Tables 13B show the presentation on additional cancer entities for selected peptides, and thus the particular relevance of the peptides as mentioned for the diagnosis and/or treatment of the cancers as indicated.

TABLE 13B

Overview of presentation of selected HLA-A*02-binding tumor-associated peptides of the present invention across entities.

| SEQ ID No. | Sequence | Peptide Presentation on cancer entities |
|---|---|---|
| 1 | LLYPEPWSV | SCLC, UEC, HNSCC |
| 2 | GLIAGVVSI | HCC, UEC, HNSCC |
| 3 | KLEENGDLYL | HCC, UEC, AML, HNSCC |
| 4 | KLMPGTYTL | MEL, HNSCC |
| 5 | GIVAHIQEV | UEC, MEL |
| 7 | ILDHEVPSL | HNSCC |
| 8 | SIYQFLIAV | UEC, BRCA, CRC, HNSCC |
| 10 | GIAGSLKTV | SCLC, MEL, AML |
| 11 | ALSPSYLTV | HNSCC |
| 12 | GLLPLLHRA | MEL, RCC |
| 13 | ALMAMLVYV | GBC_CCC, MEL, NHL, HNSCC |
| 14 | ILAKDLFEI | SCLC |
| 15 | YLDLSHNQL | OSCAR, GBC_CCC, HNSCC |
| 16 | YTLDIPVLFGV | HNSCC |
| 18 | ILLDLTDNRL | AML, HNSCC |
| 19 | SISDNVWEV | HNSCC |

TABLE 13B-continued

Overview of presentation of selected HLA-A*02-binding tumor-associated peptides of the present invention across entities.

| SEQ ID No. | Sequence | Peptide Presentation on cancer entities |
|---|---|---|
| 20 | GLSQITNQL | MEL, AML |
| 21 | AIQDEIRSV | MEL, CRC, AML |
| 22 | FVDPNTQEKV | HNSCC |
| 23 | SLFSDEFKV | MEL |
| 26 | ALQEELTEL | NSCLC, CRC, HNSCC |
| 28 | SLPNGKPVSV | OSCAR, SCLC, HNSCC |
| 29 | YLLDPSITL | HCC, SCLC, MEL, HNSCC |
| 30 | AMIEEVFEA | NSCLC, HCC, UEC, GBC_CCC, NHL, HNSCC |
| 32 | VQLDSIEDLEV | NSCLC, OC, UEC, MEL |
| 33 | YIKTELISV | HCC |
| 35 | FLLPFSTVYL | HNSCC |
| 38 | FLGPRIIGL | CRC |
| 39 | HLLEGSVGV | HCC, MEL |
| 40 | VLIDPQWVLTA | CRC |
| 42 | LLDSVSRL | CRC |
| 43 | KAIEVLLTL | NSCLC, AML |
| 44 | SLFETAWEA | UEC, CRC, HNSCC |
| 45 | SLTEVSLPL | NSCLC, CRC, HNSCC |
| 46 | SQFPLPLAV | MEL, HNSCC |
| 47 | ALLERGELFV | OSCAR, UBC, AML |
| 48 | QVIEDSTGV | OC |
| 49 | ALNIATHVL | CRC |
| 50 | ILFHGVFYA | SCLC |
| 51 | LLFSRLCGA | UEC |
| 52 | RLAVLFSGA | HCC |
| 53 | KMVGLVVAI | MEL |
| 54 | VLNPLITAV | HCC, SCLC, UEC, MEL, RCC |
| 55 | SLATKIVEA | AML |
| 56 | FLHDEKEGIYI | AML |
| 60 | ALFAPLVHL | NHL |
| 63 | SQIPAQPSV | AML, HNSCC |
| 64 | SLFPDSLIV | NSCLC, HCC, BRCA, PC |
| 66 | KLIFSVEAV | OC, UBC, BRCA |
| 67 | TLLQRLTEV | NHL |
| 69 | FLAVGLVDV | SCLC |
| 70 | LLLGDSALYL | CRC |
| 72 | FLTAINYLL | UEC, RCC, AML |
| 73 | YTLREVDTV | AML |
| 76 | AVGPVHNSV | NSCLC |
| 77 | TLIDEQDIPLV | SCLC, NHL, HNSCC |
| 85 | VLNDILVRA | UEC |
| 86 | SVDSHFQEV | NSCLC, OC |
| 87 | TIYKDFVYI | OC |
| 90 | FLQDLEQRL | HNSCC |
| 91 | KLFDESILI | HCC, HNSCC |
| 92 | GLLFSLRSV | SCLC, HNSCC |
| 93 | QVLELDVADI | HNSCC |
| 94 | LLLPAVPVGA | SCLC |
| 95 | GLLGSLFFL | GC, OSCAR, UBC, MEL, RCC, CRC, PC, HNSCC |
| 96 | LLVSHLYLV | UEC, CRC, HNSCC |
| 98 | RLFPDFFTRVAL | NSCLC |
| 100 | ALLGMIIVGV | HCC, AML |
| 106 | FINDSIVYL | NSCLC, HCC, CRC, NHL |
| 110 | FLLGVSKEV | NHL |
| 116 | TIDESGSIL | MEL, AML |
| 117 | KMPDVELFV | NSCLC, SCLC, MEL |
| 118 | QLWQFLVTL | MEL |
| 123 | VLDPALPALV | NSCLC, UEC, HNSCC |
| 126 | QMFQYFITV | UEC |
| 130 | SLLGGTFVGI | HCC |
| 134 | GLAVPTPSV | HNSCC |
| 135 | HLSTIIHEA | CLL, UEC |
| 138 | ALLAKILQI | HNSCC |
| 139 | FLLPTGAEA | GBC CCC, HNSCC |
| 140 | VLLEELEAL | HCC, CRC, HNSCC |
| 141 | FLDKVLVAA | HCC, OC, UEC, BRCA, MEL, CRC, HNSCC |
| 143 | ALLPELREV | OC, SCLC, AML, HNSCC |
| 145 | YLWATIQRI | UEC |
| 148 | MLAGIAITV | GBC CCC, NHL |
| 149 | ILNTHITEL | BRCA |
| 150 | VLYDRPLKI | HCC, SCLC, UEC, BRCA |
| 151 | SVLDSTAKV | HCC, UEC, GBC_CCC, MEL, HNSCC |

TABLE 13B-continued

Overview of presentation of selected HLA-A*02-binding tumor-associated peptides of the present invention across entities.

| SEQ ID No. | Sequence | Peptide Presentation on cancer entities |
|---|---|---|
| 152 | MMVGDLLEV | UEC, HNSCC |
| 153 | FISERVEVV | SCLC, UEC |
| 154 | RLLGTEFQV | SCLC |
| 155 | LLNPVVEFV | NSCLC, HCC, BRCA, CRC, HNSCC |
| 157 | TLTSLLAQA | NSCLC, CRC, HNSCC |
| 229 | AILAHLNTV | UEC, HNSCC |
| 230 | KLQNIMMLL | HNSCC |
| 233 | HLFDAFVSV | MEL |
| 234 | LLSPHNPAL | GB, HCC, SCLC, UEC, MEL, RCC |
| 235 | KIIDFLSAL | NSCLC, HCC, MEL, HNSCC |
| 236 | STIAILNSV | MEL |
| 237 | ALAPHLDDA | SCLC, AML |
| 238 | GLYERPTAA | GC, MCC, OSCAR, CRC, NHL |
| 239 | KMNESTRSV | GB, CRC |
| 240 | YMGEEKLIASV | UEC, NHL |
| 243 | FMADDIFSV | SCLC |
| 244 | YLLEKNRVV | HNSCC |
| 245 | SLLDLPLSL | NSCLC, RCC, AML, HNSCC |
| 247 | ALYEGYATV | AML, HNSCC |
| 248 | YLDRFLAGV | SCLC, HNSCC |
| 249 | GLCERLVSL | MEL, NHL, HNSCC |
| 250 | SLAPATPEV | BRCA, HNSCC |
| 252 | RLMEICESL | UEC, MEL |
| 253 | ALAELIDNSL | NSCLC, AML |
| 254 | KLQGKLPEL | UEC, AML |
| 255 | SLLHFTENL | NSCLC, CRC |
| 257 | GLYTDPCGV | HNSCC |
| 259 | ILLPRIIEA | GB, GC, CLL, SCLC, UEC, BRCA, MEL, CRC, PC, HNSCC |
| 260 | ILLEKILSL | GC, HCC, PCA, CLL, OC, SCLC, UEC, BRCA, GBC_CCC, MEL, PC, AML, NHL, HNSCC |
| 261 | QLQDRVYAL | MEL |
| 262 | FMVDKAIYL | UEC, MEL, HNSCC |
| 263 | VLLSEQGDVKL | UEC, AML |
| 266 | YAIGLVMRL | HCC, GBC_CCC, MEL |
| 305 | KLFTSVFGV | AML |
| 306 | ALLSSLNEL | AML, PCA, BRCA, GBC_CCC, HCC, NHL, NSCLC, OC, GB, RCC, UBC, UEC |

GB = glioblastoma,
BRCA = breast cancer,
CRC = colorectal cancer,
RCC = renal cell carcinoma,
CLL = chronic lymphocytic leukemia,
HCC = hepatocellular carcinoma,
NSCLC = non-small cell lung cancer,
SCLC = small cell lung cancer,
NHL = non-Hodgkin lymphoma,
AML = acute myeloid leukemia,
OC = ovarian cancer,
PC = pancreatic cancer,
PCA = prostate cancer and benign prostate hyperplasia,
OSCAR = esophageal cancer, including cancer of the gastric-esophageal junction,
GBC_CCC = gallbladder adenocarcinoma and cholangiocarcinoma,
MEL = melanoma,
GC = gastric cancer,
UBC = urinary bladder cancer,
UEC = uterine cancer.

TABLE 14A

Overview of presentation of selected HLA-A*24-binding tumor-associated peptides of the present invention across entities.

| SEQ ID No. | Sequence | Peptide Presentation on cancer entities |
|---|---|---|
| 158 | HYSQELSLLYL | GB, GC, NSCLC, HCC, PCA, RCC |
| 159 | LYNKGFIYL | GB, NSCLC, RCC |
| 160 | VYTLDIPVL | GC, NSCLC, HCC, PCA |
| 161 | IYLVSIPEL | GC, NSCLC, PCA |
| 162 | VFTRVSSFL | GB, GC, NSCLC |
| 163 | DYLKGLASF | GB, GC, NSCLC |
| 164 | KFSSFSLFF | GC, NSCLC, PCA |
| 165 | DYTTWTALL | GC, NSCLC |
| 166 | YYVESGKLF | GB, NSCLC, HCC |
| 167 | NYINRILKL | GC |
| 168 | KYQDILETI | NSCLC, PCA |
| 169 | AYTLIAPNI | GC, NSCLC, HCC |
| 170 | VYEDQVGKF | GB, NSCLC |
| 171 | LFIPSSKLLFL | NSCLC, HCC, RCC |
| 172 | TYTTVPRVAF | GB, RCC |
| 173 | IYSWILDHF | GC, NSCLC, HCC, RCC |
| 174 | VYGGGQIIHL | GB, GC, NSCLC |
| 175 | YYEVHKELF | GC, NSCLC, HCC |

TABLE 14A-continued

Overview of presentation of selected HLA-A*24-binding tumor-associated peptides of the present invention across entities.

| SEQ ID No. | Sequence | Peptide Presentation on cancer entities |
|---|---|---|
| 176 | EYNQWFTKL | GC, NSCLC |
| 177 | VYPWLGALL | GC |
| 178 | IFIEVFSHF | GC, NSCLC |
| 179 | MYDSYWRQF | GB, NSCLC |
| 180 | IYDDSFIRPVTF | NSCLC, HCC |
| 181 | LYLDIINLF | GC, NSCLC, PCA |
| 182 | IYQLDTASI | GC, NSCLC, PCA |
| 183 | VFTSTARAF | NSCLC, PCA |
| 184 | VFQNFPLLF | GB, GC |
| 185 | IYKVGAPTI | NSCLC |
| 186 | IFPQFLYQF | GC, NSCLC |
| 187 | TYLRDQHFL | GC, NSCLC, HCC |
| 188 | RYFKGLVF | GB |
| 189 | WYVNGVNYF | NSCLC, PCA |
| 190 | GFFIFNERF | NSCLC, PCA |
| 191 | VFKASKITF | GB |
| 192 | SYALLTYMI | NSCLC |
| 193 | RFHPTPLLL | NSCLC, HCC, PCA |
| 194 | EFGSLHLEFL | GB |
| 195 | TYSVSFPMF | GB, GC, NSCLC, HCC, PCA |
| 196 | LYIDRPLPYL | GC, NSCLC, HCC, PCA, RCC |
| 197 | EYSLFPGQVVI | GB, GC, NSCLC, HCC, PCA |
| 198 | LYLDKATLI | GB, GC, NSCLC, HCC, PCA |
| 199 | RYAEEVGIF | GC, NSCLC, HCC, PCA |
| 200 | YYGPSLFLL | GC, NSCLC, RCC |
| 201 | IYATEAHVF | GB, GC, NSCLC, HCC, PCA |
| 202 | VYWDSAGAAHF | NSCLC |
| 203 | FYSRLLQKF | GC, NSCLC |
| 204 | TYELRYFQI | GB, GC, NSCLC, HCC |
| 205 | VHIPEVYLI | GC, NSCLC |
| 206 | EYQENFLSF | NSCLC, PCA |
| 207 | AYVVFVSTL | GB, GC, NSCLC |
| 208 | TYTQDFNKF | NSCLC, HCC |
| 209 | TYKDEGNDYF | GB, NSCLC |
| 210 | IYTMIYRNL | GB, GC, NSCLC |
| 211 | YYLEVGKTLI | GC, NSCLC, HCC |
| 212 | YYTFHFLYF | GC, NSCLC, HCC |
| 213 | IFDEAEKL | NSCLC, PCA |
| 214 | LYLKLWNLI | NSCLC, HCC |
| 215 | YFDKVVTL | NSCLC, HCC |
| 216 | QYSSVFKSL | GB, GC |
| 217 | FFPPTRQMGLLF | GC |
| 218 | YYKSTSSAF | GB, GC, NSCLC, HCC, PCA |
| 219 | EYPLVINTL | GB, GC, NSCLC, HCC, RCC |
| 220 | GYIDNVTLI | GC, NSCLC, HCC |
| 221 | RYSTGLAGNLL | GB, NSCLC, HCC, PCA |
| 222 | TFSVSSHLF | GB, NSCLC, HCC |
| 223 | KYIPYKYVI | NSCLC, HCC |
| 224 | QYLENLEKL | GB, NSCLC, HCC |
| 225 | YVVYIMNHL | GB, NSCLC |
| 226 | VYRDETGELF | GB, NSCLC, HCC, PCA |
| 227 | IFLDYEAGTLSF | GC, RCC |
| 228 | KYTSWYVAL | GB, PCA |
| 267 | KYMVYPQTF | GB, GC, NSCLC, HCC, PCA |
| 268 | QYLGQIQHI | GB, GC, NSCLC, HCC |
| 269 | YFIDSTNLKTHF | GC, NSCLC, HCC |
| 270 | NYYEVHKELF | GB, GC, NSCLC |
| 271 | LYHDIFSRL | GC, NSCLC, HCC |
| 272 | QYLQDAYSF | GB, NSCLC |
| 273 | TYIKPISKL | GB, NSCLC |
| 274 | AYLHSHALI | NSCLC, PCA |
| 275 | EYINQGDLHEF | NSCLC, PCA |
| 276 | VYGFQWRHF | NSCLC |
| 277 | VYQGHTALL | GB, GC, NSCLC, PCA |
| 278 | RYISDQLFTNF | GB, GC, NSCLC, HCC, PCA, RCC |
| 279 | TYIESASEL | NSCLC, RCC |
| 280 | RYPDNLKHLYL | GC, NSCLC, HCC |
| 281 | PYRLIFEKF | NSCLC, HCC |
| 282 | KFVDSTFYL | GB, GC, NSCLC, HCC |
| 283 | TYGDAGLTYTF | GB, GC, NSCLC, PCA, RCC |
| 284 | RYLNKAFHI | PCA |

TABLE 14A-continued

Overview of presentation of selected HLA-A*24-binding tumor-associated peptides of the present invention across entities.

| SEQ ID No. | Sequence | Peptide Presentation on cancer entities |
|---|---|---|
| 285 | HYPPVQVLF | GB, GC, NSCLC, HCC, PCA |
| 286 | RYPDNLKHL | NSCLC, HCC, PCA |
| 287 | LYITEPKTI | GB, GC, NSCLC, HCC |
| 288 | VYVSDIQEL | GC, NSCLC, HCC, PCA |
| 289 | KYPVEWAKF | PCA, RCC |
| 295 | YYPGVILGF | GB, NSCLC, RCC |
| 296 | TYVDSSHTI | GB, GC, NSCLC, HCC, PCA |
| 297 | PFLQASPHF | GC, NSCLC |
| 298 | RYLEGTSCI | GB, GC, NSCLC, HCC |
| 299 | VYFVAPAKF | GC, NSCLC |
| 300 | AYVLRLETL | GB, GC, NSCLC, RCC |
| 301 | AYKPGALTF | NSCLC, HCC |
| 302 | RYMPPAHRNF | GC, NSCLC |

GB = glioblastoma,
HCC = hepatocellular carcinoma,
NSCLC = non-small cell lung cancer,
PCA = prostate cancer,
GC = gastric cancer,
CRC = colorectal cancer,
RCC = renal cell carcinoma.

Table 14B show the presentation on additional cancer entities for selected peptides, and thus the particular relevance of the peptides as mentioned for the diagnosis and/or treatment of the cancers as indicated.

TABLE 14B

Overview of presentation of selected HLA-A*24-binding tumor-associated peptides of the present invention across entities.

| SEQ ID No. | Sequence | Peptide Presentation on cancer entities |
|---|---|---|
| 162 | VFTRVSSFL | HCC |
| 163 | DYLKGLASF | PCA |
| 164 | KFSSFSLFF | PCA |
| 167 | NYINRILKL | NSCLC |
| 178 | IFIEVFSHF | HCC |
| 180 | IYDDSFIRPVTF | HCC |
| 184 | VFQNFPLLF | NSCLC |
| 206 | EYQENFLSF | GB |
| 212 | YYTFHFLYF | PCA |
| 216 | QYSSVFKSL | NSCLC, HCC |
| 218 | YYKSTSSAF | SCLC |
| 227 | IFLDYEAGTLSF | NSCLC |

GB = glioblastoma,
HCC = hepatocellular carcinoma,
NSCLC = non-small cell lung cancer,
PCA = prostate cancer,
GC = gastric cancer,
CRC = colorectal cancer,
RCC = renal cell carcinoma.

TABLE 15

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | AML | BRCA | CLL | CRC | GB | GBC_CCC | GC | HCC | MEL | NHL |
|---|---|---|---|---|---|---|---|---|---|---|
| 1 | | | | | ++++ | | | | | |
| 2 | | ++++ | ++++ | | ++++ | | ++++ | | | |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| # | GB | BRCA | CRC | RCC | CLL | HCC | NSCLC | SCLC | NHL | AML | OC | PC | PCA | OSCAR | GBC_CC | MEL | GC | UBC | UEC |
|---|----|------|-----|-----|-----|-----|-------|------|-----|-----|----|----|----|-------|--------|-----|----|-----|-----|
| 3 | | | | | | | | | | | | | | | | | | + | |
| 5 | ++ | | + | | | | | | | | | | | | | | | | |
| 6 | | | | ++++ | | | | | | | | | | | | | | | |
| 7 | ++ | | + | | | | | | | | | | + | | | | | | |
| 8 | ++++ | | ++++ | | | | ++++ | | | | | | | | | ++++ | | | |
| 9 | | | | ++++ | ++++ | | | | | | | | | | | | | | |
| 10 | ++ | | | | | | | | | | | | | | | | | | |
| 11 | | +++ | +++ | | | +++ | +++ | | | | | | | +++ | | | | | |
| 12 | | | | ++++ | | | | | | | | | | | | | | | |
| 13 | | ++++ | | | ++++ | ++++ | | | | | | | | | | | | | |
| 14 | ++++ | | | | | | | ++++ | ++++ | | | | | | | | | | |
| 15 | | ++++ | ++++ | | ++++ | | | | ++++ | ++++ | ++++ | | | | | | | | |
| 16 | | | ++++ | | | | | | ++++ | ++++ | ++++ | | | | | | | | |
| 17 | | | | | | ++++ | | | ++++ | | | | | | | | | | |
| 18 | | ++++ | | ++++ | | | | ++++ | | | | | | | | | | | |
| 19 | | ++++ | | | ++++ | | | | ++++ | ++++ | | | | | | | | | |
| 20 | | | ++++ | | | | | | ++++ | | | | | | | | | | |
| 21 | | ++++ | | ++++ | | | | | ++++ | | | | | | | | | | |
| 22 | | ++++ | | | | | ++++ | ++++ | | | | | | | | | | | |
| 23 | ++ | | | ++ | | | | | | | | | | | | | | | |
| 24 | | | | | | | | ++++ | ++++ | | | | | | | | | | |
| 25 | | | | | | | | | | | | | | | | | | | |
| 26 | ++++ | ++++ | | | ++++ | | | | ++++ | ++++ | | | | | | | | | |
| 27 | | | ++++ | | | | | | | | | | | | | | | | |
| 28 | | | | | | | | | ++++ | | | | | | | | | | |
| 29 | +++ | +++ | +++ | | | +++ | | | +++ | | | | | | | | | | |
| 30 | | +++ | | | | | | | +++ | | | | | | | | | | |
| 31 | | | | ++++ | | | | | | | | | | | | | | | |
| 32 | | ++++ | | | | | | | | | | | | | | | | | |
| 33 | | | | | | ++++ | | | ++++ | | | | | | | | | | |
| 34 | ++++ | | | | | | | | ++++ | | | | | | | | | | |
| 35 | + | | ++ | | | | | | | | | | | | | | | | |
| 36 | | | | | | | | | | ++++ | | | | | | | | | |
| 37 | ++++ | | | | | | | | | | | | | | | | | | |
| 38 | ++++ | | ++++ | | | | | | ++++ | | | | | | | | | | |
| 39 | | ++++ | | | | | | | | | | | | | | | | | |
| 40 | | | | | | | | | ++++ | | | | | | | | | | |
| 41 | | | | ++++ | | | | | | | | | | | | | | | |
| 42 | | | | ++++ | ++++ | | | | | | | | | | | | | | |
| 43 | ++++ | | | | | ++++ | | | | | | | | | | | | | |
| 44 | ++++ | | | | | | | | ++++ | ++++ | | | | | | | | | |
| 45 | ++++ | | | | ++++ | | | | ++++ | | | | | | | | | | |
| 46 | | | | | | ++++ | | | | | | | | | | | | | |
| 47 | | ++++ | | | | | | | ++++ | | | | | | | | | | |
| 48 | | | | | | ++++ | | | | | | | | | | | | | |
| 49 | | ++++ | | | | | | | ++++ | | | | | | | | | | |
| 50 | ++++ | | | | | | | | | | | | | | | | | | |
| 51 | | | | ++++ | | | | | | | | | | | | | | | |
| 52 | | | | | | ++++ | | | | | | | | | | | | | |
| 53 | +++ | | +++ | | | | | | +++ | | | | | | | | | | |
| 54 | +++ | | | | | | | | +++ | | | | | | | | | | |
| 55 | +++ | +++ | | | | | | | | | | | | | | | | | |
| 56 | | | | | | | | | ++++ | | | | | | | | | | |
| 57 | | | | | | | | | ++++ | | | | | | | | | | |
| 58 | | | ++++ | | | | | | | | | | | | | | | | |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID | GB | BRCA | CRC | RCC | CLL | HCC | NSCLC | SCLC | NHL | AML | OC | PC | PCA | OSCAR | GBC_CC | MEL | GC | UBC | UEC |
|---|---|---|---|---|---|---|---|---|---|---|---|---|---|---|---|---|---|---|---|
| 59 | | | | | | ++++ | | | | | | | | | | | | | |
| 60 | ++++ | | | | | | | | | | | | | | | | | | |
| 61 | | | | | | | | ++++ | | | | | | | | | | | |
| 62 | | | | | | ++++ | | | | | | | | | | | | | |
| 63 | | | | | | | | ++++ | | | | | | | | | | | |
| 64 | | | | | | | | | | | | | | | | | | | |
| 65 | | | | | | | | ++++ | | | | | | | | | | | |
| 66 | | ++++ | | | | | | | | | | | | | | | | | |
| 67 | +++ | | +++ | | | | | | | | | | | | | | | | |
| 68 | | | | ++++ | | | | ++++ | | | | | | | | | | | |
| 69 | ++++ | | | | | | | | | | | | | | | | | ++++ | |
| 70 | | | | | | | | | | | | | | | | | | ++++ | |
| 71 | | | ++++ | | | | | | | | | | | | | | | ++++ | |
| 72 | | | | | | | | | | | | | | | | | | | |
| 73 | | | | | | | | | | | | | | | | | | | |
| 74 | ++++ | | | | | | | | | | | | | | | | | | |
| 75 | | | | | | | | ++++ | | | | | | | | | | | |
| 76 | | | | | | | | ++++ | | | | | | | | | | | |
| 77 | | | | | | | | | | | | | | | | | | | |
| 78 | | | | | | | | ++++ | | | | | | | | | | | |
| 79 | | | | | | | | ++++ | | | | | | | | | | | |
| 80 | ++++ | | | | | | | | | | | | | | | | | ++++ | |
| 81 | | | | | | | | ++++ | | | | | | | | | | | |
| 82 | | | | | | | | ++++ | | | | | | | | | | | |
| 84 | | | | ++++ | | | | | | | | | | | | | | | |
| 85 | | | | | | | | | | | | | | | | | | | |
| 86 | | | | | | | | ++++ | | | | | | | | | | | |
| 87 | | | | | | | | ++++ | | | | | | | | | | | |
| 88 | | | | | | | | ++++ | | | | | | | | | | | |
| 89 | | ++++ | | | | | | | | | | | | | | | | ++++ | |
| 90 | | | | | | | | | | | | | | | | | | | |
| 91 | + | | | | | | | | | | | | | | | | | + | |
| 92 | | | | | | | | | | | | | | | | | | | |
| 93 | +++ | +++ | | +++ | | | | +++ | | | | | | | | | | +++ | |
| 94 | +++ | | | +++ | + | | | | | | | | | | | | | | |
| 95 | | ++ | | | | | +++ | | | | | | | | | | | ++ | |
| 96 | | +++ | | | | | | | | | | | | | | | | +++ | |
| 97 | | | | | | + | | +++ | | | | | | | | | | | |
| 98 | | | | | | | | | | | | | | | | | | | |
| 99 | | +++ | | | | | | | | | | | | | | | | +++ | |
| 100 | | +++ | | | | | | | | | | | | | | | | | |
| 101 | ++++ | | | | | | | | | | | | | | | | | | |
| 102 | ++++ | | | | | | | | | | | | | | | | | | |
| 103 | ++++ | | | | | | | | | | | | | | | | | | |
| 104 | | | | | ++++ | | | | | | | | | | | | | | |
| 105 | | | | | | | | | | | | | | | | | | ++++ | |
| 106 | ++++ | | | | | | | | | | | | | | | | | | |
| 107 | | | | | | | | | | | | | | | | | | ++++ | |
| 108 | | ++++ | | | | | | | | | | | | | | | | | |
| 109 | | | | | | | | | | | | | | | | | | | |
| 110 | | | | | | | | | | | | | | | | ++++ | | | |
| 111 | | | | | | | | ++++ | | | | | | | | | | | |
| 112 | | | | | | | | | | | | | | | | | | | |
| 113 | | | | | | | | ++++ | | | | | | | | | | | |
| 114 | | | | | | | | | | | | | | | | | | | |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| # | GB | BRCA | CRC | RCC | CLL | HCC | NSCLC | SCLC | NHL | AML | OC | PC | PCA | OSCAR | GBC_CC | MEL | GC | UBC | UEC |
|---|---|---|---|---|---|---|---|---|---|---|---|---|---|---|---|---|---|---|---|
| 115 | | | | | | | | | | | | | | | | | | | |
| 116 | | | | | | | | | | | | ++++ | | | | | | | |
| 117 | | | | | | | | | | | | | | | | | | | |
| 118 | | | | | | | | | | | | | | | | | | | |
| 119 | | | | | | | | | | | | | | | | | | | |
| 120 | | | | | | | ++++ | | | | | | | | | | | | |
| 121 | | ++++ | | | | | | | | | | | | | | | | | |
| 122 | | | | | | | ++++ | | | | | | | | | | | | |
| 123 | | | | | | | | | | | | | | | | | | | |
| 124 | | | | | | | | | | | | | | | | | | | |
| 125 | | | | ++++ | | | | | | | | | | | | | | | |
| 126 | | ++++ | | | | | | | | | | | | | | | | | |
| 127 | | | | | | | | | | | | | | | | | | | |
| 128 | | | | | | | ++++ | | | | | | | | | | | | |
| 129 | ++++ | | | | | | | | | | | | | | | | | | |
| 130 | | | | | | | | | | | | | | | | | | | |
| 131 | | ++++ | | | | | | | | | | | | | | ++++ | | | |
| 132 | | ++++ | | | | | | | | | | | | | | ++++ | | | |
| 133 | | | | | | | | | | | | | | | | | | | |
| 134 | | | | | | | | | | | | | | | | | | | |
| 135 | | ++++ | | | | | | | | | | | | | | | | | |
| 136 | | | | | | | | | | | | | | | | ++++ | | | |
| 137 | | | | +++ | | | | | | | | | | | | | | | |
| 138 | +++ | + | +++ | ++ | | | +++ | | ++ | + | | | | | | | | | |
| 139 | +++ | | + | | | | | | | | | | | | | | | | |
| 140 | ++ | | ++ | | | + | | | | + | | | | | | | | | |
| 141 | ++ | | + | | | | | | | | | | | | | | | | |
| 142 | | | | | | | | | | | | | | | | | | | |
| 143 | | | | | + | + | | + | | | | | | | | | | | |
| 144 | +++ | + | | + | +++ | | ++ | | | | | | | | | | | | |
| 145 | ++ | | | | | | | | | | | | | | | | | | |
| 146 | | | | | | | | | | | | | | | | | | | |
| 147 | | | | | | +++ | | | | | | | | | | | | | |
| 148 | | | | | +++ | | | | | | | | | | | | | | |
| 149 | | | | | | | | | | ++++ | | | | | | | | | |
| 150 | | | ++ | ++ | | | | | + | + | | | | | | | | | |
| 151 | | | | | | | | + | | | | | | | | | | | |
| 152 | +++ | | +++ | +++ | +++ | | | | + | | | | | | | | | | |
| 153 | | | + | | | | | | ++ | | | | | | | | | | |
| 154 | | | | | | | | | + | | | | | | | | | | |
| 155 | | | +++ | | | ++ | | | + | | | | | | | | | | |
| 156 | | | | | | | | | | | | | | | | | | | |
| 157 | | | | | | | | | | | | | | | | | | | |
| 229 | ++++ | ++++ | ++++ | ++++ | ++++ | | ++++ | | ++++ | | | | | | | | | | |
| 230 | ++++ | ++++ | ++++ | ++++ | | ++++ | | ++++ | ++++ | | | | | | | | | | |
| 231 | | + | | | | | | | | | | | | | | | | | |
| 232 | | | | + | | | | ++ | | | | | | | | | | | |
| 233 | ++++ | ++++ | | ++++ | | | | | ++++ | | | | | | | | | | |
| 234 | | ++++ | ++++ | | | | | | ++++ | | | | | | | | | | |
| 235 | ++++ | | | | | | | | ++++ | | | | | | | | | | |
| 236 | | | ++++ | | ++++ | | ++++ | | ++++ | | | | | | | | | | |
| 237 | | ++++ | | | ++++ | | | | ++++ | ++++ | | | | | | | | | |
| 238 | ++ | | | | | | | | | | | | | | | | | | |
| 239 | | | | | | ++++ | | | ++++ | | | | | | | | | | |
| 240 | | | ++ | | | | | | | + | | | | | | | | | |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | | | | | | | | | | | | |
|---|---|---|---|---|---|---|---|---|---|---|---|---|
| 241 | | | | | | | | | | | ++++ | |
| 242 | ++++ | | | | | | | | | | | |
| 243 | | | | | | | | | | | ++++ | |
| 244 | | | | | | | | | | | | |
| 245 | | | ++++ | | | | | | | | ++++ | |
| 246 | | | ++++ | | ++++ | | | | | | | |
| 247 | | ++ | | | | | | | | | | |
| 248 | + | | | | | | | | | | | |
| 249 | | | + | +++ | ++ | | | | | | | |
| 251 | ++++ | | | | | | | | | | | |
| 252 | ++++ | | | | | | | | | | | |
| 253 | | | ++++ | | | | | | | | | |
| 254 | | | | | | | | | | | ++++ | |
| 255 | ++++ | | | | | | | | | | ++++ | |
| 256 | | | | | | | | | | ++++ | ++++ | |
| 257 | | | | | | | | | | | ++++ | |
| 258 | | | | | | | | ++++ | | | | |
| 259 | | | | | | | | | | | | |
| 260 | | | ++ | | | | | | | | | |
| 261 | | | | + | | | | | | | | + |
| 262 | | + | ++ | | + | | | | | | +++ | |
| 263 | | + | | | | | | | | + | + | |
| 264 | + | + | | | | | | | | | | |
| 265 | | + | +++ | | | | | | | | | |
| 266 | +++ | + | | | | | | | | | | |
| 290 | | ++ | | | | | | | | | ++ | |
| 291 | ++ | | | + | | | | | + | +++ | ++ | |
| 292 | | | +++ | +++ | +++ | | | | | | ++ | |
| 293 | | | ++++ | | | | | | | | | |
| 294 | | | | | | | | | | | | |

| SEQ ID No. | NSCLC | OC | OSCAR | PC | PCA | RCC | SCLC | UBC | UEC |
|---|---|---|---|---|---|---|---|---|---|
| 1 | ++++ | ++++ | | | | | | | |
| 2 | ++++ | | | ++++ | | ++++ | | ++++ | |
| 3 | | | | | | | | +++ | |
| 5 | | + | | | | | | | |
| 6 | | | | | | | | | |
| 7 | | | +++ | | | | | | |
| 8 | ++++ | | | | | | | | |
| 9 | ++++ | | ++++ | | | | | | |
| 10 | + | | | | | | | | + |
| 11 | +++ | | | | | | | | |
| 12 | ++++ | | | | | ++++ | | | ++++ |
| 13 | ++++ | ++++ | | | | ++++ | | | |
| 14 | ++++ | | ++++ | | | | | ++++ | |
| 15 | ++++ | | | | | | | | |
| 16 | ++++ | | | | | | | | |
| 17 | ++++ | ++++ | ++++ | | | | | | |
| 18 | ++++ | | ++++ | | | ++++ | | ++++ | |
| 19 | | ++++ | ++++ | | | | | | ++++ |
| 20 | | | | | | | | ++++ | |
| 21 | ++++ | ++++ | ++++ | | | | | | |
| 22 | | ++++ | ++++ | | | | | ++++ | |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| # | GB | BRCA | CRC | RCC | CLL | HCC | NSCLC | SCLC | NHL | AML | OC | PC | PCA | OSCAR | GBC_CC | MEL | GC | UBC | UEC |
|---|---|---|---|---|---|---|---|---|---|---|---|---|---|---|---|---|---|---|---|
| 23 | + |  | + |  |  |  | + |  |  |  | +++ |  |  |  |  |  |  |  |  |
| 24 | ++++ | ++++ |  |  |  |  |  |  |  |  |  |  |  |  |  |  |  |  |  |
| 25 |  | ++++ |  |  |  |  |  |  |  |  |  |  |  |  | ++++ |  |  |  |  |
| 26 |  |  |  |  |  |  |  |  |  |  |  |  |  |  |  |  |  |  |  |
| 27 | ++++ | ++++ | ++++ |  |  |  |  |  |  |  |  |  |  |  | ++++ |  |  |  |  |
| 28 | ++++ | ++++ |  |  |  |  |  |  |  |  |  |  |  | ++++ |  |  |  |  |  |
| 29 | +++ |  |  |  |  |  |  |  |  |  |  |  |  |  |  |  |  |  |  |
| 30 |  | +++ |  |  | +++ |  | +++ | +++ |  |  |  |  |  |  |  |  |  |  |  |
| 31 |  |  |  |  |  |  |  |  |  |  |  |  |  |  |  |  |  |  |  |
| 32 |  | ++++ |  |  |  |  |  |  |  |  |  |  |  |  |  |  |  |  |  |
| 33 | ++++ | ++++ | ++++ |  |  |  |  |  |  |  |  |  |  |  |  |  |  |  |  |
| 34 |  | ++++ |  |  |  |  | ++++ |  |  |  |  |  |  |  |  |  |  |  |  |
| 35 | + | +++ |  |  |  |  |  |  |  |  |  |  |  |  |  |  |  |  |  |
| 36 |  |  |  |  |  |  | ++++ |  |  |  |  |  |  |  |  |  |  |  |  |
| 37 |  |  |  |  |  |  |  |  |  |  |  |  |  |  |  |  |  |  |  |
| 38 |  |  |  |  |  |  |  |  |  |  |  |  |  |  |  |  |  |  |  |
| 39 |  |  |  |  |  |  |  |  |  |  |  |  |  |  |  |  |  |  |  |
| 40 |  | ++++ |  |  |  |  |  |  |  |  |  |  |  |  |  |  |  |  |  |
| 41 |  |  |  |  |  |  |  |  |  |  |  |  |  |  |  |  |  |  |  |
| 42 | ++++ |  |  |  |  |  |  |  |  |  |  |  |  |  |  |  |  |  |  |
| 43 |  |  | ++++ |  |  |  |  |  |  |  |  |  |  |  |  |  |  |  |  |
| 44 | ++++ |  |  |  |  |  |  |  |  |  |  |  |  |  |  |  |  |  |  |
| 45 |  | ++++ |  |  |  |  |  |  |  |  |  |  |  |  |  |  |  |  |  |
| 46 | ++++ |  | ++++ |  |  |  |  |  |  |  | ++++ |  |  |  |  |  |  |  |  |
| 47 | ++++ | ++++ |  |  |  |  |  |  |  |  |  |  |  |  |  |  |  |  |  |
| 48 | ++++ | ++++ | ++++ |  |  |  |  |  |  |  |  |  |  |  |  |  |  |  |  |
| 49 | ++++ |  |  |  |  |  |  |  |  |  | ++++ |  |  |  |  |  |  |  |  |
| 50 | ++++ | ++++ |  |  |  |  |  |  |  |  | ++++ |  |  |  |  |  |  |  |  |
| 51 | ++++ |  |  |  |  |  |  |  |  |  |  |  |  |  |  |  |  |  |  |
| 52 | ++++ | ++++ | ++++ |  |  |  |  |  |  |  |  |  |  |  |  |  |  |  |  |
| 53 |  |  |  |  |  |  |  |  |  |  |  |  |  |  |  |  |  |  |  |
| 54 | +++ |  |  |  | +++ |  |  |  |  |  |  |  |  |  |  |  |  |  |  |
| 55 |  | +++ |  |  | +++ |  |  |  |  |  |  |  |  |  |  |  |  |  |  |
| 56 | ++++ | ++++ |  |  |  |  |  |  |  |  |  |  |  |  |  |  |  |  |  |
| 57 | ++++ | ++++ | ++++ |  |  |  |  |  |  |  |  |  |  |  |  |  |  |  |  |
| 58 |  |  |  |  |  |  |  |  |  |  |  |  |  |  |  |  |  |  |  |
| 59 | ++++ |  |  |  |  |  |  |  |  |  |  |  |  |  |  |  |  |  |  |
| 60 |  |  |  |  |  |  |  |  |  |  |  |  |  |  |  |  |  |  |  |
| 61 | ++++ |  | ++++ |  |  |  |  |  |  |  |  |  |  |  |  |  |  |  |  |
| 62 | ++++ |  |  |  | ++++ |  |  |  |  |  |  |  |  |  |  |  |  |  |  |
| 63 | ++++ |  | ++++ |  |  |  |  |  |  |  |  |  |  |  |  |  |  |  |  |
| 64 |  |  |  |  | ++++ |  |  |  |  |  |  |  |  |  |  |  |  |  |  |
| 65 | ++++ |  | ++++ |  |  |  |  |  |  |  |  |  |  |  |  |  |  |  |  |
| 66 | ++++ |  |  |  |  |  | ++++ |  | ++++ |  |  |  |  |  |  |  |  |  |  |
| 67 | +++ |  |  |  | +++ |  |  |  |  |  |  |  |  |  |  |  |  |  |  |
| 68 |  | ++++ |  |  |  |  |  |  |  |  |  |  |  |  |  |  |  |  |  |
| 69 |  |  |  |  |  |  |  |  |  |  |  |  |  |  |  |  |  |  |  |
| 70 |  |  |  |  | ++++ |  |  |  |  |  |  |  |  |  |  |  |  |  |  |
| 71 |  |  |  |  |  |  |  |  |  |  |  |  |  |  |  |  |  |  |  |
| 72 |  | ++++ |  |  | ++++ |  |  |  |  |  |  |  |  |  |  |  |  |  |  |
| 73 | ++++ | ++++ | ++++ |  |  |  |  |  |  |  |  |  |  |  |  |  |  |  |  |
| 74 |  |  |  |  |  |  |  |  |  |  |  |  |  |  |  |  |  |  |  |
| 75 | ++++ |  | ++++ |  |  |  |  |  |  |  |  |  |  |  |  |  |  |  |  |
| 76 |  | ++++ |  |  |  |  |  |  |  |  |  |  |  |  |  |  |  |  |  |
| 77 | ++++ | ++++ |  |  |  |  | ++++ |  |  |  |  |  |  |  |  |  |  |  |  |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| # | GB | BRCA | CRC | RCC | CLL | HCC | NSCLC | SCLC | NHL | AML | OC | PC | PCA | OSCAR | GBC_CC | MEL | GC | UBC | UEC |
|---|---|---|---|---|---|---|---|---|---|---|---|---|---|---|---|---|---|---|---|
| 78 |  | ++++ | ++++ |  |  |  |  |  |  |  |  |  |  |  |  |  |  |  |  |
| 79 | ++++ |  | ++++ |  |  |  |  |  |  |  |  |  |  |  |  |  |  |  |  |
| 80 | ++++ |  |  |  |  |  |  |  |  |  |  |  |  |  |  |  |  |  |  |
| 81 | ++++ |  | ++++ |  |  |  |  |  |  |  |  |  |  |  |  |  |  |  |  |
| 82 | ++++ |  | ++++ |  |  |  |  |  |  |  |  |  |  |  |  |  |  |  |  |
| 84 |  |  |  |  |  |  |  |  |  |  |  |  |  |  |  |  |  |  |  |
| 85 |  | ++++ |  |  |  |  |  |  |  |  |  |  |  |  |  |  |  | ++++ |  |
| 86 |  | ++++ | ++++ |  |  |  |  |  |  |  |  |  |  |  |  |  |  |  |  |
| 87 | ++++ |  | ++++ |  |  |  |  |  |  |  |  |  |  |  |  |  |  |  |  |
| 88 | ++++ |  | ++++ |  |  |  |  |  |  |  |  |  |  |  |  |  |  |  |  |
| 89 |  | ++++ |  |  |  |  |  |  |  |  |  |  |  |  |  |  |  |  |  |
| 90 |  |  |  |  |  |  |  |  |  |  | +++ | + |  |  |  |  |  |  |  |
| 91 | ++ | + |  |  |  |  |  |  |  |  |  |  |  |  |  |  |  |  |  |
| 92 |  |  | + |  |  | + |  |  |  |  |  |  |  |  |  |  |  |  |  |
| 93 | +++ |  |  |  |  | +++ |  |  | +++ | +++ | +++ |  |  |  |  |  |  |  |  |
| 94 | + |  |  |  |  |  |  |  |  |  |  |  |  |  |  |  |  |  |  |
| 95 | ++ | + |  |  |  |  |  | + |  |  |  |  |  |  |  |  |  |  |  |
| 96 | + |  |  |  |  |  |  |  |  | +++ |  |  |  |  |  |  |  |  |  |
| 97 |  | +++ | +++ |  |  |  |  |  |  |  |  |  |  |  |  |  |  |  |  |
| 98 | + |  |  |  |  |  |  |  |  |  |  |  |  |  |  |  |  |  |  |
| 99 |  |  |  |  |  |  |  |  |  |  |  |  |  |  |  |  |  |  |  |
| 100 |  |  |  |  |  |  |  |  |  |  |  |  |  |  |  |  |  |  |  |
| 101 |  |  |  |  |  |  |  |  |  |  |  |  |  |  |  |  |  |  |  |
| 102 |  |  |  |  |  |  |  |  |  |  |  |  |  |  |  |  |  |  |  |
| 103 |  |  |  |  |  |  |  |  |  |  |  |  |  |  |  |  |  |  |  |
| 104 |  |  |  |  |  |  |  |  |  |  |  |  |  |  |  |  |  |  |  |
| 105 |  |  |  |  |  |  |  |  |  |  |  |  |  |  |  |  |  |  |  |
| 106 |  |  |  |  |  |  |  |  |  |  |  |  |  |  |  |  |  |  |  |
| 107 |  |  |  |  |  |  |  |  |  |  |  |  |  |  |  |  |  |  |  |
| 108 |  |  |  |  |  |  |  |  |  |  |  |  |  |  |  |  |  |  |  |
| 109 |  |  |  |  |  |  |  |  |  |  |  |  |  |  |  |  |  | ++++ |  |
| 110 |  |  |  |  |  |  |  |  |  |  |  |  |  |  |  |  |  |  |  |
| 111 | ++++ |  | ++++ |  |  |  |  |  |  |  |  |  |  |  |  |  |  |  |  |
| 112 | ++++ |  |  |  |  |  |  |  |  |  |  |  |  |  |  |  |  | ++++ |  |
| 113 |  | ++++ |  |  |  |  |  |  |  |  |  |  |  |  |  |  |  | ++++ |  |
| 114 |  | ++++ |  |  |  | ++++ |  |  |  |  |  |  |  |  |  |  |  |  |  |
| 115 | ++++ | ++++ |  |  |  |  |  |  |  |  |  |  |  |  |  |  |  |  |  |
| 116 |  |  |  |  |  |  |  |  |  |  |  |  |  |  |  |  |  | ++++ |  |
| 117 | + |  |  |  |  |  |  |  |  |  |  |  |  |  |  |  |  |  |  |
| 118 |  | ++++ |  |  |  |  |  |  |  |  |  |  |  |  |  |  |  |  |  |
| 119 | ++++ | ++++ |  |  |  |  |  |  |  |  |  |  |  |  |  |  |  |  |  |
| 120 |  |  | ++++ |  |  |  |  |  |  |  |  |  |  |  |  |  |  |  |  |
| 121 |  |  |  |  |  |  |  |  |  |  |  |  |  |  |  |  |  |  |  |
| 122 | ++++ |  | ++++ |  |  |  |  |  |  |  |  |  |  |  |  |  |  |  |  |
| 123 |  | ++++ |  |  |  |  |  |  |  |  |  |  |  |  |  |  |  | ++++ |  |
| 124 | ++++ | ++++ |  |  |  |  |  |  |  |  |  |  |  |  |  |  |  |  |  |
| 125 |  |  |  |  |  |  | ++++ |  |  |  |  |  |  |  |  |  |  |  |  |
| 126 | ++++ |  |  |  |  |  |  |  |  |  |  |  |  |  |  |  |  |  |  |
| 127 | ++++ |  |  |  |  |  |  |  |  |  |  |  |  |  |  |  |  |  |  |
| 128 |  |  | ++++ |  |  |  |  |  |  |  |  |  |  |  |  |  |  |  |  |
| 129 | ++++ |  |  |  |  |  |  |  |  |  |  |  |  |  |  |  |  |  |  |
| 130 |  |  |  |  |  |  |  |  |  |  |  |  |  |  |  |  |  | ++++ |  |
| 131 |  |  |  |  |  |  |  |  |  |  |  |  |  |  |  |  |  |  |  |
| 132 |  |  |  |  |  |  |  |  |  |  |  |  |  |  |  |  |  |  |  |
| 133 |  |  | ++++ |  |  |  |  |  |  |  |  |  |  |  |  |  |  |  |  |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| # | GB | BRCA | CRC | RCC | CLL | HCC | NSCLC | SCLC | NHL | AML | OC | PC | PCA | OSCAR | GBC_CC | MEL | GC | UBC | UEC |
|---|---|---|---|---|---|---|---|---|---|---|---|---|---|---|---|---|---|---|---|
| 134 | ++++ | ++++ | | | | | | | | | | | | | | | | | |
| 135 | ++++ | | | | | | | | | | | | | | | | | | |
| 136 | | ++++ | | | | | | | | | | | | | | | | | |
| 137 | +++ | | | | | | | | | | | | | | | | | | |
| 138 | + | + | | | | | ++ | | | + | | | | | | | | | |
| 139 | | | | | | | | | | | | | | | | | | + | |
| 140 | | + | | | | | | | | | | | | | | | +++ | | |
| 141 | | | | | | | | | | | | | | | | | | | |
| 142 | +++ | | | | | + | | | | | | | | | | | | | |
| 143 | + | | | | | | | | | | | | | | | | | | |
| 144 | ++ | | +++ | | | | | | | | | | | | | | | | |
| 145 | + | +++ | + | | | | | | | | | | | | | | | | |
| 146 | | | | | | +++ | | | | | | | | | | + | | | |
| 147 | | +++ | | | | | | | | | | | | | | | | | |
| 148 | | | | | | | | | | | | | | | | | | | |
| 149 | | | | | | | | | | | | | | | | | | | |
| 150 | | | + | | | | | | | | | | | | | | | | |
| 151 | | ++ | + | | | + | | | | | | | | | | | | | |
| 152 | +++ | | | | | | | | | | | | | | | | | | |
| 153 | | ++ | + | | | | | | | | | | | + | | | | | |
| 154 | | | | | | | | | | | | | | | | | | | |
| 155 | | | | | | | | | | | | | | | | | | | |
| 156 | | | | | ++ | | | | | | | | | | | | | | |
| 157 | | | | | | | | | | | | | + | | | | | | |
| 229 | ++++ | ++++ | ++++ | | | | | | ++++ | ++++ | | | | | | | | | |
| 230 | ++++ | | | | | ++++ | | | ++++ | | | | | | | | | | |
| 231 | | | | | | | | | | | | | | | | | | | |
| 232 | | | | | | | | | ++ | | | | | | | | | | |
| 233 | ++++ | | | | | | | | ++++ | | | | | | | | | | |
| 234 | ++++ | ++++ | ++++ | | | | | | ++++ | | | | | | | | | | |
| 235 | | ++++ | | | | | | | | | | | | | | | ++++ | | |
| 236 | ++++ | | ++++ | | ++++ | | | | | | | | | | | | | | |
| 237 | ++++ | ++++ | | | | | | | | | | | | ++++ | ++++ | | | | |
| 238 | | | | | | | | | | | | | | | | | | | |
| 239 | ++++ | | | | | | | | | | | | | | | | | | |
| 240 | + | | | | | | | | | | | | + | | | | | | |
| 241 | ++++ | ++++ | | | | | | | | | | | | | | | | | |
| 242 | ++++ | | | | | | | | | | | | | ++++ | | | | | |
| 243 | | | | | | | | | | | | | | | | | | | |
| 244 | ++++ | ++++ | ++++ | | | | | | | | | | | | | | | | |
| 245 | | | | | | | | | | | | | | | | | | | |
| 246 | ++++ | | | | | | | | | | | | | | | | | | |
| 247 | | | + | | | | | | + | +++ | | | | | | | | | |
| 248 | | | | | | | | | | | | | | | | | | | |
| 249 | + | | | | | +++ | | | | | | | | | | | | | |
| 251 | | | | | | | | | | | | | | | | | | | |
| 252 | | | | | | | | | | | | | | | | | | | |
| 253 | | | | | | | | | | | | | | | | | | | |
| 254 | ++++ | | | | | | | | | | | | | | | | | | |
| 255 | | | | | | | | | | | | | | | | | | | |
| 256 | | | | | | | | | | | | | | | | | | | |
| 257 | ++++ | | | | | | | | | | | | | | | | | | |
| 258 | | | | | | ++++ | | | | | | | | | | | | | |
| 259 | ++++ | ++++ | | | | | | | | | | | | | | | | | |
| 260 | +++ | | | | | | | | | | | | | | | | | | |

TABLE 15-continued

Presentation scores: The table lists HLA-A*02 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 41), BRCA = breast cancer (N = 17), CRC = colorectal cancer (N = 28), RCC = renal cell carcinoma (N = 20), CLL = chronic lymphocytic leukemia (N = 17), HCC = hepatocellular carcinoma (N = 16), NSCLC = non-small cell lung cancer (N = 39), SCLC = small cell lung cancer (N = 19), NHL = non-Hodgkin lymphoma (N = 18), AML acute myeloid leukemia (N = 18), OC = ovarian cancer (N = 20), PC = pancreatic cancer (N = 16), PCA = prostate cancer and benign prostate hyperplasia (N = 39), OSCAR = esophageal cancer, including cancer of the gastric-esophageal junction (N = 17), GBC_CC = gallbladder adenocarcinoma and cholangiocarcinoma (N = 6), MEL = melanoma (N = 7), GC = gastric cancer (N = 29), UBC = urinary bladder cancer (N = 16), UEC = uterine cancer (N = 15). The panel of normal tissues (N = 262) considered relevant for comparison with tumors consisted of: adipose tissue, adrenal gland, artery, vein, bone marrow, brain, central and peripheral nerve, eye, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| | | | | | |
|---|---|---|---|---|---|
| 261 | + | + | | | |
| 262 | +++ | | | + | +++ |
| 263 | +++ | | + | | |
| 264 | + | | | | |
| 265 | | | | | |
| 266 | | | | | |
| 290 | | | | | |
| 291 | | ++ | | + | +++ |
| 292 | +++ | | | | +++ |
| 293 | | | | | |
| 294 | | | | ++++ | |

TABLE 16

Presentation scores: The table lists HLA-A*24 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 18), HCC = hepatocellular carcinoma (N = 15), NSCLC = non-small cell lung cancer (N = 91), PGA = prostate cancer (N = 40), GC = gastric cancer (N = 44), RCC = renal cell carcinoma (N = 2). The panel of normal tissues (N = 70) considered relevant for comparison with tumors consisted of: adrenal gland, brain, colon, rectum, heart, kidney, liver, lung, pancreas, pituitary, skin, spleen, stomach, and thymus.

| SEQ ID No. | GB | GC | HCC | NSCLC | PCA | RCC |
|---|---|---|---|---|---|---|
| 158 | ++++ | ++++ | ++++ | ++++ | ++++ | ++++ |
| 159 | ++++ | | | ++++ | | ++++ |
| 160 | | ++++ | ++++ | ++++ | ++++ | |
| 161 | | ++++ | | ++++ | ++++ | |
| 162 | ++++ | ++++ | | ++++ | | |
| 163 | ++++ | ++++ | | ++++ | | |
| 164 | | ++++ | | ++++ | ++++ | |
| 165 | | ++++ | | ++++ | | |
| 166 | ++++ | | ++++ | ++++ | | |
| 167 | | ++++ | | | | |
| 168 | | | | ++++ | ++++ | |
| 169 | | ++++ | ++++ | ++++ | | |
| 170 | ++++ | | | ++++ | | |
| 171 | | | +++ | +++ | | +++ |
| 172 | ++++ | | | | | ++++ |
| 173 | | ++++ | ++++ | ++++ | ++++ | |
| 174 | ++++ | ++++ | | ++++ | | |
| 175 | | ++++ | ++++ | ++++ | | |
| 176 | | ++++ | | ++++ | | |
| 177 | | ++++ | | | | |
| 178 | | ++++ | | ++++ | | |
| 179 | ++++ | | | ++++ | | |
| 180 | | | ++++ | ++++ | | |
| 181 | | ++++ | | ++++ | ++++ | |
| 182 | | ++++ | | ++++ | ++++ | |
| 183 | | | | ++++ | ++++ | |
| 184 | ++++ | ++++ | | | | |
| 185 | | | | ++++ | | |
| 186 | | ++++ | | ++++ | | |
| 187 | | ++++ | ++++ | ++++ | | |
| 188 | ++++ | | | | | |
| 189 | | | | ++++ | ++++ | |
| 190 | | | | ++++ | ++++ | |
| 191 | ++++ | | | | | |
| 192 | | | | ++++ | | |
| 193 | | | ++++ | ++++ | ++++ | |
| 194 | ++++ | | | | | |
| 195 | +++ | | | | + | |
| 196 | | | | + | | + |
| 197 | | + | | | + | |
| 198 | | ++ | ++ | + | | |
| 199 | | + | | | ++ | |
| 200 | | + | | | + | |
| 201 | +++ | + | | ++ | | |

TABLE 16-continued

Presentation scores: The table lists HLA-A*24 peptides that are specifically presented on tumors (++++), very highly over-presented on tumors compared to a panel of normal tissues (+++), highly over-presented on tumors compared to a panel of normal tissues (++) or over-presented on tumors compared to a panel of normal tissues (+). GB = glioblastoma (N = 18), HCC = hepatocellular carcinoma (N = 15), NSCLC = non-small cell lung cancer (N = 91), PGA = prostate cancer (N = 40), GC = gastric cancer (N = 44), RCC = renal cell carcinoma (N = 2). The panel of normal tissues (N = 70) considered relevant for comparison with tumors consisted of: adrenal gland, brain, colon, rectum, heart, kidney, liver, lung, pancreas, pituitary, skin, spleen, stomach, and thymus.

| SEQ ID No. | GB | GC | HCC | NSCLC | PCA | RCC |
|---|---|---|---|---|---|---|
| 202 | | | | + | | |
| 203 | | + | | | | |
| 204 | ++ | +++ | + | +++ | | |
| 207 | +++ | +++ | | | | |
| 208 | | | + | +++ | | |
| 209 | +++ | | | + | | |
| 210 | +++ | + | | | | |
| 211 | | +++ | | | | |
| 212 | | +++ | +++ | +++ | | |
| 213 | | | | ++ | +++ | |
| 214 | | ++++ | | ++++ | | |
| 215 | | ++++ | | ++++ | | |
| 216 | ++++ | ++++ | | | | |
| 217 | | ++++ | | | | |
| 218 | ++ | + | | ++ | | |
| 219 | +++ | | + | + | | ++ |
| 222 | | | + | + | | |
| 224 | + | | + | + | | |
| 225 | | | | ++ | | |
| 227 | | +++ | | | +++ | |
| 228 | ++ | | | | + | |
| 267 | +++ | +++ | +++ | +++ | +++ | |
| 268 | ++++ | ++++ | ++++ | ++++ | | |
| 269 | | ++++ | ++++ | ++++ | | |
| 270 | ++++ | ++++ | | ++++ | | |
| 271 | | ++++ | ++++ | ++++ | | |
| 272 | ++++ | | | ++++ | | |
| 273 | ++++ | | | ++++ | | |
| 274 | | | | ++++ | ++++ | |
| 275 | | | | ++++ | ++++ | |
| 276 | | | | ++++ | | |
| 277 | | ++ | | +++ | + | |
| 278 | + | ++ | | | | |
| 279 | | | | | | +++ |
| 280 | | + | | | | |
| 281 | | +++ | | +++ | | |
| 282 | +++ | +++ | +++ | +++ | | |
| 283 | + | ++ | | +++ | +++ | +++ |
| 284 | | | | ++++ | | |
| 285 | + | | | + | | |
| 286 | | | ++ | + | | |
| 287 | + | + | | | | |
| 288 | | + | + | + | | |
| 289 | | | | +++ | +++ | |
| 295 | ++++ | | | ++++ | | ++++ |
| 296 | | | | | | |
| 297 | | +++ | | +++ | | |
| 298 | + | | | +++ | | |
| 299 | | | | ++ | | |
| 300 | +++ | +++ | | +++ | | +++ |
| 301 | | | ++++ | ++++ | | |
| 302 | | ++++ | | ++++ | | |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

For HLA class I-binding peptides of this invention, normal tissue expression of all source genes was shown to be minimal based on a database of RNASeq data covering around 3000 normal tissue samples (Lonsdale, 2013). In addition, gene and exon expression data from tumors vs normal tissues were analyzed to assess target coverage in various tumor entities.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, MI, USA & Royston, Herts, UK); BioCat GmbH (Heidelberg, Germany); BioServe (Beltsville, MD, USA); Geneticist Inc. (Glendale, CA, USA); Istituto Nazionale Tumori "Pascale" (Naples, Italy); ProteoGenex Inc. (Culver City, CA, USA); University Hospital Heidelberg (Heidelberg, Germany).

Total RNA from tumor tissues for RNASeq experiments was obtained from:

Asterand (Detroit, MI, USA & Royston, Herts, UK); Bio-Options Inc. (Brea, CA, USA); BioServe (Beltsville, MD, USA); Center for cancer immune therapy (CCIT), Herlev Hospital (Herlev, Denmark); Geneticist Inc. (Glendale, CA, USA); Istituto Nazionale Tumori "Pascale" (Naples, Italy); Kyoto Prefectural University of Medicine (KPUM) (Kyoto, Japan); Leiden University Medical Center (LUMC) (Leiden, Netherlands); Tissue Solutions Ltd (Glasgow, UK); University Hospital Bonn (Bonn, Germany); University Hospital Geneva (Geneva, Switzerland); University Hospital Heidelberg (Heidelberg, Germany); Osaka City University (OCU) (Osaka, Japan); University Hospital Tübingen (Tübingen, Germany); Val d'Hebron University Hospital (Barcelona, Spain).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, CA, USA), which includes RNA fragmentation, cDNA conversion and addition of sequencing adaptors. Libraries derived from multiple samples are mixed equimolarly and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in different cancer are shown in FIGS. 2A-2I. Expression data for different entities and further exemplary peptides are summarized in Table 17, based on data generated by comparing tumor samples from the TCGA Research Network with normal tissue samples (Lonsdale, 2013). Expression scores for further exemplary genes are shown in Table 18, based on in-house RNASeq analyses.

TABLE 17

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 1 | | | | | | | | | | | | A | | | | | | | | | | |
| 2 | C | C | B | A | | A | A | A | A | A | | A | B | A | A | C | B | | A | B | B | C |
| 3 | A | B | B | C | A | A | A | B | A | B | A | A | C | B | A | C | C | B | C | A | B | B |
| 4 | | C | | | | C | | | | | | | | | B | C | | B | C | | | | B |
| 5 | B | | | C | B | B | | | | | A | | | C | | | | | | A | A | C |
| 6 | | | | | | | | | | | | A | | | | | | | | | | |
| 7 | A | A | A | A | A | A | A | A | | | | A | A | A | A | A | A | A | A | A | A | A |
| 8 | B | A | C | B | A | B | B | | | B | C | A | C | C | B | C | | | B | A | C | B |
| 9 | B | C | | C | | B | | A | | | B | C | | C | C | C | B | | C | C | C | |
| 10 | C | C | | | | B | | | C | | A | | | C | | | | | | B | C | C |
| 11 | B | A | A | A | | A | A | A | A | A | A | A | B | A | A | A | A | A | A | C | B | A |
| 12 | | | | | | | | | | | | | | | | | | | | | | |
| 13 | | | | | | | | | | | | | | | | | | | | | A | |
| 14 | B | B | | B | C | B | | | | | | C | C | C | C | C | C | | B | B | C | |
| 15 | C | C | C | | | C | | | | | | | | C | B | B | | | C | C | C | |
| 16 | A | B | | B | B | A | | A | | | | C | C | B | A | A | C | | B | A | A | B |
| 17 | | | | | | | | | | | | | | | | | | | | | | |
| 18 | C | C | | | | B | C | | B | C | C | | | C | C | C | C | | | B | B | |
| 19 | C | | | | | B | | | B | C | A | B | | A | | C | | | | C | B | |
| 20 | B | | | B | | A | C | | C | | A | C | | B | C | A | C | | | C | A | B |
| 21 | A | A | C | | | A | A | C | | | A | | | A | C | A | A | C | A | A | C | |
| 22 | B | B | A | A | | B | A | | A | | A | | B | C | A | C | A | B | C | | A | C |
| 23 | C | B | | C | B | A | | C | A | B | B | | | C | C | C | C | B | | B | C | |
| 24 | B | C | A | C | | C | C | | B | | | | | B | A | A | C | C | A | B | A | A |
| 25 | C | | | | | A | | | B | | A | | | A | A | | | | | A | A | A |
| 26 | | | | A | | B | | C | C | | | | | | C | A | A | A | | A | C | A |
| 27 | B | B | C | A | A | B | C | | C | | B | A | A | B | A | A | C | A | A | B | B | B |
| 28 | | | | | | A | | A | B | | A | A | | | C | | A | | | A | A | |
| 29 | A | A | A | A | A | A | A | A | A | B | B | A | A | A | A | A | A | A | A | B | A | A |
| 30 | A | B | A | A | A | B | A | | B | A | A | A | | A | A | A | A | A | A | A | A | A |
| 31 | | | | | | | | | | | | | | | | | | | | | | |
| 32 | B | C | B | B | B | B | | C | B | B | B | B | B | C | A | C | C | C | C | A | B | A |
| 33 | B | B | A | C | A | A | | | B | | | A | B | B | B | A | B | C | C | B | B | B |
| 34 | B | | | | | C | | C | C | | A | | | C | C | B | B | | | B | A | C |
| 35 | | | | | | | | | | | A | | | | | | | | | | | |
| 36 | | | | | | | | | | | A | | | | | | | | | | | |
| 37 | | | | | | | | | | | | | | | | | | | | A | | |
| 38 | | | | | | | | | | | | | | | | | | | | | | C |
| 39 | A | | | | | | | | | | | | C | | | | B | | | | | |
| 40 | | | | A | | | | | | | | | | | | | | | | | | |
| 41 | | | | | | | C | | C | | | | | | | | | | | C | | |
| 42 | C | B | A | A | | A | | B | | B | | | | A | A | B | A | C | A | A | B | B |
| 43 | B | B | C | B | A | A | B | | C | | A | | | C | A | B | | | B | B | B | B |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 44 | B | C | | | | A | C | | | | A | | | | B | C | | | B | B | B | |
| 45 | | | | | | C | | | | | C | | | | | | | | | | | |
| 46 | | | | | | C | | | | | | | | | | | | | | | | |
| 47 | B | A | A | A | B | A | B | B | C | A | B | B | B | B | B | A | B | B | A | A | A | A |
| 48 | C | C | C | C | | A | A | C | B | C | A | B | C | C | B | B | C | | C | C | C | C |
| 49 | A | A | A | A | A | A | A | A | C | A | A | A | A | A | A | A | A | B | A | A | A | A |
| 50 | A | A | B | B | A | B | B | A | C | A | A | A | C | A | C | A | A | B | B | A | A | C |
| 51 | | B | B | B | A | A | B | B | B | A | | B | B | A | O | A | A | B | B | C | A | O |
| 52 | B | C | | A | A | A | C | C | A | C | | A | C | A | C | A | C | | A | A | A | C |
| 53 | | B | | B | A | B | A | A | A | A | A | B | B | A | B | A | A | B | B | A | A | B |
| 54 | A | | A | | | | | A | | | C | A | | | | | | | | | | |
| 55 | B | | | | | | | | | | A | | | | | | | | | | C | C |
| 56 | | | | C | | C | C | | | | B | | | | | | | | | | | |
| 57 | | | | C | | B | B | | | | | | | | | | B | | | | | |
| 58 | | | | | | | A | | | | | | | | | C | | | | B | | |
| 59 | | | | | B | B | | | | | C | | | | C | B | | | | | | |
| 60 | B | B | | B | | B | B | | | | B | C | B | C | B | A | B | | B | B | C | B |
| 61 | B | C | B | A | | A | | A | | A | A | | | A | B | | | | A | B | B | C |
| 62 | C | C | | | | A | | C | C | C | | C | | B | C | A | | | | C | A | C |
| 63 | A | A | A | A | | A | A | A | A | A | A | A | | A | | A | A | A | A | A | C | A |
| 64 | B | | B | | | C | | B | | | A | | | B | | B | B | A | A | C | B | B |
| 65 | | | | | | | | | | | | | | | | A | | | | | | |
| 66 | | | | B | B | | | | C | | B | A | B | A | | A | A | | C | C | C | |
| 67 | | | | B | | | B | | B | | A | C | | | | | | | | | | |
| 68 | | | | B | | | | | C | | A | | | | | | | | | | C | |
| 69 | | | | C | | | | | B | | B | C | | | | | | | | | C | |
| 70 | | | | | | | | | B | | A | C | | | | | | | | | | |
| 71 | | | | | | | B | | C | | A | B | | | | | | | | | | |
| 72 | A | A | | A | | A | A | B | A | A | A | A | B | A | A | A | A | B | A | A | A | A |
| 73 | | | C | | | | | | | A | | C | A | | | A | | | | B | C | A |
| 74 | | | A | | | | | | | | | C | | | | A | | | | C | C | |
| 75 | B | C | | B | B | C | C | B | | C | | C | | | B | B | | C | | C | C | C |
| 76 | B | | B | B | | B | | C | | | | C | | C | C | B | C | C | B | | B | B |
| 77 | C | B | | | | C | | | | | | C | | | | | | | | | B | |
| 78 | B | | | C | A | | B | | C | | | A | | C | C | | A | | C | B | B | |
| 79 | | | | C | | | | | C | | | C | | | | C | | | | | | |
| 80 | | | C | C | | | | | | | | | | | | | | | | | B | B |
| 81 | A | A | A | A | A | A | A | A | A | A | B | B | A | A | A | A | A | A | A | A | A | A |
| 82 | B | B | B | B | A | B | B | | C | B | C | C | A | B | C | C | B | | B | C | C | B |
| 83 | | | | C | | | | | | | C | C | | | | | | | | | C | |
| 84 | | C | | | | | B | | | | | B | | | B | | | | | | | |
| 85 | | | | | | | | | | | | | | | | | | | | | | B |
| 86 | | | | C | | B | | | C | B | | | | | | B | | | C | C | C | C |
| 87 | C | C | | C | | C | B | B | C | B | B | C | | | C | C | C | B | C | C | C | C |
| 88 | | B | | C | | C | B | B | | C | | A | | | | | C | | C | C | C | B |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 89 | A | A | A | A | A | A | A | A | A | A | A | A | A | A | A | A | A | A | A | A | A | A |
| 90 |   | C |   |   |   |   |   |   |   |   |   |   |   |   |   |   |   |   |   |   |   |   |
| 91 | B | C |   | C | C |   |   | B | C | C |   | C | C | C | C | B |   | C | C | C | C | C |
| 92 | C | B | C | C |   |   | B | C |   |   |   |   |   | C | C | B |   | C | C | C | A | B |
| 93 | C |   | C | B | C | B | C |   |   |   |   |   |   | B | B | C |   |   | A | B | B | B |
| 94 |   |   |   |   |   |   |   |   |   |   |   |   |   |   |   | C |   |   |   |   |   |   |
| 95 |   |   |   |   |   |   |   |   |   |   |   |   |   | C | C |   |   |   |   |   |   |   |
| 96 | B | A | A | A | A | A | C | B | A | A | A |   | B | A | A | A | A | A | A | B | A | A |
| 97 | C | B |   | B | A | B |   |   |   |   | B |   |   | C | B | B | A |   | B | A | C | B |
| 98 |   |   |   |   |   | B |   |   |   |   | A |   |   |   |   |   |   |   |   |   | B |   |
| 99 | C |   |   |   |   |   |   |   |   |   | A |   |   |   |   |   |   |   |   |   |   |   |
| 100 |   |   |   |   |   | C |   |   |   |   | C |   |   |   |   |   |   |   |   | C |   | C |
| 101 |   |   |   |   |   |   |   |   |   |   | A |   |   |   |   |   |   |   |   |   |   |   |
| 102 |   |   |   |   |   |   |   |   |   |   | A |   |   |   |   |   |   |   |   |   |   |   |
| 103 |   |   |   |   |   |   |   |   |   |   | B |   |   |   |   |   |   |   |   |   |   |   |
| 104 |   |   |   |   |   |   | C |   |   |   |   | A |   |   |   |   |   |   |   |   |   |   |
| 105 | B |   |   |   |   |   |   | B |   |   | A | C |   | B |   | C |   |   | B | C | C | B |
| 106 |   |   |   |   | B | C |   |   |   |   |   |   |   |   |   | C |   |   |   |   |   |   |
| 107 |   |   |   |   | A |   |   |   |   |   |   |   |   |   | C | C |   |   |   |   |   |   |
| 108 | C |   |   |   |   | C |   |   |   |   |   |   | B |   |   |   | B |   |   |   |   | B |
| 109 |   | C |   | B |   | B |   |   |   |   |   |   |   | B | B | B |   |   | B | B | B | A |
| 110 |   |   |   |   |   |   |   |   |   |   |   |   |   |   |   | A |   |   |   |   |   |   |
| 111 | B | C |   | B | B | B | C | C | A | C | A |   | B | B | B | A | B | C | B | B | B | B |
| 112 |   | B |   | A |   |   | A |   | C | C |   |   | C | C | C | B | C |   | B | A | B | B |
| 113 | A | A |   | A | A | A | A | A | A | A | A | A | A | A | A | A | A |   | C | B | A | A |
| 114 | A | A | B | A | B | A | A | A | A | A | A | A |   | A | A | A | A | A | A | A | A | C |
| 115 | A | A | A | A | A | A | A | A | A | A | A | B | B | B | B | A | A |   | A | A | A | B |
| 116 | A | A | C | A | A | A | A | A | A | A | A | C |   | C | C | C | A |   | B | B | B | B |
| 117 | B | B | A | C |   | C | B | C | A | B | C | B |   | C | C | B | B | B | B | B | C | C |
| 118 | A | B |   | B | A | B | B | B | B | A | B | B | A | A | A | A | A | B | B | A | B | B |
| 119 | C | C |   | B | B | A | C | C | C | A | B | C | B | C | C | B | B | C | B | B | A | B |
| 120 | C |   |   | C |   | C |   |   |   | B | C | B |   | C | C | C | C |   | C | B | B | B |
| 121 | C |   |   | C |   | A |   |   |   |   | C |   |   |   |   |   | C |   | C | B | C | B |
| 122 |   |   |   |   |   | A |   |   |   |   |   |   |   |   |   |   | C |   |   |   | C |   |
| 123 |   |   |   |   |   |   |   |   |   |   |   |   |   |   |   |   |   |   |   |   |   |   |
| 124 | A | A | A | A | A | A | A | A | A | A | B | B | B | A | A | A | A | B | A | A | A | A |
| 125 | A | A |   |   |   | A | C |   |   |   | A | A |   | A | A | A |   |   | A | C | A | A |
| 126 | A | A | A |   |   | A | A | A | A | B | B | B |   | A | A | A | A | B | A | A | A | A |
| 127 | A | A | A |   |   | A | A | A | A | A | B | A | B | A | A | A | A |   | A | A | A | A |
| 128 |   |   | B |   |   |   | C |   | C | B | C | B | B | A | C | A | B | B | A | B | A | B |
| 129 |   |   |   |   |   |   |   |   |   |   |   |   |   |   |   |   |   |   |   |   | C |   |
| 130 |   | C |   |   |   | C |   | B | C | C | A |   | C |   |   | C |   | C | C | C | A | C |
| 131 | C |   |   |   |   | B |   |   |   |   |   |   |   |   |   | C |   |   |   | C | B |   |
| 132 |   |   | C |   |   |   |   |   |   |   | B |   |   |   |   |   |   | A |   |   |   |   |
| 133 |   |   |   |   |   |   |   |   |   |   |   |   |   |   |   |   |   |   |   |   |   |   |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 135 | A | | A | A | A | A | A | A | A | A | A | A | B | A | A | A | A | A | A | A | A | B |
| 136 | B | | | | | | | | | | | | | | | | | | | | | |
| 137 | A | B | C | | C | A | | | B | C | A | C | | C | C | | C | C | C | C | A | C |
| 138 | | | | B | C | | C | | C | C | A | B | | C | A | C | C | C | B | A | A | |
| 139 | | | | | | | | | | | A | | | | | | | | | | | |
| 140 | | | | | | | | | | | A | | | | | | | | | | | |
| 141 | C | | | | | A | | | | | A | | | | | | | C | | C | | |
| 142 | | | | | | | | | | | B | | | | | | | | | | | |
| 143 | B | | | C | | B | | B | | C | A | | B | C | | | C | B | C | C | B | |
| 144 | | | | | | | | | | | | | | | | | | B | | | | |
| 145 | | | | | | | | | | | | | | | | | | B | | | | C |
| 146 | C | | | | | | | | C | | | | | C | | | | | | | | |
| 147 | | | | | | | | | | | | | | | | | | | | | | C |
| 148 | A | B | B | B | A | B | A | C | B | A | A | A | C | B | B | A | B | A | B | A | B | A |
| 149 | A | B | A | B | C | C | | | B | B | A | B | B | C | C | C | C | | B | C | A | A |
| 150 | B | A | | A | A | A | B | | C | B | A | | B | B | B | C | A | A | B | B | B | A |
| 151 | | | | | | | | | | | | | | | | | | | | | | |
| 152 | C | | A | A | B | B | | | C | | A | B | | B | C | C | B | | A | C | B | A |
| 153 | A | A | | A | A | A | A | | C | C | B | B | B | B | A | A | | A | B | A | A | |
| 154 | | | | | | | | | | | | C | | | | | | | | | | A |
| 155 | A | B | C | B | C | A | C | | C | B | A | B | B | C | A | B | B | B | A | A | A | C |
| 156 | B | B | B | B | B | B | C | | C | C | B | | C | C | B | B | C | C | B | A | C | B |
| 157 | B | | | C | C | B | | | | | | | | | | C | A | | C | A | B | |
| 229 | B | B | B | B | A | B | B | | | | B | C | | C | B | B | | | B | C | B | B |
| 230 | B | B | | B | B | C | C | | | | A | | | B | B | C | C | | B | C | B | B |
| 231 | | | | | | | | | | | A | | | | | | | | | | | |
| 232 | B | A | B | A | A | B | C | C | A | | C | B | C | C | A | C | C | A | A | B | B | A |
| 233 | B | B | A | A | C | A | B | B | B | B | A | C | | B | C | A | C | A | B | B | A | B |
| 234 | | B | B | B | C | C | | | | | A | | A | A | C | B | | B | A | C | B | B |
| 235 | A | A | A | A | A | A | A | | A | B | A | B | | A | A | B | B | A | A | A | A | A |
| 236 | B | B | A | A | C | B | B | | B | | A | C | A | C | A | B | | A | B | B | B | B |
| 237 | B | B | B | A | C | A | A | | | B | A | | | B | C | B | | A | A | C | B | B |
| 238 | | | | | | | | | | | | | | | | | | | | | | |
| 239 | B | B | A | A | B | A | B | | B | | A | C | | C | A | B | C | | A | B | B | B |
| 240 | B | B | A | A | A | B | A | A | A | A | A | A | C | A | A | A | A | B | A | B | B | A |
| 241 | A | A | A | A | C | A | B | | C | B | B | A | A | C | C | B | A | A | A | A | A | B |
| 242 | | | | | | | | | | | | | | | | | | | | | | |
| 243 | | | | A | | | | | | | | | | | | | | | | | | B |
| 244 | B | C | B | B | | B | | A | C | | A | | | B | B | A | B | C | B | C | C | |
| 245 | | | | | | | | | | | | | | | | | | | | A | A | |
| 246 | A | A | A | A | A | A | A | | A | A | A | A | B | B | A | A | A | A | A | A | A | A |
| 247 | B | A | A | C | C | A | C | | | B | A | B | C | B | C | A | B | B | A | B | A | A |
| 248 | | | C | B | B | A | C | | C | C | C | C | | C | C | B | C | | C | A | A | C |
| 249 | A | B | | A | B | A | C | | C | | A | B | | C | C | | | | B | A | A | |
| 250 | | | | | | | | | | | | | | | | | | | | C | | |
| 251 | | | | | | | | | | | A | | | | | | | | | | | |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 252 | A |   |   | A | A | A | A | C |   | C | A | B |   |   | A | A | A | C | A | A |   | A |
| 253 | C |   |   |   | C | B |   |   | C |   | A | C |   |   |   |   |   | C | C | C | B | B |
| 254 |   |   |   | C | B | C |   |   |   |   | A |   |   |   |   | C |   |   | B | B | C | C |
| 255 |   | B |   | B | B | A | B |   |   |   | B |   |   | B | C | B |   |   | A | C | A | B |
| 256 | B |   | C | A | C | C | C |   |   |   | A |   |   |   | A | B |   |   | C | B | C | C |
| 257 |   | C |   | A | C | A | C |   | A |   | B |   |   | A | A | A |   | C | A |   | A | A |
| 258 | A |   | A | A | C | A |   | A |   |   |   |   | C | B | C | A | C | A | C | A | C |   |
| 260 | C |   |   |   | B | A | A |   |   |   |   |   |   |   |   |   | A |   | C |   | A |   |
| 261 |   |   |   |   |   |   |   |   |   |   |   |   | C |   |   | B |   |   |   |   |   |   |
| 262 |   |   |   |   |   | C |   |   |   |   |   | C |   |   |   |   |   | C |   |   |   |   |
| 263 | C |   |   | C | C | A |   |   |   |   | A | A | A | C | C | A | A | A | C | A | C | A |
| 264 | A | A | A | A | A | A | A | A | A | A | A | A | B | A | A | A | A | A | A | A | A | A |
| 265 | A | A |   | B | B | C | B | A | C | A | C | C | C | B | A | B | C |   | A | A | B | A |
| 266 | A | A | B | A | A | A | A | A | A |   | A | A |   | C | A | A | A |   | A | A | A | A |
| 290 | A | A | C | B | B | A | A |   |   |   | A |   | C | B | B | A | C |   | B | B | A | A |
| 291 | A | B | C | C | B | A | B |   |   |   | A |   | B | A | A | C | C |   | B | A | B | A |
| 292 | A | A | A | C | B | A | A | A |   |   | A | B | B | B | A | A | A |   | B | A | C | A |
| 293 |   |   |   |   |   | C |   |   |   |   | C |   |   |   |   |   |   |   |   | C |   |   |
| 294 |   |   |   |   |   | B |   |   |   |   | C |   |   |   |   |   |   | A |   | C |   |   |
| 158 | A | B | C | C | C | A | C | B |   | C | A | C | B | C | A | C | B | C | B | A | C | C |
| 159 | A | C | C | C | C | A | C |   | B | C | A | C | C | B | A | A | B | C | B | C | A | C |
| 160 | A | B | C | B | B | A | A |   | A |   | A | C | C | B | C | A | A | C | B | B | B | C |
| 161 |   |   |   |   |   |   |   |   |   |   | A |   |   |   |   |   |   |   |   |   |   |   |
| 162 |   |   |   |   |   |   |   |   |   |   | A |   |   |   |   |   |   |   |   |   |   |   |
| 163 |   |   |   |   |   |   |   |   |   |   | C |   |   |   |   |   |   |   |   |   |   |   |
| 164 |   |   |   | A |   |   |   | B |   |   | C |   |   |   |   |   |   |   |   | B |   |   |
| 165 | C | B | C | C | A | C | C | B | B | B | C | C | C | C | B | C | B | A | C | C | C | B |
| 166 | B | B | B | A | A | B | B | A | B | B | C | B | C | B | A | B | A | A | A | C | A | C |
| 167 | A | A | A | B | A | A | A | A | A |   | A | A | A | A | C | A | A | B | A | A | A | A |
| 168 | B | C | C | B | A | A | C |   | B |   | C | C |   | B | C | A | B |   | C | A | C | B |
| 169 | B | B | A | A | B | A |   | B | A |   | A |   | B | B | C | A | A |   | A | C | A | C |
| 170 | A | A | A | A | B | A | A | C | C |   | A |   | C | B | A | C | A |   | A | A | A | A |
| 171 | B | C | C | B | B | B | A |   | C |   | A |   | B | C |   | C |   |   | C | B | A | A |
| 172 |   |   |   |   |   |   |   |   |   |   |   |   |   |   |   |   |   |   |   |   |   |   |
| 173 |   |   |   |   |   |   |   |   |   |   | A |   |   |   |   |   |   |   |   |   |   |   |
| 174 | C | B | C | A | C | B | B |   | B |   | B | C | B | B | B | C | B | B | A | C | B | B |
| 175 | B | B |   | B | A | B | B |   | A |   | A | B | A | A | A | B |   |   | B | B | B | C |
| 176 |   |   | C | C | C | B |   |   |   |   | B | C | C |   | C |   |   |   | C | A | B | A |
| 177 |   |   |   | B |   | C |   | C |   |   | B |   |   |   |   |   |   |   | B |   | C |   |
| 179 |   |   |   |   |   |   |   |   |   |   |   |   |   |   |   |   |   |   |   |   |   |   |
| 180 | A | B | B | A | C | A | A | C | B |   | B | C | B |   | B | B | B | B | A | C | A | B |
| 181 | A | A | A | B | A | A | A | A | A |   | A | B | A | A | A | A | A |   | A | A | B | A |
| 182 | B | B | C | A | B | A | B | B | A |   | B | C | B | B | A | A |   |   | A | B | B | B |
| 183 |   |   |   |   |   |   |   |   |   |   | A |   |   |   |   |   |   |   |   |   |   |   |
| 184 |   |   |   |   |   |   |   |   |   |   | C |   |   |   |   |   |   |   |   |   |   |   |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 185 | | | | | | | | | | | | | | | | | | | | | | |
| 186 | | | | | C | | | | | | | | | | | | | | | | | |
| 187 | C | A | C | C | | B | | | A | B | A | | | A | | C | | | C | C | A | |
| 188 | | | C | B | A | B | C | | | | B | | C | C | B | A | | | B | C | B | A |
| 189 | | | | | | | A | | | C | | A | | | | | A | | | C | | |
| 190 | | | C | | | | | | C | | A | | C | C | | | | C | | | | |
| 191 | | | | | | | A | | | | | | | | C | | | | | C | | |
| 192 | B | B | C | B | A | C | A | | B | B | A | A | C | C | B | B | C | | B | A | B | A |
| 193 | C | A | B | B | A | B | A | | C | C | B | C | C | B | B | A | C | | B | B | C | B |
| 194 | C | B | C | C | B | B | C | A | C | C | A | B | C | B | A | | C | A | | C | | |
| 195 | A | B | B | A | A | A | A | | C | C | A | A | B | C | B | A | B | | A | B | A | B |
| 196 | B | B | B | A | B | A | A | | B | B | A | | | B | A | B | C | A | A | B | A | B |
| 197 | B | B | C | A | B | A | A | | C | C | A | A | | C | A | C | C | C | A | B | B | C |
| 198 | A | C | C | A | A | C | B | B | B | | C | B | B | C | C | C | B | A | A | B | B | C |
| 199 | B | B | B | C | B | A | C | C | C | | A | | C | C | A | B | C | C | C | B | B | B |
| 200 | A | | | A | | A | A | | B | C | A | C | | B | A | C | | C | A | B | A | |
| 201 | A | | B | A | | C | C | C | C | | C | | | B | C | A | | C | C | C | A | |
| 202 | | | | | A | | | | | | A | | | | | | | | | | | |
| 203 | A | A | B | A | A | A | A | B | A | C | A | C | C | A | A | A | A | C | A | A | A | C |
| 204 | | C | B | B | B | C | B | C | B | B | C | | B | B | C | C | C | C | C | B | B | |
| 205 | | | | | | | | | | | A | | | | | | | | | C | | |
| 206 | C | | C | | | | | | | | | B | | C | B | B | B | | C | A | C | |
| 207 | C | | A | | | B | A | B | A | | | | C | C | A | A | | C | C | C | | |
| 208 | | | | | | | | B | | | | | | C | | | | | | B | | |
| 209 | A | A | A | A | A | A | A | B | A | C | A | A | A | A | A | A | A | A | A | A | A | C |
| 210 | A | B | B | | C | A | B | B | B | B | A | C | C | B | B | C | C | C | C | B | A | B |
| 211 | B | | C | C | A | A | C | C | | C | A | | B | C | A | A | C | B | B | C | B | |
| 212 | A | C | B | C | | B | A | B | A | A | A | B | | C | B | B | C | B | B | C | B | |
| 213 | B | B | B | B | A | B | B | | B | B | C | | B | C | C | C | A | A | B | B | C | A |
| 214 | A | A | C | A | B | B | B | | B | B | A | A | | B | A | A | C | | A | C | B | |
| 215 | | | | | | | | | | | | B | | | | | | | | | | |
| 216 | C | C | A | | A | C | C | | C | A | | C | | C | C | A | B | A | A | C | C | B |
| 217 | C | B | | A | B | C | C | | B | C | B | B | C | C | A | C | C | | C | C | A | |
| 218 | | | | | | | | | | | | | | | | | | | | | | |
| 219 | | | | | | | | | | | | | | | | | | | | | | |
| 220 | C | B | C | | | A | A | C | A | C | A | | A | B | A | C | C | A | B | A | A | B |
| 221 | A | A | A | A | A | A | B | B | C | C | A | A | | A | A | A | A | B | A | B | A | B |
| 222 | | | | | | | | | | | | | | | | | | | | | | |
| 223 | B | C | | | A | A | C | | B | | | | | C | | B | | | | C | A | |
| 224 | C | | | | | C | | | | | | | | | | | | | | C | | |
| 225 | | | | | | | | A | | | | | | | | | | | | | | |
| 226 | | | | | | | B | | B | | | | | | | | | | | | | |
| 227 | A | A | A | A | A | A | A | A | A | A | A | A | A | A | A | A | A | A | A | A | A | C |
| 228 | C | | | | | | C | C | C | C | A | A | | | C | | C | | | C | C | A |
| 267 | B | | | B | C | C | B | B | | | | | | | C | B | | | B | C | B | |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 268 | B | A | A | A | A | A | A |   | A | B | A | C | B | B | A | A | C |   | B | A | A | A |
| 269 | A | A | A | A | A | A | A |   | A | A | C | A | A | A | A | A | A | A | A | A | A | A |
| 270 | B | B | C | B | B | A | B |   |   |   | B | C |   | C | A | B | B |   | B | B | B | C |
| 271 | C | B |   | A | C | B |   | A | C |   |   |   |   | B | B | C |   | A | A | C | B | C |
| 272 | B | B | B | B | B | A | C |   |   |   | A |   |   | C | A | A | B |   | B | B | A | C |
| 273 |   |   |   |   |   | C |   |   |   |   | B |   |   |   |   |   |   |   |   |   |   |   |
| 274 |   |   |   |   |   | C |   |   |   |   |   |   |   |   |   |   |   | B |   |   |   |   |
| 275 |   |   |   |   |   | C |   |   |   |   | A | C |   |   |   | C |   |   |   |   |   |   |
| 276 | B | A | B | A | A | A | A |   | A | B | A | C | B | B | A | A | C | B | B | A | B | B |
| 277 | B | B | C | B |   | B |   |   |   | C |   |   | B | A | A | A | B | B | B | B | C | A |
| 278 |   |   |   |   |   | B |   |   |   |   |   |   |   |   |   |   | C |   | B |   |   |   |
| 279 |   | C |   |   |   |   |   |   | A | A |   |   |   | C | C | C |   |   |   |   |   |   |
| 280 | A | A | A | A | A | A | A | A | A | A | A | B | B | C | A | A | B | B | A | B | A | B |
| 281 | B | B | C | B | C | A | C | C | C | B | A | A | C | A | A | B | C | C | B | A | A | C |
| 282 | B | A | B | A | A | A | A |   | C | C | A | B | C | B | A | A | B | A | A | A | B | A |
| 283 | C | C | C | C | A |   | B |   |   | B | A | B | B | B | C | C |   | B | C | C | B | B |
| 284 | B | C |   | B | C | A | C |   | A |   | A | C |   | C | C | B |   | A | B | C | A | C |
| 285 | A | A | A | A | A | A | A | A | A | B | A | B | A | A | A | A | B | A | A | A | B | A |
| 286 | B | A | A | A | A | B | A | A | A | B | A | B | B | B | A | A | B | B | A | B | A | B |
| 287 | A | A | B | A | B | A | A | A | A | A | B | A | B | B | A | A |   | B | A | A | B | A |
| 288 | B |   |   | C |   | B |   | C |   |   |   |   |   | C | C | B |   |   | C | C | B | C |
| 289 | C |   |   |   |   |   |   | C |   |   |   |   |   |   |   |   |   |   |   |   |   |   |

TABLE 17-continued

Target coverage within various tumor entities, for expression of source genes of selected peptides: A gene was considered over-expressed if its expression level in a tumor sample was more than 2-fold above the highest 75% percentile of expression levels determined from high and medium risk normal tissue samples. Over-expression categories are indicated as "A" (>=50% of tumors above the cutoff), "B" (>=20% of tumors above the cutoff, but <50%), and "C" (>=5% of tumors above the cutoff, but <20%).

| SEQ ID No. | BRCA | BLCA | CHOL | COAD | DLBC | ESCA | GBM | KICH | KIRC | KIRP | LAML | LGG | LIHC | LUAD | LUSC | OV | PAAD | PRAD | READ | SKCM | STAD | UCEC |
|---|---|---|---|---|---|---|---|---|---|---|---|---|---|---|---|---|---|---|---|---|---|---|
| 295 |  |  |  |  |  |  | A | A |  |  | B |  |  |  |  |  |  |  |  |  |  |  |
| 296 |  |  |  |  |  |  | A |  |  | C | B | A |  |  |  |  |  |  |  |  |  |  |
| 297 |  | B |  |  |  | C |  |  |  |  |  |  |  | C | C |  |  |  |  |  |  |  |
| 298 | C |  |  | C |  | B |  |  |  |  |  |  |  | A | A | C |  |  |  |  |  |  |
| 299 | C |  | A | A |  | A |  |  |  | B |  |  |  | A | A | A | A | C | C | C | A | B |
| 300 |  |  |  |  |  |  |  |  | B |  |  |  | A |  |  |  |  |  |  |  |  |  |
| 301 |  |  |  |  |  |  |  | C |  |  | A |  |  |  |  |  |  |  |  |  |  | C |
| 302 | B | B |  | B | A | B |  | C | A |  |  |  |  | A | A | A | C | C | B | B | B | A |

BLCA = Bladder urothelial carcinoma (N = 408),
BRCA = Breast cancer (N = 1104),
CHOL = Cholangiocarcinoma (N = 36),
COAD = Colon and rectal adenocarcinoma (N = 462),
DLBC = Lymphoid neoplasm diffuse large B-cell lymphoma (N = 48),
ESCA = Esophageal cancer (N = 185),
GBM = Glioblastoma multiforme (N = 169),
KICH = Kidney chromophobe (N = 66),
KIRC = Clear cell kidney carcinoma (N = 534),
KIRP = Papillary kidney carcinoma (N = 291),
LAML = Acute Myeloid Leukemia (N = 173),
LGG = Lower grade glioma (N = 534),
LIHC = Liver hepatocellular carcinoma (N = 374),
LUAD = Lung adenocarcinoma (N = 517),
LUSC = Lung squamous cell carcinoma (N = 503),
OV = Ovarian serous cystadenocarcinoma (N = 309),
PAAD = Pancreatic ductal adenocarcinoma (N = 179),
PRAD = Prostate adenocarcinoma (N = 498),
READ = Colon and rectal adenocarcinoma (N = 167),
SKCM = Skin cutaneous melanoma (N = 473),
STAD = Stomach adenocarcinoma (N = 415),
UCEC = Uterine corpus endometrial carcinoma (N = 546).

TABLE 18

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| SEQ ID No. | AML | BRCA | CLL | CRC | GB | GBC_CCC | GC | HCC | NHL |
|---|---|---|---|---|---|---|---|---|---|
| 1 | | | | | +++ | | | | |
| 2 | | | + | + | +++ | ++ | + | | |
| 4 | | | | | ++ | | | | |
| 5 | + | | + | | | | | | + |
| 6 | | | | +++ | | | | | |
| 8 | | | | | + | | | | + |
| 9 | | +++ | | + | | +++ | ++ | | |
| 10 | +++ | | + | | + | | | | |
| 11 | | + | | | | | | | + |
| 12 | | | | | + | | | | |
| 13 | | + | | | | | + | | |
| 14 | + | +++ | | ++ | ++ | + | + | + | ++ |
| 15 | | + | + | | | + | | | |
| 16 | | + | | + | | + | | | + |
| 17 | | | + | | | | | | |
| 18 | | | | | | ++ | + | | |
| 19 | | | | | + | | | | + |
| 20 | | + | + | | + | | | | + |
| 21 | + | + | | + | + | + | + | | +++ |
| 22 | | ++ | | + | | +++ | ++ | | |
| 23 | | | | | | + | | | |
| 24 | | +++ | | | +++ | | | +++ | |
| 25 | | | | | | | | | |
| 26 | + | | | | + | | | | ++ |
| 27 | + | ++ | | +++ | | + | + | | + |
| 28 | | | | | | | | | |
| 29 | | | | | + | | | | |
| 31 | | | | | +++ | | | | |
| 32 | +++ | +++ | | +++ | +++ | +++ | +++ | ++ | +++ |
| 33 | | ++ | | | | | + | | +++ |
| 34 | | + | | | + | | | | |
| 35 | + | | ++ | | | | | | |
| 37 | + | | | | | | | | |
| 38 | + | | + | | | | | | |
| 39 | | +++ | | | | | | + | |
| 40 | | | | | | | | | + |
| 41 | | | | | + | | | | |
| 42 | | | | ++ | | +++ | +++ | | |
| 43 | | | | + | + | | | | ++ |
| 44 | + | + | ++ | + | + | | | | +++ |
| 45 | | + | | | + | + | | | ++ |
| 46 | | | | | + | | | | |
| 47 | | | | | | | | | + |
| 48 | | | | + | | + | | | |
| 49 | | | | | | | | | |
| 50 | | | | | | | | | + |
| 51 | | | | | | | + | | |
| 52 | | | | | | | + | | + |
| 53 | + | | | | | | | | + |
| 54 | | | | | | | | | |
| 55 | | + | | | | | | | |
| 56 | + | | | | | | | | + |
| 57 | | | | | ++ | | | | + |
| 58 | | | | | +++ | | | | |
| 59 | | | | | +++ | | | | + |
| 60 | +++ | | | | | | | | |
| 61 | | + | | | + | + | | | + |
| 62 | | | | + | ++ | ++ | ++ | + | |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| # | C1 | C2 | C3 | C4 | C5 | C6 | C7 | C8 | C9 |
|---|----|----|----|----|----|----|----|----|----|
| 63 |  | + | + |  | + | + |  |  |  |
| 64 |  |  |  |  |  |  |  |  |  |
| 65 |  |  |  |  | + |  |  | + |  |
| 67 | ++ |  | ++ |  |  |  |  | ++ |  |
| 68 |  |  | +++ |  | + |  | ++ |  |  |
| 69 | + |  |  |  |  |  |  |  |  |
| 70 |  |  |  |  |  |  |  | + |  |
| 71 | + |  |  | + |  |  |  |  |  |
| 72 | +++ | + |  |  |  |  |  |  |  |
| 73 | + |  |  |  |  |  |  |  |  |
| 74 | +++ |  |  |  |  |  |  | ++ |  |
| 75 |  | + |  | + | + | + |  | + |  |
| 76 |  | + | + |  | + |  |  | + |  |
| 78 | + |  |  |  | + |  |  |  |  |
| 79 |  | + | + |  |  |  | + |  |  |
| 80 | + |  |  |  |  |  |  |  |  |
| 81 |  |  |  |  |  |  | + |  |  |
| 82 |  | + |  |  |  |  |  | ++ |  |
| 83 |  |  | ++ |  | + | +++ |  |  |  |
| 84 |  |  |  | + |  |  |  |  |  |
| 85 |  | + |  |  |  |  |  |  |  |
| 86 |  |  |  | + |  |  |  | + |  |
| 90 |  | + |  |  |  |  |  |  |  |
| 91 |  | + | + |  |  |  |  | + |  |
| 93 |  |  | + |  |  |  |  |  |  |
| 94 | ++ |  |  |  |  |  |  |  |  |
| 95 |  | + |  |  |  | + |  |  |  |
| 96 |  |  |  |  |  |  |  |  |  |
| 97 | + | + | + | + | + |  | + | +++ |  |
| 98 |  |  |  |  |  |  |  |  |  |
| 99 | + |  | +++ | + | + | + |  | + |  |
| 100 |  |  |  |  |  |  | +++ |  |  |
| 101 | +++ |  |  |  |  |  |  |  |  |
| 102 | +++ |  |  |  |  |  |  |  |  |
| 104 |  |  |  | +++ |  |  |  |  |  |
| 105 |  |  | +++ | +++ |  |  |  | +++ |  |
| 106 | +++ | +++ | + | +++ | + |  |  | + | +++ |
| 107 |  |  | + |  |  |  |  | +++ |  |
| 108 |  | +++ |  |  |  |  | +++ |  |  |
| 109 |  |  |  |  | +++ | + |  |  |  |
| 111 | +++ | + | ++ |  | + |  |  | +++ |  |
| 112 |  |  |  |  |  |  |  |  |  |
| 113 | + |  |  |  | + |  |  | + |  |
| 114 |  |  |  |  |  |  |  |  |  |
| 115 |  |  |  |  | + |  |  |  |  |
| 116 |  | + |  | + | + |  |  | + |  |
| 117 |  |  |  |  |  | + |  |  |  |
| 118 |  |  |  |  | + |  |  |  |  |
| 119 |  |  | + |  |  |  |  | + |  |
| 120 | + |  |  |  | + |  |  | + |  |
| 121 |  |  |  |  |  |  |  |  |  |
| 122 |  | ++ |  | + |  | +++ | ++ |  |  |
| 123 |  |  |  | ++ |  | + | +++ |  |  |
| 127 |  | + |  | + | + |  | + |  |  |
| 128 |  | +++ |  |  |  |  | + |  |  |
| 129 |  |  | + |  | + |  |  | ++ |  |
| 130 |  |  | ++ |  |  | + |  | + |  |
| 133 | ++ |  |  |  |  | + |  |  |  |
| 134 |  |  |  |  |  | + |  |  |  |
| 135 |  |  |  |  |  |  |  |  |  |
| 136 |  | + |  |  |  | + |  |  |  |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| # | 1 | 2 | 3 | 4 | 5 | 6 | 7 |
|---|---|---|---|---|---|---|---|
| 137 |  |  | + | + | + |  | + |
| 138 | + | + |  | + | + | + |  | + |
| 140 |  |  |  |  |  |  |  |
| 141 | + | + | + |  | + |  |  |
| 142 |  |  |  | +++ | + |  |  |
| 144 |  | + |  | + |  | + |  |
| 145 | + |  |  |  | + | + |  |
| 146 |  |  |  |  |  | + |  |
| 147 |  |  |  |  |  |  |  |
| 148 |  |  |  | ++ |  |  |  |
| 149 |  | +++ |  | + | +++ | +++ | +++ |
| 150 | + | + | ++ | + |  |  | + |
| 151 |  | + |  | + | + | + |  |
| 152 | + |  | + |  |  |  | + |
| 153 |  | + |  | + |  |  |  |
| 154 |  |  |  |  |  | ++ |  |
| 155 | + | + | + | + | + |  | + |
| 156 |  | + |  | + |  | + |  |
| 157 |  | ++ |  | + | +++ | ++ |  |
| 229 |  | + | ++ | ++ | + |  | ++ |
| 230 | + | + | + | + | + | + | +++ |
| 231 | + |  | + |  |  |  |  |
| 232 | + |  |  | + |  | + | ++ |
| 233 |  | + | + | + | + |  | +++ |
| 234 |  | ++ |  |  |  |  |  |
| 235 | + | + |  |  |  |  | + |
| 236 |  |  |  |  |  |  | + |
| 237 |  | + |  | + | + | + | + |
| 238 | + |  |  |  |  |  |  |
| 239 | + | + |  | + | + |  | + |
| 240 |  |  |  |  |  |  | + |
| 241 |  | + |  |  |  |  | + |
| 242 |  |  |  |  | ++ |  | ++ |
| 243 |  |  | ++ |  |  |  | +++ |
| 244 |  |  |  | + | + | + |  |
| 245 |  |  |  |  |  | + |  |
| 246 |  | + |  |  |  |  |  |
| 247 | + | + |  |  |  | + | + |
| 248 |  |  |  | + | ++ |  | + |
| 249 | + | + |  | + | + | + | + |
| 250 |  |  |  |  |  |  | ++ |
| 251 | +++ |  |  |  |  |  | + |
| 252 | + | ++ |  | ++ | +++ | ++ | + | +++ |
| 253 | + |  | +++ |  | + |  |  |
| 254 | + |  |  |  | + |  | + | ++ |
| 255 | + | + |  | + | ++ | + | ++ | +++ |
| 256 |  |  |  | + | + | + | + | ++ |
| 257 |  |  |  |  |  |  |  |
| 259 |  |  |  |  |  |  |  |
| 263 | ++ |  | + |  |  |  | + |
| 264 |  |  |  |  |  |  |  |
| 265 |  |  |  |  |  |  | + |
| 266 | + |  | + |  |  |  |  |
| 290 | + | + |  | + | + |  | + | +++ |
| 291 | + | ++ | ++ | ++ | + | + | +++ |
| 292 |  |  |  |  |  |  |  |
| 293 |  |  |  | +++ |  |  |  |
| 294 |  |  |  | +++ |  | ++ |  |
| 158 |  | + | + | + |  |  | + |
| 159 | + | + | + | + | + | + |  |
| 160 |  | + |  | + |  | + |  | + |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| # | 1 | 2 | 3 | 4 | 5 | 6 | 7 | 8 |
|---|---|---|---|---|---|---|---|---|
| 161 | + | | + | | | | | |
| 163 | + | | + | | | | | |
| 164 | | + | | | | + | | + |
| 165 | | + | | | + | | | ++ |
| 166 | | | | | + | | | + |
| 167 | | | | | | | + | ++ |
| 168 | | | | | | | | |
| 169 | | | | | + | | + | + |
| 170 | | | | | + | | | |
| 172 | | | | | +++ | | + | |
| 173 | + | | + | | + | | | + |
| 174 | | | | | ++ | + | | |
| 175 | | | | | + | | | + |
| 176 | | | | | | | | |
| 177 | | | | | +++ | +++ | +++ | |
| 178 | | | | | | | | +++ |
| 179 | | | | ++ | | | | |
| 180 | | | | | + | + | + | + + |
| 182 | | | | | | | | |
| 183 | ++ | | | | | | | + |
| 184 | | | | | | + | | |
| 185 | | | | | | | | |
| 186 | | | | | | | | |
| 187 | | | | | | | | + |
| 188 | | | | | +++ | | | |
| 189 | | | | | + | | ++ | |
| 190 | | | + | | | | | |
| 191 | | | | | +++ | | | |
| 192 | + | | | | + | | | ++ |
| 193 | | + | | + | | + | | + |
| 194 | | | | | + | | | |
| 195 | | | | | + | | | + |
| 196 | | | | | | | | |
| 197 | | | | | | | | + |
| 198 | + | + | | + | + | + | | ++ |
| 199 | | | | | | | | |
| 200 | | + | | | + | | | |
| 201 | | + | | + | + | + | + | ++ |
| 202 | + | | | | | | | |
| 203 | | | | + | + | + | + | + |
| 204 | | + | | + | | | + | ++ |
| 205 | + | | +++ | | | | | ++ |
| 206 | | + | | | | | | |
| 207 | | | | | + | | | |
| 208 | | | | | | | +++ | |
| 210 | + | + | | | ++ | +++ | | + |
| 211 | | + | | + | | | | |
| 213 | | + | | | | | | ++ |
| 214 | + | ++ | | | | | | |
| 215 | | | | | + | | | |
| 216 | | | | | + | | | |
| 217 | | + | | ++ | + | | ++ | |
| 218 | | | | | ++ | + | | |
| 219 | | | | | ++ | | | |
| 220 | | | | | +++ | +++ | +++ | |
| 221 | | | | | | | | |
| 222 | | | | | | | | |
| 223 | | + | | | | | | + |
| 224 | | + | | | | | | |
| 225 | | | | | | | | |
| 226 | | | | | | | | |

TABLE 18-continued

Expression scores. The table lists peptides from genes that are very
highly over-expressed in tumors compared to a panel of normal tissues (+++),
highly over-expressed in tumors compared to a panel of normal tissues (++)
or over-expressed in tumors compared to a panel of normal tissues (+).
AML = acute myeloid leukemia (N = 11), CLL = chronic lymphocytic leukemia
(N = 10), CRC = colorectal cancer (N = 20), GB = glioblastoma (N = 24),
GBC_CCC = gallbladder adenocarcinoma and cholangiocarcinoma (N = 3), GC =
gastric cancer (N = 11), HCC = hepatocellular carcinoma (N = 15), NHL = non-
Hodgkin lymphoma (N = 10), NSCLC = non-small cell lung cancer (N = 11), OC =
ovarian cancer (N = 12), OSCAR = esophageal cancer, including cancer of the gastric-
esophageal junction (N = 11), PC = pancreatic cancer (N = 26), PCA = prostate cancer
and benign prostate hyperplasia (N = 5), RCC = renal cell carcinoma (N = 10), SCLC =
small cell lung cancer (N = 10), UBC = urinary bladder cancer (N = 10), UEC =
uterine cancer (N = 10). The baseline for this score was calculated from measurements
of the following relevant normal tissues: adipose tissue, adrenal gland, artery,
blood cells, bone marrow, brain, cartilage, colon, esophagus, gallbladder, heart,
kidney, liver, lung, lymph node, pancreas, pituitary, rectum, skeletal muscle, skin,
small intestine, spleen, stomach, thyroid gland, trachea, urinary bladder, and vein.

| SEQ ID No. | | | | | | | | |
|---|---|---|---|---|---|---|---|---|
| 267 | ++ | | | | | | | |
| 268 | + | | | + | | | | ++ |
| 270 | | | | + | | | | + |
| 271 | ++ | | +++ | | +++ | + | + | ++ |
| 272 | | | | | | | | + |
| 274 | + | | | + | | | | + |
| 275 | | | + | | | | | |
| 276 | + | | | + | | | | ++ |
| 277 | ++ | | + | | ++ | + | | |
| 278 | | +++ | + | | | + | | |
| 279 | | | | | | | | |
| 281 | | + | | + | + | + | | + |
| 282 | | | | | | | | + |
| 283 | | | | + | | | + | |
| 284 | | | | + | | | | + |
| 285 | + | + | | | | | | + |
| 287 | | | | + | | | | |
| 288 | ++ | | + | | | | | ++ |
| 295 | | | | +++ | | | | |
| 296 | | | | +++ | + | | | |
| 297 | | | | | ++ | | | |
| 298 | ++ | | + | | +++ | ++ | | |
| 299 | + | | ++ | | +++ | +++ | | |
| 302 | + | | | | | | | + |

| SEQ ID No. | NSCLC | OC | OSCAR | PC | PCA | RCC | SCLC | UBC | UEC |
|---|---|---|---|---|---|---|---|---|---|
| 1 | | | | | | | | | |
| 2 | +++ | + | | + | | +++ | | | + |
| 4 | ++ | +++ | +++ | | | | + | | ++ |
| 5 | | + | | | | | + | | |
| 6 | | | | | | | | | |
| 8 | + | + | + | | | | + | | + |
| 9 | ++ | + | +++ | ++ | | | | + | ++ |
| 10 | + | + | + | | | | + | ++ | |
| 11 | + | ++ | + | + | | | + | | |
| 12 | | + | + | | | | | | |
| 13 | | + | | | | | + | | |
| 14 | ++ | + | ++ | + | | | +++ | + | + |
| 15 | + | | + | + | | | | | |
| 16 | + | ++ | + | | | | +++ | | |
| 17 | | | | | | | | | |
| 18 | ++ | | +++ | | | + | | | |
| 19 | | | | | | | | | |
| 20 | + | + | | | | | + | | + |
| 21 | + | + | + | + | | | ++ | + | + |
| 22 | + | +++ | +++ | + | | | + | ++ | |
| 23 | + | | | + | + | | | +++ | + |
| 24 | +++ | | +++ | + | | | +++ | | |
| 25 | | +++ | | + | | | | | ++ |
| 26 | | + | + | | | | + | | |
| 27 | + | +++ | +++ | + | | ++ | + | + | + |
| 28 | ++ | + | +++ | | | | | ++ | |
| 29 | | | + | | | | | | |
| 31 | | | | | | | | | |
| 32 | +++ | +++ | +++ | +++ | | +++ | +++ | +++ | +++ |
| 33 | ++ | +++ | ++ | + | | ++ | + | + | |
| 34 | + | + | + | | | | + | | |
| 35 | | | | | | | | | |
| 37 | | | | | | | | | |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| # | C1 | C2 | C3 | C4 | C5 | C6 | C7 | C8 | C9 |
|---|---|---|---|---|---|---|---|---|---|
| 38 |  |  |  |  |  |  |  |  |  |
| 39 |  |  |  |  | +++ |  |  |  | + |
| 40 |  | + |  |  | + |  |  |  |  |
| 41 |  |  |  |  |  |  |  |  |  |
| 42 | +++ | +++ | +++ | +++ |  | ++ |  | +++ | +++ |
| 43 | + | + | + |  |  | ++ |  |  |  |
| 44 | ++ | + | + |  |  |  | +++ | + | + |
| 45 | + | + |  |  |  | ++ |  |  | + |
| 46 |  |  |  |  |  | + |  |  |  |
| 47 |  | + |  |  |  |  |  | + |  |
| 48 | ++ | + | + | + |  | + |  | + | + |
| 49 |  | + |  |  |  |  |  | + |  |
| 50 |  |  |  |  |  |  |  |  |  |
| 51 |  | + |  |  |  |  |  |  | + |
| 52 |  | + | + |  |  | ++ |  |  |  |
| 53 |  | + | + |  |  |  |  | + |  |
| 54 |  |  |  |  |  | + |  |  |  |
| 55 |  |  |  |  |  |  |  |  |  |
| 56 |  |  |  |  |  |  |  |  |  |
| 57 | ++ | +++ |  |  |  |  |  |  | +++ |
| 58 |  |  |  |  |  |  |  | + |  |
| 59 | +++ |  | +++ |  |  |  |  | + |  |
| 60 |  |  |  |  |  |  |  |  |  |
| 61 | + | ++ | + |  |  |  | +++ |  | + |
| 62 | +++ | + |  | + |  | +++ |  | + |  |
| 63 | + | + | + |  |  | + | + | + | + |
| 64 | + |  |  |  | +++ |  |  |  |  |
| 65 |  | +++ | ++ |  |  |  |  | + | + |
| 67 |  |  |  |  |  |  |  |  |  |
| 68 |  | ++ | +++ | +++ |  |  |  | +++ | ++ |
| 69 |  |  |  |  |  |  |  |  |  |
| 70 |  |  |  |  |  |  |  |  |  |
| 71 |  |  |  |  |  |  |  |  |  |
| 72 |  | +++ |  |  |  | +++ |  |  | +++ |
| 73 |  |  | + |  |  |  |  |  |  |
| 74 |  |  |  |  |  |  |  |  |  |
| 75 | + | ++ | + |  |  |  | +++ | + | + |
| 76 | + | + |  |  |  |  |  |  |  |
| 78 |  |  |  |  |  |  |  |  |  |
| 79 |  |  | + |  |  |  |  |  |  |
| 80 |  |  |  |  |  |  |  |  |  |
| 81 |  | + |  |  |  |  |  |  |  |
| 82 |  | + | + |  |  |  |  |  | + |
| 83 | + | + | + | +++ |  |  |  | +++ |  |
| 84 |  |  |  |  |  |  |  |  |  |
| 85 |  | +++ |  |  |  |  |  |  | +++ |
| 86 |  |  |  |  |  |  |  |  |  |
| 90 | + | ++ | + |  |  |  | +++ | +++ | + |
| 91 | + | + |  |  |  |  | + |  |  |
| 93 | + | + |  |  |  |  | + |  |  |
| 94 | + | + |  | + |  |  | + |  | ++ |
| 95 |  | + |  |  |  |  | + |  |  |
| 96 |  |  | + |  |  |  |  |  |  |
| 97 | + | ++ | ++ |  |  |  | +++ | + |  |
| 98 |  |  |  |  |  |  |  |  |  |
| 99 | + | + |  |  | + | + | ++ |  | + |
| 100 |  |  |  |  | ++ | +++ |  |  | + |
| 101 |  |  |  |  |  |  |  |  |  |
| 102 |  |  |  |  |  |  |  |  |  |
| 104 |  |  |  |  |  |  |  |  |  |
| 105 |  | +++ |  |  |  |  |  | + | +++ |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| # | | | | | | | | |
|---|---|---|---|---|---|---|---|---|
| 106 | +++ | +++ | ++ | +++ | | +++ | | ++ |
| 107 | | | | | | | | |
| 108 | | +++ | | | | | | +++ |
| 109 | | +++ | +++ | + | | | | +++ |
| 111 | ++ | ++ | + | | | ++ | | |
| 112 | | + | | + | +++ | | + | + |
| 113 | + | + | + | | | ++ | + | |
| 114 | | +++ | | | +++ | | | |
| 115 | | | | | | | | |
| 116 | ++ | + | + | | | ++ | + | |
| 117 | | + | + | | + | + | | |
| 118 | | | | | | | | |
| 119 | | | | | | | | |
| 120 | + | + | + | | | | + | |
| 121 | | | + | | | | | |
| 122 | + | +++ | +++ | + | | | + | ++ |
| 123 | + | + | + | +++ | | | +++ | |
| 127 | + | + | + | | | | + | + |
| 128 | + | + | | + | | + | | |
| 129 | | | | | | | | |
| 130 | | + | + | | | | + | |
| 133 | | | | + | +++ | | + | |
| 134 | | + | + | | | | | |
| 135 | | | | | | | | |
| 136 | | + | | | | + | | |
| 137 | + | + | + | | | + | | + |
| 138 | ++ | ++ | + | + | | ++ | + | |
| 140 | | + | + | | | + | | |
| 141 | | | | | | | | |
| 142 | + | | | + | | | | |
| 144 | | | | + | | | | + |
| 145 | | + | | + | + | | | +++ |
| 146 | | | | | | | | |
| 147 | | | | | | + | | |
| 148 | | | | | | + | | |
| 149 | +++ | | +++ | +++ | | + | + | ++ |
| 150 | + | + | + | | | + | | |
| 151 | | + | + | + | + | + | | + | + |
| 152 | | + | + | | | + | | |
| 153 | | + | + | | | + | + | |
| 154 | | | | +++ | | | | |
| 155 | + | + | + | | | + | | |
| 156 | + | + | + | + | + | | | + |
| 157 | + | +++ | +++ | + | | + | ++ | |
| 229 | ++ | +++ | +++ | | + | +++ | + | + |
| 230 | ++ | ++ | ++ | + | + | +++ | + | ++ |
| 231 | | | | | | | | |
| 232 | + | + | + | | | + | + | + |
| 233 | + | + | ++ | | | +++ | | + |
| 234 | | | | | | | | |
| 235 | + | ++ | + | | | ++ | + | |
| 236 | + | + | | | +++ | + | | |
| 237 | | + | + | + | | | + | + |
| 238 | | | | | | | | |
| 239 | + | + | + | | | ++ | + | |
| 240 | | | + | | | | | |
| 241 | + | + | + | | | + | | + |
| 242 | ++ | +++ | | | | | | +++ |
| 243 | + | ++ | | | + | + | | |
| 244 | + | ++ | ++ | + | | + | + | + |
| 245 | | + | | | | | | |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| # | AML | CLL | CRC | GB | GBC_CCC | GC | HCC | NHL | NSCLC | OC | OSCAR | PC | PCA | RCC | SCLC | UBC | UEC |
|---|---|---|---|---|---|---|---|---|---|---|---|---|---|---|---|---|---|
| 246 | | | | | | | | | | | | | | | | | + |
| 247 | + | + | ++ | | | | | | | | | + | + | + | | | |
| 248 | | | | | | | | | | | | | | | | | |
| 249 | ++ | + | + | + | | | | | | | | ++ | + | + | | | |
| 250 | | + | | | | | | | | | | | | + | | | |
| 251 | | | | | | | | | | | | | | | | | |
| 252 | +++ | +++ | +++ | + | | | | | | | | +++ | ++ | +++ | | | |
| 253 | + | | | | | | | | | | | ++ | | | | | |
| 254 | + | + | | | | | | | | | | + | | + | | | |
| 255 | ++ | + | ++ | | | | | | | | | ++ | | ++ | | | |
| 256 | + | | + | | | | | | | | | ++ | | + | | | |
| 257 | | | | + | | | | | | | | | + | | | | |
| 259 | | + | | | | | | | | | | | | | | | |
| 263 | | | | | | | | | | | | | | | | | |
| 264 | | | | | | | | | | | | + | | | | | |
| 265 | | | | | | | | | | | | + | | | | | |
| 266 | | | | | | | | | | | | | | | | | |
| 290 | + | ++ | ++ | | | | | | | | | +++ | + | + | | | |
| 291 | +++ | ++ | +++ | + | | | | | | | | +++ | + | + | | | |
| 292 | | + | | | | | | | | | | | | | | | |
| 293 | | | | | | | | | | | | | | | | | |
| 294 | | | | + | +++ | | | | | | | +++ | | + | | | |
| 158 | + | + | + | | | | | | | | | + | | | | | |
| 159 | ++ | + | + | + | | | + | | | | | + | | | | | |
| 160 | + | ++ | + | | | | | | | | | +++ | | | | | |
| 161 | + | | | | | | | | | | | | | | | | |
| 163 | | | | | | | | | | | | | | | | | |
| 164 | + | | | + | | ++ | | | | | | + | | | | | |
| 165 | + | + | + | | | | | | | | | ++ | + | | | | |
| 166 | + | + | + | | | | | | | | | + | | | | | |
| 167 | | + | | | | | | | | | | | + | | | | |
| 168 | | + | | + | | | | | | | | + | | | | | + |
| 169 | + | + | ++ | + | | | | | | | | | + | | | | |
| 170 | + | + | + | | | | | | | | | | + | | | | |
| 172 | | + | | | | +++ | ++ | | | | | | | | | | |
| 173 | | | | | | | | | | | | | | | | | |
| 174 | | | | | | | | | | | | + | | | | | |
| 175 | + | + | ++ | | | | | | | | | ++ | + | | | | |
| 176 | | + | | | | | | | | | | | | | | | + |
| 177 | | +++ | ++ | + | + | | | | | | | + | | | | | |
| 178 | | | | | | | | | | | | +++ | | | | | |
| 179 | + | | | | | | | | | | | | | | | | |
| 180 | + | | | + | | | | | | | | + | | + | | | |
| 182 | | + | + | +++ | | | | | | | | + | | + | | | |
| 183 | | | | | | | | | | | | | | | | | |
| 184 | | | | | | | | | | | | + | | | | | |
| 185 | | + | | | | | | | | | | | | | | | |
| 186 | + | | | | | + | | | | | | | | | | | |
| 187 | + | +++ | + | | | | | | | | | ++ | + | + | | | |
| 188 | | | | | | | | | | | | | | | | | |
| 189 | | | | +++ | | | | | | | | +++ | | | | | |
| 190 | | | | | | | | | | | | | | | | | |
| 191 | | | | | | | | | | | | | | | | | |
| 192 | + | + | + | | | | | | | | | +++ | + | | | | |
| 193 | + | + | + | | | | | | | | | + | | | | | |
| 194 | | | | | | | | | | | | | | | | | |
| 195 | + | + | | | | | | | | | | + | | + | | | |
| 196 | | + | | | | | | | | | | | | | | | |
| 197 | | + | | | | | | | | | | | | | | | |
| 198 | | | | | | | | | | | | + | | + | | | |
| 199 | | | | + | | | | | | | | | | | | | |

TABLE 18-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). AML = acute myeloid leukemia (N = 11), CLL = chronic lymphocytic leukemia (N = 10), CRC = colorectal cancer (N = 20), GB = glioblastoma (N = 24), GBC_CCC = gallbladder adenocarcinoma and cholangiocarcinoma (N = 3), GC = gastric cancer (N = 11), HCC = hepatocellular carcinoma (N = 15), NHL = non-Hodgkin lymphoma (N = 10), NSCLC = non-small cell lung cancer (N = 11), OC = ovarian cancer (N = 12), OSCAR = esophageal cancer, including cancer of the gastric-esophageal junction (N = 11), PC = pancreatic cancer (N = 26), PCA = prostate cancer and benign prostate hyperplasia (N = 5), RCC = renal cell carcinoma (N = 10), SCLC = small cell lung cancer (N = 10), UBC = urinary bladder cancer (N = 10), UEC = uterine cancer (N = 10). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, skeletal muscle, skin, small intestine, spleen, stomach, thyroid gland, trachea, urinary bladder, and vein.

| ID | C1 | C2 | C3 | C4 | C5 | C6 | C7 | C8 |
|---|---|---|---|---|---|---|---|---|
| 200 | + | + | + |  |  | + |  |  |
| 201 | + | ++ | ++ | + |  | ++ | + | + |
| 202 |  |  |  |  |  |  |  |  |
| 203 | + | + | + |  |  | + | + | + |
| 204 |  |  |  |  |  |  | + |  |
| 205 |  |  |  |  |  |  |  |  |
| 206 |  |  |  |  |  |  |  |  |
| 207 | + |  |  |  |  |  |  |  |
| 208 |  |  | +++ |  |  | +++ |  |  |
| 210 | + |  | + |  | + |  | + | + |
| 211 |  |  |  | + |  |  |  | + |
| 213 |  | + | + |  |  |  |  | + |
| 214 | + | +++ | ++ | + |  | +++ | + | + |
| 215 |  |  |  |  |  |  |  |  |
| 216 |  |  |  |  |  |  |  |  |
| 217 |  | + | + | ++ | +++ | + | + |  | + |
| 218 | + |  |  |  | + |  |  |  |
| 219 | ++ |  |  |  |  |  |  |  |
| 220 | +++ | +++ | +++ | +++ |  |  | +++ | +++ |
| 221 |  |  |  |  |  |  | + | + |
| 222 |  |  |  | + |  |  |  |  |
| 223 | + | ++ | + | + |  | + |  |  |
| 224 |  |  |  |  |  |  |  |  |
| 225 |  |  |  |  |  | +++ |  |  |
| 226 |  |  |  |  |  | + |  |  |
| 267 |  |  |  |  |  |  |  |  |
| 268 |  | ++ | + |  |  | ++ | + |  |
| 270 | + | + | ++ |  |  | ++ | + |  |
| 271 | ++ | +++ | +++ | ++ |  | + | + | ++ | +++ |
| 272 | + | ++ | + |  |  | + |  |  |
| 274 |  |  |  |  |  |  |  |  |
| 275 |  |  |  |  |  |  |  |  |
| 276 |  | + | + |  |  | ++ | + |  |
| 277 | +++ | ++ | +++ | + | + |  | ++ | ++ | +++ |
| 278 |  |  |  |  |  |  |  | + |
| 279 | + |  | + |  | +++ |  | + |  |
| 281 | + | + | + |  |  | + |  |  |
| 282 |  |  |  |  |  | + |  |  |
| 283 |  | + |  |  |  |  |  |  |
| 284 | + | + |  |  | +++ | + |  |  |
| 285 | + | ++ | + |  |  | ++ | + |  |
| 287 |  |  |  |  |  |  |  |  |
| 288 | + | + | + |  |  | + |  |  |
| 295 |  |  |  |  |  |  |  |  |
| 296 | + |  | + |  |  |  |  |  |
| 297 | +++ | + | +++ | + |  |  | +++ |  |
| 298 | + | +++ | +++ | + |  | + | ++ |  |
| 299 | +++ | +++ | +++ | +++ |  |  | +++ | +++ |
| 302 | +++ | +++ | ++ | + |  | + | ++ | + | ++ |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201 restricted TUMAPs of the invention, demonstrating that these peptides are T-cell epitopes against which CD8+ precursor T cells exist in humans (Table 19).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nurnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 303) from modified Melan-A/MART-1) and A*0201/DDX5-001 (YLLPAIVHI from DDX5, SEQ ID NO. 304), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Different Cancer Peptides

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A and 3B together with corresponding negative controls. Results for 10 peptides from the invention are summarized in Table 19A. Exemplary flow cytometry results after TUMAP-specific multimer staining for seven peptides of the invention are shown in FIGS. 4A-4D and 5A-5C together with corresponding negative controls. Results for 60 peptides from the invention are summarized in Table 19B.

TABLE 19A in vitro immunogenicity of HLA class I peptides of the invention
Exemplary results of in vitro immunogenicity experiments conducted by the applicant for the peptides of the invention.

| SEQ ID No. | Sequence | Wells positive [%] |
|---|---|---|
| 290 | KIVDFSYSV | ++ |
| 291 | KLDETGNSL | + |
| 292 | GMMTAILGV | + |
| 293 | FLVDGSWSI | + |
| 295 | YYPGVILGF | ++ |
| 296 | TYVDSSHTI | + |
| 297 | PFLQASPHF | ++ |
| 298 | RYLEGTSCI | + |
| 300 | AYVLRLETL | + |
| 301 | AYKPGALTF | + |

<20% = +;
20%-49% = ++;
50%-69% = +++;
>=70% = ++++

TABLE 19B in vitro immunogenicity of HLA class I peptides of the invention
Exemplary results of in vitro immunogenicity experiments conducted by the applicant for the peptides of the invention.

| SEQ ID No | Sequence | Wells positive [%] |
|---|---|---|
| 1 | LLYPEPWSV | ++ |
| 2 | GLIAGVVSI | ++ |
| 4 | KLMPGTYTL | + |
| 5 | GIVAHIQEV | + |
| 6 | ALFDSLRHV | ++ |
| 7 | ILDHEVPSL | ++ |
| 11 | ALSPSYLTV | ++ |
| 12 | GLLPLLHRA | ++++ |
| 14 | ILAKDLFEI | ++ |
| 18 | ILLDLTDNRL | + |

TABLE 19B-continued in vitro immunogenicity of HLA class I peptides of the invention
Exemplary results of in vitro immunogenicity experiments conducted by the applicant for the peptides of the invention.

| SEQ ID No | Sequence | Wells positive [%] |
|---|---|---|
| 20 | GLSQITNQL | ++ |
| 23 | SLFSDEFKV | ++++ |
| 26 | ALQEELTEL | + |
| 27 | RLMEENWNA | +++ |
| 29 | YLLDPSITL | + |
| 31 | TITETTVEV | + |
| 35 | FLLPFSTVYL | + |
| 90 | FLQDLEQRL | + |
| 92 | GLLFSLRSV | ++ |
| 96 | LLVSHLYLV | ++ |
| 138 | ALLAKILQI | ++ |
| 141 | FLDKVLVAA | + |
| 144 | ALLAFFPGL | +++ |
| 149 | ILNTHITEL | + |
| 150 | VLYDRPLKI | ++ |
| 151 | SVLDSTAKV | ++ |
| 229 | AILAHLNTV | ++ |
| 230 | KLQNIMMLL | ++++ |
| 232 | KIFPAALQLV | ++ |
| 233 | HLFDAFVSV | ++ |
| 235 | KIIDFLSAL | +++ |
| 247 | ALYEGYATV | ++ |
| 248 | YLDRFLAGV | ++ |
| 249 | GLCERLVSL | + |
| 251 | ALSVLRLAL | ++ |
| 158 | HYSQELSLLYL | + |
| 159 | LYNKGFIYL | ++++ |
| 160 | VYTLDIPVL | ++ |
| 161 | IYLVSIPEL | ++ |
| 162 | VFTRVSSFL | ++ |
| 163 | DYLKGLASF | + |
| 165 | DYTTWTALL | + |
| 166 | YYVESGKLF | +++ |
| 167 | NYINRILKL | + |
| 168 | KYQDILETI | ++ |
| 169 | AYTLIAPNI | +++ |
| 173 | lYSWILDHF | ++ |
| 176 | EYNQWFTKL | +++ |
| 196 | LYIDRPLPYL | ++++ |
| 197 | EYSLFPGQVVI | + |
| 199 | RYAEEVGIF | ++ |
| 200 | YYGPSLFLL | ++ |
| 204 | TYELRYFQI | + |
| 207 | AYVVFVSTL | + |
| 218 | YYKSTSSAF | + |
| 222 | TFSVSSHLF | ++ |
| 268 | QYLGQIQHI | + |
| 269 | YFIDSTNLKTHF | + |
| 281 | PYRLIFEKF | +++ |
| 285 | HYPPVQVLF | + |

<20% = +;
20%-49% = ++;
50%-69% = +++;
>=70% = ++++

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with NH2SO4. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 20

MHC class I binding scores.

| SEQ ID No | Sequence | Peptide exchange |
|---|---|---|
| 1 | LLYPEPWSV | ++++ |
| 2 | GLIAGVVSI | +++ |
| 3 | KLEENGDLYL | ++++ |
| 4 | KLMPGTYTL | ++++ |
| 5 | GIVAHIQEV | +++ |
| 6 | ALFDSLRHV | +++ |
| 7 | ILDHEVPSL | +++ |
| 9 | FLVDGSYSI | +++ |
| 10 | GIAGSLKTV | +++ |
| 11 | ALSPSYLTV | +++ |
| 12 | GLLPLLHRA | ++++ |
| 13 | ALMAMLVYV | ++ |
| 14 | ILAKDLFEI | ++++ |
| 15 | YLDLSHNQL | +++ |
| 16 | YTLDIPVLFGV | ++++ |
| 18 | ILLDLTDNRL | +++ |
| 19 | SISDNVWEV | +++ |
| 20 | GLSQITNQL | +++ |
| 21 | AIQDEIRSV | +++ |
| 22 | FVDPNTQEKV | ++ |
| 23 | SLFSDEFKV | +++ |
| 24 | TLDEKVAEL | +++ |
| 25 | TMDSVLVTV | +++ |
| 26 | ALQEELTEL | +++ |
| 27 | RLMEENWNA | +++ |
| 28 | SLPNGKPVSV | +++ |
| 29 | YLLDPSITL | +++ |
| 30 | AMIEEVFEA | ++ |
| 31 | TITETTVEV | +++ |
| 32 | VQLDSIEDLEV | +++ |
| 33 | YIKTELISV | +++ |
| 34 | FLLATEVVTV | ++++ |
| 35 | FLLPFSTVYL | +++ |
| 36 | SLADTNSLAVV | +++ |
| 37 | ILAPFSVDL | +++ |
| 38 | FLGPRIIGL | +++ |
| 39 | HLLEGSVGV | +++ |
| 40 | VLIDPQWVLTA | +++ |
| 41 | ALFENTPKA | ++ |
| 42 | LLDSVSRL | + |
| 43 | KAIEVLLTL | +++ |
| 44 | SLFETAWEA | +++ |
| 45 | SLTEVSLPL | +++ |
| 46 | SQFPLPLAV | ++ |
| 47 | ALLERGELFV | +++ |
| 48 | QVIEDSTGV | ++ |
| 49 | ALNIATHVL | +++ |
| 50 | ILFHGVFYA | +++ |
| 51 | LLFSRLCGA | ++++ |
| 53 | KMVGLVVAI | +++ |
| 54 | VLNPLITAV | +++ |
| 55 | SLATKIVEA | +++ |
| 56 | FLHDEKEGIYI | +++ |
| 57 | TVFTDHMLTV | ++ |
| 58 | YLLPLLPAL | +++ |
| 59 | KLLDPQEFTL | +++ |
| 60 | ALFAPLVHL | +++ |
| 61 | AIVKEIVNI | ++ |
| 62 | ALNPELVQA | ++ |
| 63 | SQIPAQPSV | ++ |
| 64 | SLFPDSLIV | ++ |
| 65 | SVVPDVRSV | ++ |
| 66 | KLIFSVEAV | +++ |
| 67 | TLLQRLTEV | +++ |
| 68 | SLSNRLYYL | +++ |

TABLE 20-continued

MHC class I binding scores.

| SEQ ID No | Sequence | Peptide exchange |
|---|---|---|
| 69 | FLAVGLVDV | +++ |
| 70 | LLLGDSALYL | +++ |
| 71 | VLHSKFWVV | +++ |
| 72 | FLTAINYLL | +++ |
| 73 | YTLREVDTV | ++ |
| 74 | TLFGYSVVL | +++ |
| 75 | AVIKFLELL | +++ |
| 76 | AVGPVHNSV | ++ |
| 77 | TLIDEQDIPLV | +++ |
| 78 | TVVTRLDEI | ++ |
| 79 | VTFKEYVTV | ++ |
| 80 | KLYEADFVL | ++ |
| 81 | NALDKVLSV | +++ |
| 82 | FIFDEAEKL | + |
| 83 | GQASYFYVA | ++ |
| 84 | ALCPRIHEV | ++++ |
| 85 | VLNDILVRA | +++ |
| 86 | SVDSHFQEV | ++ |
| 87 | TIYKDFVYI | ++ |
| 88 | AQADHLPQL | ++ |
| 89 | QLAPVFQRV | ++ |
| 90 | FLQDLEQRL | +++ |
| 92 | GLLFSLRSV | ++++ |
| 94 | LLLPAVPVGA | +++ |
| 95 | GLLGSLFFL | ++++ |
| 96 | LLVSHLYLV | ++ |
| 98 | RLFPDFFTRVAL | ++ |
| 99 | YLLQSVNQLLL | ++ |
| 100 | ALLGMIIVGV | + |
| 101 | ALADFMLSL | +++ |
| 102 | VLLDIQEVFQI | +++ |
| 103 | YLVSEIFKA | +++ |
| 104 | ALISWQPPRA | +++ |
| 105 | ALLGTKILL | +++ |
| 106 | FINDSIVYL | +++ |
| 107 | LLVPTSGIYFV | +++ |
| 108 | ILLKNLVTI | ++ |

TABLE 20-continued

MHC class I binding scores.

| SEQ ID No | Sequence | Peptide exchange |
|---|---|---|
| 109 | SLDPSVTHL | ++ |
| 110 | FLLGVSKEV | +++ |
| 111 | AIVDLIHDI | ++ |
| 112 | SLGKFTFDV | ++++ |
| 113 | FLERGLESA | ++ |
| 114 | 0LIQTLHAV | +++ |
| 115 | SLDPDTLPAV | ++ |
| 117 | KMPDVELFV | +++ |
| 118 | QLWQFLVTL | +++ |
| 119 | FII0GLRSVGA | +++ |
| 120 | VTPVTVSAV | + |
| 121 | FTIFRTISV | +++ |
| 122 | GVVDPVHGV | ++ |
| 123 | VLDPALPALV | ++ |
| 124 | KVMATIEKV | ++ |
| 125 | SLADYEHFV | ++++ |
| 126 | QMFQYFITV | ++++ |
| 127 | KLDGNELDL | +++ |
| 128 | TQSPATLSV | ++ |
| 129 | RLQDILWFL | ++++ |
| 130 | SLLGGTFVGI | +++ |
| 131 | VTSNSGILGV | +++ |
| 132 | ILGEVLAQL | +++ |
| 133 | ALLPRLHQL | ++++ |
| 134 | GLAVPTPSV | +++ |
| 135 | HLSTIIHEA | +++ |
| 136 | FLFGGVLMTL | ++ |
| 138 | ALLAKILQI | +++ |
| 139 | FLLPTGAEA | ++ |
| 141 | FLDKVLVAA | +++ |
| 142 | ILVEGISTV | +++ |
| 143 | ALLPELREV | +++ |
| 144 | ALLAFFPGL | +++ |
| 145 | YLWATIQRI | +++ |
| 146 | ALHFSEDEI | ++ |
| 147 | YLMDDTVEI | ++++ |
| 148 | MLAGIAITV | +++ |
| 149 | ILNTHITEL | +++ |

TABLE 20-continued

MHC class I binding scores.

| SEQ ID No | Sequence | Peptide exchange |
|---|---|---|
| 150 | VLYDRPLKI | +++ |
| 151 | SVLDSTAKV | ++ |
| 152 | MMVGDLLEV | +++ |
| 153 | FISERVEVV | ++++ |
| 154 | RLLGTEFQV | +++ |
| 155 | LLNPVVEFV | +++ |
| 156 | ILGDLSHLL | +++ |
| 157 | TLTSLLAQA | +++ |
| 229 | AILAHLNTV | ++++ |
| 230 | KLQNIMMLL | ++ |
| 231 | MLDKYSHYL | +++ |
| 232 | KIFPAALQLV | +++ |
| 233 | HLFDAFVSV | +++ |
| 234 | LLSPHNPAL | +++ |
| 235 | KIIDFLSAL | +++ |
| 236 | STIAILNSV | +++ |
| 237 | ALAPHLDDA | +++ |
| 238 | GLYERPTAA | ++ |
| 239 | KMNESTRSV | ++ |
| 240 | YMGEEKLIASV | +++ |
| 241 | KTIQQLETV | ++ |
| 242 | WLYGEDHQI | ++ |
| 243 | FMADDIFSV | +++ |
| 244 | YLLEKNRVV | ++ |
| 245 | SLLDLPLSL | ++++ |
| 246 | TVSDVLNSV | +++ |
| 247 | ALYEGYATV | +++ |
| 248 | YLDRFLAGV | ++++ |
| 249 | GLCERLVSL | ++++ |
| 250 | SLAPATPEV | +++ |
| 251 | ALSVLRLAL | +++ |
| 252 | RLMEICESL | +++ |
| 253 | ALAELIDNSL | +++ |
| 254 | KLQGKLPEL | ++ |
| 255 | SLLHFTENL | +++ |
| 256 | SLGEEQFSV | ++ |
| 257 | GLYTDPCGV | ++++ |
| 258 | LLSERFINV | ++++ |
| 259 | ILLPRIIEA | +++ |
| 260 | ILLEKILSL | +++ |
| 261 | QLQDRVYAL | +++ |
| 262 | FMVDKAIYL | +++ |
| 263 | VLLSEQGDVKL | ++ |
| 264 | KLFPQETLFL | +++ |
| 265 | NTCPYVHNI | +++ |
| 266 | YAIGLVMRL | +++ |

Binding of HLA-class I restricted peptides to HLA-A*02 was ranged by peptide exchange yield:
<20% = +;
20%-49% = ++;
50%-75% = +++;
>75% = ++++

TABLE 21

MHC class I binding scores.

| SEQ ID No | Sequence | Peptide exchange |
|---|---|---|
| 172 | TYTTVPRVAF | ++++ |
| 177 | VYPWLGALL | ++++ |
| 178 | IFIEVFSHF | +++ |
| 179 | MYDSYWRQF | ++++ |
| 180 | IYDDSFIRPVTF | +++ |
| 181 | LYLDIINLF | ++++ |
| 182 | IYQLDTASI | +++ |
| 183 | VFTSTARAF | +++ |
| 184 | VFQNFPLLF | ++++ |
| 185 | IYKVGAPTI | +++ |
| 186 | IFPQFLYQF | ++++ |
| 187 | TYLRDQHFL | ++++ |
| 188 | RYFKGLVF | +++ |
| 189 | WYVNGVNYF | ++ |
| 190 | GFFIFNERF | +++ |
| 191 | VFKASKITF | +++ |
| 192 | SYALLTYMI | ++++ |
| 193 | RFHPTPLLL | ++++ |
| 194 | EFGSLHLEFL | + |
| 198 | LYLDKATLI | +++ |
| 203 | FYSRLLQKF | +++ |

TABLE 21-continued

MHC class I binding scores.

| SEQ ID No | Sequence | Peptide exchange |
|---|---|---|
| 205 | VHIPEVYLI | +++ |
| 206 | EYQENFLSF | +++ |
| 208 | TYTQDFNKF | +++ |
| 210 | IYTMIYRNL | ++++ |
| 211 | YYLEVGKTLI | ++++ |
| 214 | LYLKLWNLI | +++ |
| 215 | YFDKVVTL | ++ |
| 216 | QYSSVFKSL | ++++ |
| 217 | FFPPTRQMGLLF | ++++ |
| 219 | EYPLVINTL | +++ |
| 220 | GYIDNVTLI | ++++ |
| 221 | RYSTGLAGNLL | +++ |
| 223 | KYIPYKYVI | +++ |
| 224 | QYLENLEKL | +++ |
| 225 | YYVYIMNHL | +++ |
| 226 | VYRDETGELF | +++ |
| 227 | IFLDYEAGTLSF | ++++ |
| 228 | KYTSWYVAL | ++++ |
| 267 | KYMVYPQTF | ++++ |
| 271 | LYHDIFSRL | ++++ |
| 272 | QYLQDAYSF | ++++ |
| 273 | TYIKPISKL | +++ |
| 274 | AYLHSHALI | ++++ |
| 275 | EYINQGDLHEF | +++ |
| 276 | VYGFQWRHF | ++++ |
| 278 | RYISDQLFTNF | ++++ |
| 279 | TYIESASEL | +++ |
| 280 | RYPDNLKHLYL | ++++ |
| 282 | KFVDSTFYL | ++++ |
| 283 | TYGDAGLTYTF | +++ |
| 284 | RYLNKAFHI | +++ |
| 286 | RYPDNLKHL | ++ |
| 288 | VYVSDIQEL | +++ |
| 289 | KYPVEWAKF | ++++ |
| 158 | HYSQELSLLYL | ++++ |
| 159 | LYNKGFIYL | ++++ |
| 160 | VYTLDIPVL | ++++ |
| 161 | IYLVSIPEL | ++++ |
| 162 | VFTRVSSFL | +++ |
| 163 | DYLKGLASF | ++++ |
| 164 | KFSSFSLFF | +++ |
| 165 | DYTTWTALL | ++++ |
| 166 | YYVESGKLF | ++++ |
| 167 | NYINRILKL | ++++ |
| 168 | KYQDILETI | ++++ |
| 169 | AYTLIAPNI | +++ |
| 170 | VYEDQVGKF | ++ |
| 171 | LFIPSSKLLFL | +++ |
| 173 | IYSWILDHF | ++++ |
| 174 | VYVGGGQIIHL | +++ |
| 175 | YYEVHKELF | ++++ |
| 176 | EYNQWFTKL | +++ |
| 195 | TYSVSFPMF | ++++ |
| 196 | LYIDRPLPYL | +++ |
| 197 | EYSLFPGQVVI | +++ |
| 199 | RYAEEVGIF | +++ |
| 200 | YYGPSLFLL | +++ |
| 201 | IYATEAHVF | +++ |
| 202 | VYWDSAGAAHF | ++++ |
| 204 | TYELRYFQI | ++++ |
| 207 | AYVVFVSTL | ++ |
| 209 | TYKDEGNDYF | +++ |
| 218 | YYKSTSSAF | +++ |
| 222 | TFSVSSHLF | +++ |
| 268 | QYLGQIQHI | +++ |
| 269 | YFIDSTNLKTHF | +++ |
| 270 | NYYEVHKELF | +++ |
| 277 | VYQGHTALL | ++++ |
| 281 | PYRLIFEKF | ++ |
| 285 | HYPPVQVLF | +++ |
| 287 | LYITEPKTI | +++ |

Binding of HLA-class I restricted peptides to HLA-A*24 was ranged by peptide exchange yield:
<20% = +;
20%-49% = ++;
50%-75% = +++;
>75% = ++++

Example 6

Absolute Quantitation of Tumor Associated Peptides Presented on the Cell Surface

The generation of binders, such as antibodies and/or TCRs, is a laborious process, which may be conducted only for a number of selected targets. In the case of tumor-associated and -specific peptides, selection criteria include but are not restricted to exclusiveness of presentation and the density of peptide presented on the cell surface. In addition to the isolation and relative quantitation of peptides as described above and in the figures, the inventors did analyze absolute peptide copies per cell as described. The quantitation of TUMAP copies per cell in solid tumor samples requires the absolute quantitation of the isolated TUMAP, the efficiency of TUMAP isolation, and the cell count of the tissue sample analyzed.

Peptide Quantitation by nanoLC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments. The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression. For the quantitation of tumor-associated peptides from tissue samples, the respective samples were also spiked with the internal standard, the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell number for selected peptides are shown in Table 22.

TABLE 22

Absolute copy numbers. The table lists the results of absolute peptide quantitation in tumor samples. The median number of copies per cell are indicated for each peptide: $<100$ = +; $>=100$ = ++; $>=1,000$ +++; $>=10,000$ = ++++. The number of samples, in which evaluable, high quality MS data is available is indicated.

| SEQ ID No. | Peptide Code | Copies per cell (median) | Number of samples |
|---|---|---|---|
| 2 | MET-007 | + | 15 |
| 24 | MAGEC2-001 | + | 16 |
| 32 | PRAME-006 | ++ | 17 |
| 39 | ABCC11-001 | + | 14 |
| 251 | SPINK2-001 | ++ | 16 |

REFERENCE LIST

Abdelmalak, C. A. et al., Clin Lab 60 (2014): 55-61
Accardi, L. et al., Int. J Cancer 134 (2014): 2742-2747
Alcoser, S. Y. et al., BMC. Biotechnol. 11 (2011): 124
Allison, J. P. et al., Science 270 (1995): 932-933 American Cancer Society, (2015)
Ampie, L. et al., Front Oncol. 5 (2015): 12
Andersen, R. S. et al., Nat. Protoc. 7 (2012): 891-902
Anderson, N. L. et al., J Proteome. Res 11 (2012): 1868-1878
Appay, V. et al., Eur. J Immunol. 36 (2006): 1805-1814
Avigan, D. et al., Clin Cancer Res. 10 (2004): 4699-4708
Banchereau, J. et al., Cell 106 (2001): 271-274
Beard, R. E. et al., Clin Cancer Res 19 (2013): 4941-4950
Beatty, G. et al., J Immunol 166 (2001): 2276-2282
Beggs, J. D., Nature 275 (1978): 104-109
Benjamini, Y. et al., Journal of the Royal Statistical Society. Series B (Methodological), Vol. 57 (1995): 289-300
Berman, R. S. et al., National Cancer Institute: PDQ(R) Colon Cancer Treatment (2015a)

Berman, R. S. et al., National Cancer Institute: PDQ(R) Rectal Cancer Treatment (2015b)
Bill, K. L. et al., Lab Invest (2015)
Borel, F. et al., Hepatology 55 (2012): 821-832
Boulter, J. M. et al., Protein Eng 16 (2003): 707-711
Braumuller, H. et al., Nature (2013)
Bray, F. et al., Int J Cancer 132 (2013): 1133-1145
Brossart, P. et al., Blood 90 (1997): 1594-1599
Bruckdorfer, T. et al., Curr. Pharm. Biotechnol. 5 (2004): 29-43
Bujas, T. et al., Eur. J Histochem. 55 (2011): e7
Butterfield, L. H. et al., Clin Cancer Res 12 (2006): 2817-2825
Butterfield, L. H. et al., Clin Cancer Res 9 (2003): 5902-5908
Carballido, E. et al., Cancer Control 19 (2012): 54-67
Card, K. F. et al., Cancer Immunol Immunother. 53 (2004): 345-357
Chang, Y. S. et al., Cancer Chemother. Pharmacol. 59 (2007): 561-574
Chanock, S. J. et al., Hum Immunol. 65 (2004): 1211-1223
Chapiro, J. et al., Radiol. Med. 119 (2014): 476-482
Chen, T. et al., Proteins 77 (2009): 209-219
ClinicalTrials.gov, (2015)
Cliteur, V. P. et al., Clin Sarcoma. Res 2 (2012): 3
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Coosemans, A. et al., Anticancer Res 33 (2013): 5495-5500
Counter, C. M. et al., Blood 85 (1995): 2315-2320
Dannenmann, S R et al., Cancer Immunol. Res. 1 (2013): 288-295
Dengjel, J. et al., Clin Cancer Res 12 (2006): 4163-4170
Denkberg, G. et al., J Immunol 171 (2003): 2197-2207
Dyrskjot, L. et al., Br. J Cancer 107 (2012): 116-122
Economopoulou, P. et al., Ann. Transl. Med. 4 (2016): 173
Edwards, S. et al., Br. J Cancer 92 (2005): 376-381
Emens, L. A., Expert. Rev. Anticancer Ther. 12 (2012): 1597-1611
Estey, E. H., Am. J Hematol. 89 (2014): 1063-1081
Evans, R. L. et al., Cancer Prev. Res (Phila) 7 (2014): 545-555
Falk, K. et al., Nature 351 (1991): 290-296
Ferlay et al., GLOBOCAN 2012 v1.0, Cancer Incidence and Mortality Worldwide: IARC CancerBase No. 11 [Internet], (2013)
Finocchiaro, G. et al., Ann. Transl. Med. 3 (2015): 83
Follenzi, A. et al., Nat Genet. 25 (2000): 217-222
Fong, L. et al., Proc. Natl. Acad. Sci. U.S.A 98 (2001): 8809-8814
Forsey, R. W. et al., Biotechnol. Lett. 31 (2009): 819-823
Fuge, O. et al., Res Rep. Urol. 7 (2015): 65-79
Gabrilovich, D. I. et al., Nat Med. 2 (1996): 1096-1103
Gandhi, A. V. et al., Ann Surg. Oncol 20 Suppl 3 (2013): S636-S643
Gattinoni, L. et al., Nat Rev. Immunol 6 (2006): 383-393
Giannopoulos, K. et al., Leukemia 24 (2010): 798-805
Giannopoulos, K. et al., Int. J Oncol 29 (2006): 95-103
Gnjatic, S. et al., Proc Natl Acad. Sci. U.S.A 100 (2003): 8862-8867
Godkin, A. et al., Int. Immunol 9 (1997): 905-911
Goede, V. et al., N. Engl. J Med. 370 (2014): 1101-1110
Gomes, I. M. et al., Mol. Cancer Res 10 (2012): 573-587
Gonen-Korkmaz, C. et al., Exp. Ther. Med 8 (2014): 1695-1700
Granziero, L. et al., Blood 97 (2001): 2777-2783
Green, M. R. et al., Molecular Cloning, A Laboratory Manual 4th (2012)
Greenfield, E. A., Antibodies: A Laboratory Manual 2nd (2014)
Grivas, P. D. et al., Semin Cancer Biol 35 (2015): 125-132
Grunewald, T. G. et al., Biol Cell 104 (2012): 641-657
Gunawardana, C. et al., Br. J Haematol. 142 (2008): 606-609
Guo, Y. et al., Clin Cancer Res 15 (2009): 1762-1769
Gustafsson, C. et al., Trends Biotechnol. 22 (2004): 346-353
Hallek, Michael et al., ASH Annual Meeting Abstracts 112 (2008): 325
Hao, J. et al., Oncotarget. 6 (2015): 42028-42039
Harig, S. et al., Blood 98 (2001): 2999-3005
Hemminger, J. A. et al., Mod. Pathol. 27 (2014): 1238-1245
Hinrichs, C. S. et al., Nat. Biotechnol. 31 (2013): 999-1008
Hlavata, I. et al., Mutagenesis 27 (2012): 187-196
Holtl, L. et al., Clin. Cancer Res. 8 (2002): 3369-3376
Honorat, M. et al., BMC. Struct. Biol 13 (2013): 7
Horig, H. et al., Cancer Immunol Immunother. 49 (2000): 504-514
Hung, C. F. et al., Immunol. Rev 222 (2008): 43-69
Hus, I. et al., Oncol Rep. 20 (2008): 443-451
Hwang, M. L. et al., J Immunol. 179 (2007): 5829-5838
Inoue, H. et al., Int. J Cancer 63 (1995): 523-526
Jones, R. T. et al., Urol. Clin North Am. 43 (2016): 77-86
Jung, G. et al., Proc Natl Acad Sci USA 84 (1987): 4611-4615
Kalos, M. et al., Sci. Transl. Med. 3 (2011): 95ra73
Kanthan, R. et al., J Oncol 2015 (2015): 967472
Kaufman, H. L. et al., Clin Cancer Res 14 (2008): 4843-4849
Kibbe, A. H., Handbook of Pharmaceutical Excipients rd (2000)
Kimura, H. et al., Int. J Oncol 30 (2007): 171-179
Knollman, H. et al., Ther. Adv. Urol. 7 (2015): 312-330
Koido, S. et al., World J Gastroenterol. 19 (2013): 8531-8542
Kono, K. et al., Cancer Sci. 100 (2009): 1502-1509
Krackhardt, A. M. et al., Blood 100 (2002): 2123-2131
Krieg, A. M., Nat Rev. Drug Discov. 5 (2006): 471-484
Kronenberger, K. et al., J Immunother. 31 (2008): 723-730
Kuball, J. et al., Blood 109 (2007): 2331-2338
Lajmi, N. et al., Br. J Haematol. 171 (2015): 752-762
Lee, W. C. et al., J Immunother. 28 (2005): 496-504
Liang, Z. et al., Zhonghua Zhong. Liu Za Zhi. 27 (2005): 534-537
Liddy, N. et al., Nat Med. 18 (2012): 980-987
Liu, H. et al., Oncotarget. (2016)
Ljunggren, H. G. et al., J Exp. Med. 162 (1985): 1745-1759
Llovet, J. M. et al., N. Engl. J Med. 359 (2008): 378-390
Longenecker, B. M. et al., Ann N. Y. Acad. Sci. 690 (1993): 276-291
Lonsdale, J., Nat. Genet. 45 (2013): 580-585
Lukas, T. J. et al., Proc. Natl. Acad. Sci. U.S.A 78 (1981): 2791-2795
Lundblad, R. L., Chemical Reagents for Protein Modification 3rd (2004)
Mantia-Smaldone, G. M. et al., Hum. Vaccin. Immunother. 8 (2012): 1179-1191
Marten, A. et al., Cancer Immunol. Immunother. 51 (2002): 637-644
Massari, F. et al., Cancer Treat. Rev. 41 (2015): 114-121
Matsueda, S. et al., World J Gastroenterol. 20 (2014): 1657-1666

Maus, M. V. et al., Blood 123 (2014): 2625-2635
Mayr, C. et al., Exp. Hematol. 34 (2006): 44-53
Mayr, C. et al., Blood 105 (2005): 1566-1573
Meziere, C. et al., J Immunol 159 (1997): 3230-3237
Mitsuhashi, K. et al., Int. J Hematol. 100 (2014): 88-95
Miyagi, Y. et al., Clin Cancer Res 7 (2001): 3950-3962
Molina, J. R. et al., Mayo Clin Proc. 83 (2008): 584-594
Morgan, R. A. et al., Science 314 (2006): 126-129
Mori, M. et al., Transplantation 64 (1997): 1017-1027
Mortara, L. et al., Clin Cancer Res. 12 (2006): 3435-3443
Moulton, H. M. et al., Clin Cancer Res 8 (2002): 2044-2051
Mueller, L. N. et al., J Proteome. Res 7 (2008): 51-61
Mueller, L. N. et al., Proteomics. 7 (2007): 3470-3480
Muller, M. R. et al., Blood 103 (2004): 1763-1769
Mumberg, D. et al., Proc. Natl. Acad. Sci. U.S.A 96 (1999): 8633-8638
National Cancer Institute, (5 Jun. 2015)
National Cancer Institute (NCI), (19 Jan. 2011)
O'Prey, J. et al., J Virol. 82 (2008): 5933-5939
Ohigashi, Y. et al., Clin Cancer Res. 11 (2005): 2947-2953
Okuno, K. et al., Exp. Ther Med. 2 (2011): 73-79
Palma, M. et al., Cancer Immunol Immunother. 57 (2008): 1705-1710
Palmer, D. H. et al., Hepatology 49 (2009): 124-132
Palomba, M. L., Curr. Oncol Rep. 14 (2012): 433-440
Parikh, S. A. et al., Blood 118 (2011): 2062-2068
Petrini, I., Ann. Transl. Med. 3 (2015): 82
Phan, G. Q. et al., Cancer Control 20 (2013): 289-297
Pinheiro, J. et al., nlme: Linear and Nonlinear Mixed Effects Models (2015)
Plebanski, M. et al., Eur. J Immunol 25 (1995): 1783-1787
Porta, C. et al., Virology 202 (1994): 949-955
Porter, D. L. et al., N. Engl. J Med. 365 (2011): 725-733
Qin, Y. et al., Chin Med. J (Engl.) 127 (2014): 1666-1671
Quillien, V. et al., Anticancer Res. 17 (1997): 387-391
Quinn, D. I. et al., Urol. Oncol. (2015)
Rakic, M. et al., Hepatobiliary. Surg. Nutr. 3 (2014): 221-226
Rammensee, H. et al., Immunogenetics 50 (1999): 213-219
RefSeq, The NCBI handbook [Internet], Chapter 18, (2002
Reinisch, W. et al., J Immunother. 25 (2002): 489-499
Reinmuth, N. et al., Dtsch. Med. Wochenschr. 140 (2015): 329-333
Reynolds, P. A. et al., Genes Dev. 17 (2003): 2094-2107
Richards, S. et al., J Natl. Cancer Inst. 91 (1999): 861-868
Rini, B. I. et al., Cancer 107 (2006): 67-74
Robak, T. et al., Expert. Opin. Biol. Ther 14 (2014): 651-661
Rock, K. L. et al., Science 249 (1990): 918-921
Rouanne, M. et al., Crit Rev Oncol Hematol. 98 (2016): 106-115
S3-Leitlinie Lungenkarzinom, 020/007, (2011)
Saiki, R. K. et al., Science 239 (1988): 487-491
Salman, B. et al., Oncoimmunology. 2 (2013): e26662
Sangro, B. et al., J Clin Oncol 22 (2004): 1389-1397
Savas, S. et al., PLoS. One. 6 (2011): e18306
Schmidt, S. M. et al., Cancer Res 64 (2004): 1164-1170
Schmitt, T. M. et al., Hum. Gene Ther. 20 (2009): 1240-1248
Scholten, K. B. et al., Clin Immunol. 119 (2006): 135-145
Schuetz, C. S. et al., Cancer Res 66 (2006): 5278-5286
Seeger, F. H. et al., Immunogenetics 49 (1999): 571-576
Sherman, F. et al., Laboratory Course Manual for Methods in Yeast Genetics (1986)
Shi, M. et al., World J Gastroenterol. 10 (2004): 1146-1151
Siegel, S. et al., Blood 102 (2003): 4416-4423
Silva, L. P. et al., Anal. Chem. 85 (2013): 9536-9542
Simmen, F. A. et al., Reprod. Biol Endocrinol. 6 (2008): 41
Singh-Jasuja, H. et al., Cancer Immunol. Immunother. 53 (2004): 187-195
Small, E. J. et al., J Clin Oncol. 24 (2006): 3089-3094
Sowalsky, A. G. et al., Mol. Cancer Res. 13 (2015): 98-106
Spaner, D. E. et al., Cancer Immunol Immunother. 54 (2005): 635-646
Srivastava, N. et al., Cancer Manag. Res. 6 (2014): 279-289
Stanbrough, M. et al., Cancer Res 66 (2006): 2815-2825
Steinberg, R. L. et al., Urol. Oncol (2016a)
Steinberg, R. L. et al., Urol. Oncol (2016b)
Steinway, S. N. et al., PLoS. One. 10 (2015): e0128159
Stevanovic, S. et al., J Clin Oncol 33 (2015): 1543-1550
Stintzing, S., F1000Prime. Rep. 6 (2014): 108
Sturm, M. et al., BMC. Bioinformatics. 9 (2008): 163
Su, Z. et al., Cancer Res. 63 (2003): 2127-2133
Szczepanski, M. J. et al., Oral Oncol 49 (2013): 144-151
Szczepanski, M. J. et al., Biomark. Med. 7 (2013): 575-578
Takayama, T. et al., Cancer 68 (1991): 2391-2396
Takayama, T. et al., Lancet 356 (2000): 802-807
Tan, P. et al., Biochem. Biophys. Res Commun. 419 (2012): 801-808
Tan, Q. et al., Cell Physiol Biochem. 38 (2016): 469-486
Tanaka, F. et al., Int. J Oncol 10 (1997): 1113-1117
Teufel, R. et al., Cell Mol Life Sci. 62 (2005): 1755-1762
Thakkar, J. P. et al., Cancer Epidemiol. Biomarkers Prev. 23 (2014): 1985-1996
Toh, U. et al., Int. J Clin Oncol 7 (2002): 372-375
Toh, U. et al., Clin Cancer Res. 6 (2000): 4663-4673
Toomey, P. G. et al., Cancer Control 20 (2013): 32-42
Tran, E. et al., Science 344 (2014): 641-645
Triulzi, T. et al., Oncotarget. 6 (2015): 28173-28182
Tsuchiya, T. et al., Chemotherapy 61 (2016): 77-86
Uemura, T. et al., Cancer Sci. 101 (2010): 2404-2410
Vici, P. et al., J Exp. Clin Cancer Res 33 (2014): 29
von Rundstedt, F. C. et al., Transl. Androl Urol. 4 (2015): 244-253
Walter, S. et al., J Immunol 171 (2003): 4974-4978
Walter, S. et al., Nat Med. 18 (2012): 1254-1261
Wang, L. et al., Cancer Res 70 (2010): 5818-5828
Whiteland, H. et al., Clin Exp. Metastasis 31 (2014): 909-920
Wierda, W. G. et al., Blood 118 (2011): 5126-5129
Wilhelm, S. M. et al., Cancer Res 64 (2004): 7099-7109
Willcox, B. E. et al., Protein Sci. 8 (1999): 2418-2423
Wilson, P. M. et al., Nat Rev. Clin Oncol 11 (2014): 282-298
Wittig, B. et al., Hum. Gene Ther. 12 (2001): 267-278
World Cancer Report, (2014)
World Health Organization, (2014)
Yamada, A. et al., Breast Cancer Res Treat. 137 (2013): 773-782
Yang, F. et al., Breast Cancer Res Treat. 145 (2014): 23-32
Yao, J. et al., Cancer Immunol. Res. 2 (2014): 371-379
Yeh, I. et al., Nat. Commun. 6 (2015): 7174
Zaremba, S. et al., Cancer Res. 57 (1997): 4570-4577
Zhang, W. et al., Acta Haematol. 130 (2013): 297-304
Zou, C. et al., Cancer 118 (2012): 1845-1855
Zufferey, R. et al., J Virol. 73 (1999): 2886-2892

The invention claimed is:

1. A peptide consisting of the amino acid sequence AYTLIAPNI (SEQ ID NO: 169) in the form of a pharmaceutically acceptable salt.

2. The peptide of claim 1, wherein said peptide has the ability to bind to an MHC class-I molecule, and wherein said peptide, when bound to said MHC, is capable of being recognized by CD8 T cells.

3. The peptide of claim 1, wherein the pharmaceutically acceptable salt is chloride salt.

4. The peptide of claim 1, wherein the pharmaceutically acceptable salt is acetate salt.

5. A composition comprising the peptide of claim 1 and a pharmaceutically acceptable carrier.

6. The composition of claim 5, wherein the peptide is in the form of a chloride salt.

7. The composition of claim 5, wherein the peptide is in the form of an acetate salt.

8. The composition of claim 5, further comprising an adjuvant selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The composition of claim 8, wherein the adjuvant is IL-2.

10. The composition of claim 8, wherein the adjuvant is IL-7.

11. The composition of claim 8, wherein the adjuvant is IL-12.

12. The composition of claim 8, wherein the adjuvant is IL-15.

13. The composition of claim 8, wherein the adjuvant is IL-21.

14. A pegylated peptide consisting of the amino acid sequence of AYTLIAPNI (SEQ ID NO: 169) or a pharmaceutically acceptable salt thereof.

15. The peptide of claim 14, wherein the pharmaceutically acceptable salt is chloride salt.

16. The peptide of claim 14, wherein the pharmaceutically acceptable salt is acetate salt.

17. A composition comprising the pegylated peptide of claim 14 or pharmaceutically acceptable salt thereof, and a pharmaceutically acceptable carrier.

18. The composition of claim 5, wherein the pharmaceutically acceptable carrier is selected from the group consisting of saline, Ringer's solution, dextrose solution, and sustained release preparation.

19. The peptide in the form of a pharmaceutically acceptable salt of claim 1, wherein said peptide is produced by solid phase peptide synthesis or produced by a yeast cell or bacterial cell expression system.

20. A composition comprising the peptide of claim 1, wherein the composition is a pharmaceutical composition and comprises water and a buffer.

\* \* \* \* \*